(12) United States Patent
McHale et al.

(10) Patent No.: US 10,856,791 B2
(45) Date of Patent: Dec. 8, 2020

(54) SYSTEMS, DEVICES, AND METHODS FOR BODILY FLUID SAMPLE COLLECTION

(71) Applicant: Labrador Diagnostics LLC, Healdsburg, CA (US)

(72) Inventors: Patricia McHale, Palo Alto, CA (US); Michael Chen, Sunnyvale, CA (US); Pey-Jiun Ko, Redwood City, CA (US); Tammy Burd, Palo Alto, CA (US); Adrit Lath, Palo Alto, CA (US); Elizabeth A. Holmes, Palo Alto, CA (US); Joy Roy, Palo Alto, CA (US)

(73) Assignee: Labrador Diagnostics LLC, Wilmington, DE (US)

( * ) Notice: Subject to any disclaimer, the term of this patent is extended or adjusted under 35 U.S.C. 154(b) by 52 days.

(21) Appl. No.: 15/244,990

(22) Filed: Aug. 23, 2016

(65) Prior Publication Data
US 2017/0042460 A1 Feb. 16, 2017

Related U.S. Application Data

(63) Continuation of application No. PCT/US2015/020307, filed on Mar. 12, 2015.
(Continued)

(51) Int. Cl.
*A61B 5/15* (2006.01)
*G01N 1/10* (2006.01)
(Continued)

(52) U.S. Cl.
CPC .... *A61B 5/150946* (2013.01); *A61B 5/15003* (2013.01); *A61B 5/154* (2013.01);
(Continued)

(58) Field of Classification Search
CPC ...................................................... A61B 5/155
See application file for complete search history.

(56) References Cited

U.S. PATENT DOCUMENTS 3,405,706 A   10/1968   Paul
3,604,410 A   9/1971    Whitacre
(Continued)

FOREIGN PATENT DOCUMENTS

CN   2128870        3/1993
EA   200600893 A1   12/2006
(Continued)

OTHER PUBLICATIONS

BD Diagnostics. product catalogue 2010/2011.
(Continued)

*Primary Examiner* — Paul S Hyun

(57) ABSTRACT

Bodily fluid sample collection systems, devices, and method are provided. The device may comprise a first portion comprising at least a sample collection channel configured to draw the fluid sample into the sample collection channel via a first type of motive force. The sample collection device may include a second portion comprising a sample container for receiving the bodily fluid sample collected in the sample collection channel, the sample container operably engagable to be in fluid communication with the collection channel, whereupon when fluid communication is established, the container provides a second motive force different from the first motive force to move a majority of the bodily fluid sample from the channel into the container.

22 Claims, 61 Drawing Sheets

Related U.S. Application Data

(60) Provisional application No. 62/051,906, filed on Sep. 17, 2014, provisional application No. 61/952,130, filed on Mar. 12, 2014, provisional application No. 61/952,125, filed on Mar. 12, 2014.

(51) Int. Cl.
| | |
|---|---|
| *A61B 10/00* | (2006.01) |
| *A61B 5/154* | (2006.01) |
| *A61B 5/151* | (2006.01) |
| *A61B 5/155* | (2006.01) |
| *B01L 3/00* | (2006.01) |
| *G01N 1/14* | (2006.01) |

(52) U.S. Cl.
CPC ........ *A61B 5/155* (2013.01); *A61B 5/150022* (2013.01); *A61B 5/15074* (2013.01); *A61B 5/150099* (2013.01); *A61B 5/15117* (2013.01); *A61B 5/150213* (2013.01); *A61B 5/150343* (2013.01); *A61B 5/150351* (2013.01); *A61B 5/150389* (2013.01); *A61B 5/150503* (2013.01); *A61B 5/150755* (2013.01); *A61B 5/150763* (2013.01); *A61B 5/150786* (2013.01); *A61B 5/150992* (2013.01); *A61B 10/0045* (2013.01); *B01L 3/50273* (2013.01); *B01L 3/502715* (2013.01); *G01N 1/10* (2013.01); *G01N 1/14* (2013.01); *A61B 2010/008* (2013.01); *B01L 2200/0605* (2013.01); *B01L 2300/041* (2013.01); *B01L 2300/0838* (2013.01); *B01L 2300/0861* (2013.01); *B01L 2300/16* (2013.01); *B01L 2400/0406* (2013.01); *B01L 2400/0487* (2013.01); *G01N 2001/149* (2013.01)

(56) References Cited

U.S. PATENT DOCUMENTS

| | | | |
|---|---|---|---|
| 3,679,129 A | 7/1972 | Livshitz et al. | |
| 3,848,581 A | 11/1974 | Cinqualbre et al. | |
| 3,960,139 A | 6/1976 | Bailey | |
| 4,150,089 A | 4/1979 | Linet | |
| 4,250,893 A | 2/1981 | White | |
| 4,292,817 A | 10/1981 | Loucks | |
| 4,318,406 A * | 3/1982 | McLeod | B01D 46/10 604/333 |
| 4,434,802 A | 3/1984 | Rilliet | |
| 4,474,033 A | 10/1984 | Baker | |
| 4,492,634 A | 1/1985 | Villa-Real | |
| 4,650,662 A | 3/1987 | Goldfinger et al. | |
| 4,676,256 A | 6/1987 | Golden | |
| 4,703,762 A | 11/1987 | Rathbone et al. | |
| 4,844,098 A | 7/1989 | Mitchen | |
| 4,932,533 A | 6/1990 | Collier | |
| 4,951,685 A | 8/1990 | Blair | |
| 4,964,509 A | 10/1990 | Insley et al. | |
| 4,976,271 A | 12/1990 | Blair | |
| 5,033,476 A | 7/1991 | Kasai | |
| 5,057,282 A | 10/1991 | Linder | |
| 5,086,780 A | 2/1992 | Schmitt | |
| 5,104,375 A | 4/1992 | Wolf et al. | |
| 5,199,795 A | 4/1993 | Russo et al. | |
| 5,249,584 A | 10/1993 | Karkar et al. | |
| 5,277,198 A | 1/1994 | Kanner et al. | |
| 5,314,412 A | 5/1994 | Rex | |
| 5,360,423 A | 11/1994 | McCormick | |
| 5,447,417 A | 9/1995 | Kuhl et al. | |
| 5,505,721 A | 4/1996 | Leach et al. | |
| 5,569,210 A | 10/1996 | Moen | |
| 5,578,269 A | 11/1996 | Yaremko et al. | |
| 5,707,876 A | 1/1998 | Levine | |
| 5,785,662 A | 7/1998 | Alexander | |
| 5,833,057 A | 11/1998 | Char et al. | |
| 5,833,630 A | 11/1998 | Kloth | |
| 5,897,508 A | 4/1999 | Konrad | |
| 6,056,925 A | 5/2000 | Sarstedt | |
| 6,221,672 B1 | 4/2001 | Baugh et al. | |
| 6,521,460 B1 | 2/2003 | Strasser et al. | |
| 6,531,098 B1 | 3/2003 | Kenney | |
| 6,541,243 B1 | 4/2003 | Harris et al. | |
| 6,555,064 B2 | 4/2003 | Baugh et al. | |
| 6,555,066 B2 | 4/2003 | Baugh et al. | |
| 6,555,381 B2 | 4/2003 | Baugh et al. | |
| 6,569,676 B1 | 5/2003 | Tripp et al. | |
| 6,626,863 B1 | 9/2003 | Berler | |
| 6,662,941 B2 | 12/2003 | Lowry et al. | |
| 6,852,290 B2 | 2/2005 | Hager et al. | |
| 6,875,405 B1 | 4/2005 | Mathus et al. | |
| 6,899,227 B2 | 5/2005 | Miersch | |
| 7,118,538 B2 | 10/2006 | Konrad | |
| 7,223,346 B2 | 5/2007 | Dorian et al. | |
| 7,305,896 B2 | 12/2007 | Howell et al. | |
| 7,335,188 B2 | 2/2008 | Graf | |
| 7,378,054 B2 | 5/2008 | Karmali | |
| 7,413,910 B2 | 8/2008 | Kearney et al. | |
| 7,699,966 B2 | 4/2010 | Qin et al. | |
| 7,785,773 B1 | 8/2010 | Anderson et al. | |
| 7,810,348 B2 | 10/2010 | Shewchuk | |
| 8,158,062 B2 | 4/2012 | Dykes et al. | |
| 8,474,228 B2 | 7/2013 | Adair et al. | |
| 8,801,918 B2 | 8/2014 | Qin et al. | |
| 8,841,118 B2 | 9/2014 | Robinson et al. | |
| 9,224,120 B2 | 12/2015 | Grabiner et al. | |
| 2001/0031932 A1 | 10/2001 | Blake et al. | |
| 2002/0004647 A1 | 1/2002 | Leong | |
| 2003/0185707 A1 | 10/2003 | Iwaki et al. | |
| 2004/0030353 A1 | 2/2004 | Schmelzeisen-Redeker et al. | |
| 2005/0036907 A1 | 2/2005 | Shoji | |
| 2005/0059163 A1 | 3/2005 | Dastane et al. | |
| 2005/0232813 A1 | 10/2005 | Karmali | |
| 2005/0236346 A1 | 10/2005 | Whitney | |
| 2006/0228258 A1 | 10/2006 | Samsoondar | |
| 2006/0233676 A1 | 10/2006 | Stein | |
| 2007/0016102 A1 | 1/2007 | Askin | |
| 2007/0104616 A1 | 5/2007 | Keenan et al. | |
| 2007/0154895 A1 | 7/2007 | Spaid et al. | |
| 2008/0025872 A1 | 1/2008 | Dykes et al. | |
| 2008/0299663 A1 | 12/2008 | Hudson | |
| 2008/0312555 A1 | 12/2008 | Boecker | |
| 2008/0318259 A1 | 12/2008 | Ranby | |
| 2009/0047179 A1 | 2/2009 | Ping et al. | |
| 2009/0088336 A1 | 4/2009 | Burd et al. | |
| 2009/0139925 A1 | 6/2009 | Sternberg | |
| 2009/0162941 A1 | 6/2009 | Winkler et al. | |
| 2009/0208923 A1 | 8/2009 | Gelfand et al. | |
| 2009/0240165 A1 | 9/2009 | Yoneya et al. | |
| 2009/0259145 A1 | 10/2009 | Bartfeld et al. | |
| 2009/0306543 A1 | 12/2009 | Slowey et al. | |
| 2010/0184056 A1 | 7/2010 | Weinberger et al. | |
| 2010/0185322 A1 | 7/2010 | Bylsma et al. | |
| 2010/0249652 A1 | 9/2010 | Rush et al. | |
| 2011/0009717 A1 * | 1/2011 | Davis | A61B 5/1405 600/309 |
| 2011/0124025 A1 | 5/2011 | Castracane et al. | |
| 2011/0244595 A1 * | 10/2011 | Chung | B01L 3/5027 436/501 |
| 2011/0284110 A1 | 11/2011 | Gagnon | |
| 2011/0312481 A1 | 12/2011 | Nguyen et al. | |
| 2012/0029384 A1 | 2/2012 | Crosman | |
| 2012/0045826 A1 | 2/2012 | Yantz et al. | |
| 2012/0101407 A1 | 4/2012 | Chan | |
| 2012/0123297 A1 | 5/2012 | Brancazio | |
| 2012/0271123 A1 | 10/2012 | Castle et al. | |
| 2012/0277629 A1 | 11/2012 | Bernstein et al. | |
| 2013/0019697 A1 | 1/2013 | McKeen et al. | |
| 2013/0172780 A1 | 7/2013 | Kuenstner | |
| 2014/0073990 A1 | 3/2014 | Holmes et al. | |
| 2014/0323911 A1 | 3/2014 | Sloan | |
| 2014/0171829 A1 | 6/2014 | Holmes et al. | |
| 2014/0219886 A1 | 8/2014 | Choi et al. | |
| 2014/0234949 A1 | 8/2014 | Wasson et al. | |

(56) References Cited

U.S. PATENT DOCUMENTS

| | | | |
|---|---|---|---|
| 2014/0316300 A1 | 10/2014 | Holmes et al. |
| 2014/0323913 A1 | 10/2014 | Holmes et al. |
| 2014/0342371 A1 | 11/2014 | Holmes |
| 2014/0358036 A1 | 12/2014 | Holmes |
| 2015/0231627 A1 | 8/2015 | Sloan et al. |
| 2017/0000826 A1 | 1/2017 | Tucker et al. |

FOREIGN PATENT DOCUMENTS

| | | | |
|---|---|---|---|
| EP | 0203930 B1 | 7/1990 |
| EP | 0550950 A2 | 7/1993 |
| EP | 1005910 A2 | 6/2000 |
| EP | 2052807 A1 | 4/2009 |
| GB | 2409411 | 6/2005 |
| JP | 63148868 | 9/1988 |
| JP | 2007167123 A | 7/2007 |
| SU | 1088789 A | 4/1984 |
| WO | 1986003008 A1 | 5/1986 |
| WO | 2005076733 A2 | 8/2005 |
| WO | 2009053432 A | 4/2009 |
| WO | 2014039909 A | 3/2014 |
| WO | 2014145330 A2 | 9/2014 |
| WO | 2014145935 A1 | 9/2014 |
| WO | 2015070247 A1 | 5/2015 |
| WO | 2014088606 | 7/2015 |

OTHER PUBLICATIONS

Biosigma. Disposable Labware for Life Science. catalogue 2009.
Bush et al. The Evolution of Evacuated Blood Collection Tubes. BD Vacutainer(R) LabNotes—vol. 19, No. 1, 2009.
Centers for Disease Control and Prevention. "Capillary Blood Sampling Protocol" 1997.
Deschka. "Blood Collection in Practice. A guideline for phlebotomists", Sep. 2009.
Home Blood Tests UK. "Home blood test kits. Collect at home, send to our laboratory." dated Jun. 13, 2012.
http://www.metzner.com/en/products/cable-processing-corrugated-tubes/corrugated-tube-processing/metzner-sm-4000-cutting-corrugated-tubes.html.
International Report and Written Opinion dated Nov. 20, 2014 for PCT/US2014/030070.
International Search Report and Written Opinion dated Aug. 28, 2014 for Application No. PCT/US2014/030792.
International Search Report and Written Opinion dated Aug. 6, 2015 for PCT/US2015/020307.
Massachusetts Department of Public Health. "Instructions for fingerstick sample collection for lead testing", Sep. 2012.
Medichecks. "Collection of a finger prick blood sample", Sep. 2012.
Notice of Allowance dated Feb. 23, 2016 for U.S. Appl. No. 14/098,177.
Notice of Allowance dated Jun. 13, 2016 for U.S. Appl. No. 14/320,471.
Notice of Allowance dated Aug. 10, 2015 for U.S. Appl. No. 14/320,471.
Office Action dated Jan. 11, 2016 for U.S. Appl. No. 14/447,099.
Office Action dated Oct. 14, 2014 for U.S. Appl. No. 14/447,099.
Office Action dated Nov. 28, 2014 for U.S. Appl. No. 14/320,471.
Office Action dated Nov. 14, 2015 for U.S. Appl. No. 14/020,435.
Office Action dated Mar. 20, 2015 for U.S. Appl. No. 14/320,471.
Office Action dated Mar. 22, 2016 for U.S. Appl. No. 14/020,435.
Office Action dated Mar. 25, 2015 for U.S. Appl. No. 14/447,099.
Office Action dated Apr. 21, 2016 for U.S. Appl. No. 14/446,080.
Office Action dated Apr. 6, 2015 for U.S. Appl. No. 14/446,080.
Office Action dated May 5, 2016 for U.S. Appl. No. 14/214,774.
Office Action dated Jun. 16, 2015 for U.S. Appl. No. 14/020,435.
Office Action dated Jul. 30, 2015 for U.S. Appl. No. 14/446,080.
Office Action dated Aug. 15, 2016 for U.S. Appl. No. 14/447,099.
Office Action dated Aug. 5, 2015 for U.S. Appl. No. 14/098,177.
Office Action dated Sep. 22, 2016 for U.S. Appl. No. 14/020,435.
Ram Scientific. Safe-T-Fill Capillary Blood Collection Tubes. 2006.
Sarstedt. comprehensive catalogue. Cover page and pp. 1-43. last modified 2007.
Sarstedt. comprehensive catalogue. last modified 2007.
The International Search Report and the Written Opinion dated Feb. 13, 2014 for Application No. PCT/US2013/058627.
The International Search Report and the Written Opinion dated Jun. 10, 2014 for Application No. PCT/US13/00268.
U.S. Appl. No. 61/697,797, filed Sep. 6, 2012.
U.S. Appl. No. 61/733,886, filed Dec. 5, 2012.
U.S. Appl. No. 61/786,351, filed Mar. 15, 2013.
U.S. Appl. No. 61/798,873, filed Mar. 15, 2013.
U.S. Appl. No. 61/852,489, filed Mar. 15, 2013.
U.S. Appl. No. 61/875,030, filed Sep. 7, 2013.
U.S. Appl. No. 61/948,542, filed Mar. 5, 2014.
U.S. Appl. No. 61/952,112, filed Mar. 12, 2014.
U.S. Appl. No. 61/952,125, filed Mar. 12, 2014.
U.S. Appl. No. 61/952,130, filed Mar. 12, 2014.
U.S. Appl. No. 62/011,023, filed Jun. 11, 2014.
International Search Report dated Dec. 8, 2016 for PCT/US2016/043435.
Office Action dated Mar. 8, 2017 for U.S. Appl. No. 14/737,412.
Notice of Allowance dated Jan. 27, 2017 for U.S. Appl. No. 13/214,774.
Notice of Allowance dated Feb. 27, 2017 for U.S. Appl. No. 14/020,435.
Office Action dated Dec. 29, 2016 for U.S. Appl. No. 14/446,080.
Gamez et al. Toward PKU Enzyme Replacement Therapy: PEGylation with Activity Retention for Three Forms of Recombinant Phenylalanine Hydroxylase. Molecular Therapy 9(1) 2004 124-129.
Office Action dated Apr. 17, 2018 for U.S. Appl. No. 15/216,658.
Office Action dated Apr. 4, 2019 for U.S. Appl. No. 15/216,658.
Phenulketonuria, National Institute of Health, 2019, pp. 1-6.
Notice of Allowance dated Nov. 3, 2017 for U.S. Appl. No. 14/737,412.
Office Action dated May 15, 2017 for U.S. Appl. No. 14/447,099.
Office Action dated Feb. 27, 2020 for U.S. Appl. No. 15/851,411.
Office Action dated Jan. 10, 2020 for U.S. Appl. No. 15/216,658.
Office Action dated Sep. 26, 2019 for U.S. Appl. No. 14/447,099.
Sigma-Aldrich, Natural Gravitation Forces and Centrifugation, pp. 1-3, 2011.

* cited by examiner

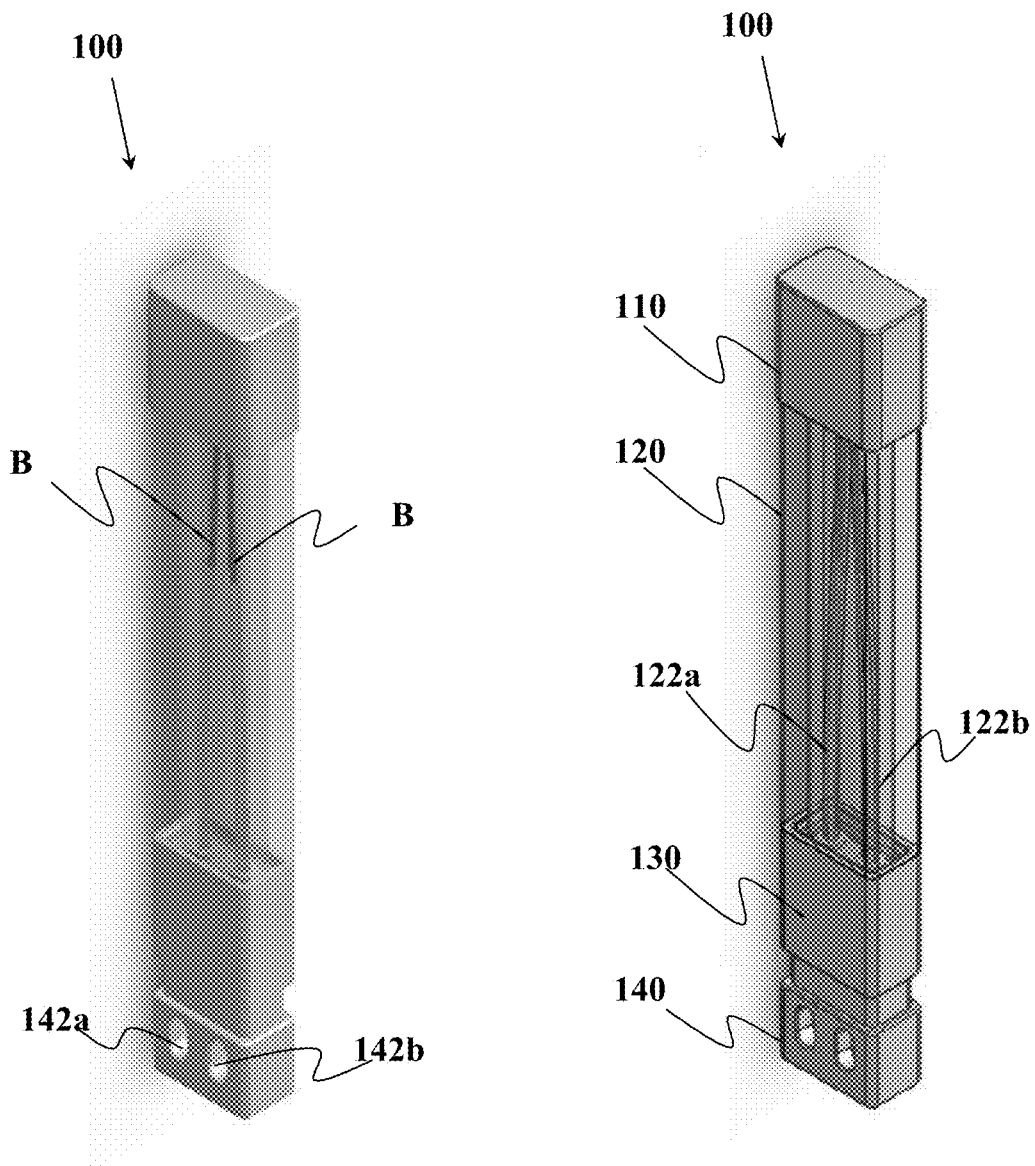

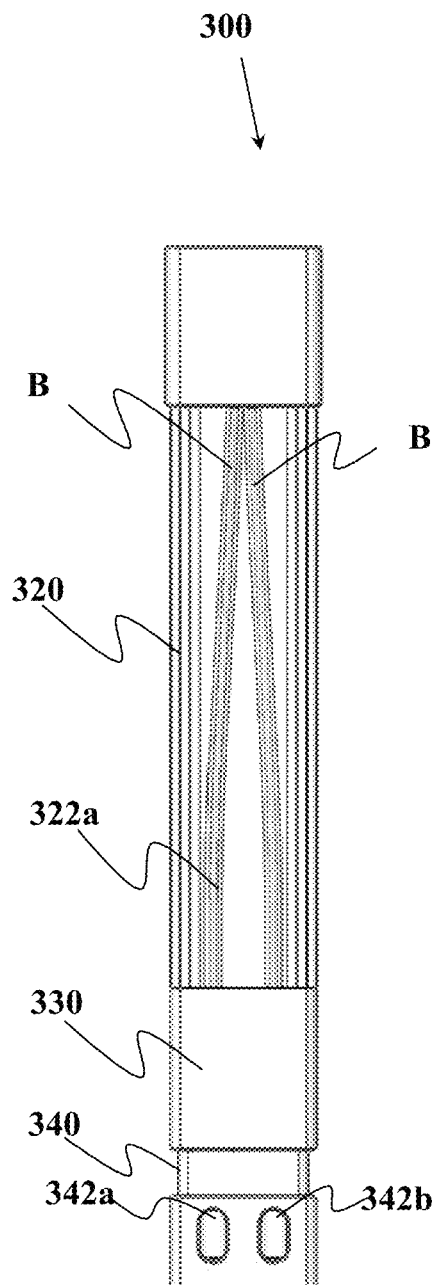
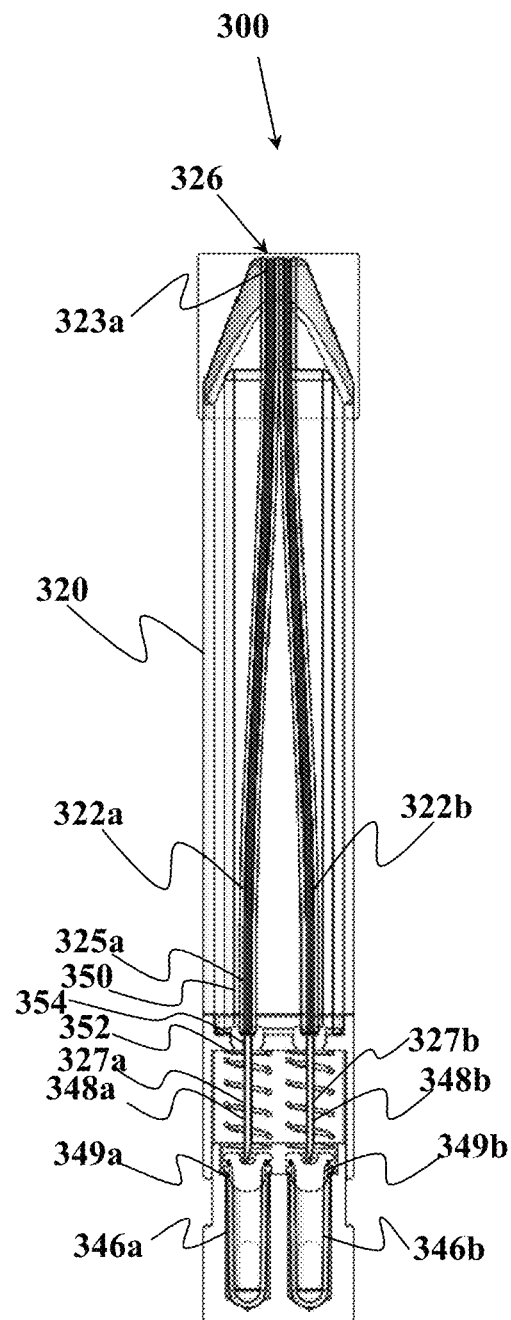
FIG. 3A
FIG. 3B

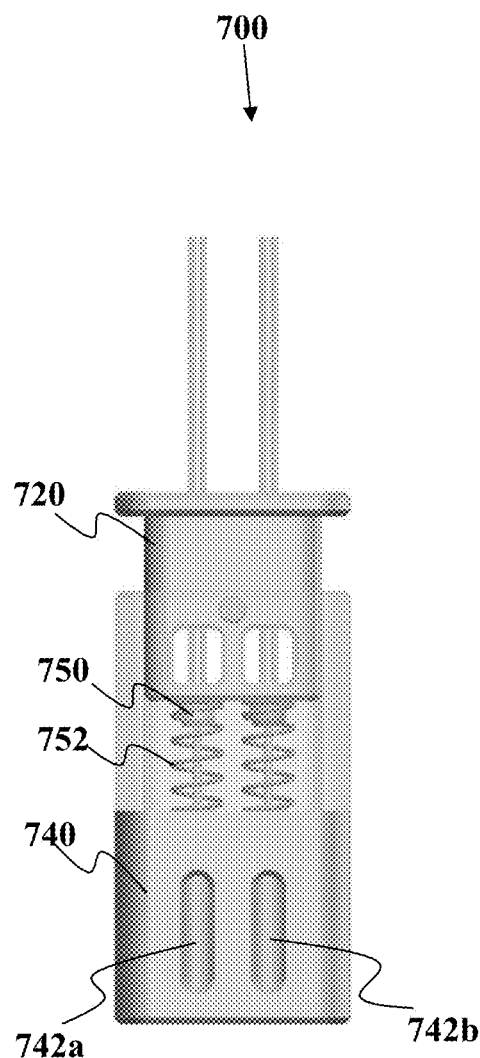
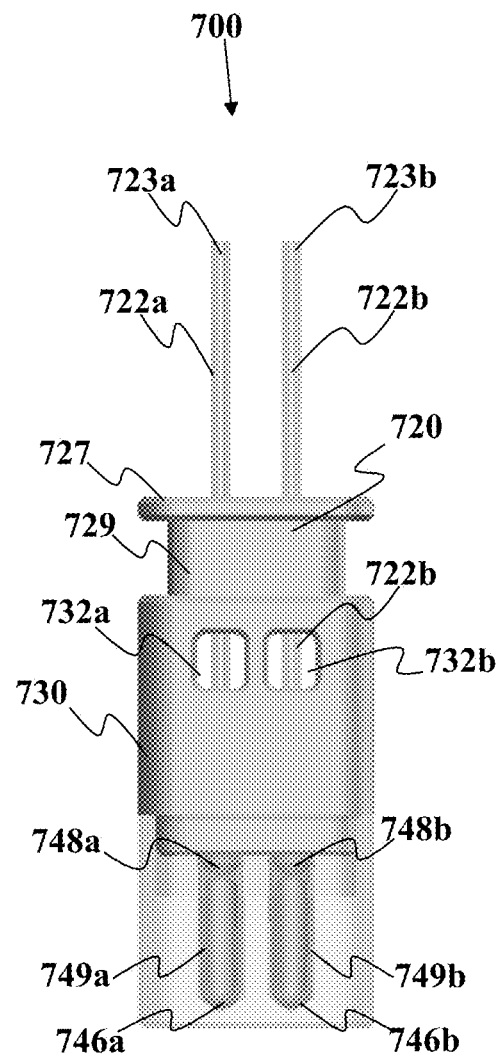
FIG. 7A
FIG. 7B

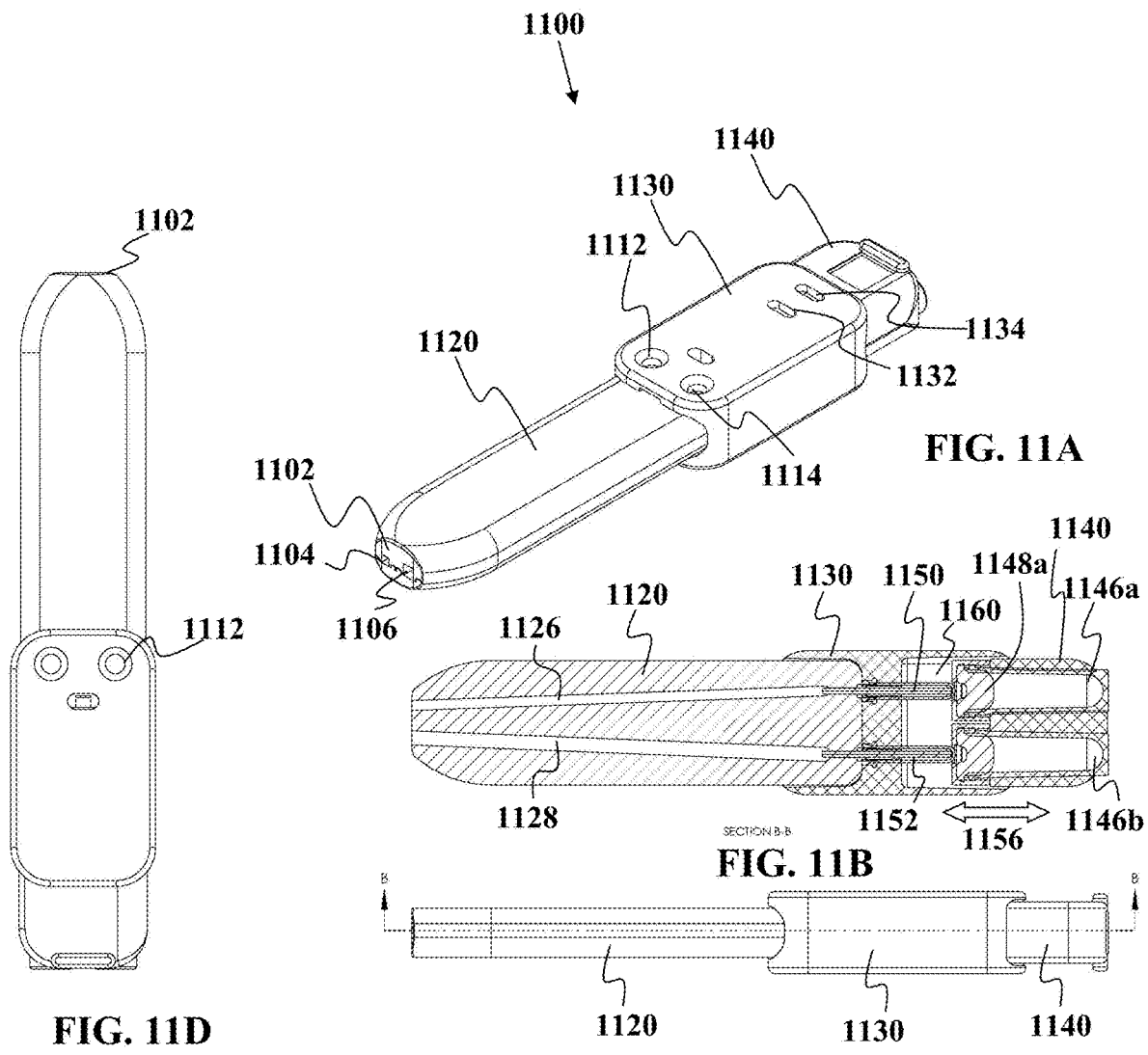

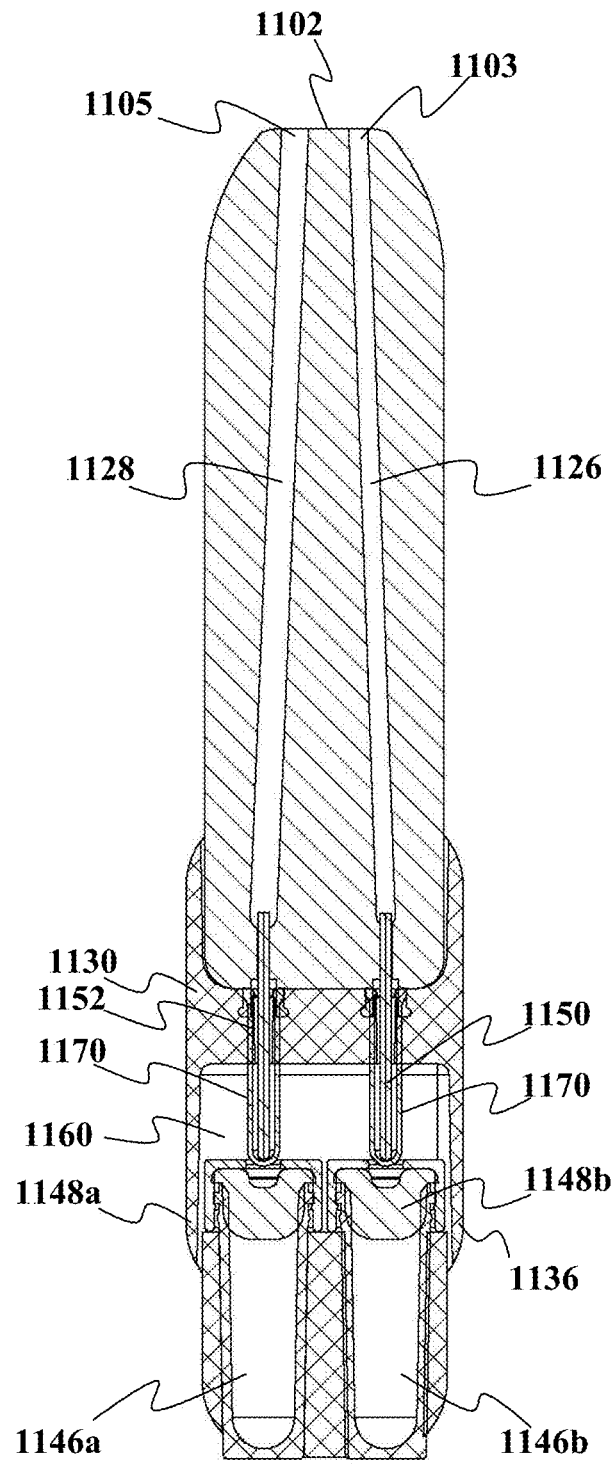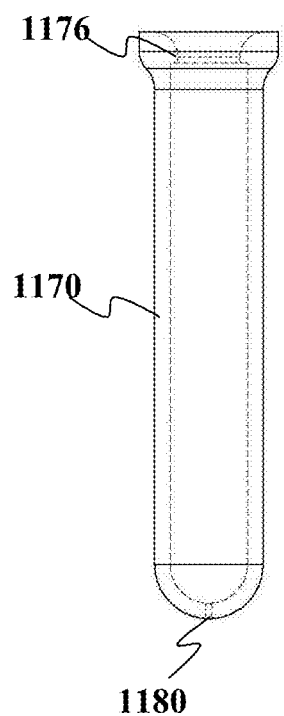
FIG. 11E
FIG. 11F

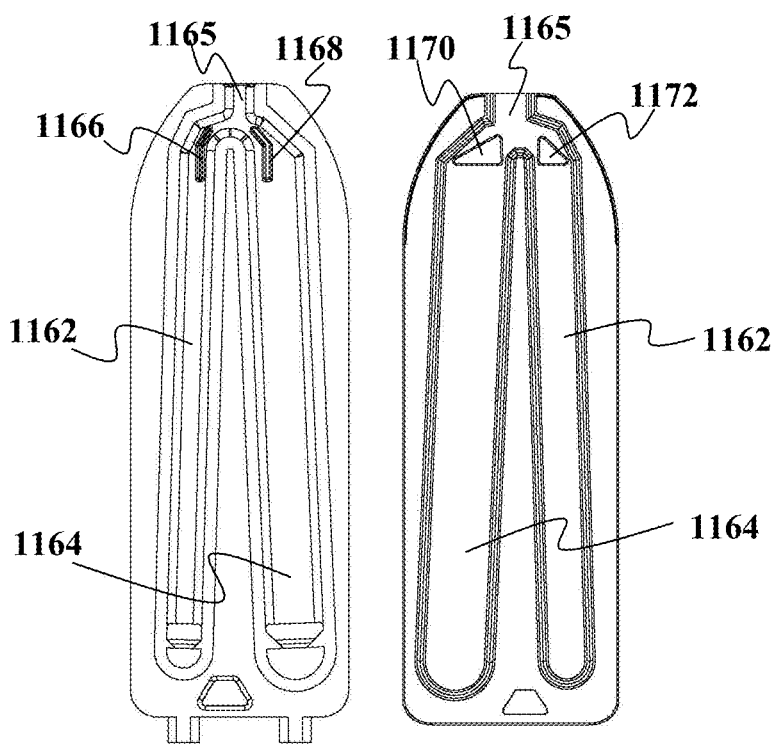
FIG. 11L  FIG. 11M
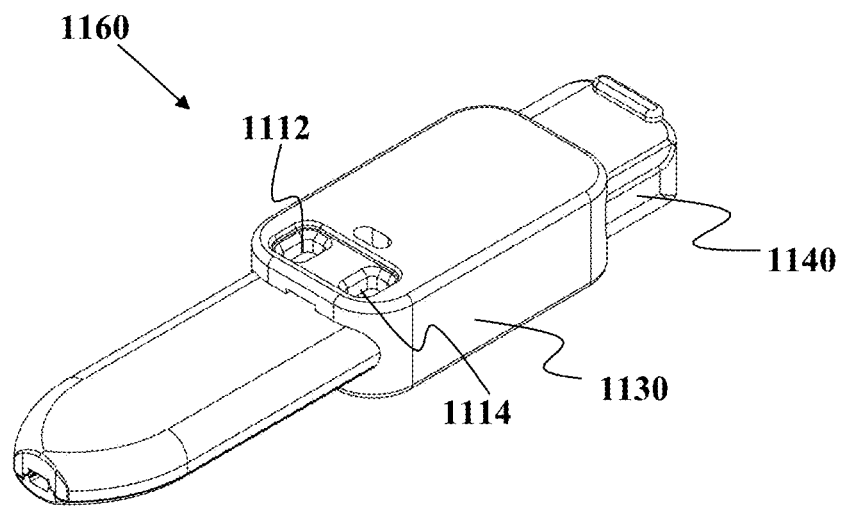
FIG. 11N

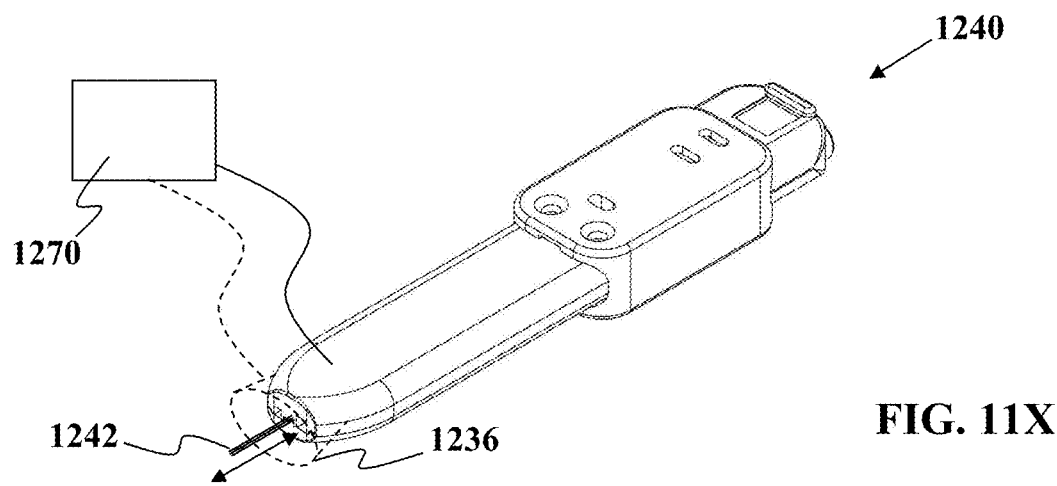
FIG. 11X
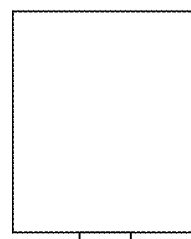
FIG. 11Y
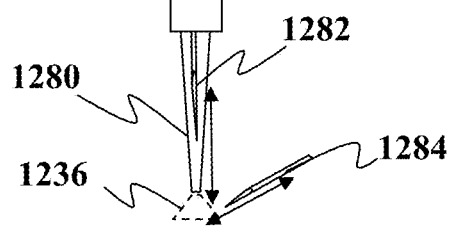
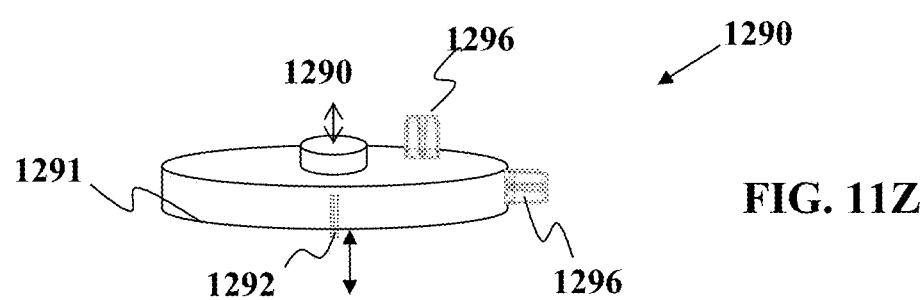
FIG. 11Z

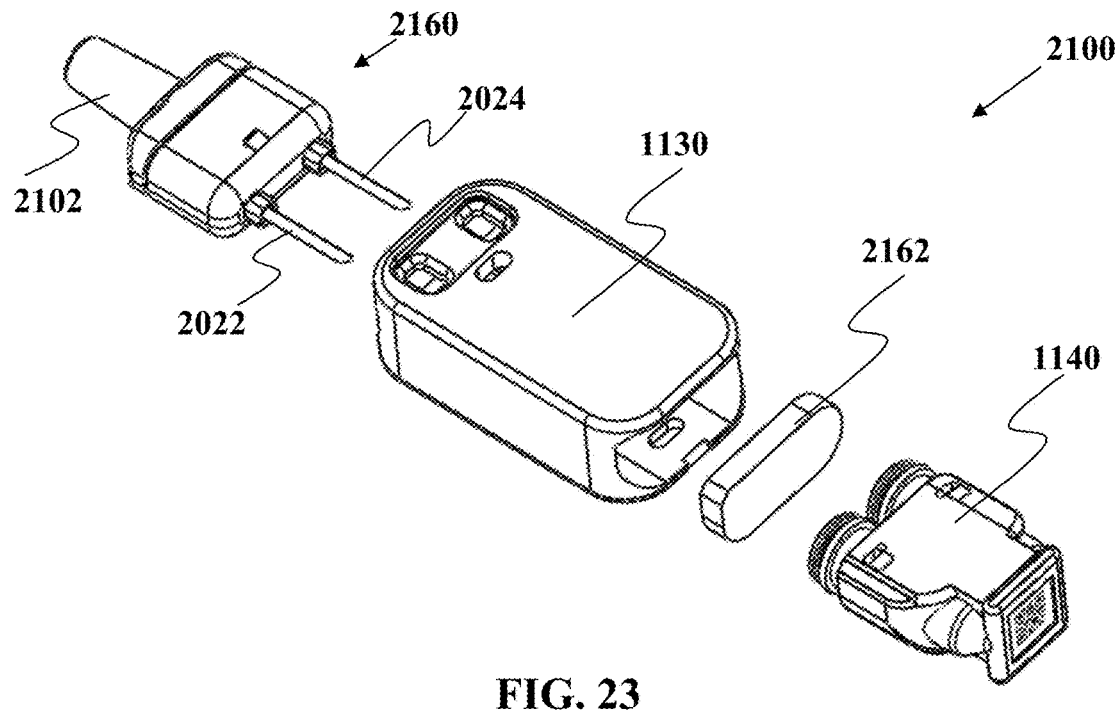
FIG. 23
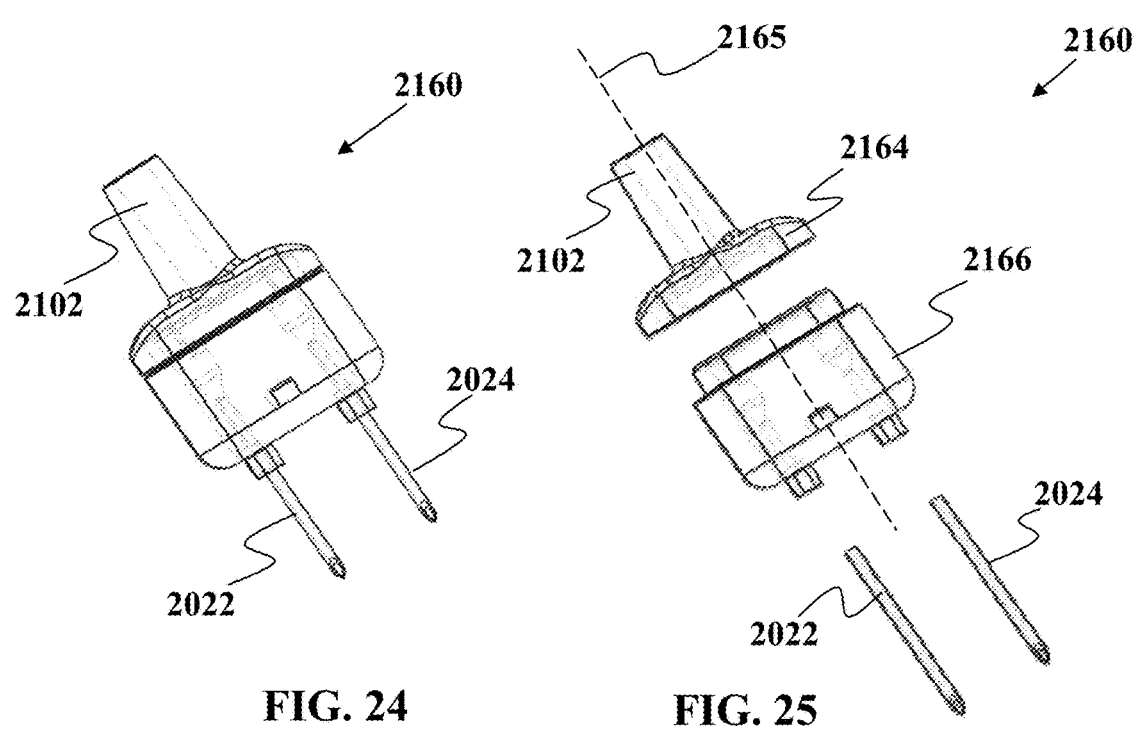
FIG. 24  FIG. 25

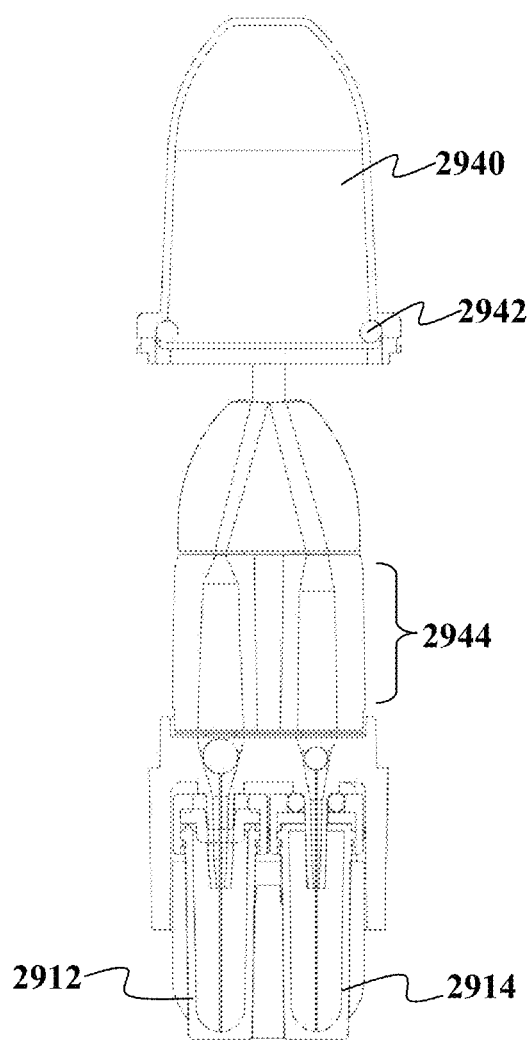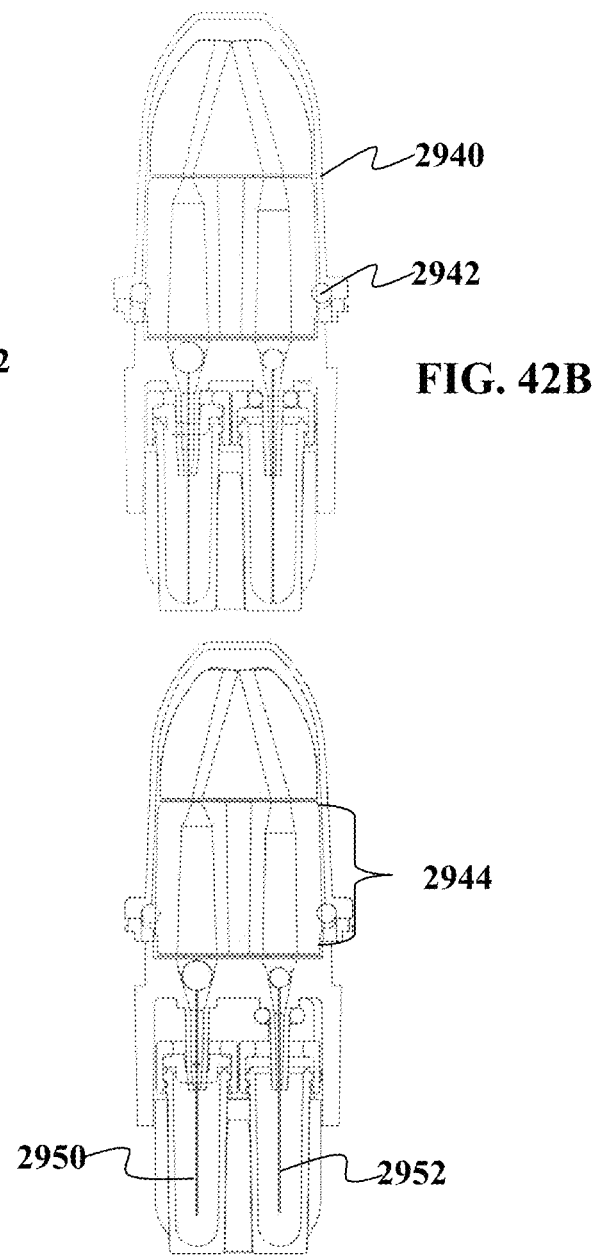
FIG. 42A
FIG. 42B
FIG. 42C

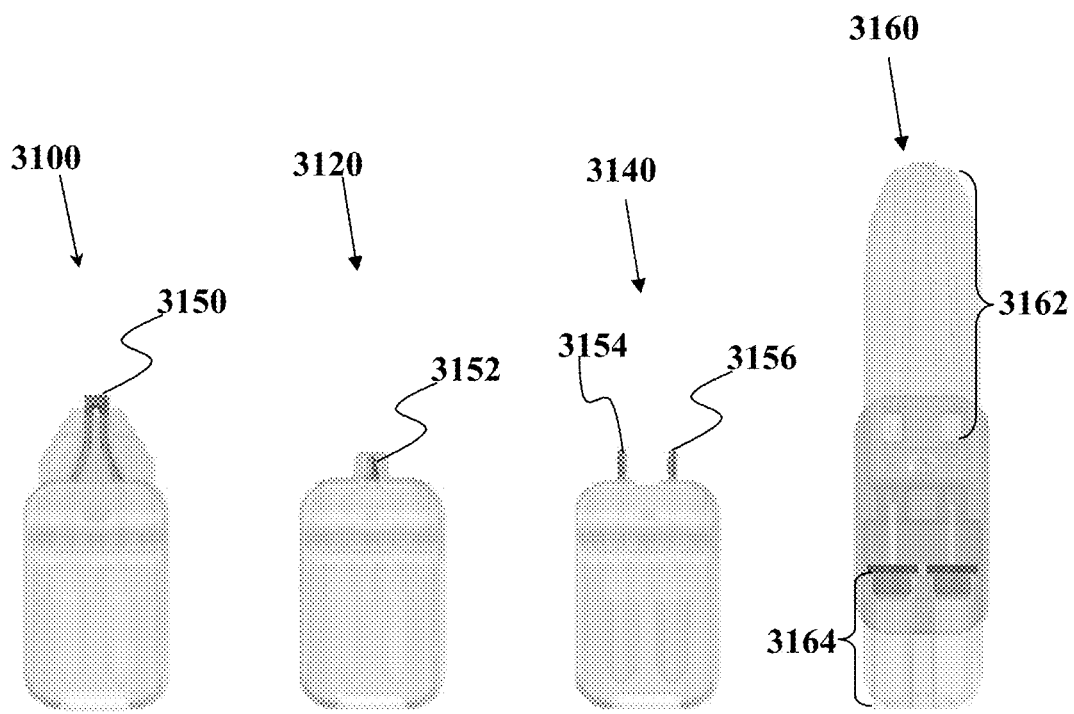
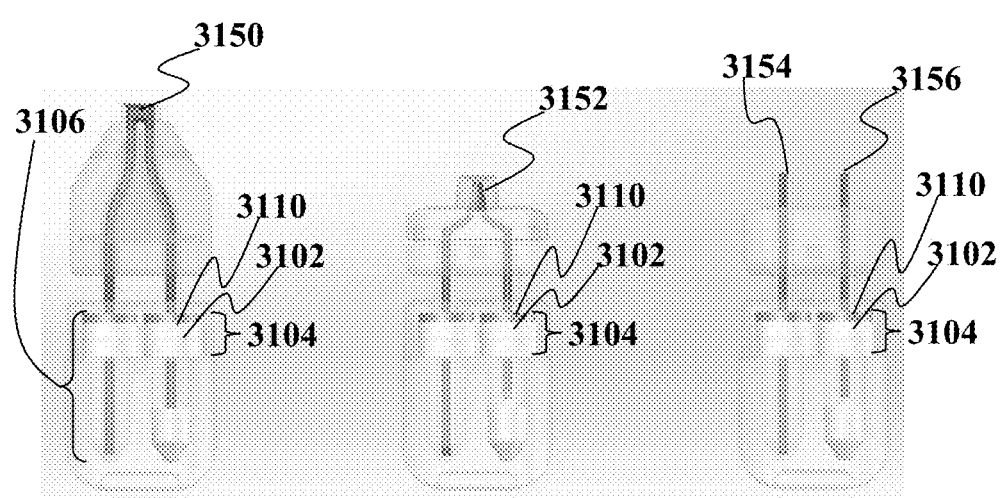

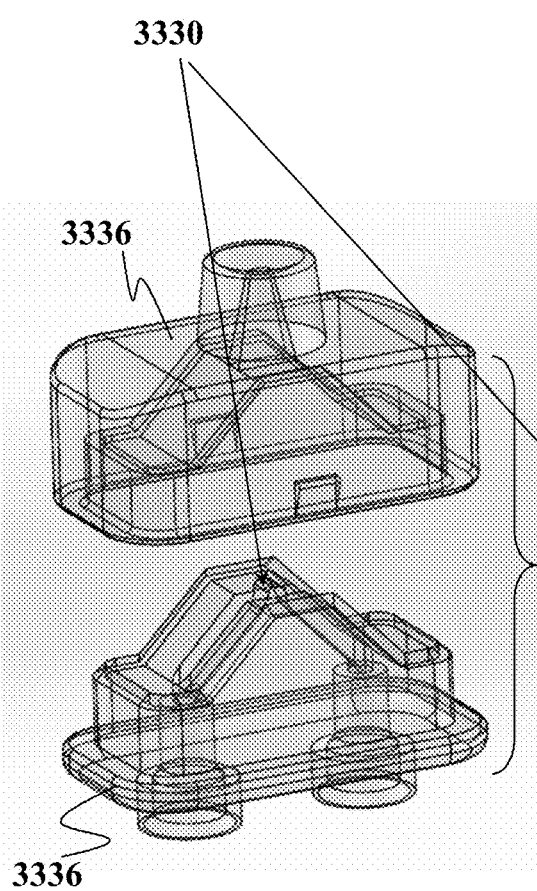
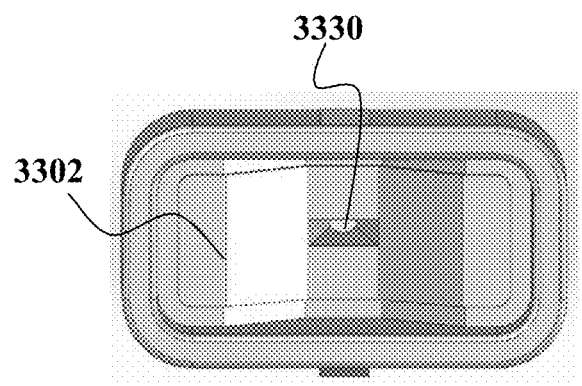
FIG. 57B
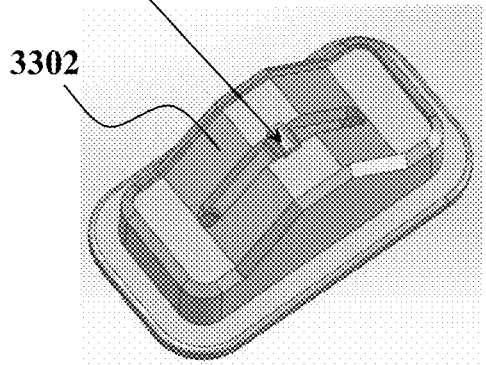
FIG. 57C
FIG. 57A

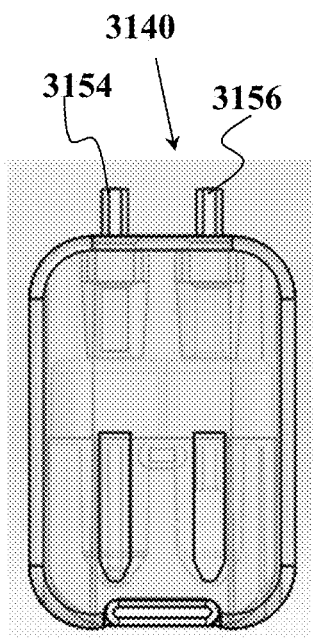
FIG. 58A
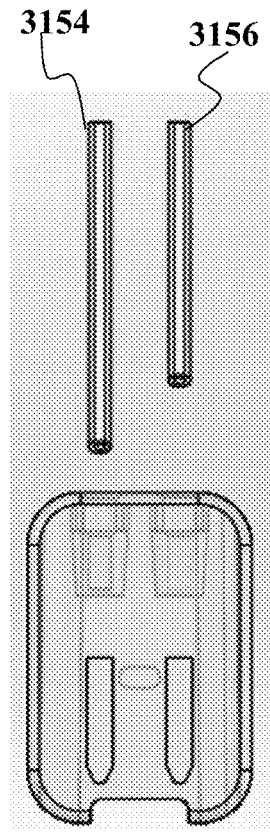
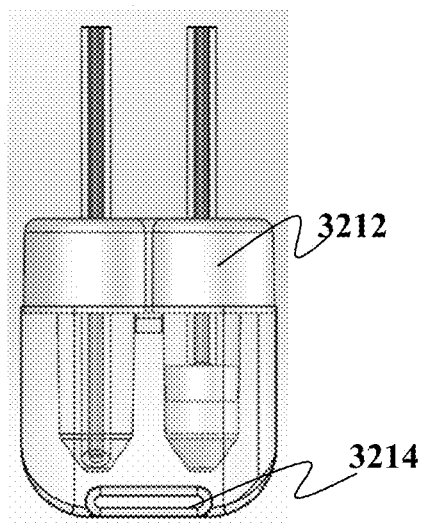
FIG. 58B
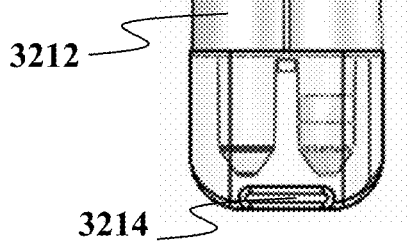
FIG. 58C

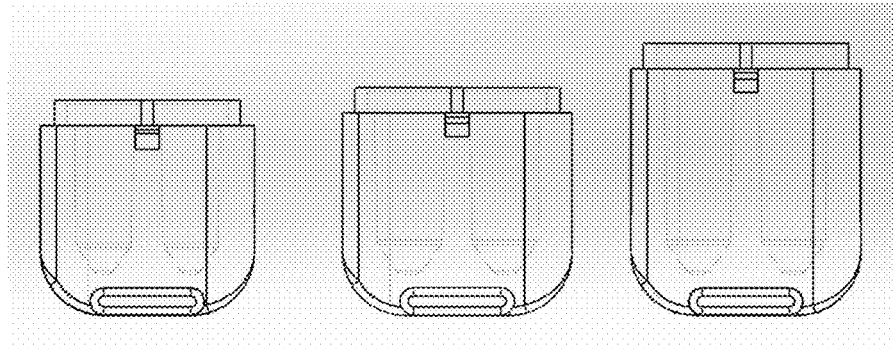
FIG. 61A    FIG. 61B    FIG. 61C
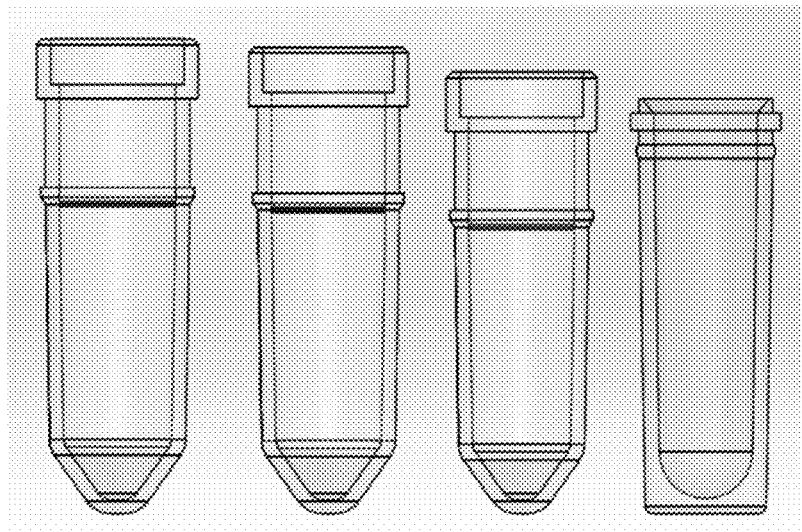
FIG. 62A  FIG. 62B  FIG. 62C
                              FIG. 62D

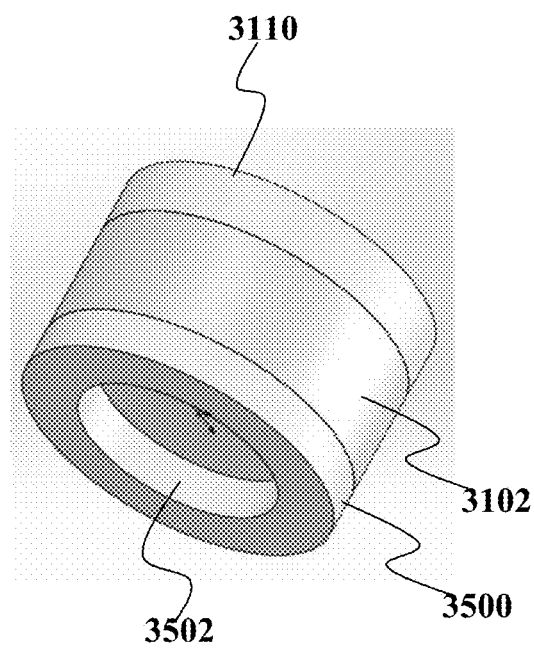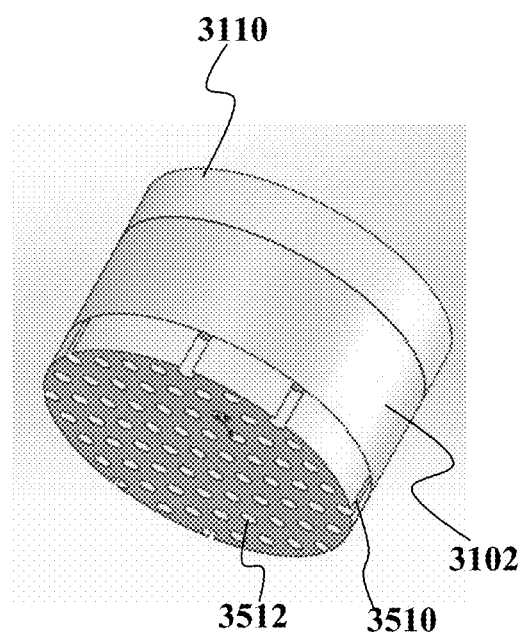
FIG. 65
FIG. 66

SYSTEMS, DEVICES, AND METHODS FOR BODILY FLUID SAMPLE COLLECTION

BACKGROUND

A blood sample for use in laboratory testing is often obtained by way of venipuncture, which typically involves inserting a hypodermic needle into a vein on the subject. Blood extracted by the hypodermic needle may be drawn directly into a syringe or into one or more sealed vials for subsequent processing. When a venipuncture may be difficult or impractical such as on a newborn infant, a non-venous puncture such as a heel stick or other alternate site puncture may be used to extract a blood sample for testing. After the blood sample is collected, the extracted sample is typically packaged and transferred to a processing center for analysis.

Unfortunately, conventional sample collection and testing techniques of bodily fluid samples have drawbacks. For instance, except for the most basic tests, blood tests that are currently available typically require a substantially high volume of blood to be extracted from the subject. Because of the high volume of blood, extraction of blood from alternate sample sites on a subject, which may be less painful and/or less invasive, are often disfavored as they do not yield the blood volumes needed for conventional testing methodologies. In some cases, patient apprehension associated with venipuncture may reduce patient compliance with testing protocol. Furthermore, the traditional collection technique adds unnecessary complexity when trying to separate a single blood sample into different containers for different pre-analytical processing.

SUMMARY

At least some of disadvantages associated with the prior art are overcome by at least some or all of the embodiments described in this disclosure. Although the embodiments herein are typically described in the context of obtaining a blood sample, it should be understood that the embodiments herein are not limited to blood samples and can also be adapted to acquire other fluid(s) or bodily sample(s) for analysis.

In one embodiment described herein, a device is provided for collecting a bodily fluid sample. This embodiment may be useful for accurately collecting small volumes of bodily fluid sample that are often associated with non-venous blood draws. In one non-limiting example, the sample volume is about 1 mL or less. Optionally, the sample volume is about 900 uL or less. Optionally, the sample volume is about 800 uL or less. Optionally, the sample volume is about 700 uL or less. Optionally, the sample volume is about 600 uL or less. Optionally, the sample volume is about 500 uL or less. Optionally, the sample volume is about 400 uL or less. Optionally, the sample volume is about 300 uL or less. Optionally, the sample volume is about 200 uL or less. Optionally, the sample volume is about 100 uL or less. Optionally, the sample volume is about 90 uL or less. Optionally, the sample volume is about 80 uL or less. Optionally, the sample volume is about 70 uL or less. Optionally, the sample volume is about 60 uL or less. Optionally, the sample volume is about 50 uL or less.

In one non-limiting example, this device can be used to split the bodily fluid sample directly into two or more different portions that are then deposited into their respective containers. In one non-limiting example, the device comprises a first portion having at least two sample collection channels configured to draw the fluid sample into the sample collection channels via a first type of motive force, wherein one of the sample collection channels has an interior coating designed to mix with the fluid sample and another of the sample collection channels has another interior coating chemically different from said interior coating. The sample collection device includes a second portion comprising a plurality of sample containers for receiving the bodily fluid sample collected in the sample collection channels, the sample containers operably engagable to be in fluid communication with the collection channels, whereupon when fluid communication is established, the containers provide a second motive force different from the first motive force to move a majority of the bodily fluid sample from the channels into the containers. The containers may be arranged such that mixing of the fluid sample between the containers does not occur. Because this device may be used with non-venous draws, it may take a longer period of time to obtain a desired volume of sample and the early introduction of a material such as an anti-coagulant which may coat the channels, can prevent premature clogging of the channels during collection.

In another embodiment described herein, a device is provided for collecting a bodily fluid sample. The device comprises a first portion comprising a plurality of sample collection channels, wherein at least two of the channels are configured to simultaneously draw the fluid sample into each of the at least two sample collection channels via a first type of motive force. The device may also include a second portion comprising a plurality of sample containers for receiving the bodily fluid sample collected in the sample collection channels, wherein the sample containers have a first condition where the sample containers are not in fluid communication with the sample collection channels, and a second condition where the sample containers are operably engagable to be in fluid communication with the collection channels, whereupon when fluid communication is established, the containers provide a second motive force different from the first motive force to move bodily fluid sample from the channels into the containers.

In a still further embodiment described herein, a method is provided comprising metering a minimum amount of sample into at least two channels by using a sample collection device with at least two of the sample collection channels configured to simultaneously draw the fluid sample into each of the at least two sample collection channels via a first type of motive force. After a desired amount of sample fluid has been confirmed to be in the collection channels, fluid communication is established between the sample collection channels and the sample containers, whereupon the containers provide a second motive force different from the first motive force use to collect the samples to move bodily fluid sample from the channels into the containers. In some alternative embodiments, devices that use only a single channel to collect the body fluid or devices that have a plurality of channels but do not collect them simultaneously are not excluded. Optionally, the collection of sample fluid is performed without the use of a wicking material.

In one embodiment, there is a discrete amount of time between sample collection and introduction of the sample into a sample pre-processing device. In one non-limiting example, the process is a non-continuous process. The sample collection occurs in one processing station and then the sample is taken to a second station. This second station may be in the sample building. Optionally, the second station may be located at another location where the sample needs to be walked, driven, flown, conveyor-ed, placed in a transport device, or placed in a transport container to reach the second location. In this manner, there is a discrete break in the processing to allow for time associated with sample transport.

In another embodiment herein, separator gel(s) can also be included in the sample containers such that the gels will separate cell-free fractions of whole blood from the cellular or other solid or semi-solid portions of the sample. Such a gel or other similar separator material may be included in the sample container prior to, during, or after sample has been introduced into the sample container. The separator material may have a density between that of the cells and solution components, so that the material separates the sample components by flowing to a position between the solution and non-solution sample layers during separation such as by centrifugation. Following centrifugation, the separator material stops flowing and remain as a soft barrier between the layers. In some embodiments, the separator material can be further processed to harden into a more rigid barrier. In on non-limiting example, the separator material may be a UV-curable material such as but not limited to thixotropic gel of sorbitol-based gelator in a diacrylate oligomer. The sample container may have the entire vessel or optionally, on that portion with the UV-curable material exposed to UV light for a period of time such as but not limited to 10 to 30 seconds to harden the material. Such hardening may involve cross-linking of material in the UV-curable material. Optionally, the UV curable material may be used in conjunction with traditional separator gel material such that only one side (the solution side or the solid side) is in contact with the UV cured material. Optionally, the UV cured material may be used with a third material such that the UV cured material is between two separator materials and is not in direct contact with the solution and non-solution portions of the sample.

In one non-limiting example, a device is provided for collecting a sample from a non-venous wound on a subject.

In one non-limiting example, a method is provided for using a device for collecting a sample from a subject and outputting at least one aliquot into a first sample container.

In one non-limiting example, a method is provided for using a device for collecting a sample from a subject and outputting at least one aliquot into a first sample container and at least a second aliquot into a second sample container.

In one non-limiting example, a method is provided for using a device for collecting a sample from a subject and outputting at least one aliquot into a first sample container and at least a second aliquot into a second sample container, wherein the sample is obtained from a single point of contact with the subject.

In one non-limiting example, a method is provided for using a device for collecting a sample from a subject and outputting at least one aliquot into a first sample container and at least a second aliquot into a second sample container, wherein the sample is obtained from a single collection event.

In one embodiment described herein, a device is provided for collecting a bodily fluid sample. This embodiment may be useful for accurately collecting small volumes of bodily fluid sample that are often associated with non-venous blood draws. In one non-limiting example, the sample volume is about 1 mL or less. Optionally, the sample volume is about 900 uL or less. Optionally, the sample volume is about 800 uL or less. Optionally, the sample volume is about 700 uL or less. Optionally, the sample volume is about 600 uL or less. Optionally, the sample volume is about 500 uL or less. Optionally, the sample volume is about 400 uL or less. Optionally, the sample volume is about 300 uL or less. Optionally, the sample volume is about 200 uL or less. Optionally, the sample volume is about 100 uL or less. Optionally, the sample volume is about 90 uL or less. Optionally, the sample volume is about 80 uL or less. Optionally, the sample volume is about 70 uL or less. Optionally, the sample volume is about 60 uL or less. Optionally, the sample volume is about 50 uL or less.

In one non-limiting example, this device can be used to split the bodily fluid sample directly into two or more different portions that are then deposited into their respective containers. In one non-limiting example, the device comprises a first portion having at least two sample collection channels configured to draw the fluid sample into the sample collection channels via a first type of motive force, wherein one of the sample collection channels has an interior coating designed to mix with the fluid sample and another of the sample collection channels has another interior coating chemically different from said interior coating. The sample collection device includes a second portion comprising a plurality of sample containers for receiving the bodily fluid sample collected in the sample collection channels, the sample containers operably engagable to be in fluid communication with the collection channels, whereupon when fluid communication is established, the containers provide a second motive force different from the first motive force to move a majority of the bodily fluid sample from the channels into the containers. The containers may be arranged such that mixing of the fluid sample between the containers does not occur. Because this device may be used with non-venous draws, it may take a longer period of time to obtain a desired volume of sample and the early introduction of a material such as an anti-coagulant which may coat the channels, can prevent premature clogging of the channels during collection.

In another embodiment described herein, a device is provided for collecting a bodily fluid sample. The device comprises a first portion comprising a plurality of sample collection channels, wherein at least two of the channels are configured to simultaneously draw the fluid sample into each of the at least two sample collection channels via a first type of motive force. The device may also include a second portion comprising a plurality of sample containers for receiving the bodily fluid sample collected in the sample collection channels, wherein the sample containers have a first condition where the sample containers are not in fluid communication with the sample collection channels, and a second condition where the sample containers are operably engagable to be in fluid communication with the collection channels, whereupon when fluid communication is established, the containers provide a second motive force different from the first motive force to move bodily fluid sample from the channels into the containers.

In a still further embodiment described herein, a method is provided comprising metering a minimum amount of sample into at least two channels by using a sample collection device with at least two of the sample collection channels configured to simultaneously draw the fluid sample into each of the at least two sample collection channels via a first type of motive force. After a desired amount of sample fluid has been confirmed to be in the collection channels, fluid communication is established between the sample collection channels and the sample containers, whereupon the containers provide a second motive force different from the first motive force use to collect the samples to move bodily fluid sample from the channels into the containers. In some alternative embodiments, devices that use only a single channel to collect the body fluid or devices that have a plurality of channels but do not collect them simultaneously are not excluded. Optionally, the collection of sample fluid is performed without the use of a wicking material.

In one embodiment, there is a discrete amount of time between sample collection and introduction of the sample into a sample pre-processing device. In one non-limiting example, the process is a non-continuous process. The sample collection occurs in one processing station and then the sample is taken to a second station. This second station may be in the sample building. Optionally, the second station may be located at another location where the sample needs to be walked, driven, flown, conveyor-ed, placed in a transport device, or placed in a transport container to reach the second location. In this manner, there is a discrete break in the processing to allow for time associated with sample transport.

In another embodiment herein, separator gel(s) can also be included in the sample containers such that the gels will separate cell-free fractions of whole blood from the cellular or other solid or semi-solid portions of the sample. Such a gel or other similar separator material may be included in the sample container prior to, during, or after sample has been introduced into the sample container. The separator material may have a density between that of the cells and solution components, so that the material separates the sample components by flowing to a position between the solution and non-solution sample layers during separation such as by centrifugation. Following centrifugation, the separator material stops flowing and remain as a soft barrier between the layers. In some embodiments, the separator material can be further processed to harden into a more rigid barrier. In on non-limiting example, the separator material may be a UV-curable material such as but not limited to thixotropic gel of sorbitol-based gelator in a diacrylate oligomer. The sample container may have the entire vessel or optionally, on that portion with the UV-curable material exposed to UV light for a period of time such as but not limited to 10 to 30 seconds to harden the material. Such hardening may involve cross-linking of material in the UV-curable material. Optionally, the UV curable material may be used in conjunction with traditional separator gel material such that only one side (the solution side or the solid side) is in contact with the UV cured material. Optionally, the UV cured material may be used with a third material such that the UV cured material is between two separator materials and is not in direct contact with the solution and non-solution portions of the sample.

In one embodiment, a device for collecting a bodily fluid sample, the device comprises a first portion comprising a plurality of capillary sample collection channels; a second portion comprising a plurality of sample containers for receiving the bodily fluid sample collected in the sample collection channels, wherein the sample containers have gas permeable and penetration re-sealable enclosure, wherein the gas permeable closure allows for sample to be transferred from the capillary channels to the containers without having to use a separate motive force.

In one embodiment, a device for collecting a bodily fluid sample, the device comprises a first portion comprising a plurality of capillary sample collection channels; a second portion comprising a plurality of sample containers for receiving the bodily fluid sample collected in the sample collection channels, wherein the sample containers have gas permeable and penetration re-sealable enclosure, wherein the gas permeable closure allows for sample to be transferred from the capillary channels to the containers without having to use a separate motive force, wherein a flow facilitator to provide a favorable pathway to from the channels into the container.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

INCORPORATION BY REFERENCE

All publications, patents, and patent applications mentioned in this specification are herein incorporated by reference to the same extent as if each individual publication, patent, or patent application was specifically and individually indicated to be incorporated by reference. However, in the event of a conflict between the content of the present express disclosure and the content of a document incorporated by reference herein, the content of the present express disclosure controls.

BRIEF DESCRIPTION OF THE DRAWINGS

FIGS. 1A-1B show perspective views of a sample collection device according to one embodiment as described herein.

FIGS. 3A-3B show side and cross-sectional views of a sample collection device according to one embodiment as described herein.

FIGS. 7A-7B and 8A-8B show side and cross-sectional views of a sample collection device according to one embodiment as described herein.

FIG. 23-28 show various view of collection devices for use with various sample collectors according to embodiments described herein.

FIGS. 33 to 43 show various views of other embodiments as described herein.

FIGS. 44A and 44B show side and cross-sectional views of another embodiment of a device as described herein.

FIGS. 45A and 45B show side and cross-sectional views of another embodiment of a device as described herein.

FIGS. 46A and 46B show side and cross-sectional views of another embodiment of a device as described herein.

FIG. 47 shows a side view of another embodiment of a device as described herein.

FIGS. 57A to 57C show various views of an embodiment of portions of a device as described herein.

FIGS. 58A to 58C show various views of another embodiment of a device as described herein.

FIGS. 61A to 61C show various embodiments of sample collection containers as described herein.

FIGS. 62A to 62D show various embodiments of a sample collection container as described herein.

FIGS. 65 to 66 show various embodiments of a portion of the device as described herein.

DESCRIPTION OF THE SPECIFIC EMBODIMENTS

Figure 2A:
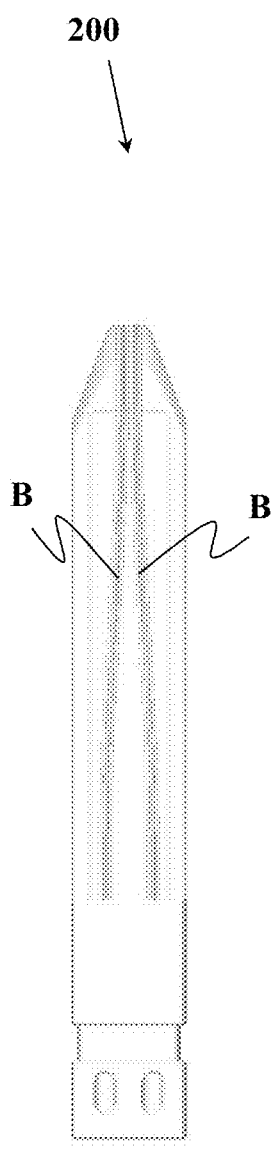
FIGS. 2A-2C show perspective views of a sample collection device without a cap according to one embodiment as described herein.

It is to be understood that both the foregoing general description and the following detailed description are exemplary and explanatory only and are not restrictive of the invention, as claimed. It may be noted that, as used in the specification and the appended claims, the singular forms "a", "an" and "the" include plural referents unless the context clearly dictates otherwise. Thus, for example, reference to "a material" may include mixtures of materials, reference to "a compound" may include multiple compounds, and the like. References cited herein are hereby incorporated by reference in their entirety, except to the extent that they conflict with teachings explicitly set forth in this specification.

This document contains material subject to copyright protection. The copyright owner (Applicant herein) has no objection to facsimile reproduction of the patent documents and disclosures, as they appear in the US Patent and Trademark Office patent file or records, but otherwise reserves all copyright rights whatsoever. The following notice shall apply: Copyright 2013-2014 Theranos, Inc.

In this specification and in the claims which follow, reference will be made to a number of terms which shall be defined to have the following meanings:

"Optional" or "optionally" means that the subsequently described circumstance may or may not occur, so that the description includes instances where the circumstance occurs and instances where it does not. For example, if a device optionally contains a feature for a sample collection well, this means that the sample collection well may or may not be present, and, thus, the description includes both structures wherein a device possesses the sample collection well and structures wherein sample collection well is not present.

Referring now to FIGS. 1A-1B, one embodiment of a sample collection device 100 will now be described. In this non-limiting example, the sample collection device 100 may include a collection device body 120, support 130, and base 140. In some instances, a cap 110 may be optionally provided. In one embodiment, the cap may be used to protect the opening, keeping it clean, and for covering up the bloody tip after collection. Optionally or alternatively, the cap may also be used to limit flow rate during transfer of sample fluid into the sample containers by controlling the amount of venting provided to the capillaries. Some embodiments may include vents pathways (permanently open or operably closable) in the cap while others do not. Optionally, the collection device body 120 can include a first portion of the device 100 having one or more collection pathways such as but not limited to collection channels 122a, 122b therein, which may be capable of receiving sample B. FIG. 1A shows that sample B only partially filling the channels 122a, 122b, but it should be understood that, although partial fills are not excluded in some alternative embodiments, in most embodiments, the channels will be fully filled with sample B when the fill process is completed. In this embodiment, the base 140 may have one or more fill indicators 142a, 142b, such as but not limited to optical indicators, that may provide an indication of whether sample has reached one or more container housed in the base. It should be understood that although this indication may be by way of a visual indication, other indication methods such as audio, vibratory, or other indication methods may be used in place of or in combination with the indication method. The indicators may be on at least one of the containers. There may be variations and alternatives to the embodiments described herein and that no single embodiment should be construed to encompass the entire invention.

Although not shown for ease of illustration, the support 130 may also include one or more fill indicators showing whether a desired fill level has been reached in the channels 122a and 122b. This may be in place of or in addition to fill indicators 142a, 142b. Of course, the one or more pathway fill indicators can be positioned on a different part and is not limited to being on support 130. It should be understood that although this indication of fill level in one or more of the channels 122a and 122b may be by way of a visual indication, other indication methods such as audio, vibratory, or other indication methods may be used in place of or in combination with the indication method. The indicator may be on at least one of the collection pathways. Optionally, indicators are on all of the collection pathways.

In the present embodiment, the support 130 can be used to join the body 120 and the base 140 to form an integrated device. It should be understood that although the device body 120, support 130, and base 140 are recited as separate parts, one or more of those parts may be integrally formed to simplify manufacturing and such integration is not excluded herein.

In some embodiments herein, a cap 110 may be optionally provided. In one non-limiting example, the cap may be fitted over a portion of the collection device body 120. The cap 110 may be detachable from the collection device body 120. In some instances, the cap 110 may be completely separable from the collection device body 120, or may retain a portion that is connected to the collection device body, such as but not limited to being hinged or otherwise linked to the collection device. The cap 110 may cover a portion of the collection device body 120 containing exposed ends of one or more channels therein. The cap 110 may prevent material, such as air, fluid, or particulates, from entering the channels within the device body, when the cap is in place. Optionally, the cap 110 may attach to the collection body 120 using any technique known or later developed in the art. For instance, the cap may be snap fit, twist on, friction-fit, clamp on, have magnetic portions, tie in, utilize elastic portions, and/or may removably connect to the collection device body. The cap may form a fluid-tight seal with the collection device body. The cap may be formed from an opaque, transparent, or translucent material.

In one embodiment, a collection device body 120 of a sample collection device may contain at least a portion of one or more collection pathways such as but not limited to channels 122a, 122b therein. It should be understood that collection pathways that are not channels are not excluded. The collection device body may be connected to a support 130 that may contain a portion of one or more channels therein. The collection device body may be permanently affixed to the support or may be removable with respect to the support. In some instances, the collection device body and the support may be formed of a single integral piece. Alternatively, the collection device body and support may be formed from separate pieces. During the operation of the device the collection device and support do not move relative to one another.

Optionally, the collection device body 120 may be formed in whole or in part from an optically transmissive material. For example, the collection device body may be formed from a transparent or translucent material. Optionally, only select portions of the body are transparent or translucent to visualize the fluid collection channel(s). Optionally, the body comprises an opaque material but an opening and/or a window can be formed in the body to show fill levels therein. The collection device body may enable a user to view the channels 122a, 122b within and/or passing through the device body. The channels may be formed of a transparent or translucent material that may permit a user to see whether sample B has traveled through the channels. The channels may have substantially the same length. In some instances a support 130 may be formed of an opaque material, a transparent material, or a translucent material. The support may or may not have the same optical characteristics of the collection device body. The support may be formed from a different material as the collection device body, or from the same material as the collection device body.

The collection device body 120 may have any shape or size. In some examples, the collection device body may have a circular, elliptical, triangular, quadrilateral (e.g., square, rectangular, trapezoidal), pentagonal, hexagonal, octagonal, or any other cross-sectional shape. The cross-sectional shape may remain the same or may vary along the length of the collection device body. In some instances, the collection device body may have a cross-sectional area of less than or equal to about $10 \text{ cm}^2$, $7 \text{ cm}^2$, $5 \text{ cm}^2$, $4 \text{ cm}^2$, $3 \text{ cm}^2$, $2.5 \text{ cm}^2$, $2 \text{ cm}^2$, $1.5 \text{ cm}^2$, $1 \text{ cm}^2$, $0.8 \text{ cm}^2$, $0.5 \text{ cm}^2$, $0.3 \text{ cm}^2$, or $0.1 \text{ cm}^2$. The cross-sectional area may vary or may remain the same along the length of the collection device body 120. The collection device body may have a length of less than or equal to about 20 cm, 15 cm, 12 cm, 10 cm, 9 cm, 8 cm, 7 cm, 6 cm, 5 cm, 4 cm, 3 cm, 2 cm, 1 cm, 0.5 cm, or 0.1 cm. The collection device body 120 may have a greater or lesser length than the cap, support or base, or an equal length to the cap, support, or base. There may be variations and alternatives to the embodiments described herein and that no single embodiment should be construed to encompass the entire invention.

In one embodiment, the collection pathways such as but not limited to channels 122a, 122b may also have a selected cross-sectional shape. Some embodiments of the channels may have the same cross-sectional shape along the entire length of the channel. Optionally, the cross-sectional shape may remain the same or may vary along the length. For example, some embodiments may have one shape at one location and a different shape at one or more different locations along the length of the channel. Some embodiments may have one channel with one cross-sectional shape and at least one other channel of a different cross-sectional shape. By way of non-limiting example, some may have a circular, elliptical, triangular, quadrilateral (e.g., square, rectangular, trapezoidal), pentagonal, hexagonal, octagonal, or any other cross-sectional shape. The cross-sectional shape may be the same for the body, support, and base, or may vary. Some embodiments may select a shape to maximize volume of liquid that can be held in the channels for a specific channel width and/or height. Some may have one of the channels 122a, 122b with one cross-sectional shape while another channel has a different cross-sectional shape. In one embodiment, the cross-sectional shape of the channel can help maximize volume therein, but optionally, it can also optimize the capillary pulling forces on the blood. This will allow for maximized rate of filling. It should be understood that in some embodiments, the cross-sectional shape of the channel can directly affect the capillary forces. By way of non-limiting example, a volume of sample can be contained in a shallow but wide channel, or a rounded channel, both containing the same volume, but one might be desirable over the other for filling speed, less possibility of air entrapment, or factors related the performance of the channel.

Although the channels may have any shape or size, some embodiments are configured such that the channel exhibits a capillary action when in contact with sample fluid. In some instances, the channel may have a cross-sectional area of less than or equal to about $10 \text{ mm}^2$, $7 \text{ mm}^2$, $5 \text{ mm}^2$, $4 \text{ mm}^2$, $3 \text{ mm}^2$, $2.5 \text{ mm}^2$, $2 \text{ mm}^2$, $1.5 \text{ mm}^2$, $1 \text{ mm}^2$, $0.8 \text{ mm}^2$, $0.5 \text{ mm}^2$, $0.3 \text{ mm}^2$, or $0.1 \text{ mm}^2$. The cross-sectional size may remain the same or may vary along the length. Some embodiments may tailor for greater force along a certain length and then less in a different length. The cross-sectional shape may remain the same or may vary along the length. Some channels are straight in configuration. Some embodiments may have curved or other shaped path shapes alone or in combination with straight portions. Some may have different orientations within the device body 120. For example, when the device is held substantially horizontally, one or more channels may slope downward, slope upward, or not slope at all as it carries fluid away from the initial collection point on the device.

The channels 122a, 122b may be supported by the device body 120 and/or the support 130. In some instances, the entire length of the channels may be encompassed within the combination of the device body and the support. In some instances, a portion of the channels may be within the device body and a portion of the channels may be within the support. The position of the channels may be affixed by the device body and/or the support. In some embodiments, the channels may be defined as lumens inside a hollow needle. In some embodiments, the channels are only defined on three sides, with at least one side that is open. Optionally, a cover layer separate from the body may define the side that would otherwise be open. Some embodiments may define different sides of the channel with different materials. These materials can all be provided by the body or they may be provided by different pieces of the collection device. Some embodiments may have the channels all in the same plane. Optionally, some may have a shape that takes at least a portion of the channel to a different plane and/or orientation. Optionally, some channels may be entirely in a different plane and/or orientation.

In some instances, a plurality of channels may be provided. In some embodiments, one channel splits into two or more channels. Optionally, some channels split into an even larger number of channels. Some channels may include a control mechanism such as but not limited to a valve for directing flow in the channel(s). At least a portion of the channels may be substantially parallel to one another. Alternatively, no portion of the channels need be parallel to one another. In some instances, at least a portion of the channels are not parallel to one another. Optionally, the channels may be slightly bent. Optionally, channels may have one cross-sectional area at one location and a smaller cross-sectional area at a different location along the channel. Optionally, channels may have one cross-sectional area at one location and a larger cross-sectional area at a different location along the channel. For some embodiments of the Y design, it may be desirable that the channels would have vents placed appropriately to define the sample for each vial such that there would not be sample pulled or cross contamination from other channels. By way of non-limiting example, one embodiment with vents is shown in FIG. 11I.

A base 140 may be provided within the sample collection device. The base may be connected to the support 130. In some instances, a portion of the base may insertable within the support and/or a portion of the support may be insertable within the base. The base may be capable of moving relative to the support. In some instances, a sample collection device may have a longitudinal axis extending along the length of the sample collection device. The base and/or support may move relative to one another in the direction of the longitudinal axis. The base and/or support may be capable of moving a limited distance relative to one another. Alternatively, the base may be fixed relative to the support. The base may be provided at an end of the sample collection device opposite an end of the sample collection device comprising a cap 110. Optionally, some embodiments may include an integrated base/container part so that there are no longer separate containers that are assembled into the base pieces. There may be variations and alternatives to the embodiments described herein and that no single embodiment should be construed to encompass the entire invention.

A base 140 may house one or more container therein. The containers may be in fluidic communication with the channels and/or may be brought into fluidic communication with the channels. An end of a channel may be within the container or may be brought within the container. A base may have one or more optical indicator 142a, 142b that may provide a visual indication of whether sample has reached one or more container housed in the base. In some embodiments, the optical indicators may be optical windows that may enable a user to see into the base. The optical window may be formed from a transparent and/or translucent material. Alternatively, the optical window may be an opening without any material therein. The optical window may enable a user to directly view a container within the base. The container within the base may be formed from a transparent and/or translucent material that may enable a user to see if a sample has reached the container of the base. For example, if blood is transported along the channel to the containers, the containers may visually indicate the presence of blood therein. In other embodiments, the optical indicators may include other features that may indicate the container has been filled. For example, one or more sensors may be provided within the base or container that may determine whether a sufficient amount of sample has been provided within the container. The one or more sensors may provide a signal to an optical indicator on the base that may indicator whether the sample has been provided to the container and/or the amount of sample that has been provided to the container. For example, the optical indicator may include a display, such as but not limited to an LCD display, light display (e.g., LED display), plasma screen display that may provide an indication that the containers have been sufficiently filled. In alternative embodiments, an optical indicator need not be provided, but alternative indicators may be provided, such as but not limited to an audio indicator or temperature controlled indicator can be used to indicate when the containers have been filed.

Figure 2B:
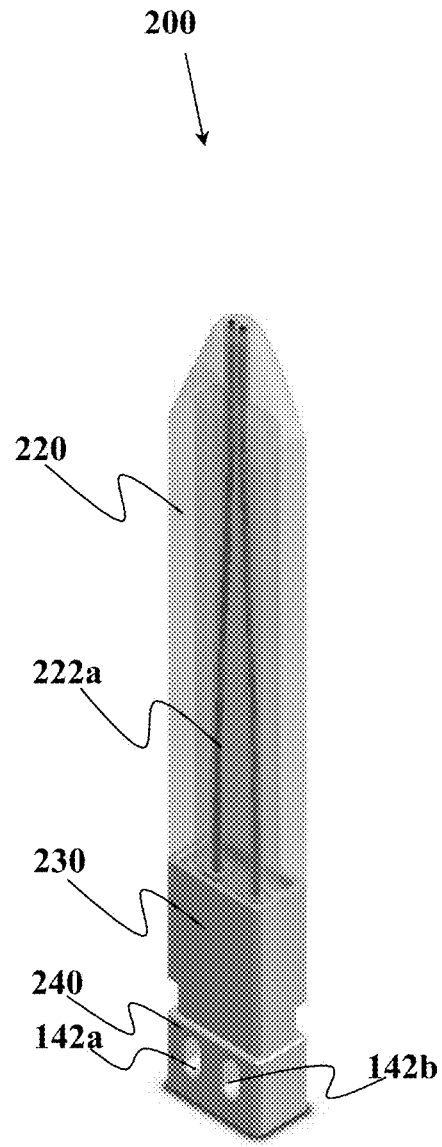
Figure 2C:
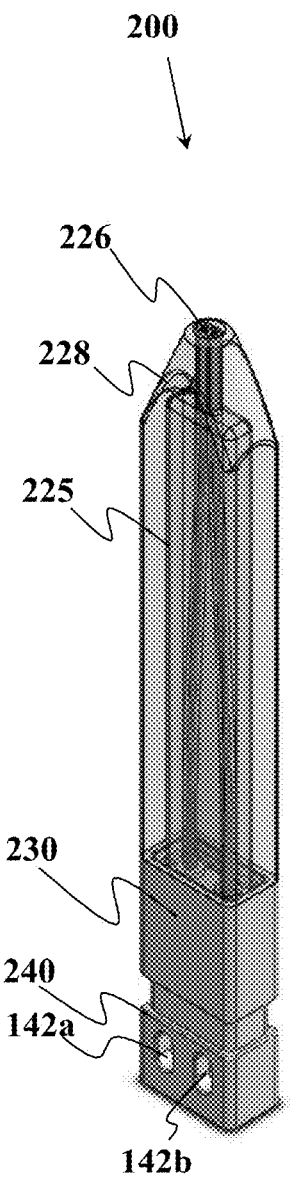

FIGS. 2A-2C provide views of a sample collection device 200 without a cap 110. The sample collection device 200 may include a body 220, support 230, and base 240. The body may be connected to the support. In the present embodiment, the base 240 may be connected to the support at an end opposing the end connected to the body. The body may support and/or contain at least a portion of one, two, or more channels 222a, 222b. The channels may be capable of receiving a sample 224a, 224b from a sample receiving end 226 of the device.

The body 220 may have a hollow portion 225 therein. Alternatively, the body may be formed from a solid piece. The channels 222a, 222b may be integrally formed into the body. For example, they may be passageways that pass through a solid portion of the body. The passageways may have been drilled through, or formed using lithographic techniques. Alternatively, the channels may be separate structures that may be supported by the body. For example, the channels may be formed of one or more tube that may be supported by the body. In some instances, the channels may be held in place at certain solid portions of the body and may pass through one or more hollow portion of the body. Optionally, the body 220 may be formed from two pieces joined together to define the channels 222a and 222b therein.

The channels 222a, 222b may include one or more features or characteristics mentioned elsewhere herein. At least a portion of the channels may be substantially parallel to one another. Alternatively, the channels may be at angles relative to one another. In some embodiments, the channels may have a first end that may be at a sample receiving end 226 of the sample collection device. The first end of a channel may be an open end capable of receiving a sample. In some embodiments, the ends of each of the channels may be provided at the sample receiving end of the sample collection device. One, two, or more channels may have a first end at the sample receiving end of the sample collection device. Separate channels can be used to minimize the risk of cross contamination of blood between one channel and another channel. Optionally, the channels may have an inverted Y configuration with the channels starting with a common channel and the splitting into two or more separate channels. This Y configuration may be useful in situation where contamination is not an issue. Optionally, an alternative method to a Y configuration would be a straight channel and have the sample collection vessels move to sequentially to engage the same needle from a straight channel.

In some instances, a plurality of channels may be provided. The ends of the channels at the sample receiving end may be in close proximity to one another. The ends of the channels at the sample receiving end may be adjacent to one another. The ends of the channels at the sample receiving end may be contacting one another, or may be within about 0.5 mm, 1 mm, 2 mm, 3 mm, 4 mm, 5 mm, 6 mm, 7 mm, 8 mm, 9 mm, 10 mm, 12 mm, 15 mm, or 20 mm of one another edge to edge, or center to center. The channels may diverge from one another from the sample receiving end. For example, the other ends of the channels opposing the ends of the channels at the sample receiving ends may be further apart from one another. They may be greater than or equal to about 3 mm, 4 mm, 5 mm, 6 mm, 7 mm, 8 mm, 9 mm, 10 mm, 12 mm, 15 mm, 20 mm, 25 mm, or 30 mm apart from one another edge to edge or center to center.

In some embodiments, the body 220 may have an elongated shape. The body may have one or more tapered portion 228 at or near the sample receiving end 226. The sides of the body may converge at the sample receiving end. The tapered portion and/or sample receiving end may be curved. Alternatively, edges may be provided. A surface of the tapered portion may be provided at any angle relative to the longitudinal axis of the device. For example, the tapered portion may be about 5 degrees, 10 degrees, 15 degrees, 30 degrees, 45 degrees, 60 degrees, or 75 degrees relative to the longitudinal axis.

The sample receiving end 226 of the device may be contacted to a sample. The sample may be provided directly from the subject. The sample receiving end may contact the subject or a sample that is contacting or being exuded from the subject. For example, the sample receiving end may contact a drop of blood on a subject's finger. The blood may enter the channels. The blood may be transported through the channels via capillary action, pressure differential, gravity, or any other motive force. The blood may travel through the channels from a sample receiving end to a sample delivery end. The sample delivery end may be in fluid communication or may be brought into fluid communication with one or more containers housed within a base of the device. The sample may pass from the channels to the containers. The sample may be driven into the containers via pressure differential, capillary action, gravity, friction, and/or any other motive force. Optionally, the sample might also be blood introduced with a pipette, syringe, etc. . . . . . It should be understood that although FIG. 2B shows that sample B only partially filling the channels 222a, 222b, but in most embodiments, the channels will be fully filled with sample B when the fill process is completed.

FIGS. 3A-3B show an example of a sample collection device 300 prior to bringing the channels 322a, 322b into fluid communication with one or more containers 346a, 346b housed within a base 340 of the device. The sample collection device may include a cap 310, body 320, support 330, and base 340. The body and/or support may support and/or encompass at least a portion of one, two, or more channels. The base may support and/or encompass one, two, or more containers.

In one embodiment, a body 320 and/or support 330 may support one or more channels 322a, 322b in the sample collection device. In one example, two channels are provided, although descriptions relating to a two-channel embodiment may apply to any number of channels including but not limited to 1, 3, 4, 5, 6, or more channels. Each of the channels may have a first end 323a, 323b that may be provided at a sample receiving end 326 of the device. The first ends of the respective channels may be open. The channels may be open to ambient air. When the first ends of the channels contact a fluid, such as blood, the fluid may be drawn into the channels. Blood may be drawn in via capillary action, or any other of the techniques described elsewhere herein. The blood may travel along the length of the channels to the respective second ends 325a, 325b of the channels. The channels may be fluidically segregated from one another. For example, a fluid may enter a first channel 322a via a first end 323a, pass through the length of the channel, and exit the first channel at the second end 325a. Similarly, fluid may enter a second channel 322b via a first end 323b, pass through the length of the channel, and exit the second channel at the second end 325b. The first and second channels may be fluidically segregated so that fluid from the first channel does not pass into the second channel and vice versa. In some embodiments, the fluid may pass to the second ends of the channels without exiting initially.

The channels 322a, 322b may have a diverging configuration. For example, the first ends 323a, 323b of the channels may be closer together than the second ends 325a, 325b of the channels. More space may be provided between the second ends of the channels than between the first ends of the channels. The first ends of the channels may or may not be in contact with one another. The first ends of the channels may be adjacent to one another.

A base 340 may be connected to a support 330 of the sample collection device. The base 340 may or may not directly contact the support. The base may be movable relative to the support during use of the device. In some embodiments, the base may slide in a longitudinal direction relative to the support. In some instances, the base may slide in a longitudinal direction relative to the support without rotating. In some instances, the base may slide co-axially with the support without rotating. In some instances, a base may rotate while moving relative to the support. A portion of the base may fit within a portion of the support, or vice versa. For example, a portion of the base may be insertable into a portion of the support and/or a portion of the support may be insertable into the base. One or more stop feature may be provided in the base and/or the frame to provide a controlled degree of movement between the base and the support. The stop feature may include a shelf, protrusion or groove.

The base 340 may be capable of supporting one or more containers 346a, 346b. The base may have a housing that may at least partially surround the one or more containers. In some instances, the containers may be completely surrounded when the base is engaged with a support 330. The base may have one or more indentation, protrusion, groove, or shaped feature to accept the containers. The base may be formed with a shape that is complementary to the shape of the containers. The containers may be maintained in an upright position relative to the base.

The same number of containers may be provided as the number of channels. For example, if N channels are provided, then N containers may be provided, wherein N is a positive whole number (e.g., 1, 2, 3, 4, 5, 6, 7, 8, or more). Each channel may correspond to a respective container. In one example, a sample collection device may have a first channel and a second channel, as well as a respective first container and second container. A first channel 322a may be in or may be configured to be brought into fluid communication with a first container 346a, and a second channel 322b may be in or may be configured to be brought into fluid communication with a second container 346b.

In some embodiments, each container may have a body 349a, 349b and a cap 348a, 348b. In some instances, the container body may be formed from a transparent or translucent material. The container body may permit a sample provided within the container body to be visible when viewed from outside the container. The container body may have a tubular shape. In some instances, the container body may have a cylindrical portion. The bottom of the container may be flat, tapered, rounded, or any combination thereof. The containers may comprise an open end and a closed end. The open end may be a top end of the container, which may be at the end of the container closer to one or more channel. The closed end may be a bottom end of the container, which may be at the end of the container further from one or more channel. Various embodiments of containers may be described in greater detail elsewhere herein.

A base 340 may have one or more optical indicators, such as optical windows 342a, 342b. The optical windows may be positioned over the containers 346a, 346b. In some instances, the optical windows may be positioned over the container bodies. A single window may provide a view to a single container or to multiple containers. In one example, the same number of optical windows may be provided as containers. Each optical window may correspond to a respective container. Both the optical window and containers may be formed of an optically transmissive material that may permit a user to view whether a sample has reached the container from outside the sample collection device.

In some embodiments, there may be optical windows of the channels 322a and 322b so that a user may observe when a desired fill level has been reached in the channels. Some embodiments where the body 320 is entirely transparent or translucent, there may be a marker or indicator mark along the channels to note when a desired fill level has been reached.

The containers may be sized to contain a small fluid sample. In some embodiments, the containers may be configured to contain no more than about 5 ml, 4 ml, 3 ml, 2 ml, 1.5 mL, 1 mL, 900 uL, 800 uL, 700 uL, 600 uL, 500 uL, 400 uL, 300 uL, 250 uL, 200 uL, 150 uL, 100 uL, 80 uL, 50 uL, 30 uL, 25 uL, 20 uL, 10 uL, 7 uL, 5 uL, 3 uL, 2 uL, 1 uL, 750 nL, 500 nL, 250 nL, 200 nL, 150 nL, 100 nL, 50 nL, 10 nL, 5 nL, or 1 nL. The containers may be configured to contain no more than several drops of blood, a drop of blood, or no more than a portion of a drop of blood.

The containers may contain a cap 348a, 348b. The plug may be configured to fit over an open end of the container. The cap may block the open end of the container. The cap may fluidically seal the container. The cap may form a fluid-tight seal with the container body. For example, the cap may be gas and/or liquid impermeable. Alternatively, the cap may permit certain gases and/or liquids to pass through. In some instances, the cap may be gas permeable while being liquid impermeable. The cap may be impermeable to the sample. For example, the cap may be impermeable to whole blood, serum or plasma. In some instances, a portion of the cap may fit into a portion of the container body. The cap may form a stopper with the container body. The cap may include a lip or shelf that may hang over a portion of the container body. The lip or shelf may prevent the cap from sliding into the container body. In some instances, a portion of a cap may overlie a top and/or side of the container body. Any description herein of containers may be applied in combination with the sample collection device. Optionally, some embodiments may include an additional part in the vessel assembly such as cap holder. In one embodiment, the purpose of the cap holder is to maintain a tight seal between the cap and container. In one embodiment, the cap holder engages an attachment, lip, indentation, or other attachment location on the outside of the container to hold the cap in position. Optionally, some embodiments can combine the function of both the cap and the cap holder into one component.

One or more engagement assemblies may be provided. The engagement assembly may include a channel holder 350 and/or a force-exerting component, such as a spring 352 or elastic. In one embodiment, the holder 350 may keep the adapter channel 354 affixed to the support. As will be described elsewhere herein, the adaptor channel 354 may be formed integrally with the collection channel or may be a discrete element that may be a stand-alone piece, part of the collection channel, or part of the container. In one embodiment, the holder 350 may prevent the adapter channel 354 from sliding relative to the support. The holder 350 may optionally provide a support upon which a force-exerting component, such as a spring, may rest.

In one example, the engagement assemblies may each include a spring 352 which may exert a force so that the base 340 is at an extended state, when the spring is at its natural state. When the base is at its extended state, space may be provided between the containers 346a, 346b and the engagement assemblies. In some instances, when the base 340 is in its extended state, the second ends of the channels may or may not contact the caps of the containers. The second ends of the channels 325a, 325b may be in a position where they are not in fluid communication with the interiors of the containers.

A sample collection device may have any number of engagement assemblies. For example, the same number of engagement assemblies may be provided as number of channels. Each channel may have an engagement assembly. For example, if a first channel and a second channel are provided, a first engagement assembly may be provided for the first channel, and a second engagement assembly may be provided for the second channel. The same number of engagement assemblies and containers may be provided.

In one embodiment, the engagement assembly may house an adapter channel 354 such as but not limited to an elongate member with angled, tapered or pointed end 327a and 327b. It should be understood that in some embodiments, the ends 327a and 327b are part of a needle that is formed separate from the channels 322a and 322b and then coupled to the channels 322a and 322b. The needles may be formed of the same or different material from the body defining the channels 322a and 322b. For example, some may use a metal to form the needles and a polymer or plastic material for the body defining channels 322a and 322b. Optionally, some embodiments may form the ends 327a and 327b on a member that is integrally formed with the channels 322a and 322b. In some instances, the second end of the channel may be configured to penetrate a material, such as a cap 348a, 348b of the container. In some embodiments, a portion of the adaptor channel 354 may be insertable within the collection channel or a portion of the collection channel may be insertable within the adaptor channel, or the two may be configured to align flush. Optionally, some embodiments may integrally form the adapter channel 354 with the collection channel 322a. It should be understood that FIGS. 3B (and 4B) shows that sample B only partially filling the channels 122a, 122b, but, in most embodiments, the channels will be fully filled with sample B when the fill process is completed. There may be variations and alternatives to the embodiments described herein and that no single embodiment should be construed to encompass the entire invention.

Figure 4A:
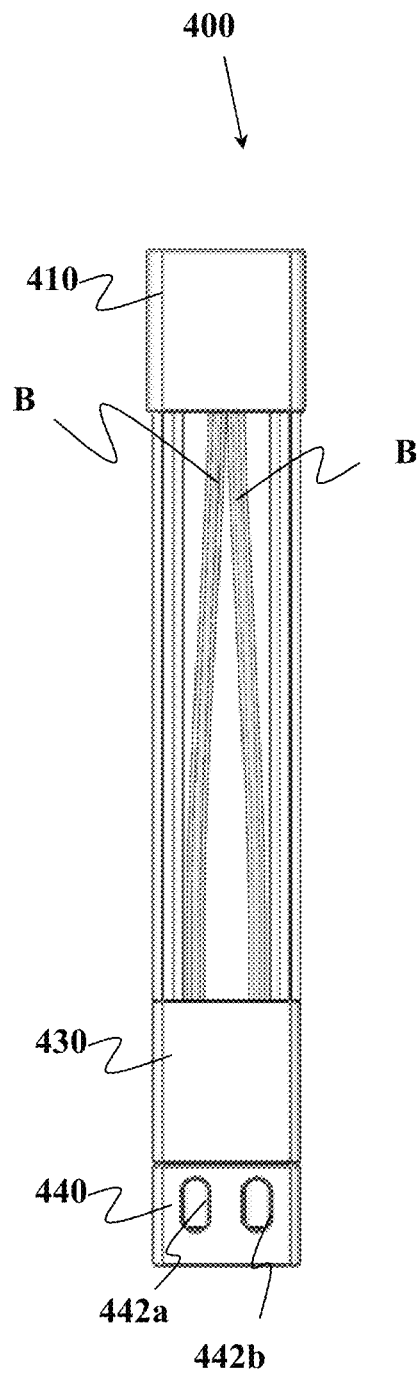
FIGS. 4A-4B show side and cross-sectional views of a sample collection device according to one embodiment as described herein.
Figure 4B:
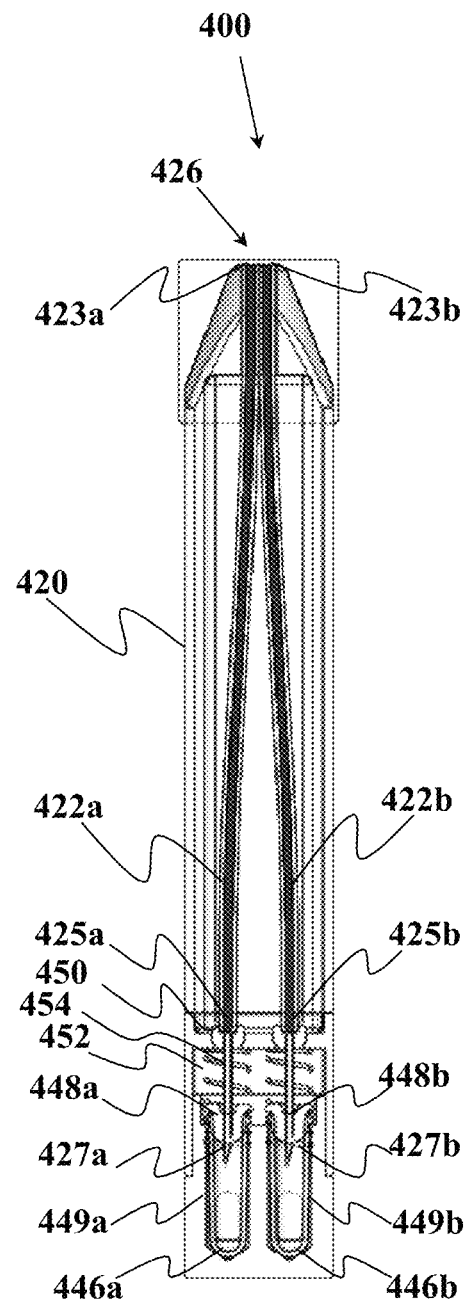

FIGS. 4A-4B show an example of a sample collection device 400 having channels 422a, 422b that are in fluid communication with the interior of containers 446a, 446b within the device. The sample collection device may include a cap 410, body 420, support 430, and base 440. The body and/or support may support and/or encompass at least a portion of one, two, or more channels. The base may support and/or encompass one, two, or more containers.

In one embodiment, a body 420 and/or support 430 may support one or more channels 422a, 422b in a sample collection device. For example, a first channel and second channel may be provided. Each of the channels may have a first end 423a, 423b that may be provided at a sample receiving end 426 of the device. The first ends of the respective channels may be open. The channels may be open to ambient air. When the first ends of the channels contact a fluid, such as blood, the fluid may be drawn into the channels. The fluid may be drawn in via capillary action, or any other of the techniques described elsewhere herein. The fluid may travel along the length of the channels to the respective second ends 425a, 425b of the channels. In some embodiments, the fluid may reach the second ends of the channels via capillary action or other techniques described herein. In other embodiments, the fluid need not reach the second ends of the channels. The channels may be fluidically segregated from one another.

In some embodiments, the fluid may pass to the second ends of the channels without exiting when the channels are not in fluid communication with the interiors of the containers 446a, 446b. For example, the fluid may be drawn into the channel via capillary action, which may cause the fluid to flow to or near the end of the channel without causing the fluid to exit the channel.

A base 440 may be connected to a support 430 of the sample collection device. The base may be movable relative to the support during use of the device. In some embodiments, the base may slide in a longitudinal direction relative to the support. In one example, the base may have (i) an extended position where the channels are not in fluid communication with the interior of the containers, and (ii) a compressed position where the channels are in fluid communication with the interior of the containers. A sample collection device may be initially provided in an extended state, as shown in FIG. 3. After the sample has been collected and flown through the length of the channel, a user may push the base in to provide the sample collection device in its compressed state, as shown in FIG. 4. Once the base has been pushed in, the base may naturally remain pushed in, or may spring back out to an extended state, once the pushing force is removed. In some instances, a base may be pulled out to an extended state, or may be pulled out completely to provide access to containers therein.

The base 440 may be capable of supporting one or more containers 446a, 446b. The base may have a housing that may at least partially surround the one or more containers. In some instances, the containers may be completely surrounded when the base is engaged with a support 430. The base may have one or more indentation, protrusion, groove, or shaped feature to accept the containers. The base may be formed with a shape that is complementary to the shape of the containers. The containers may be maintained in an upright position relative to the base.

The same number of containers may be provided as the number of channels. Each channel may correspond to a respective container. In one example, a sample collection device may have a first channel and a second channel, as well as a respective first container and second container. A first channel 422a may be in or may be configured to be brought into fluid communication with a first container 446a, and a second channel 422b may be in or may be configured to be brought into fluid communication with a second container 446b. The first channel may initially not be in fluid communication with a first container and the second channel may initially not be in fluid communication with the second container. The first and second channels may be brought into fluid communication with the interiors of the first and second containers respectively when the base is pushed in relative to the support. The first and second channels may be brought into fluid communication with the first and second containers simultaneously. Alternatively, they need not be brought into fluid communication simultaneously. The timing of the fluid communication may depend on the height of the container and/or the length of the channel. The timing of the fluid communication may depend on the relative distances between the second end of the channel and the container.

In some embodiments, each container may have a body 449a, 449b and a cap 448a, 448b. The container body may have a tubular shape. In some instances, the container body may have a cylindrical portion. The bottom of the container may be flat, tapered, rounded, or any combination thereof. The containers may comprise an open end and a closed end. The open end may be a top end of the container, which may be at the end of the container closer to one or more channel. The closed end may be a bottom end of the container, which may be at the end of the container further from one or more channel.

A base 440 may have one or more optical indicators, such as optical windows 442a, 442b. The optical windows may be positioned over the containers 446a, 446b. In some instances, the optical windows may be positioned over the container bodies. Both the optical window and containers may be formed of an optically transmissive material that may permit a user to view whether a sample has reached the container from outside the sample collection device. In some embodiments, the containers may incorporate markings on the containers themselves to indicate fill level requirements.

The containers may contain a cap 448a, 448b. The cap may be configured to fit over an open end of the container. The cap may block the open end of the container. The cap may fluidically seal the container. The cap may form a fluid-tight seal with the container body. For example, the cap may be impermeable to whole blood, serum or plasma. In some instances, a portion of the cap may fit into a portion of the container body. The cap may include a lip or shelf that may hang over a portion of the container body. In some embodiments, the cap may have a hollow or depression. The hollow or depression may assist with guiding a second end of the channel to a center of the cap. In some instances, when the sample collection device is in an extended state, a second end of a channel 425a, 425b may lie above the cap of the container. The second end of the channel may or may not contact the container cap. In some instances, the second end of the channel may rest within a hollow or depression of the cap. In some instances, the second end of the channel may partially penetrate the cap without reaching the interior of the container. Optionally, some embodiments of the cap might include a crimping piece to hold vacuum.

A second end of a channel may have an angled, tapered or pointed end 427a and 427b. It should be understood that in some embodiments, the ends 427a and 427b are part of a needle that is formed separate from the channels 422a and 422b and then coupled to the channels 422a and 422b. The needles may be formed of the same or different material from the body defining the channels 422a and 422b. For example, some may use a metal to form the needles and a polymer or plastic material for the body defining channels 422a and 422b. Optionally, some embodiments may form the ends 427a and 427b on a member that is integrally formed with the channels 422a and 422b. In some instances, the second end of the channel may be configured to penetrate a material, such as a cap 448a, 448b of the container. The cap may be formed of a material that may prevent sample from passing through in the absence of a penetrating member. The cap may be formed from a single solid piece. Alternatively, the cap may include a slit, opening, hole, thin portion, or any other feature that may accept a penetrating member. A slit or other opening may be capable of retaining sample therein, when the penetrating member is not in the slit or opening, or when the penetrating member is removed from the slit or opening. In some instances, the cap may be formed from a self-healing material, so that when a penetrating member is removed, the opening formed by the penetrating member closes up. The second end of the channel may be a penetrating member that may pass through the cap and into the interior of the container. In some embodiment, it should be clear that the penetrating member may be hollow needles that allow sample to pass through, and not just needles for piercing. In some embodiments, the piercing tip can be a non-coring design such as but not limited to a tapered cannula that pierces without coring the cap material.

One or more engagement assemblies may be provided. The engagement assembly may include a channel holder 450 and/or a force-exerting component, such as a spring 452 or elastic. In one embodiment, the holder 450 may keep the adaptor channel 454 affixed to the support. As will be described elsewhere herein, the adaptor channel 454 may be formed integrally with the collection channel or may be a discrete element that may be a stand-alone piece, part of the collection channel, or part of the container. In one embodiment, the holder 450 may prevent the adaptor channel 454 from sliding relative to the support. The holder 450 may optionally provide a support upon which a force-exerting component, such as a spring, may rest.

In one example, the engagement assemblies may include a spring 452 which may exert a force so that the base is at its extended state, when the spring is at its natural state. When the base is at its extended state, space may be provided between the containers 446a, 446b and the engagement assemblies. The second ends of the channels 425a, 425b may be in a position where they are not in fluid communication with the interiors of the containers.

A sample collection device may have any number of engagement assemblies. For example, the same number of engagement assemblies may be provided as number of channels. Each channel may have an engagement assembly. For example, if a first channel and a second channel are provided, a first engagement assembly may be provided for the first channel, and a second engagement assembly may be provided for the second channel. In one embodiment, the same number of engagement assemblies and containers may be provided.

When the base is pressed in, the spring 452 may be compressed. The second ends 425a, 425b of the channels may penetrate the caps of the containers. The second ends of the channels may enter the interior of the container. In some instances, a force may be provided to drive the fluid from the channels into the containers. For example, a pressure differential may be generated between the first and second ends of the channels. A positive pressure may be provided at the first end 423a, 423b of the channels and/or a negative pressure may be provided at the second end of the channels. The positive pressure may be positive relative to the pressure at the second end of the channel, and/or ambient air. The negative pressure may be negative relative to the pressure at the first end of the channel and/or ambient air. In one example, the containers may have a vacuum therein. When the second end of a channel penetrates a container, the negative pressure within the container may pull the sample into the container. In alternative embodiments, the sample may enter the container driven by capillary forces, gravity, or any other motive force. There may be variations and alternatives to the embodiments described herein and that no single embodiment should be construed to encompass the entire invention.

In some instances, different types of motive forces may be used at different stages of sample collection. Thus, one type of motive force may be used to draw the sample into the channel, and then a different type of motive force may be used to move sample from the channel into the container. For example, a capillary force may draw the sample into a channel, and a pressure differential may drive the sample from the channel into the container. Any combinations of motive forces may be used to draw sample into the channel and into the container. In some embodiments, the motive force(s) used to draw sample into the channel is different from motive force(s) used to draw sample into the container. In some alternative embodiments, the motive force(s) may be the same for each stage. In some embodiments, the motive force(s) are applied sequentially or at defined time periods. By way of non-limiting example, motive force(s) to draw sample into the container is not applied until the at least one channel has reach a minimum fill level. Optionally, motive force(s) to draw sample into the container is not applied until the at least two channels have each reach a minimum fill level for that channel. Optionally, motive force(s) to draw sample into the container is not applied until all channels have each reach a minimum fill level for that channel. In some embodiments, the motive force(s) are applied simultaneously.

Some embodiments may use a pressurized gas source coupled to the sample collection device and configured to push collected bodily fluid from the one or more channels into their respective containers. Optionally, some may use a vacuum source not associated with the containers to pull sample fluid towards the containers.

Additional, some embodiments of the channel may be configured such that there is sufficient capillary force within the channel such that once filled, the force is greater than that of gravity so that sample does not escape from the channel based only on gravitation force. An additional motive force is used to break the hold of the capillary action of the channel(s). Optionally, as described elsewhere herein, a device such as but not limited to a sleeve may contain the bodily fluid from exiting the channel at the end closest to the container, thus minimizing any loss until transfer to the container is initiated.

Optionally, other materials such as but not limited to a lyosphere, sponge, or other motive force provider may be used to provide motive force that draws sample into the container. When multiple forces are being used, this may be a primary, secondary, or tertiary motive force to draw sample into the container. Optionally, some embodiments may include a push-type motive force provider such as but not limited to a plunger to move the sample in a desired manner.

Some time may elapse after a sample has been introduced to a channel for traveling along the length of the channel. A user may introduce a sample to the sample collection device and may wait for the sample to travel the length of the channel. One or more optical indicator may be provided, which may indicate whether the sample has reached a desired fill level, such as not limited to the end of the channel. In other embodiments, the user may wait a predetermined amount of time before pushing in the base. The base may be pushed in after the user has determined the sample has traveled a sufficient length of the channel and/or a sufficient amount of time has passed since the sample was introduced. After the base is pushed in, the channels may be brought into fluid communication with the containers, and sample may flow from the channel into the containers. An optical indicator may be provided so that a user may know when the containers have been filled.

Once the containers have been filled, they may be transferred to a desired location, using systems and methods described elsewhere herein. In some instances, the entire sample collection device may be transferred. The cap may be placed on the sample collection device for transfer. In other embodiments, the base portion and/or support portion may be removable from the rest of the device. In one example, the base may be removed from the sample collection device, and the containers may be transferred along with the base. Alternatively, the base may be removed from the sample collection device to provide access to the containers, and the containers may be removed from the device and transmitted. The removal of the base may involve some disassembly of the sample collection device to detach the base. This may involve using sufficient force to overcome detents or stops built into the device to prevent accidental disengagement. Optionally, some other positive act such as but not limited to disengaging a latch or other locking mechanism may be performed by a user before detaching the base. Optionally, some embodiments may allow for removal of the containers without removal of the base, but allow for access to the containers by way of openings, access ports, or open-able covers on the base.

In some embodiments, one or more of the channels and/or containers may comprise features described elsewhere herein, such as separation members, coatings, anti-coagulants, beads, or any other features. In one example, the sample introduced to the sample collection device may be whole blood. Two channels and respective containers may be provided. In this non-limiting example, each of the channels has a coating such as but not limited to an anti-coagulant coating in the channel. Such an anti-coagulant coating can serve one or more of the following functions. First, the anti-coagulant can prevent whole blood from clotting inside the channel during the sample collection process. Depending on the amount of whole blood to be collected, clotting could prematurely clog the channel before sufficient amount of blood has been brought into the channel. Another function is to introduce anti-coagulant into the whole blood sample. By have the anti-coagulant in the channel, this process can begin earlier in the collection process versus some embodiments which may only have it the containers 446a or 446b. This early introduction of anti-coagulant may also be advantageous in case the whole blood sample will be led along a pathway that may have portions that are not coated with anti-coagulant, such as but not limited to, the inner surfaces of a needle connected to the channels 422a or 422b. Optionally, some embodiments may include surfactants that can be used to modify the contact angle (wettability) of a surface.

In some embodiments the inner surface of the channel and/or other surfaces along the fluid pathway such as but not limited to the sample inlet to the interior of a sample collection vessel may be coated with a surfactant and/or an anti-coagulant solution. The surfactant provides a wettable surface to the hydrophobic layers of the fluidic device and facilitate filling of the metering channel with the liquid sample, e.g., blood. The anti-coagulant solution helps prevent the sample, e.g., blood, from clotting when provided to the fluidic device. Exemplary surfactants that can be used include without limitation, Tween, TWEEN®20, Thesit®, sodium deoxycholate, Triton, Triton®X-100, Pluronic and/or other non-hemolytic detergents that provide the proper wetting characteristics of a surfactant. EDTA and heparin are non-limiting anti-coagulants that can be used. In one non-limiting example, the embodiment the solution comprises 2% Tween, 25 mg/mL EDTA in 50% Methanol/50% H2O, which is then air dried. A methanol/water mixture provides a means of dissolving the EDTA and Tween, and also dries quickly from the surface of the plastic. The solution can be applied to the channel or other surfaces along the fluid flow pathway by any technique that will ensure an even film over the surfaces to be coated, such as, e.g., pipetting, spraying, printing, or wicking.

It should also be understood for any of the embodiments herein that a coating in the channel may extend along the entire path of the channel. Optionally, the coating may cover a majority but not all of the channel. Optionally, some embodiments may not cover the channel in the areas nearest the entry opening to minimize the risk of cross-contamination, wherein coating material from one channel migrates into nearby channels by way of the channels all being in contact with the target sample fluid at the same time and thus having a connecting fluid pathway.

Although embodiments herein are shown with two separate channels in the sample collection device, it should be understood that some embodiments may use more than two separate channels. Optionally, some embodiments may use less than two fully separate channels. Some embodiments may only use one separate channel. Optionally, some embodiments may use an inverted Y-channel that starts initially as one channel and then splits into two or more channels. Any of these concepts may be adapted for use with other embodiments described herein.

Collection Device with Self-Supporting Collection Channels

Figures 5A, 5B:
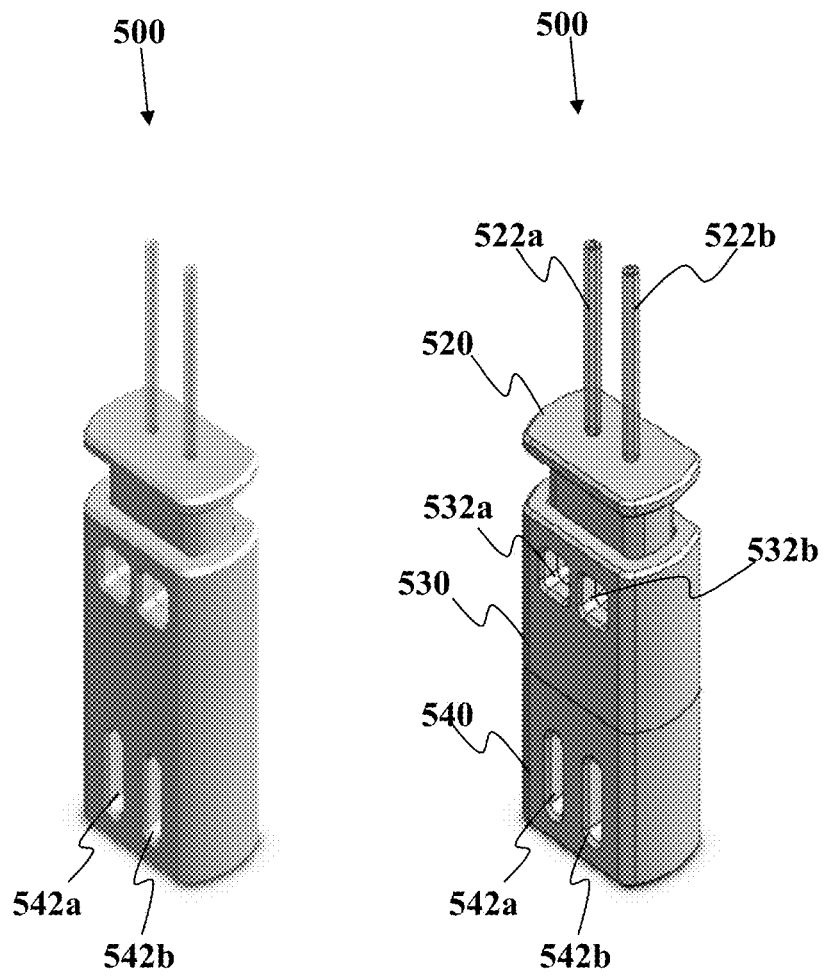
FIGS. 5A-5B show perspective views of a sample collection device according to another embodiment as described herein.

FIGS. 5A-5B provide another example of a sample collection device 500 provided in accordance with an embodiment described herein. The sample collection device may include a collection device body 520, support 530, and base 540. In some instances, a cap may be optionally provided. The collection device body may contain one or more collection channels 522a, 522b defined by collection tubes, which may be capable of receiving sample. A base may have one or more optical indicator 542a, 542b that may provide a visual indication of whether sample has reached one or more container housed in the base. A support may have one or more optical indicator 532a, 532b that may provide a visual indication of whether sample has reached or passed through a portion of the channels.

A collection device body 520 of a sample collection device may contain at least a portion of one or more tubes with channels 522a, 522b therein. Optionally, the device collection body 520 may also define channels that couple to channels 522a, 522b defined by the tubes. In some embodiments, a portion of the channels may extend beyond the collection device body. The channels may extend beyond one end or two ends of the collection device body.

The collection device body 520 may be connected to a support 530. The support may contain a portion of one or more channels therein. The collection device body may be permanently affixed to the support or may be removable with respect to the support. In some instances, the collection device body and the support may be formed of a single integral piece. Alternatively, the collection device body and support may be formed from separate pieces.

During the operation of the device the collection device body 520 and support 530 may move relative to one another. In some instances, a portion of the body 520 may be insertable within the support 530 and/or a portion of the support may be insertable within the body. The body may be capable of moving relative to the support. In some instances, a sample collection device may have a longitudinal axis extending along the length of the sample collection device. The body and/or support may move relative to one another in the direction of the longitudinal axis. The body and/or support may be capable of moving a limited distance relative to one another. The body and/or support may move co-axially without rotational motion. Alternatively, rotational motion may be provided.

The collection device body 520 may be formed from an optically transmissive material. For example, the collection device body may be formed from a transparent or translucent material. Alternatively, the body may be formed from an opaque material. The support 530 may be formed from an optically opaque, translucent, or transparent material. The support may or may not have the same optical characteristics of the collection device body. The support may be formed from a different material as the collection device body, or from the same material as the collection device body. There may be variations and alternatives to the embodiments described herein and that no single embodiment should be construed to encompass the entire invention.

The collection device body, support, and/or base may have any shape or size. In some examples, the collection device body, support, and/or base may have a circular, elliptical, triangular, quadrilateral (e.g., square, rectangular, trapezoidal), pentagonal, hexagonal, octagonal, or any other cross-sectional shape. The cross-sectional shape may remain the same or may vary along the length. The cross-sectional shape may be the same for the body, support, and base, or may vary. In some instances, the collection device body, support, and/or base may have a cross-sectional area of less than or equal to about 10 cm2, 7 cm2, 5 cm2, 4 cm2, 3 cm2, 2.5 cm2, 2 cm2, 1.5 cm2, 1 cm2, 0.8 cm2, 0.5 cm2, 0.3 cm2, or 0.1 cm2. The cross-sectional area may vary or may remain the same along the length. The cross-sectional size may be the same for the collection body, support, and/or base, or may vary. The collection device body, support, and/or base may have a length of less than or equal to about 20 cm, 15 cm, 12 cm, 10 cm, 9 cm, 8 cm, 7 cm, 6 cm, 5 cm, 4 cm, 3 cm, 2 cm, 1 cm, 0.5 cm, or 0.1 cm. The collection device body may have a greater or lesser length than support or base, or an equal length to the support, or base.

The channels 522a, 522b may be supported by the device body 520 and/or the support 530. In some instances, the entire length of the tubes or the channels therein may be encompassed within the combination of the device body and the support. Alternatively, the channels may extend beyond the device body and/or support as seen in FIG. 5. In some instances, the channels may extend beyond one end of the device body/support combination, or beyond both ends. In some instances, a portion of the channels may be within the device body and a portion of the channels may be within the support. The position of the channels may be affixed by the device body and/or the support. In some instances, the channels may be affixed to device body and/or not move relative to the device body. The channels may be movable relative to the support. In some instances, a plurality of channels may be provided. At least a portion of the channels may be substantially parallel to one another. The channels may be parallel to one another and/or a longitudinal axis extending along a length of the sample collection device. Alternatively, no portion of the channels need be parallel to one another. In some instances, at least a portion of the channels are not parallel to one another. The channels may be slightly bent. Optionally, they may be straight, but aligned to be closer to one another as they near the sample collection point. It should be understood that the tubes defining the channels 522a and 522b may be made of optically transparent, transmissive, or other material sufficient to provide a detectable change that sample has reached a desired fill level in at least one channel. Optionally, the detectable change can be used to detect when both channels reach at least the desired fill level.

A base 540 may be provided within the sample collection device. The base may be connected to the support 530. In some instances, a portion of the base 540 may insertable within the support 530 and/or a portion of the support may be insertable within the base. The base may be fixed relative to the support or may be movable relative to the support. The base may be provided at an end of the support opposite an end of the support connected to the body. The base may be formed as a separate piece from the support. The base may be separable from the support. Alternatively, the base may be affixed to the support and/or formed as an integral piece with the support.

A base 540 may house one or more container therein. The containers may be in fluidic communication with the channels and/or may be brought into fluidic communication with the channels. An end of a channel may be within the container or may be brought within the container. A base may have one or more optical indicator 542a, 542b that may provide a visual indication of whether sample has reached one or more container housed in the base. In some embodiments, the optical indicators may be optical windows that may enable a user to see into the base. The optical window may be formed from a transparent and/or translucent material. Alternatively, the optical window may be an opening without any material therein. The optical window may enable a user to directly view a container within the base. The container within the base may be formed from a transparent and/or translucent material that may enable a user to see if a sample has reached the container of the base. For example, if blood is transported along the channel to the containers, the containers may show the blood therein. In other embodiments, the optical indicators may include other features that may indicate the container has been filled. For example, one or more sensor may be provided within the base or container that may determine whether a sufficient amount of sample has been provided within the container. The sensor may provide a signal to an optical indicator on the base that may indicator whether the sample has been provided to the container and/or the amount of sample that has been provided to the container. For example, the optical indicator may include a display, such as an LCD display, light display (e.g., LED display), plasma screen display that may provide an indication that the containers have been sufficiently filled. In alternative embodiments, an optical indicator need not be provided, but alternative indicators may be provided, such as but not limited to, an audio indicator, temperature controlled indicator, or other device that may indicate by a detectable signal, such as one detectable by a user, when the containers have been filed.

A support 530 may have one or more optical indicator 532a, 532b that may provide a visual indication of whether sample has reached or pass through a portion of a channel housed by the support. In some embodiments, the optical indicators may be optical windows that may enable a user to see into the support. The optical window may be formed from a transparent and/or translucent material. Alternatively, the optical window may be an opening without any material therein. The optical window may enable a user to directly view a portion of a channel within the support. The channels may be formed from a transparent and/or translucent material that may enable a user to see if a sample has reached the portion of the channel underlying the optical window. In other embodiments, the optical indicators may include other features that may indicate the sample has passed through a portion of the channel, such as sensors described elsewhere herein.

Figure 6A:
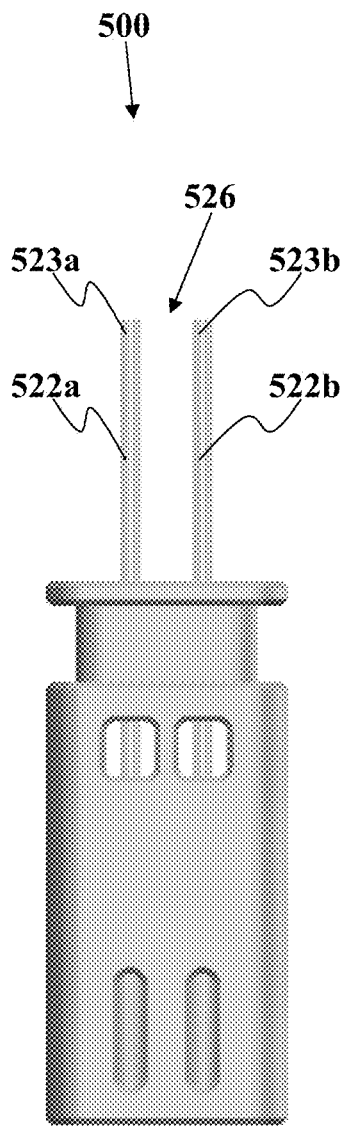
FIGS. 6A-6B show side views of a sample collection device according to one embodiment as described herein.
Figure 6B:
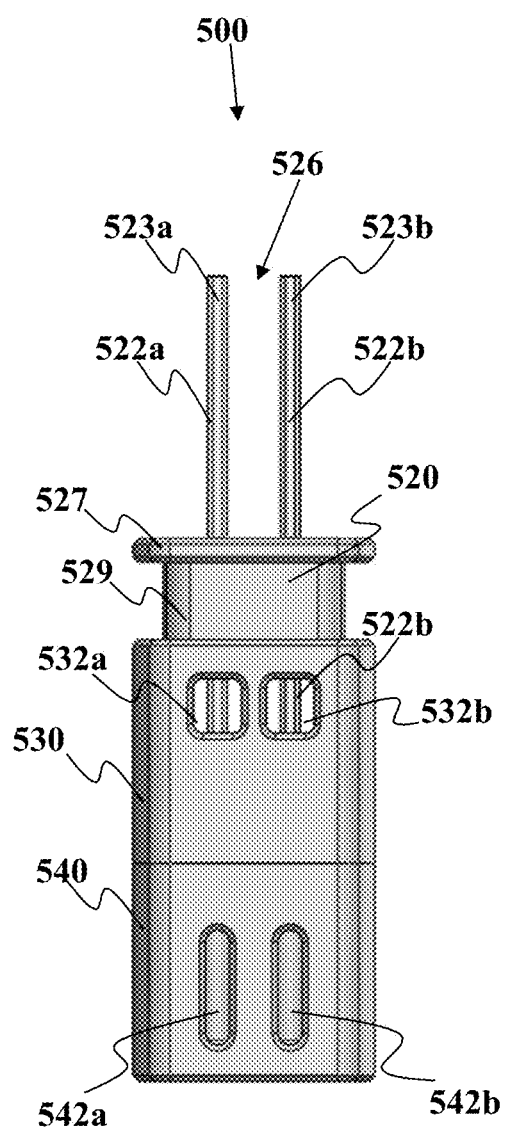

Referring now to FIGS. 6A-6B, additional views of a sample collection device 500 are provided in accordance with one embodiment described herein.

In some embodiments, a portion of the tubes containing channels 522a, 522b may extend beyond the collection device body 520. The portion of the channels that extend beyond may include portions of the channels that are configured to receive a sample from the subject. In one example, the channels may have a first end 523a, 523b that may be a sample receiving end of the channels.

The channels may optionally be defined by a rigid material. Alternatively, the channels may be defined by a flexible material or may have flexible components. The channels may or may not be designed to bend or curve. The channels may or may not be substantially parallel to one another. In some instances, the first ends of the channels may be some distance apart when in a relaxed state. The first ends of the channels may remain that distance apart during operation of the device. Alternatively, the first ends of the channels may be brought closer together. For example, the first ends of the channels may be squeezed together. Each open end of the channels may separately receive a sample. The sample may be received sequentially. The sample may be from the same subject. Alternatively, the channels may be capable of receiving the same sample simultaneously.

The channels 522a, 522b may include one or more features or characteristics mentioned elsewhere herein. At least a portion of the channels may be substantially parallel to one another. Alternatively, the channels may be at angles relative to one another. In some embodiments, the channels may have a first end that may be at a sample receiving end 526 of the sample collection device. The first end of a channel may be an open end capable of receiving a sample. In some embodiments, the ends of each of the channels may be provided at the sample receiving end of the sample collection device. One, two, or more channels may have a first end at the sample receiving end of the sample collection device.

In some embodiments, the device body 520 may be movable relative to the support 530. A portion of the device body may be insertable within the support or vice versa. In one example, the device body may have a lip 527 and an interior portion 529. The lip may have a greater cross-sectional area than the interior portion. The interior portion may be capable of being inserted into the support. The lip may act as a stop to prevent the entire body from being inserted into the support. The lip may rest on a shoulder of the support.

FIGS. 7A-7B shows partial cutaway views of an example of a sample collection device 700 provided in accordance with an embodiment described herein. The sample collection device in an extended state, prior to bringing the channels 722a, 722b into fluid communication with one or more containers 746a, 746b housed within a base 740 of the device. The sample collection device may include a body 720, support 730, and base 740. The body and/or support may support and/or encompass at least a portion of one, two or more channels. The base may support and/or encompass one, two or more containers. There may be variations and alternatives to the embodiments described herein and that no single embodiment should be construed to encompass the entire invention.

In one embodiment, a body 720 and/or support 730 may support one or more channels 722a, 722b in a sample collection device. In one example, two channels are provided, though descriptions relating to a two-channel embodiment may apply to any number of channels including but not limited to 1, 3, 4, 5, 6 or more channels. Each of the channels may have a first end 723a, 723b that may be a sample receiving end of the device. The first ends of the respective channels may be open. The channels may be open to ambient air. When the first ends of the channels contact a fluid, such as blood, the fluid may be drawn into the channels. Fluid may be drawn in via capillary action, or any other of the techniques described elsewhere herein. The fluid may travel along the length of the channels to the respective second ends of the channels. The channels may be fluidically segregated from one another. For example, a fluid may enter a first channel 722a via a first end 723a, pass through the length of the channel, and exit the first channel at the second end. Similarly, fluid may enter a second channel 722b via a first end 723b, pass through the length of the channel, and exit the second channel at the second end. The first and second channels may be fluidically segregated so that fluid from the first channel does not pass into the second channel and vice versa. In some embodiments, the fluid may pass to the second ends of the channels without exiting initially.

The channels 722a, 722b may have a parallel configuration. For example, the first ends 723a, 723b of the channels may be about the same distance apart as the second ends of the channels. The first ends of the channels may or may not be in contact with one another.

A support 730 may have one or more optical indicators, such as optical windows 732a, 732b. The optical windows may be positioned over the channels 722a, 722b. In some instances, the optical windows may be positioned over portions of the channels. A single window may provide a view to a single channel portion or to multiple channel portions. In one example, the same number of optical windows may be provided as channels. Each optical window may correspond to a respective channel. Both the optical window and channels may be formed of an optically transmissive material that may permit a user to view whether a sample has reached and/or passed through the underlying portion of the channel from outside the sample collection device. Such determination may be useful in determining when to compress the sample collection device.

A base 740 may be connected to a support 730 of the sample collection device. The base may or may not directly contact the support. The base may be fixed relative to the support during use of the device. In some instances, the base may be removable from the support. A portion of the base may be insertable into the support and/or vice versa. In some embodiments, the base may slide out from the support in a longitudinal direction relative to the support. In some instances, the base may slide co-axially with the support without rotating. In some instances, a base may rotate while moving relative to the support.

The base 740 may be capable of supporting one or more containers 746a, 746b. The base may have a housing that may at least partially surround the one or more containers. In some instances, the containers may be completely surrounded when the base is engaged with a support 730. The height of the base may extend beyond the height of the containers. Alternatively, the height of the base may extend to the same degree or less than the height of the containers. The base may have one or more indentation, protrusion, groove, or shaped feature to accept the containers. The base may be formed with a shape that is complementary to the shape of the containers. For example, the base may have one or more tube shaped indentation into which tube shaped containers may snugly fit. The containers may friction-fit into the base. The containers may be maintained in an upright position relative to the base. There may be variations and alternatives to the embodiments described herein and that no single embodiment should be construed to encompass the entire invention.

The same number of containers may be provided as the number of channels. For example, if N channels are provided, then N containers may be provided, wherein N is a positive whole number (e.g., 1, 2, 3, 4, 5, 6, 7, 8, or more). Each channel may correspond to a respective container. In one example, a sample collection device may have a first channel and a second channel, as well as a respective first container and second container. A first channel 722a may be in or may be configured to be brought into fluid communication with a first container 746a, and a second channel 722b may be in or may be configured to be brought into fluid communication with a second container 746b.

In some embodiments, each container may have a body 749a, 749b and a cap 748a, 748b. The containers may have any features or characteristics as described elsewhere herein.

A base 740 may have one or more optical indicators, such as optical windows 742a, 742b. The optical windows may be positioned over the containers 746a, 746b. In some instances, the optical windows may be positioned over the container bodies. A single window may provide a view to a single container or to multiple containers. In one example, the same number of optical windows may be provided as containers. Each optical window may correspond to a respective container. Both the optical window and containers may be formed of an optically transmissive material that may permit a user to view whether a sample has reached the container from outside the sample collection device. Such visual assessment may be useful in determining when the sample has reached the containers, and when the base can be removed from the sample collection device.

One or more engagement assemblies may be provided. The engagement assembly may include a channel holder 750 and/or a force-exerting component, such as a spring 752 or elastic. In one embodiment, the holder 750 may keep the adaptor channel 754 affixed to the support. As will be described elsewhere herein, the adaptor channel 754 may be formed integrally with the collection channel or may be a discrete element that may be a stand-alone piece, part of the collection channel, or part of the container. In one embodiment, the holder 750 may prevent the adaptor channel 754 from sliding relative to the support. The holder 750 may optionally provide a support upon which a force-exerting component, such as a spring, may rest.

In one example, the engagement assemblies may include a spring 752 which may exert a force so that the body 720 is at an extended state, when the spring is at its natural state. When the body is at its extended state, space may be provided between the containers 746a, 746b and the engagement assemblies. When a body is in its extended state, the interior portion 729 of the body may be exposed and/or uncovered by the support 730. In some instances, when the body is in its extended state, the second ends of the channels 722a, 722b may or may not contact the caps of the containers. The second ends of the channels may be in a position where they are not in fluid communication with the interiors of the containers. There may be variations and alternatives to the embodiments described herein and that no single embodiment should be construed to encompass the entire invention.

A sample collection device may have any number of engagement assemblies. For example, the same number of engagement assemblies may be provided as number of channels. Each channel may have an engagement assembly. For example, if a first channel and a second channel are provided, a first engagement assembly may be provided for the first channel, and a second engagement assembly may be provided for the second channel. The same number of engagement assemblies and containers may be provided.

Figure 8A:
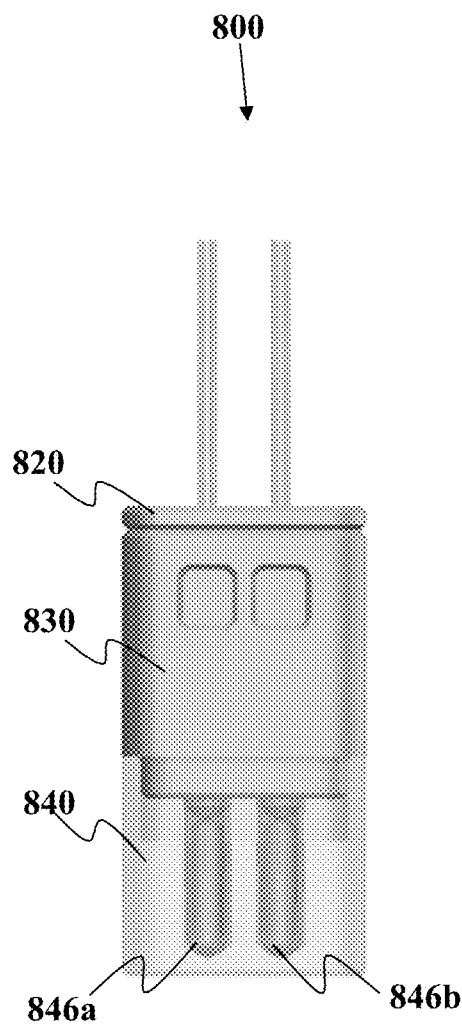
Figure 8B:
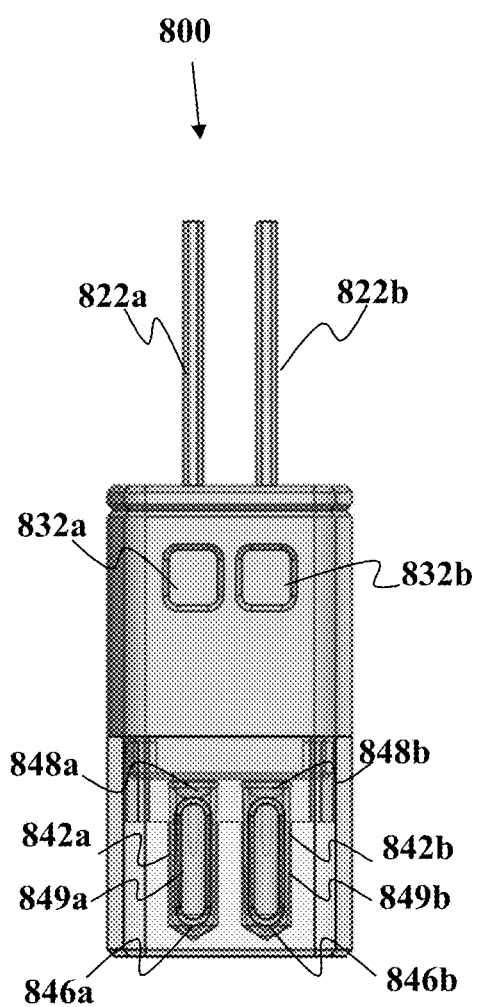

FIGS. 8A-8B provide an example of a sample collection device 800 having channels 822a, 822b that are in fluid communication with the interior of containers 846a, 846b within the device. The sample collection device may include a body 820, support 830, and base 840. The body and/or support may support and/or encompass at least a portion of one, two or more channels. The channels may extend beyond an end of the body. The base may support and/or encompass one, two or more containers.

In one embodiment, a body 820 and/or support 830 may support one or more channels 822a, 822b in a sample collection device. For example, a first channel and second channel may be provided. Each of the channels may have a first end 823a, 823b that may be provided at a sample receiving end of the device that may extend beyond the body. The first ends of the respective channels may be open. The channels may be open to ambient air. The channels may be rigid or may be flexible. In some embodiments, the channels may have a length that may permit them to be bent into contact with one another. When the first ends of the channels contact a fluid, such as blood, the fluid may be drawn into the channels. Each channel end may be separately contacted to a fluid, which is drawn into the respective channel. This may involve angling the sample collection device so that only one opening into the channel is in contact with the sample fluid at any one time. Alternatively, all channels may be simultaneously contacted to the same sample which is simultaneously drawn into the respective channels. Alternatively, multiple but not all channels may be simultaneously contacted to the same sample which is then simultaneously drawn into the respective channels. The fluid may be drawn in via capillary action, or any other of the techniques described elsewhere herein. The fluid may travel along the length of the channels to the respective second ends of the channels. In some embodiments, the fluid may reach the second ends of the channels via capillary action or other techniques described herein. In other embodiments, the fluid need not reach the second ends of the channels. The channels may be fluidically segregated from one another.

In some embodiments, the fluid may pass to the second ends of the channels without exiting when the channels are not in fluid communication with the interiors of the containers 846*a*, 846*b*. For example, the fluid may be drawn into the channel via capillary action, which may cause the fluid to flow to or near the end of the channel without causing the fluid to exit the channel.

The body 820 may be movable relative to the support 830 during use of the device. In some embodiments, the body may slide in a longitudinal direction relative to the support. In one example, the body may have (i) an extended position where the channels are not in fluid communication with the interior of the containers, and (ii) a compressed position where the channels are in fluid communication with the interior of the containers. A sample collection device may be initially provided in an extended state, as shown in FIG. 7. After the sample has been collected and flown through the length of the channel, a user may push the body in to provide the sample collection device in its compressed state, as shown in FIG. 8. In some instances, when the body is in an extended state, an interior portion of the body is exposed. When the body is in a compressed state, the interior portion of the body may be covered by the support. A lip of the body may contact the support. Once the body has been pushed in, the body may naturally remain pushed in, or may spring back out to an extended state, once the pushing force is removed. In some instances, a body may be pulled out to an extended state, or may be pulled out completely to provide access to containers therein. Optionally, in some assemblies, removal of the body will not provide access to the containers.

A base 840 may be connected to a support 830 of the sample collection device. The base 840 may be capable of supporting one or more containers 846*a*, 846*b*. The base may have a housing that may at least partially surround the one or more containers. In some instances, the containers may be completely surrounded when the base is engaged with a support 830. The base may have one or more indentation, protrusion, groove, or shaped feature to accept the containers. The base may be formed with a shape that is complementary to the shape of the containers. The containers may be maintained in an upright position relative to the base.

The same number of containers may be provided as the number of channels. Each channel may correspond to a respective container. In one example, a sample collection device may have a first channel and a second channel, as well as a respective first container and second container. A first channel 822*a* may be in or may be configured to be brought into fluid communication with a first container 846*a*, and a second channel 822*b* may be in or may be configured to be brought into fluid communication with a second container 846*b*. The first channel may initially not be in fluid communication with a first container and the second channel may initially not be in fluid communication with the second container. The first and second channels may be brought into fluid communication with the interiors of the first and second containers respectively when the body is pushed in relative to the support. The first and second channels may be brought into fluid communication with the first and second containers simultaneously. Alternatively, they need not be brought into fluid communication simultaneously. The timing of the fluid communication may depend on the height of the container and/or the length of the channel. The timing of the fluid communication may depend on the relative distances between the second end of the channel and the container.

In some embodiments, each container may have a body 849*a*, 849*b* and a cap 848*a*, 848*b*. The container body may have a tubular shape. In some instances, the container body may have a cylindrical portion. The bottom of the container may be flat, tapered, rounded, or any combination thereof. The containers may comprise an open end and a closed end. The open end may be a top end of the container, which may be at the end of the container closer to one or more channel. The closed end may be a bottom end of the container, which may be at the end of the container further from one or more channel. There may be variations and alternatives to the embodiments described herein and that no single embodiment should be construed to encompass the entire invention.

A support 830 may have one or more optical indicators, such as optical windows 832*a*, 832*b*. The optical windows may be positioned over portions of the channels 822*a*, 822*b*. The optical windows may provide an indicator of whether a sample has reached and/or passed through the portion of the channels shown by the optical windows. This may be useful to assess whether the sample has flowed sufficiently for the user to push the body into the sample collection device. In some instances, it may be desirable for the sample to reach the second end of the channels, or to near the second end of the channels, before causing the channels to enter into fluid communication with the containers. In some instances, it may be desirable that the reach a certain portion of the channel before pushing the body in to bring the channels into fluid communication with the containers. The certain portion of the channel may underlie the optical windows.

A base 840 may have one or more optical indicators, such as optical windows 842*a*, 842*b*. The optical windows may be positioned over the containers 846*a*, 846*b*. In some instances, the optical windows may be positioned over the container bodies. The optical windows may provide an indicator of whether a sample has entered the containers. The optical windows may show how much sample has filled the containers. This may be useful to assess whether a sufficient amount of sample has entered the containers. In some instances, it may be desirable for a particular amount of sample to enter the containers before removing the containers from fluid communication with the channels. A predetermined volume of sample in the containers may be desired before removing a base of the device, thereby bringing the containers out of fluid communication with the channels.

The containers and/or interfaces with the channels may have any characteristic or feature, such as those described elsewhere herein. In some instances, a second end of the channel may penetrate a cap of the container, thereby bringing the channel into fluid communication with the container. In some instances, the channel may be withdrawn from the container, and the cap of the container may form a fluid-tight seal, thereby permitting a fluid-tight environment within the container when the channel is brought out of fluid communication with the container.

One or more engagement assembly may be provided. The engagement assembly may include a channel holder and/or a force-exerting component, such as a spring or elastic. The holder may keep the channel affixed to the body. The holder may prevent the channel from sliding relative to the body. The holder may optionally provide a support upon which a force-exerting component, such as a spring, may rest.

In one example, the engagement assemblies may include a spring which may exert a force so that the body is at its extended state, when the spring is at its natural state. When the body is at its extended state, space may be provided between the containers 846a, 846b and the bottom portion of the sample body 820. The second ends of the channels may be in a position where they are not in fluid communication with the interiors of the containers.

Figure 9A:
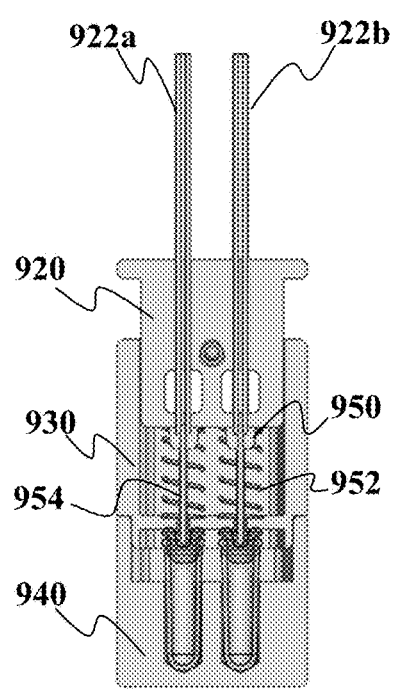
FIGS. 9A-9C show side cross-sectional views of a sample collection device at various stages of use according to one embodiment as described herein.
Figure 9B:
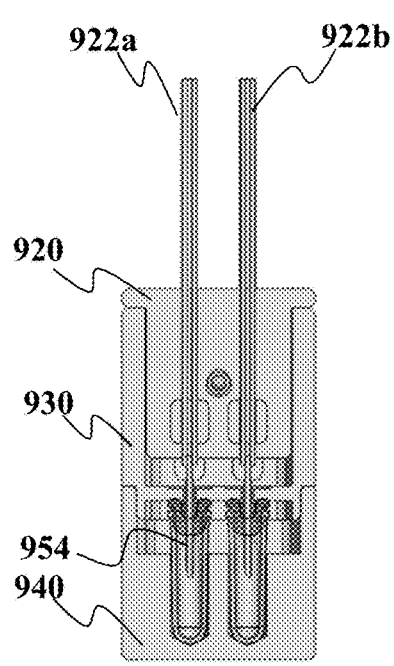
Figure 9C:
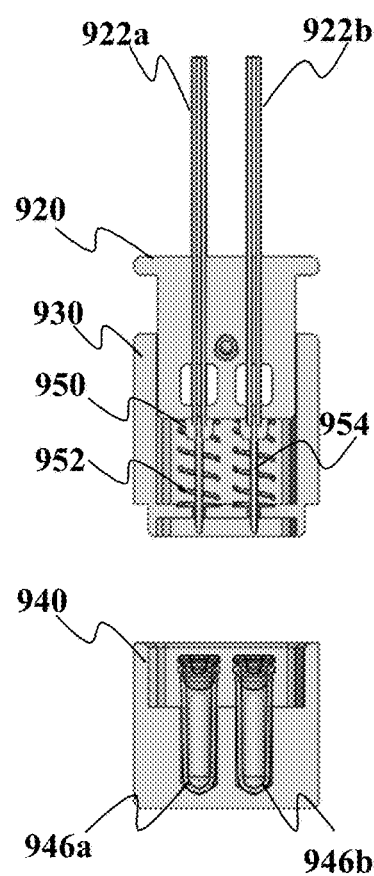

When the body is pressed in, the spring 852 may be compressed (see also FIGS. 9A-9C). The second ends of the channels may penetrate the caps of the containers. The second ends of the channels may enter the interior of the container. In some instances, a force may be provided to drive the fluid from the channels into the containers. For example, a pressure differential may be generated between the first and second ends of the channels. A positive pressure may be provided at the first end 823a, 823b of the channels and/or a negative pressure may be provided at the second end of the channels. The positive pressure may be positive relative to the pressure at the second end of the channel, and/or ambient air. The negative pressure may be negative relative to the pressure at the first end of the channel and/or ambient air. In one example, the containers 846a and 846b may each have a vacuum therein. When the second end of a channel penetrates a container, the negative pressure within the container may suck the sample into the container. In alternative embodiments, the sample may enter the container driven by capillary forces, gravity, or any other motive force. Optionally, there may be single or multiple combinations of forces to fill the container with fluid.

In some instances, different types of motive forces may be used to draw the sample into the channel, and from the channel into the container. For example, a capillary force may draw the sample into a channel, and a pressure differential may drive the sample from the channel into the container. Any combinations of motive forces may be used to draw sample into the channel and into the container.

Some time may elapse after a sample has been introduced to a channel for traveling along the length of the channel. A user may introduce a sample to the sample collection device and may wait for the sample to travel the length of the channel. One or more optical indicator along the length of the channel may be provided, which may indicate whether the sample has reached the end of the channel. In other embodiments, the user may wait a predetermined amount of time before pushing in the body. The body may be pushed in after the user has determined the sample has traveled a sufficient length of the channel and/or a sufficient amount of time has passed since the sample was introduced. The body may have a flat surface which may be easy for the user to push. In some instances, the flat surface may have a cross-sectional area that may be sufficient for a user's fingers to press down on the body. After the body is pushed in, the channels may be brought into fluid communication with the containers, and sample may flow from the channel into the containers. An optical indicator may be provided so that a user may know when the containers have been filled.

Once the containers have been filled, they may be transferred to a desired location, using systems and methods described elsewhere herein. As previously described, the entire sample collection device may be transferred. In other embodiments, the base portion may be removable from the rest of the device. In one example, the base may be removed from the sample collection device, and the containers may be transferred along with the base. Alternatively, the base may be removed from the sample collection device to provide access to the containers, and the containers may be removed from the device and transmitted Referring now to FIGS. 9A-9C, examples of a sample collection device 900 and method of use will now be described. In one nonlimiting example, the device may have a body 920, support 930, and base 940. The body 920, support 930, and base 940 may be movable relative to one another. In some instances, the various components of the devices may be movable during different stages of use. Examples of stages of use may include when the device is in an extended state, compressed state, and separated state.

FIG. 9A shows an example of the device 900 in an extended state. The body 920 may be extended relative to the support. Channels 922a, 922b configured to transport a sample may be affixed to the body. A first end of a channel may extend out from the body and/or the rest of the sample collection device. A second end of the channel may be within and/or encompassed by a portion of the sample collection device. The channel may be fluidically isolated from a respective container housed by the base 940. The support 930 may be positioned between the body and base. The support may at least partially encompass a portion of the channel. In some instances, the support may encompass the second end of the channel.

When in an extended state, the device may have an extended length. The length of the device may be from the bottom of the base to the first end of the channels. Alternatively, the length of the device may be measured from the bottom of the base to the top of the body.

As seen in FIG. 9A, the device 900 may be in an extended state when the sample is introduced to the device. For example, a sample may be contacted by at least a first end of a channel. The sample may be drawn into the channel via capillary action or any other technique or motive force described herein. The forces may act alone or in combination to draw sample into the device. The device 900 may remain in an extended state while the sample is traversing the channel. The sample may fill the entire length of the channel, a portion of the length of the channel, or at least a minimum portion to meet a desired sample acquisition volume.

FIG. 9B shows an example of the device 900 in a compressed state. The body 920 may be compressed relative to the support. The channels 922a, 922b may be affixed to the body. The channels may be fluidic communication with their respective containers. When the device is brought into a compressed state, a first channel may be brought into fluid communication with an interior of a first container, and a second channel may be brought into fluid communication with an interior of a second container.

By way of nonlimiting example, a user may push the body 920 toward the support 930 (or vice versa) to bring the device into a compressed state. The relative motion between parts may involve movement of both pieces. Optionally, movement may involve moving only one of them. In the present example, the body 920 may be pushed all the way to the support 930 so that no interior portion of the body is exposed and/or a lip of the body contacts the support. Any stop mechanism may be used that may be engaged when the device is completely compressed. Alternatively, the body may only be partially pushed. For example, a portion of the interior portion of the body may be exposed. The support may be positioned between the body and base. The support may at least partially encompass a portion of the channel. In some instances, the second end of the channel may extend beyond the support of the device.

When in a compressed state, it should be understood that the device 900 may have a compressed length. The length of the device 900 may be from the bottom of the base to the first end of the channels. Alternatively, the length of the device may be measured from the bottom of the base to the top of the body. The compressed length of the device may be less than the extended length of the device. In some embodiments, the compressed length of the device may be at least about 0.1 cm, 0.5 cm, 1.0 cm, 1.5 cm, 2.0 cm, 2.5 cm, 3.0 cm, 3.5 cm, 4.0 cm, or 5.0 less than the extended length of the device. The compressed length of the device may be less than or equal to about 50%, 60%, 70%, 75%, 80%, 85%, 90%, 95%, 97% or 99% of the extended length of the device.

One or more engagement assemblies may be provided with the device 900. The engagement assembly may include a channel holder 950 and/or a force-exerting component, such as a spring 952 or elastic. The holder 950 may keep the adaptor channel 954 affixed to the support. As will be described elsewhere herein, the adaptor channel 954 may be formed integrally with the collection channel or may be a discrete element that may be a stand-alone piece, part of the collection channel, or part of the container. In one embodiment, the holder 950 may prevent the adaptor channel 954 from sliding relative to the support. The holder 950 may optionally provide a support upon which a force-exerting component, such as a spring, may rest. The force-exerting component, such as a spring may be in a compressed state when the device is in a compressed state. The spring may exert a force on the body of the device when the device is in a compressed state.

The device may be in a compressed state when the sample is transferred from the channels to the respective containers. In some examples, the transfer may occur via pressure differential between the channels and the interiors of the containers, when they are brought into fluidic communication. For example, a second end of the channel may be brought into fluidic communication with the interior of the container. The container may have a vacuum and/or negative pressure therein. The sample may be sucked into the container when the channel is brought into fluidic communication with the container. The device may remain in a compressed state while the sample is being transferred to the container. The sample may fill the entire container or a portion of the container. The entirety of the sample (and/or greater than 90%, 95%, 97%, 98%, 99%, 99.5% or 99.9% of the sample) from the channels may be transferred to the containers. Alternatively, only a portion of the sample from the channels may be transferred to the containers.

Referring now to FIG. 9C, an example of a device 900 in a separated state will now be described. The base 940 may be separated from the rest of the device 900. The body 920 may be extended or compressed relative to the support 930. In one example, the extended state may be the natural state, so that when the force is no longer exerted on the body by the user, the body may extend back to the extended state. The channels 922a, 922b may be affixed to the body.

When the device 900 is in a separated state, the base 940 may be separated from the support 930 of the device. The channels 922a, 922b may be removed from fluidic communication with their respective containers 946a, 946b. When the device 900 is brought into the separated state, a first channel may be brought out of fluid communication with an interior of a first container, and a second channel may be brought out of fluid communication with an interior of a second container. This may occur sequentially or simultaneously. When the channels are removed from the containers, the containers may assume a sealed state to prevent undesired material from entering the containers. In some embodiments, the containers may be fluid-tight after removal of the channels. Optionally, the containers may be gas-tight after removal of the channels.

A user may separate the base 940 from the support 930 to bring the device into a separated state to remove the containers therein. In some embodiments, the base may be separated from the support or vice versa. Separating the base from the support may expose the containers 946a, 946b that are supported by the base. The containers may be press-fit or otherwise held within the base. The containers 946a, 946b may be removable from the base. By way of non-limiting example, removing the containers 946a, 946b allows them to be placed with other containers in a climate controlled container for transport to an analysis site. Optionally, the containers 946a, 946b may be removed to allow for pretreatment such as but not limited to centrifugation prior to being sent on for processing at an analysis site. Alternatively, the containers 946a, 946b may remain with the base.

Figures 10A, 10B:
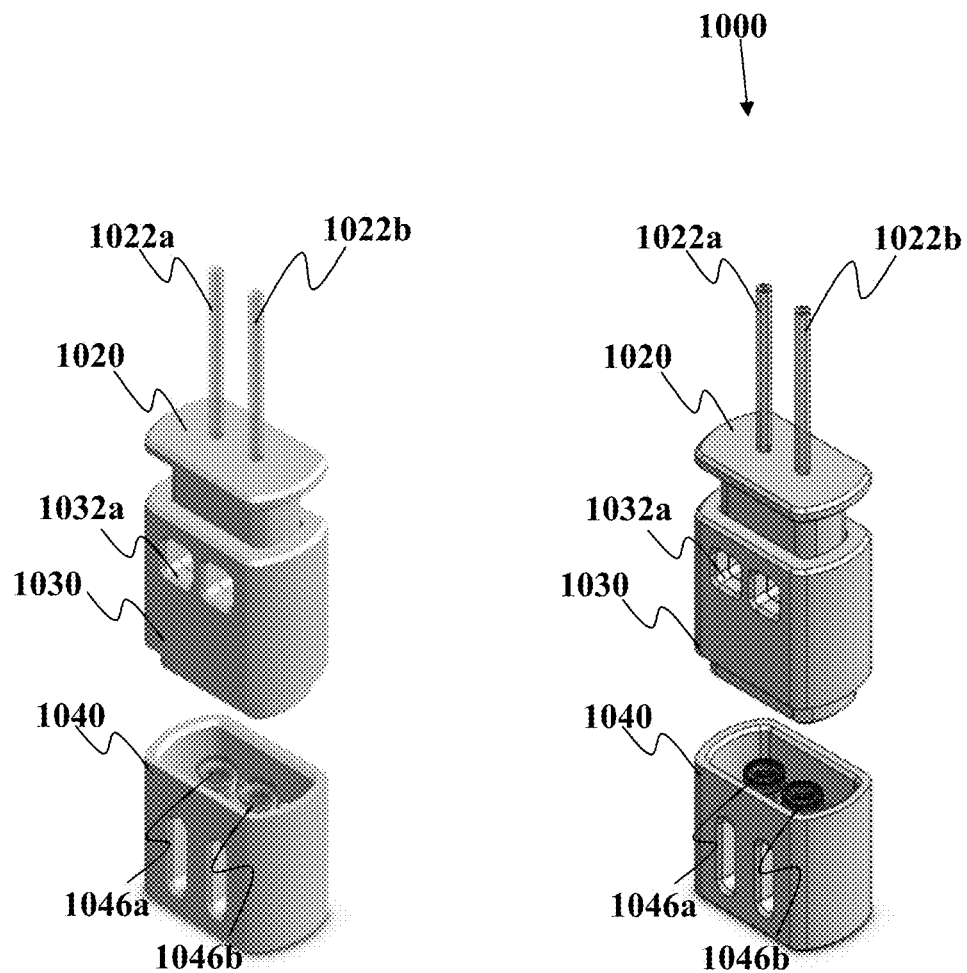
FIGS. 10A-10B show perspective views of a sample collection device according to one embodiment as described herein.

FIGS. 10A-10B provide additional views of a sample collection device 1000 in a separated state. When in a separated state, the base 1040 may be separated (partially or completely) from the support 1030 and/or body 1020 of the device. This allows for the removal of the containers 1046a and 1046b through the end of base 1040 previously not externally exposed when the device 1000 was not in a separate state.

When the device is in a separated state, one or more channels 1022a, 1022b may be fluidically isolated from one or more containers 1046a, 1046b housed by the base 1040. The containers may be fluidically sealed from their environment. The containers may contain sample therein, that had been transported through the collection channels, reached a minimum fill level, and then substantially fully deposited into the respective containers. The base 1040 may include one or more optical indicator 1046a, 1046b. The optical indicator may show a portion of the containers therein such that the device 1000 is not moved into the separate state until a minimum fill level has been reached in the containers. By way of non-limiting example, the containers may have an optically transmissive material that may permit a user to view the sample within the containers from outside the base.

In some embodiments, the base 1040 may encompass at least a portion of the containers. The base may have a hollow interior and walls surrounding the hollow interior. The base may have one or more shaped feature that may support the containers. The containers may be provided within the hollow interior. The walls may surround the container. The base may have an open top though which the containers may be exposed. The containers may or may not be removed through the open top.

Collection Device with Multiple Collection Channels

Referring now to FIGS. 11A-11F, a still further embodiment as described herein will now be described. This embodiment provides a bodily fluid sample collection device 1100 for use in collecting a fluid sample that may be pooled or otherwise formed on a surface, such as but not limited to the skin or other target area of a subject. Although this embodiment shows a device body which defines at least two collection channels of different volumes therein, it should be understood that devices with fewer or greater numbers of collection channels are not excluded. Embodiments where the same collection volume is used for one or more the channels are also not excluded. There may be variations and alternatives to the embodiments described herein and that no single embodiment should be construed to encompass the entire invention.

Figures 11G, 11H:
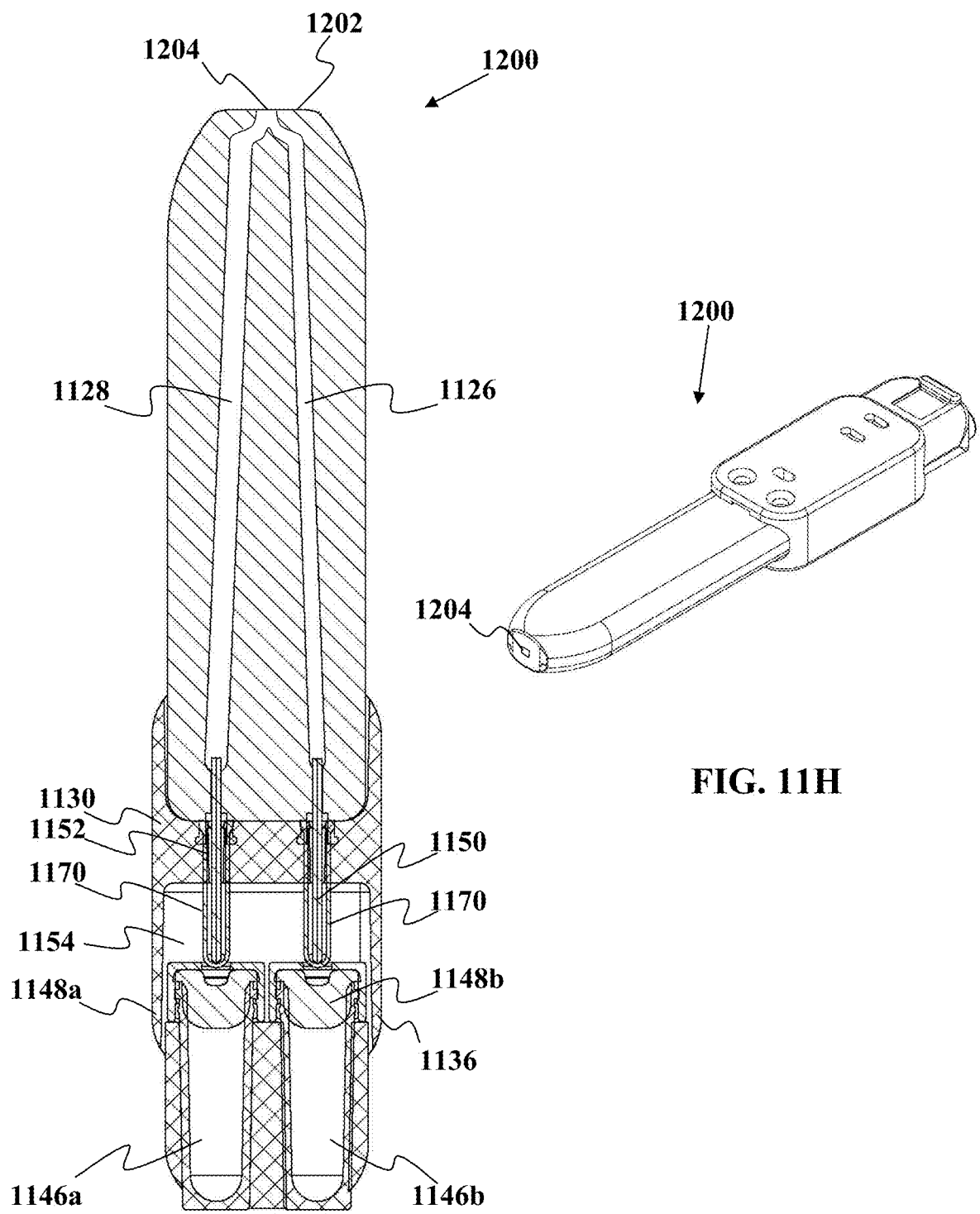
FIGS. 11A-11AB show views of various examples of sample collection devices according embodiment as described herein.
Figure 11I:
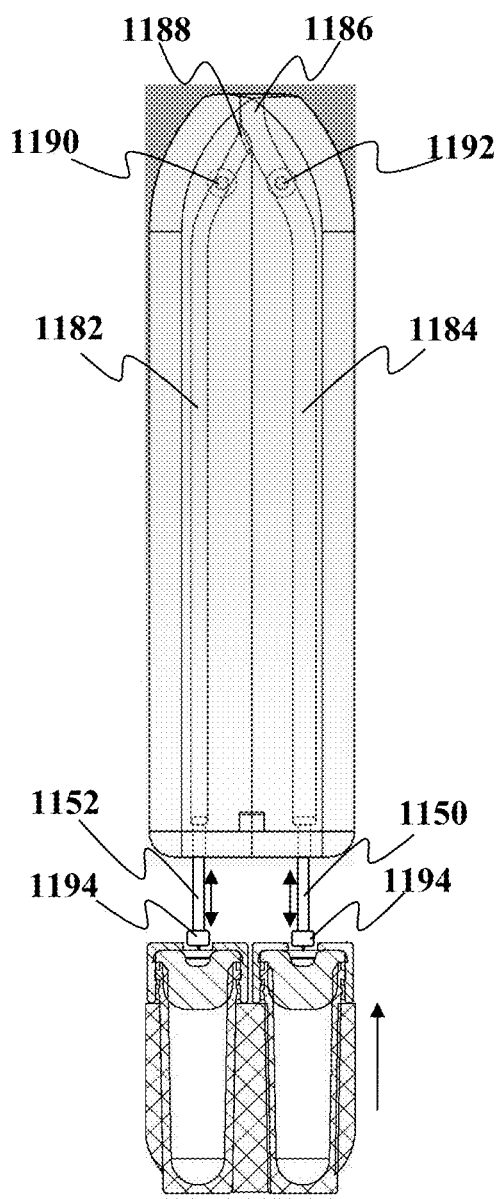
Figure 11J:
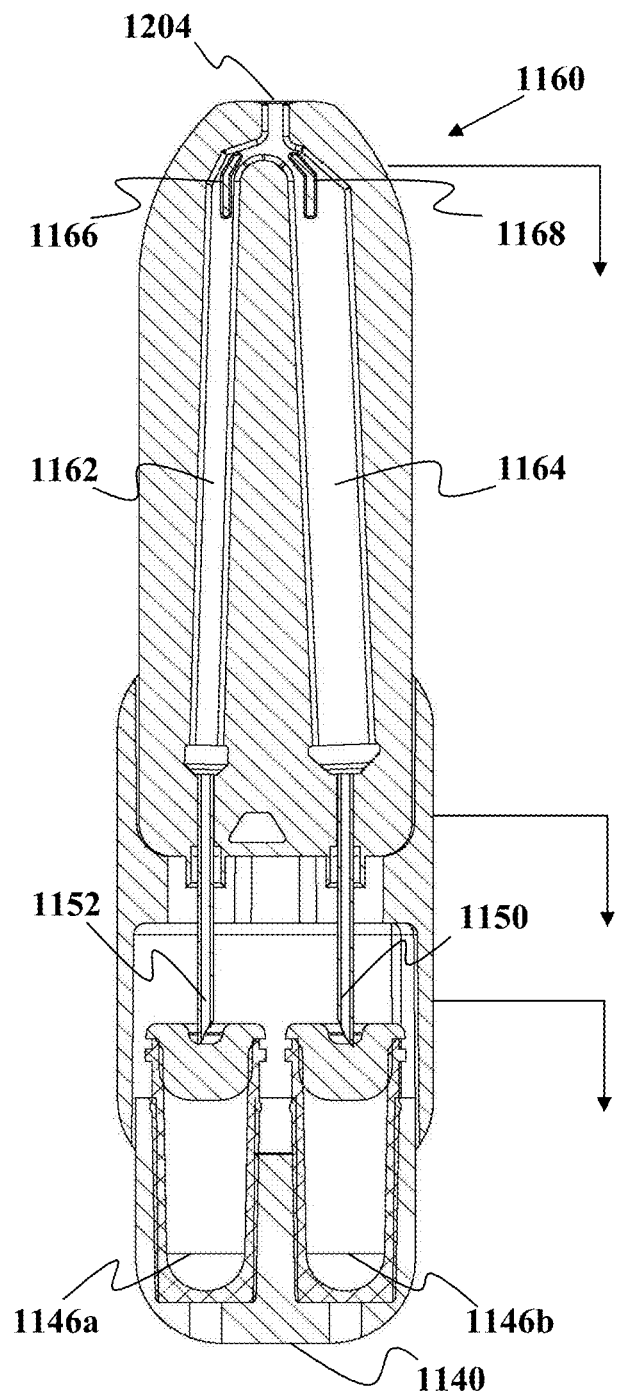
Figure 11K:
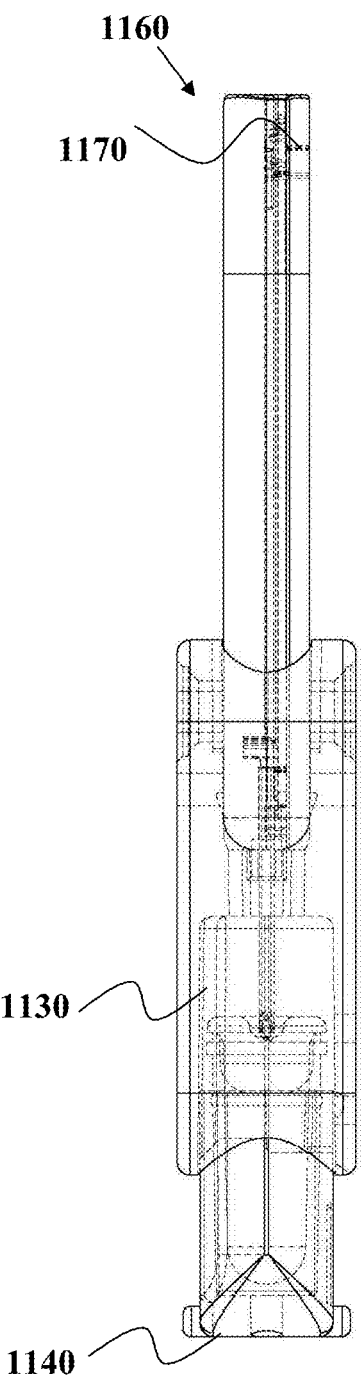
Figure 11O:
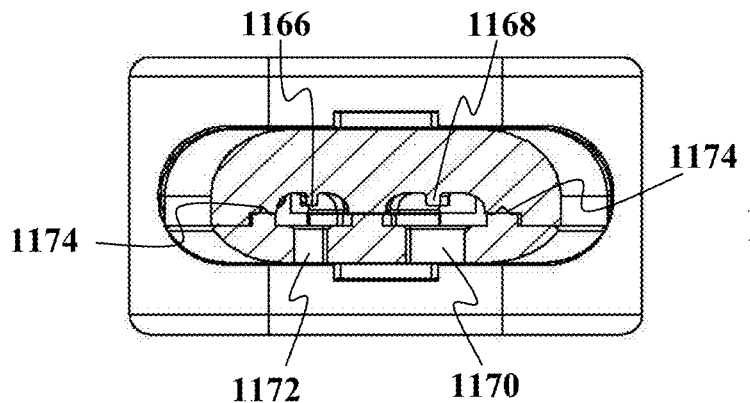
Figure 11P:
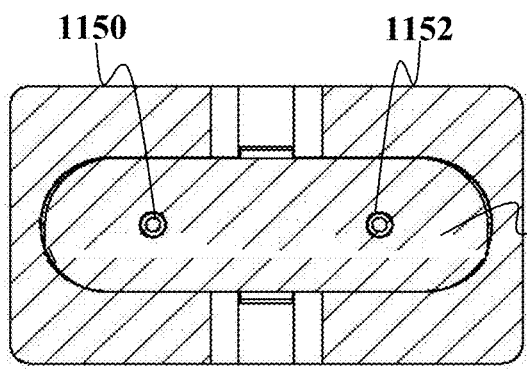
Figure 11Q:
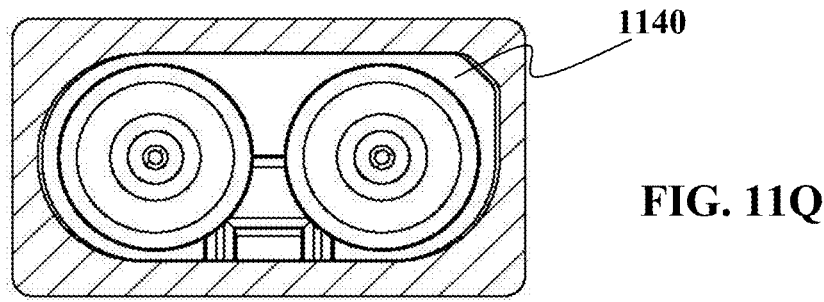
Figure 11R:
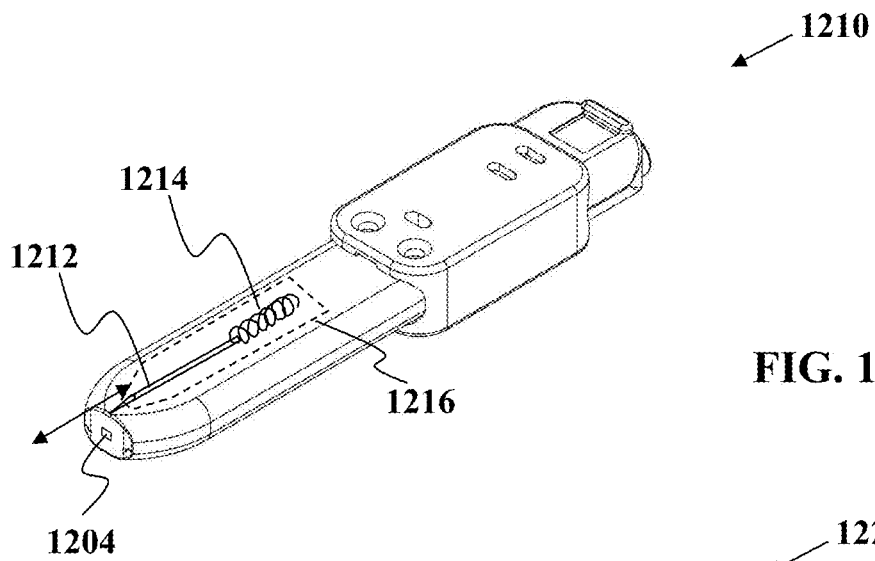
Figure 11S:
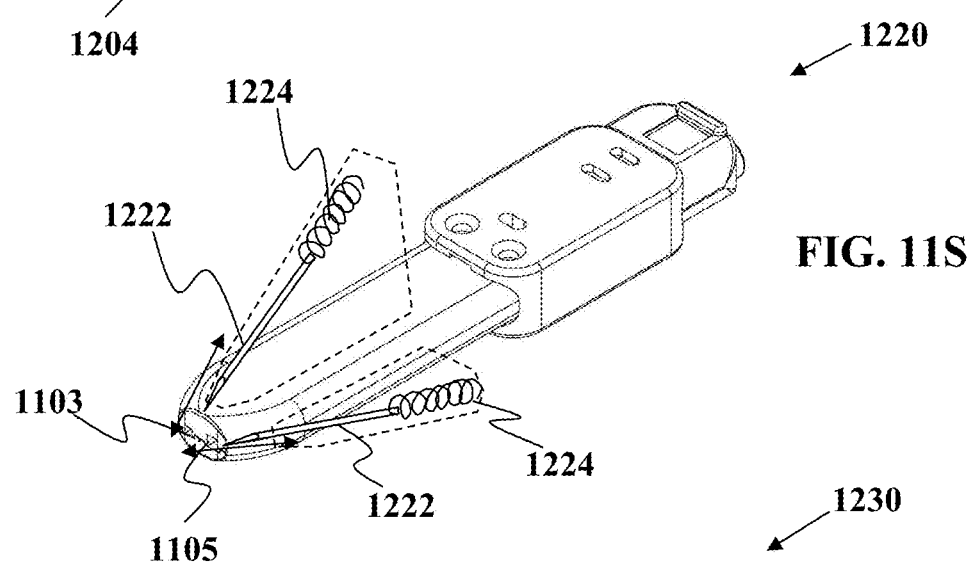
Figure 11T:
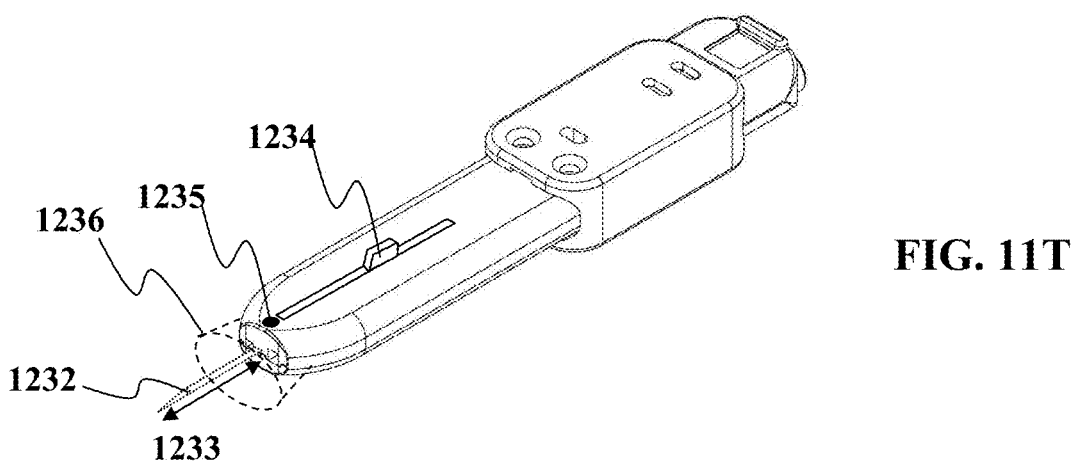
Figure 11U:
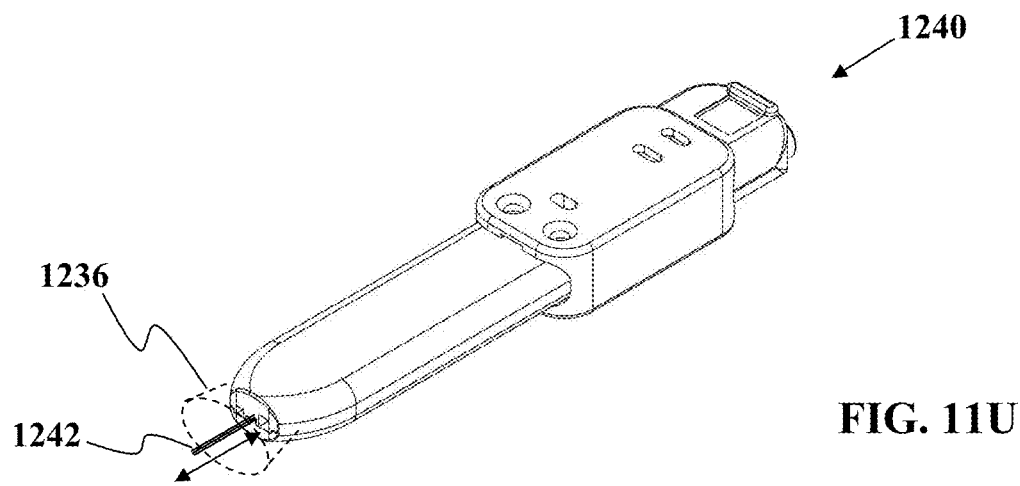
Figure 11V:
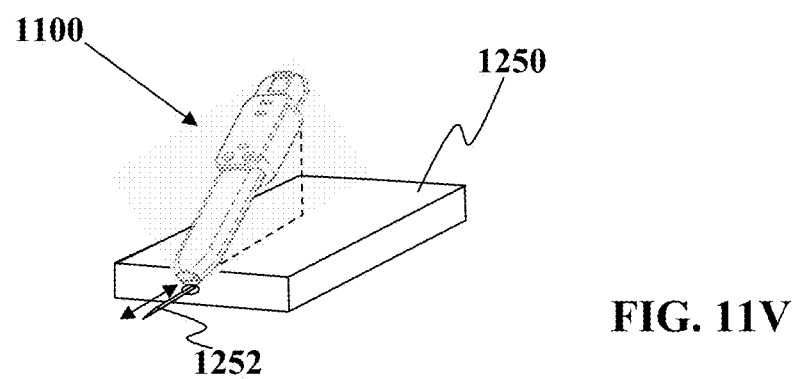
Figure 11W:
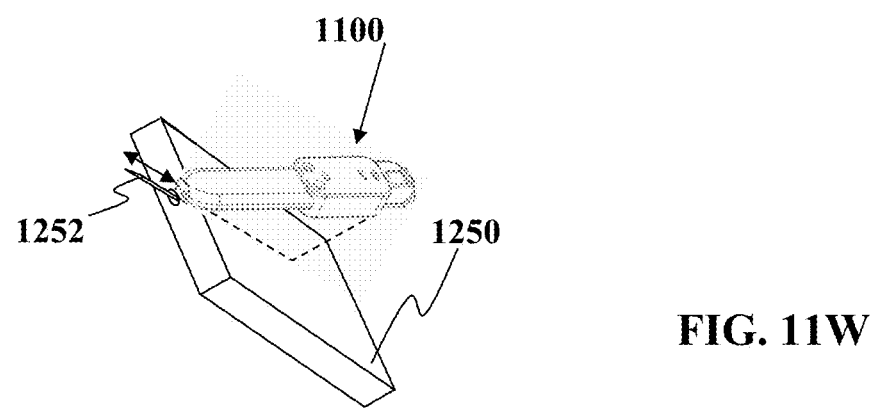
Figure 11A:
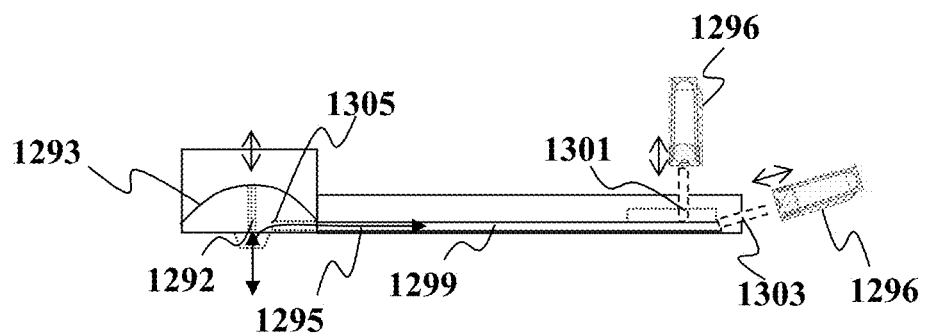
Figure 11A:
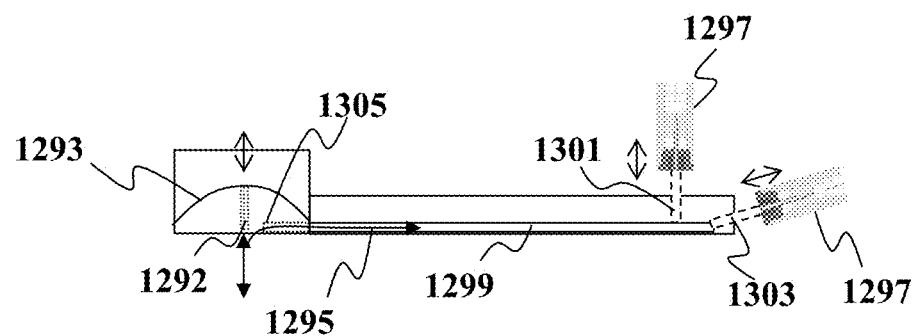

FIG. 11A shows a perspective view of one embodiment of a bodily fluid sample collection device 1100 with a distal end 1102 configured to engage a fluid sample on a surface. In this embodiment, the distal end 1102 may have a configuration designed to better engage a droplet or pool of bodily fluid or sample formed on a surface. Some embodiments, in addition to a desired shape, may also have surface treatments at the distal end 1102, such as but not limited to, chemical treatments, texturing, surface features, or coatings to encourage fluid flow towards the one or more openings 1104 and 1106 on the distal end 1102 leading to the channels in the device 1100.

As seen in FIG. 11A, this embodiment of the sample collection device 1100 has two openings 1104 and 1106 for receiving the sample fluid. It should be understood that some embodiments may have more than two openings at the distal end. Some embodiments may only have one opening at the distal end. Optionally, some embodiments may have additional openings along a side or other surfaces leading away from the distal end 1102 of the device 1100. The openings 1104 and 1106 may have any cross-sectional shape. In some non-limiting examples, the openings may have a circular, elliptical, triangular, quadrilateral (e.g., square, rectangular, trapezoidal), pentagonal, hexagonal, octagonal, or any other cross-sectional shape. The cross-sectional shape may remain the same or may vary along the length of the collection device body. In some instances, the openings may have a cross-sectional area of less than or equal to about 2 mm$^2$, 1.5 mm$^2$, 1 mm$^2$, 0.8 mm$^2$, 0.5 mm$^2$, 0.3 mm$^2$, or 0.1 mm$^2$. Some embodiments have the opening be the same shape. Others may use different shapes for the one or more openings.

The sample fill portion 1120 which may be the body of the sample collection device 1100 may be formed from a transparent and/or translucent material that may enable a user to see if a sample has entered sample collection channel(s) (see FIG. 11B) in the sample fill portion 1120. In some embodiments, the entire sample fill portion 1120 is transparent or translucent. Alternatively, some embodiments may only have all areas over the channel or only select portions of the channel or sample fill portion 1120 be transparent or translucent to allow a user to visualize the filling of sample into the sample collection device 1100. Optionally, the sample fill portion is made of an opaque material but has an opening or a window to allow for visualization of fill level therein. The device 1100 may further include one or more visualization windows 1112 and 1114 to allow a user to see when a desired fill level has been reached. The visualization window may be formed from a transparent and/or translucent material. Alternatively, the visualization window may be an opening without any material therein. Additional visualization windows can also be used to determine of all of the fluid in the collection channels have been emptied into the containers 1146a and 1146b (see FIG. 11B).

FIG. 11A also shows that some embodiments of support 1130 may have optical windows 1132 and 1134 which are positioned to show fill levels in the containers 1146a and 1146b to show if the containers in base 1140 have been moved into position to receive sample fluid. Optionally, the windows 1132 and 1134 may be cutouts that act as guides for the snap feature of based in order to define the start and end positions during activation. It should be understood that the base can be configured to hold one or more sample containers. By way of example and not limitation, the entire base 1140 can be removed from the sample collection device before or after sample fill. The base 1140 can be used as holder to retain the sample containers therein during transport, and in such an embodiment, the base 1140 along with the sample containers would be loaded into a shipping tray or other holder for transport. Alternatively, some embodiments may remove the sample containers from the base 1140 and then transport the containers without the base 1140 holding them.

FIG. 11B shows a cross-sectional view along section lines B-B of the embodiment shown in FIG. 11C. FIG. 11B shows the channels 1126 and 1128 in the portion 1120. The sample fill portion 1120 may be formed from two or more pieces which join together to define the portion 1120. Some may define the channels in one piece and then have another piece which mates to the first piece to define an opposing or top wall surface of the channel. In terms of manufacturing, this allows one piece to have channels molded or otherwise formed into the body and the opposing piece will mate to act as a cover for the channels or may also include portions of the channel too. The channels 1126 and 1128 may be formed only in portion 1120 or may also extend into support 1130 that has features to connect with the containers held in base or carrier 1140. Some embodiments may integrally form portions 1120 and 1130 together. Support 1130 may also be configured to hold adapter channel 1150 which will fluidically connect the channels 1126 and 1128 with their respective containers 1146a and 1146b.

Although these embodiments herein are described using two channels and two containers, it should be understood that other numbers of channels and containers are not excluded. Some embodiments may have more channels than containers, wherein some channels will couple to the same container. Some embodiments may have more containers than channels, in which case multiple containers may operably couple to the same channel.

As seen in FIG. 11B, the channels 1126 and 1128 may be of different sizes. This allows for different fluid volumes to be collected in each channel before they are simultaneously transferred into the containers 1146a and 1146b. Optionally, some embodiments may have the channels 1126 and 1128 sized to contain the same volume of fluid. In some embodiments, the fluid pathway of the channels 1126 and 1128 are shaped and/or angled so that openings near the distal end 1102 are closer together than proximal ends, which may be further apart to align them for entry into the containers 1146a and 1146b. There may be variations and alternatives to the embodiments described herein and that no single embodiment should be construed to encompass the entire invention.

FIG. 11B also shows that some embodiments may use needles for the adapter channels 1150 and 1152 in the body 1130 which are in communication with the channels 1126 and 1128. The needles each has a channel to allow for fluid to pass therethrough from the collection channels 1126 and 1128 to the ends of the needles. As seen in FIG. 11B, the containers 1146a and 1146b in the base 1140 are slidable relative to the support 1130 as indicated by arrow 1156. Relative motion between support 1130 and base 1140 can close the gap 1154. Closing the gap 1154 brings the adapter channels 1150 into the cap 1148a of the container 1146a until there is fluid communication between the interior of container 1146a and the collection channel 1126. At that time, motive force in the form will then move fluid in the channel 1126 into the container 1146a.

By way of example and not limitation, any combinations of motive forces may be used to draw sample into the container. Some embodiment may use pull from vacuum in the containers 1146a to draw sample into the container. Some may use pushing force from external pressure to move fluid into the container. Some embodiments may use both. Some may rely on capillary and/or gravity. In some embodiments, the motive force(s) used to draw sample into the channel is different from motive force(s) used to draw sample into the container. In some alternative embodiments, the motive force(s) may be the same for each stage. In some embodiments, the motive force(s) are applied sequentially or at defined time periods. By way of non-limiting example, motive force(s) to draw sample into the container is not applied until the at least one channel has reach a minimum fill level. Optionally, motive force(s) to draw sample into the container is not applied until the at least two channels have each reach a minimum fill level for that channel. Optionally, motive force(s) to draw sample into the container is not applied until all channels have each reach a minimum fill level for that channel. In some embodiments, the motive force(s) are applied simultaneously. This features recited may be applicable to any of the embodiments herein.

Referring now to FIG. 11E, an enlarged cross-sectional view of the device 1100 is shown. This embodiment shows that the support 1130 has a lip portion 1136 sized to extend over the adapter channels 1150 and 1152 in an amount sufficient to prevent a user from inserting a finger into the gap 1154 and piercing the finger on one of the needle.

Additionally, as shown in FIGS. 11B and 11E, the present embodiment has at least two channels in the sample collection device 1100. This allows for each of the channels 1128 and 1126 to each introduce a different material into the sample. By way of non-limiting example, if the sample is whole blood, one channel can introduce heparin into the blood while another channel introduces ethylenediaminetetraacetic acid (EDTA). Not only do these anti-coagulants prevent premature clogging of the channels during fill, but also introduce anti-coagulant into the whole blood in preparation for transport in the containers 1146a and 1146b. Optionally, the channel(s) may also be plasma coated in addition to or in place of the anti-coagulants. The plasma coating can reduce the flow resistance of the body fluid sample in the channels. Such a coating can be applied in patterns such as but not limited to strips, rings, or other patterns along with any other coating(s) to be used in the channels.

Optionally, there is sufficient quantity of anti-coagulant in the respective channel such that the sample fluid will contain a desired level of anti-coagulant in the sample fluid after only a single pass of the fluid through the channel. In traditional blood vials, the blood sample does not contain anti-coagulant until it enters the vial and once in the vial, the technician typically repeatedly tilts, shakes, and/or agitates the vial to enable mixing of anti-coagulant in the vials. In the present embodiment, the sample fluid will contain anti-coagulant prior to entering the sample container and it will do so without having to repeatedly tilt or agitate the sample collection device. In the embodiment herein, a single pass provides enough time and sufficient concentration of additive such as anti-coagulant into the sample fluid. In one embodiment, an EDTA channel has a volume of 54 uL coated by 200 mg/mL EDTA; a channel for Heparin has a volume of about 22 uL coated by 250 units/mL Heparin. In another embodiment, the EDTA channel has a volume of 70 uL coated by 300 mg/mL EDTA; the channel for Heparin has a volume of about 30 uL and is coated by 250 units/mL Heparin. By way of non-limiting example, a channel of volume from 50 to 70 uL can be coated by EDTA in the range from about 200 to 300 mg/mL EDTA. Optionally, a channel of volume from 70 to 100 uL can be coated by EDTA in the range from about 300 to 450 mg/mL EDTA. Optionally, a channel of volume from 20 to 30 uL can be coated by Heparin in the range from 250 units/mL Heparin. By way of example, the material may be solution coated onto the target surface for less than 1 hour and then dried overnight. There may be variations and alternatives to the embodiments described herein and that no single embodiment should be construed to encompass the entire invention.

Referring now to FIG. 11G, a still further embodiment will now be described. The embodiment of FIG. 11G shows that at a distal end 1202 of the sample collection device 1200, instead of having one opening 1204 for each of the channels, the sample collection device 1200 merges two or more of the channels into a single channel. The embodiment of FIG. 11G shows that there is common channel portion prior to the split of the common channel into to a plurality of separate channels. As will be described below in FIG. 11I, optionally, there may be back flow preventer such as but not limited to a vent positioned along the separate channel to reduce the possibility of drawing sample from one channel into another channel during filling and/or extraction of sample from the channels into the sample container(s).

As seen in FIG. 11H, this use of common flow paths can result in a reduced number of openings on the exterior of the sample collection device 1200, which may make it align the opening 1204 to engage the bodily fluid sample. It may also increase the capillary force for drawing bodily fluid sample into the sample collection device 1200 by having more capillaries pulling on the same channel where the bodily fluid sample enters the collection device.

Referring now to FIG. 11I, a cross-sectional view of select components of a sample collection device will now be described. FIG. 11I shows that the sample collection device can have two channels 1182 and 1184 that have a common portion 1186 leading towards an inlet opening on the device. In some embodiments, the common portion 1186 is a continuation of one of the channels 1182 or 1184 in terms of size, shape, and/or orientation. Optionally, the common portion 1186 is not of the same size, shape, and/or orientation of any of the channels 1182, 1184, or any other channel that may be in fluid communication with the common portion 1186. FIG. 11I shows that in one non-limiting example, there may be a step at the interface 1188 between the channel 1182 and 1184. This interface 1188 may be configured to ensure flow into both of the channels so that they will both reach a full fill. In one embodiment, the interface 1188 has a size greater than the channel 1182 leading away from the interface 1188. Although other sizes are not excluded, this interface 1188 of greater size may ensure that sufficient flow will enter the channel 1182, which in the present embodiment, has a smaller diameter and reduced volume relative to the channel 1184. There may be variations and alternatives to the embodiments described herein and that no single embodiment should be construed to encompass the entire invention.

FIG. 11I also shows that there may be vents 1190 and 1192 that can be used to prevent cross-flow between channels, particularly when sample is being transferred into the sample containers. In one embodiment, the vents 1190 and 1192 are open at all times. In another embodiment, the vents 1190 and 1192 may be open only at select times, such as but not limited to after the channels 1182 and 1184 are filled or substantially filled. Some embodiments may use a dissolvable material the plugs the vents 1190 and 1192 until they are in contact with sample fluid. Optionally, some embodiments may use a slidable covers one or more of the vents 1190 and 1192 such that they are only opened at times selected by the user. In one embodiment, the covers are linked to the sample containers such that movement of the sample containers to move into fluid communication with the channels will also open one or more vents 1190 and 1192 to reduce the risk of cross-flow between channels. Optionally, other anti-crossflow mechanisms such as but not limited to valves, gates, or plugs can also be used to prevent fluid transfer between channels 1190 and 1192.

FIG. 11I also shows that there may be anti-leakage devices 1194 positioned over the adapters 1150 and 1152. In this embodiment, the anti-leakage devices 1194 are frits which may be slidably moved from a first position where they prevent sample from leaking out from the adapters 1150 and 1152 to a second position wherein they allow the adapters to deliver fluid into the sample containers. In one non-limiting example, the anti-leakage devices 1194 will slide when they are engaged by the sample containers or the housing that holds the sample containers. The movement of the sample containers or the housing in this non-limiting example shows that the movement of those elements will also cause movement of the anti-leakage devices 1194.

Referring now FIG. 11J, yet another embodiment of a sample collection device 1160 will now be described. This embodiment of the sample collection device 1160 shows that the device 1160 has a sample entry location 1204 that leads to a plurality of channels 1162 and 1164 in the device 1160. Although FIG. 11J show that the channels 1162 and 1164 may have different shapes and/or sizes, some embodiments may be configured to have the same volumes and/or shapes. It should also be understood that the sample entry location 1204 can be on the surface of the device 1160, or optionally, it can be part of a tip, nozzle, stub, or other protrusion that extends from the body of the device 1160. This protrusion may be in the same plane and aligned parallel with the body of the device or optionally, it may be angled so that the axis of the protrusion intersects the plane of the device 1160.

FIG. 11J further shows that for some embodiments, there may be sample flow features 1166 and 1168 to draw or otherwise preferentially direct sample in a desired direction. In some embodiments, the features 1166 and 1168 are guides that operate to decrease channel dimension in at least one axis, such as but not limited to width or height, and thus increase capillary action through those areas of reduced dimension. In one non-limiting example, these flow features 1166 and 1168 can assist fluid flow through the channel areas positioned near the anti-crossflow features 1170 during sample entry into the channels. In one embodiment, the flow features 1166 and 1168 are sized so as to preferentially improve flow in the inbound direction when flow is drawn primarily by capillary action. Outbound flow, in one scenario, is not based on capillary force but on vacuum pulling force (such as from an adjacent channel), and these flow features 1166 and 1168 of the present embodiment are not configured to provide assistance under those vacuum, non-capillary flow conditions. Thus, some but not all embodiments of flow features 1166 and 1168 are configured to assist under at least one type of flow condition but not certain other flow condition(s). Optionally, some embodiments may use other techniques alone or in combination with the guides, such as but not limited to, shaped features, hydrophobic material(s), hydrophilic material(s), or other techniques to push/pull samples towards a desired location.

FIG. 11J also shows that in the one or more embodiments herein, there may be angled side wall features 1167 that conically or otherwise narrow the cross-sectional area of the channel in a manner that funnels sample to minimize the amount of sample that may be retained in the channel and not collected. FIG. 11J also shows that there may be locating feature(s) 1169 to facilitate joining of parts together in a define location and orientation during manufacturing.

FIG. 11K shows a side view of this embodiment of the sample collection device 1160. The side view of the device 1160 shows that there are embodiments where there are one or more anti-crossflow features 1170 such as but not limited to vents to minimize undesired crossflow of sample between the channels 1162 and 1164, particularly once a desired fill level has been reached in the respective channels. The anti-crossflow features 1170 and 1172 can prevent crossflow due to the break in fluid pathway created by the vents. The crossflow issue presents itself most commonly when the containers in the holder 1140 are engaged and provide an additional motive force to pull the sample from the channels into the containers. This "pulling" effect may inadvertently draw sample from one channel to an adjacent channel. To minimize crossflow, forces associated with pulling sample from the channel into the container will pull from the vent and not fluid in an adjacent channel, thus minimizing undesired comingling of sample.

FIG. 11K also shows that in some embodiments herein, there may be common portions 1130 and 1140 which can be adapted for use with different sample fill portions 1120. Some may use different capillary fill portions 1120. Some embodiments may use fill portions that use different types of capture techniques, such as but not limited to, samples acquired from venous draws, arterial draws, or other sample drawn from an interior location or target site of the subject.

Referring now to FIG. 11L, one embodiment of the sample flow features 1166 and 1168 are shown. This cross-sectional view of sample collection portion with the channels 1162 and 1164 and the sample flow features 1166 and 1168 near the common inlet pathway 1165 shows that the features are desired in one embodiment near where the sample is entering the channels. FIG. 11L also shows, for channels of different volumes, it can be desirable to position the inlet 1165 closer to the channel 1164 that has the larger volume, as seen by the asymmetric location of inlet 1165. It can also be seen that in some embodiments, location(s) of the sample flow features 1166 and 1168 can also be selected to control filling rate, filling volume, or the like in the sample collection device 1160. It should be understood that one or more of features described can be adapted for use with other embodiments herein.

Referring now to FIG. 11M, channels 1162 and 1164 with sample anti-crossflow features are shown. In one embodiment, the sample anti-crossflow features are vents 1170 and 1172 located on at least one surface of the channels 1162 and 1164. In one nonlimiting example, these sample anti-crossflow features are located near any sample flow features 1166 and 1168 in the device. In one embodiment, these anti-crossflow features are configured to prevent flow between channels. These anti-crossflow features can be located near the maximum fill locations of each of the channels such that as the channel is at or near its maximum sample capacity, the anti-crossflow features 1170 and 1172 are positioned to prevent overfilled sample from causing sample that has been treated in one channel from entering another channel and undesirably mixing samples from two channels together.

FIG. 11N shows a perspective view of the sample collection device 1160 with sample fill indicators 1112 and 1114. In one embodiment, these indicators 1112 and 1114 are openings or transparent portions of the device 1160 that allows for observation of at least one portion of the channel(s) 1162 or 1164. When sample is visible in at least one of the indicators 1112 and 1114, it provides a cue to the user to then take another action such as but not limited to engaging the sample containers in the holder 1140. In some embodiments, there is only one sample fill indicator which is a proxy for sufficient fill of sample in two or more of the channels. In some embodiments, the action to engage the sample containers is only taken when indicated by indicators 1112 and 1114. In some embodiments, the action to engage the sample containers is only taken when indicated by only one of the indicators.

Referring now to FIGS. 11O, 11P, and 11Q, cross-section at various locations along one embodiment of the device 1160 in FIG. 11J are shown. FIG. 11O shows a cross-section showing the sample flow features 1166 and 1168. The anti-crossflow features 1170 and 1172 are also shown. Engagement features 1174 can also be provided to enable mating of pieces together to form the device 1160.

FIG. 11P shows that the adapter channels 1150 and 1152 are positioned to extend into or at least be in fluid communication with the sample channels 1162 and 1164. Optionally, some embodiments may have multi-lumen adapter channels 1150 or 1152. Optionally, some embodiments may have multiple adapter channels per sample channel, wherein such additional channels may be parallel to, angled, wrapped, or otherwise oriented relatively to each other.

FIG. 11Q shows that in some embodiments, the container holder 1140 can be shaped asymmetrically (in the cross-sectional plane) or otherwise shaped to enable only one orientation that the holder 1140 can be received in the device 1160. This can be particularly desirable when it is desired to direct sample from a certain channel into a selected container. If the holder 1140 can be inserted in various orientations, the sample from one channel may end up in the wrong container. Optionally, other features such as alignment features, slots, visual cues, texture cues, and/or the like may be used to encourage a preferred orientation of sample containers in the device.

Integrated Tissue Penetrating Member

Referring now to FIG. 11R, yet another embodiment of a sample collection device will now be described. This sample collection device 1210 comprises features similar to that shown in FIG. 11G, except that it further includes a tissue penetrating member 1212 that is mounted to the sample collection device 1210. An actuation mechanism 1214 such as but not limited to a spring actuator can be used to launch the tissue penetrating member. FIG. 11R shows the actuation mechanism 1214 in a resting state and that it can be a spring that can be compressed to launch a tissue penetrating member 1212 towards target tissue. The tissue penetrating member 1212 can be housed inside a housing 1216 (shown in phantom). In one embodiment, the housing 1216 comprises a portion that can be peeled back, pierced, released or otherwise opened to allow the tissue penetrating member 1212 to exit the housing but also maintain sterility of the tissue penetrating member 1212 prior to its use. In some embodiments, the portion may be a foil, a cap, a polymer layer, or the like. There may be variations and alternatives to the embodiments described herein and that no single embodiment should be construed to encompass the entire invention.

In one embodiment, the tissue penetrating member 1212 path can be controlled along both the "normal" (i.e., forward direction of the tissue penetrating member) and "orthogonal" (i.e., perpendicular to main motion vector) of the trajectory. Some embodiments may have not have a hard stop or bang stop at the deepest point of penetration (i.e., return point), which is the main cause for spontaneous pain. Some embodiments may use a cushion, a cam pathway, or other non-hardstop mechanism to prevent pain associated with the shockwave of a sudden stop. Such a shockwave is detrimental even if the tissue penetrating member successfully avoids hitting nerves near the wound location as the shockwave can activate such nerves even if direct contact was avoided. Optionally, some embodiments may have the tissue penetrating member follow a non-jitter path, to prevent a rough wound channel (residual pain). This may be achieved in some embodiments through tighter tolerance in any guide pathway used with tissue penetrating member or a pin associated with the tissue penetrating member. This may be a non-jitter path when penetrating the tissue. Optionally, this may be a non-jitter path for the tissue penetrating member both outside the tissue and when it is inside the tissue. This can reduce overall motion "wobble" of the tissue penetrating member that may cause residual pain, long-lasting trauma, and scarring.

Some embodiments may have a controlled outbound speed to prevent slow and delayed wound closure and after bleeding. By way of nonlimiting example, the controlled outbound speed of the tissue penetrating member can be controlled by mechanical mechanisms such as but not limited cams or higher friction materials.

Some embodiments may also include anti-bouncing mechanisms to prevent unintended re-lancings that can be associated with an uncontrolled tissue penetrating member that rebounds into the tissue after initial wound creation. Some embodiments herein may have "parking" mechanisms or lock-out mechanisms that will engage the tissue penetrating member or its attachments to prevent re-entry of the tissue penetrating member once it has retracted out of the tissue or some other desired distance.

The abruptness with which the lancet comes to a stop in the skin at maximum depth, before it starts its outbound motion and returning to its starting position, is an inherent issue of this design. With the lancet at its deepest point of penetration, the greatest amount of force is applied to the skin. The drive mechanism simply bounces off the end of the device like a ball bounces back from the floor. The lancet, coming to an abrupt stop at the end point of its inbound motion, sends a shockwave into the skin, causing many pain receptors in the vicinity of the lancet to fire, even though they are not directly struck. This amplifies spontaneous pain substantially.

As mentioned, instead of simple spring actuated tissue penetrating members, some embodiments may use mechanical cam actuation. Devices with cam-actuation design can minimize "hard stopping" of the tissue penetrating member. A cam mechanism is usually spring driven and generally offers a better guided actuation. The trajectory of the tissue penetrating member is tightly controlled through a guided path of the tissue penetrating member holder via a pin riding in a cam. The cam mechanism allows for a predetermined speed profile with a softer return and distinct speed control for the tissue penetrating member outbound trajectory. This mechanism also effectively avoids a bounce back of the lancet into the skin when the mechanism reaches its motion end point. In addition, the mechanical oscillation (or jitter/wobble) of the lance path in both directions is reduced when fired in air. Some embodiments herein may also minimize any mechanical wobble of the drive mechanism (e.g., due to uneven or rough cam slots) to prevent transfer of such drive mechanism wobble directly into the tissue because of its "forced motion profile."

Optionally, some embodiments may use electronic actuation through an electronically controlled drive mechanism. This technology uses a miniaturized electronic motor (e.g., voice coil, solenoid) coupled with a very accurate position sensor, moving the tissue penetrating member into and out of the skin with precisely controlled motion and velocity. Following rapid entry, the device decelerates the tissue penetrating member to an exact, preset depth to return smoothly, without jitter, and relatively slowly. This allows quick wound closure and avoids long-term trauma. With this device, the force required to penetrate the lancet into the skin is controlled while the tissue penetrating member is progressing. The benefit of tightly controlling the tissue penetrating member actuation "profile" is a reproducible painless lancing that yields a sufficient and consistent blood sample for testing.

In terms of puncture site creation for blood sample extraction, it may be desirable to elect the appropriate puncture site on one of the patient's fingers (ring or middle) on their non-dominant hand. The puncture sites may be on the sides of the tips of the fingers. In one nonlimiting example, it may be desirable to hold the hand warmer strip against the patient's selected finger for 15 seconds. Optionally, some may warm the patient's finger(s) from 10 to 60 seconds. Others may warm for longer. The warming will increase blood flow to the target site. To prepare the target site, it may be desirable to wipe the side tip of the selected finger or surface of the subject with an alcohol wipe or similar cleaning agent, being sure to wipe the selected puncture site. In some embodiments, it is desirable to wait until the skin is completely dry. Typically, one does not dry with gauze or blow air on the fingertip to accelerate drying.

After a puncture has been formed, hold the finger downward, below the patient's waist, in order to allow blood to flow. Massage the finger lightly from base to tip until a blood drop has formed. Carefully fill the blood collection device by touching the tip of the device to the bead of blood on the finger. Make sure the device is completely filled. Once the blood collection device is filled, press the bleeding area of the finger against the gauze pad on the table. Transfer the blood sample into the collection containers. Place a bandage over the finger. Place the containers with the sample into the shipping box inside the refrigerator. Discard all supplies in the biohazard sharps container. All supplies are single-use only.

If enough blood is not obtained from the first puncture, carefully place the blood collection device on the table surface, ensuring that the device remains horizontal. Place a bandage over the finger that was punctured. Select the appropriate puncture site on a different finger on the patient's same hand. If the ring finger was punctured first, choose a new puncture site on the middle finger, and vice versa. Hold the hand warmer strip against the patient's selected finger for 60 seconds. Optionally, some may warm the patient's finger(s) from 30 to 90 seconds. This will increase blood flow to the finger. These techniques for blood collection using a sample collection device such as any of those herein can enable sufficient sample collection of capillary blood for use in laboratory testing at Clinical Laboratory Improvement Amendments (CLIA) certified facility and/or standards.

Referring now to FIG. 11S, yet another embodiment of a sample collection device 1220 will now be described. In this embodiment, the tissue penetrating member 1222 may be mounted at an angled relative to the sample collection device 1220. This angled configuration allows for tissue penetrating member to create a wound at a location that aligns with sample acquisition opening(s) 1103 and 1105. Although a standard spring-launched actuator is shown as the drive mechanism 1224 for the tissue penetrating member 1222, it should be understood that cam and/or electrical drive systems may also be used in place of or in combination with the spring launcher. When the drive mechanism 1224 is a spring, the spring can be compressed to move the tissue penetrating member 1222 to a launch position and the released to penetrate into the target tissue. FIG. 11S shows the tissue penetrating member 1222 in a resting position. Although the figures show a spring for the drive mechanism 1224, it should be understood that other drive mechanism suitable for use in launching a tissue penetrating member to create a healable wound on a subject are not excluded. There may be variations and alternatives to the embodiments described herein and that no single embodiment should be construed to encompass the entire invention.

A housing 1226, similar to that described for housing 1216, may be formed around the tissue penetrating member 1222. Although FIG. 11S shows two tissue penetrating members 1222 mounted on the sample collection device, it should be understood that devices with more or fewer tissue penetrating members are not excluded. For example, some embodiments may have only one tissue penetrating member 1222 mounted to the sample collection device 1220. There may be variations and alternatives to the embodiments described herein and that no single embodiment should be construed to encompass the entire invention.

Referring now to FIG. 11T, another embodiment of a sample collection device 1230 will now be described. This embodiment shows that the tissue penetrating member 1232 is contained within the sample collection device 1230 and as seen in FIG. 11T, it is actually co-axially aligned with the central axis of the sample collection device. This positions the tissue penetrating member 1232 to extend outward from the sample collection device 1230 at a location close to where openings 1103 and 1105 are positioned on the sample collection device 1230. Of course, devices having more or fewer openings are not excluded and the embodiment of FIG. 11T is exemplary and non-limiting. FIG. 11T shows that in one embodiment of the sample collection device, a firing button 1234 may be mounted on the sample collection device 1230. Optionally, some embodiments may have the shaped front end 1236 function as the actuation button, wherein upon pressing the tissue against the front end 1236 to a certain depth and/or certain pressure, the tissue penetrating member will be actuated.

Once fired, the tissue penetrating member 1232 moves as indicated by arrow 1233. In some embodiments, the tissue penetrating member 1232 is fully contained inside the sample collection device 1230 prior to actuation. Some embodiments may have a visual indicator 1235 on the device 1230 to help guide the user on where the tissue penetrating member 1232 will exit the device and where approximately the wound will be formed.

In this non-limiting example, the entire device 1230 may be in a sterile pouch or package that is only opened before the device 1230 is used. In this manner, sterile conditions are maintained for the tissue penetrating member and the collection device prior to use. This external sterile pouch or package is also applicable to any of the other embodiments herein. FIG. 11L also shows that a shaped front end 1236 (shown in phantom) that can be integrally formed or separately attached to the sample collection device 1230. This shaped front end 1236 can provide suction to draw sample fluid into the sample collection device 1230. Optionally, the shaped front end 1236 can be used to stretch the target tissue and/or force it into the shaped front end to apply pressure to increase sample fluid yield from wound formed by the tissue penetrating member 1232. It should be understood that any of the embodiments herein can be adapted to have a shaped front end 1236. Optionally, the shaped front end may have select hydrophobic area(s) to direct sample fluid to towards one or more collection areas on the front end. Optionally, the shaped front end may have select hydrophilic area(s) to direct sample fluid to towards one or more collection areas on the front end.

Referring now to FIG. 11U, yet another embodiment of a sample collection device will now be described. This embodiment is similar to that of FIG. 11T except that, instead of single tissue penetrating member such as a lancet, the embodiment of FIG. 11T uses a plurality of tissue penetrating members 1242. In one embodiment, these tissue penetrating members are microneedles 1242 that are of reduced diameter as compared to traditional lancets. A plurality of microneedles 1242 can be simultaneously actuated for device 1240 and create multiple wound sites on the tissue. The spacing of the microneedles 1242 can result in more capillary loops being pierced and more channels being available for blood to reach the tissue surface. This also allows for a more "square" penetration profile as compared to a lancet which has a pointed tip and a tapered profile. This may enable the microneedles 1242 to engage more capillary loops over a larger area without penetrating too deep into deeper tissue layers that are more densely populated with nerve endings.

Referring now to FIGS. 11V and 11W, a still further embodiment of a sample collection device will now be described. In the embodiment shown in these figures, the sample collection device 1100 may be mounted angled to a dedicated wound creation device 1250 that has a tissue penetrating member 1252 configured to extend outward from the device 1250. The sample collection device 1100, which may optionally be configured to have a shaped front end 1236 (with or without an opening to accommodate the tissue penetrating member 1252), can be removably mounted to the wound creation device 1250. Optionally, the sample collection device 1100 may be flat mounted to the device 1250. Optionally, there may be a shaped cut-out on device 1250 for press-fit holding the sample collection device 1100. It should be understood that other techniques for removably mounting the sample collection device 1100 are not excluded. This de-coupling of the collection device and the wound creation device allows for the use of a more sophisticated, possible non-disposable wound creation device 1250 that can create a more controlled, reduced-pain wound creation experience.

FIG. 11W shows that the sample collection device 1100 can be aligned to be more or less horizontal to be neutral with regards to gravity effects on the sample collection. Other mounting configurations of device 1100 to would creation device 1250 are not excluded.

Referring now to FIGS. 11X to 11Z, still further embodiments of various sample collection devices will now be described. FIG. 11X shows a sample collection device 1240 where a shaped front end 1236 may be used with the device 1240. This shaped front end 1236 is similar to that previously described. A vacuum source 1270 can be used to assist in drawing bodily fluid sample into the device 1240. The vacuum source 1270 may be linked to the body of device 1240 and/or to the shaped front end 1236. It should be understood that any of the embodiments described in this disclosure can be adapted for use with a sample acquisition assist device such as but not limited to a vacuum source 1270.

FIG. 11Y shows yet another embodiment of a sample collection device. This embodiment uses a pipette system having a tip 1280 for collecting sample fluid. The tip may include a coaxially mounted tissue penetrating member 1282. Optionally, a side mount or angled tissue penetrating member 1284 is shown to create the wound at the target site. The pipette system with tip 1280 can apply vacuum to pull sample fluid from the subject. Optionally, a shaped front end 1236 may be used with the tip 1280 to assist in skin stretching or tissue reshaping at the target site.

FIG. 11Z shows that some embodiments may use a diaphragm 1291 linked actuation mechanism to create a vacuum for drawing blood sample. This linkage allows for the diaphragm to create a vacuum on the return stroke of the tissue penetrating member 1292 from the target site. In one embodiment, the tissue penetrating members 1292 are microneedles. The actuation of the tissue penetrating members as indicated by arrows 1294 launches the tissue penetrating members 1292 and on the return path, creates the vacuum due to the motion of the diaphragm linked to the motion of the tissue penetrating member 1292. One or more containers 1296 can be coupled to hold fluid collected by the device 1290. Some embodiments may have only one container 1296. Some embodiments may have one set of containers 1296. Some embodiments may have multiple sets of containers 1296. Some embodiments may be mounted externally on device 1290. Some embodiments may be mounted internally in device 1290. There may be variations and alternatives to the embodiments described herein and that no single embodiment should be construed to encompass the entire invention.

FIG. 11AA shows a side cross-sectional view of a sample collection device having a plurality of tissue penetrating members 1292 mounted to an actuation mechanism 1293. In one embodiment, the tissue penetrating members 1292 are microneedles. In one embodiment, the actuation mechanism 1292 can be a spring-like device in a dome, curved, or other shape. Although a mechanical actuation method is shown, it should be understood that other types of actuation techniques such as but not limited to electromechanical, pneumatic, mechanical cam, or other technique known or developed in the future may be used for actuation. It should also be understood that some embodiments may use a tissue interface (shown in phantom) to facilitate interaction with the tissue. FIG. 11AA shows that the sample obtained from a wound or wounds created by tissue penetrating members 1292 may flow as indicated by arrow 1295 to a channel 1299. In one embodiment, the channel 1299 may be coated with at least one anticoagulant. Optionally, some embodiments may have two channels 1299 that may draw sample along two pathways, wherein each channel may have the same, or optionally different, coatings on the surface of the channels 1299. Optionally, some embodiments may have surfaces of the device uncoated but instead have the additive material in the container 1296 or 1297. As seen in FIG. 11AA, the sample may flow to a location such as but not limited to a chamber (shown in phantom), one end of the channel 1299 or other location wherein a conduit such as pathway 1301 or 1303 (shown in phantom) may be used to fluidically couple the sample collected in channel 1299 to transfer the sample container 1296 or 1297 as shown in FIG. 11AB. It should be understood that some embodiments may have containers 1296 in both locations as shown in FIG.

11AA or only at one but not the other. Optionally, some may have multiple containers at one location and none or fewer containers at the other location. Optionally, some of these may be unitized so that multiple vessels are integrally formed or otherwise joined together. As seen in FIG. 11AA, the container 1296 may be actuated by sliding the container 1296 to contact the pathway 1301 in a manner that allows sub-atmospheric environment inside the container 1296 to draw sample therein. Optionally, other actuation methods such as but not limited to using a valve, breaking a seal, or the like can be used to activate sample transfer from the device to the container 1296. Although FIG. 11AA show that the channel 1299 has a certain length and aspect ratio, it should be understood that the channels of different cross-sectional shape, different length (longer or shorter), and curved vs linear may also be used. Some embodiments may keep the channel 1299 in one horizontal plane or may optionally have portions in one plane and portions in another plane. Optionally, instead of or in combination with capillary action from channel 1299 for drawing sample therein from the wound site, a suction or other sample pulling device can be used to draw sample into the channel 1299. The embodiment of FIG. 11AA may optionally be modified to locate the entry port of channel 1299 closer to the wound site such as but not limited a channel extension 1305, forming the channel closer to the wound site, or positioning or orienting the tissue penetration members to form a wound closer to the inlet of channel 1299.

FIG. 11AB shows a still further embodiment wherein containers 1297 having a reverse-syringe design is used. As seen herein, the movement of engaging the container 1297 with pathway 1301 or 1303 can be used to push the plunger 2828 to create a reduced pressure environment that draws sample into the container 1297. It should be understood that some embodiments may have containers 1297 in both locations as shown in FIG. 11AB or only at one but not the other. Optionally, some may have multiple containers at one location and none or fewer containers at the other location. Optionally, some of these may be unitized so that multiple vessels are integrally formed or otherwise joined together. Optionally, some embodiments may have one type of container 1296 at one location and a different type of container 1297 at a different location shown in FIG. 11AB. Optionally, some may have at least two different types of container at one location. Optionally, other features discussed regarding the embodiment of FIG. 11AA may also be configured for use on the embodiment herein.

Referring still to FIG. 11AB, some embodiments may use a push element 1307 that provide a cap or other seal that when moved as indicated over feature 1305 will cause a pressurized air bolus to push sample in the channel 1299 outward into the containers 1297 that may be attached to 1301 or 1303.

Vertical Outflow Restrictors

FIG. 11E also more clearly shows that there are sleeves 1156 around the adapter 1150 and 1152. Although only shown in FIGS. 11A-11F, it should be understood that sleeves with or without vents may be configured for use with any of the embodiments contemplated herein. As seen in the embodiment of FIG. 11E, the channels may be defined by needles. These sleeves 1156 prevent premature flow of fluid sample out from the adapter channels 1150 and 1152 before the containers 1146a and 1146b engage the needles. Because of the low volumes of sample fluid being acquired, preventing premature flow reduces the amount of fluid loss associated with transfer of fluid from the channels to the containers. In one embodiment, the sleeves 1156 can minimize that fluid loss by providing a sleeve that is liquid tight, but not air tight. If the sleeve were airtight, it may prevent the capillary action of the channels from working properly. Optionally, some embodiments may locate vents near the base of the needle, away from the tip, such that the sleeve can contain the sample at locations away from the vents.

FIG. 11F shows that in an exemplary embodiment, the sleeve 1156 is configured to have an opening 1158 through the sleeve. This provides an improved embodiment over traditional sleeves which are typically loosely fitted over a needle. Because of the loose fit, in traditional sleeves, there is sleeve space in the tip and in side wall space between the needle and the sleeve within which fluid sample can accumulate. Although a sleeve of this design can help prevent greater loss of fluid by restricting the loss to a defined amount as compared to a needle without a sleeve which can lose fluid continuously, the fluid accumulating in the sleeve area along the tip and side wall is still lost and not collected by the containers 1146a or 1146b. The sleeve 1156 may also include a narrowed area 1176 to facilitate engagement of the sleeve against the device providing fluid communication with the channels 1126 and 1128, such as but not limited to the needle, probe, tube, channel, or other adapter channel 1150.

In the embodiment of FIG. 11F, the opening 1158 is sized based on calculations which are sufficient to withstand fluid pressure associated with the flow from the capillary action of the channels in sample fill portion 1120. This forces allows the opening 1158 to be there to vent air from the channel but also prevent fluid from exiting the sleeve until the containers 1146a and 1146b are pushed to engage the adapter channels 1150 and 1152. Because of the vent effect created by the opening 1158, the side wall and other areas of the sleeve can be made to much more tightly engage the needle than in traditional sleeves. This reduces the gap space between the needle and the sleeve and thus minimizes the amount of fluid that can be lost as compared to sleeves without a vent hole which have a much greater gap space due to the looseness of the fit. Additionally, the opening 1158 can also be sized such once fluid reaches the opening, that it provides enough resistance so that flow out from the channel or needle is also stopped so that here is minimal fluid loss in any gap between the sleeve and the needle tip.

Figure 12:
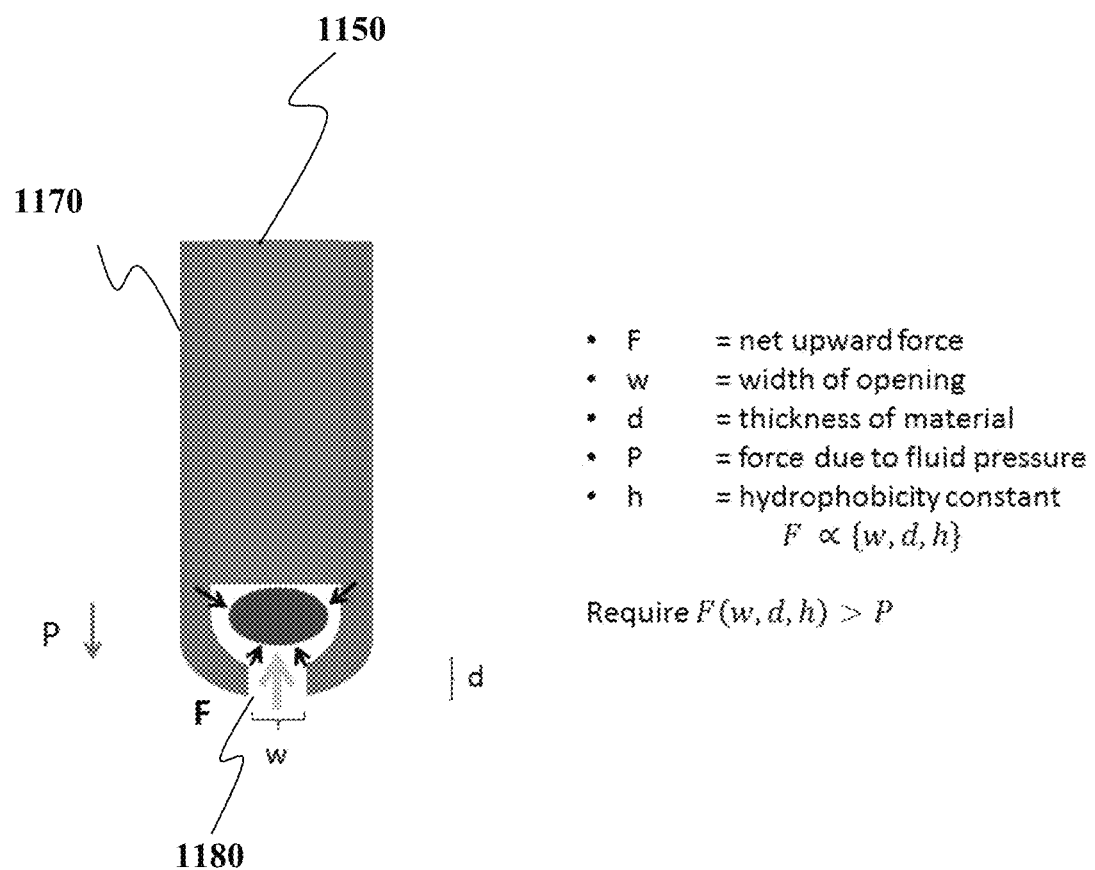
FIG. 12 shows a schematic of a tip portion of a sleeve and associated balance of forces associated with one embodiment as described herein.

The calculations for sizing the opening are as shown in FIG. 12. The desire is to balance the forces such that there is sufficient leak-prevention force associated with the hydrophobic material defining the vent to contain outflow of sample fluid outside of the sleeve. In FIG. 12, the side walls of the sleeve 1156 may be in direct contact with the needle or in some embodiments, there may be a gap along the sidewall with the sleeve. In one embodiment, the sleeve 1156 comprises a hydrophobic material such as but not limited to thermoplastic elastomer (TPE), butyl rubber, silicone, or other hydrophobic material. In one embodiment, the thickness of the sleeve will also determine the length of the side walls of the opening or vent 1158 in the sleeve 1156.

The opening 1158 may be located at one or more positions along the sleeve 1156. Some may have it as shown in FIG. 12. Alternatively, some embodiments may have the opening 1158 on a side wall of the sleeve. Other locations are not excluded. Optionally, the sleeve 1156 may have multiple openings through the sleeve, but configured such that fluid does not exit from the sleeve and resistance from the openings is sufficient to prevent additional outflow from the channel until the containers 1146a or 1146b are engaged and in fluid communication with the channels.

With regards to how the device 1100 is used to collect a sample, in one technique, the sample collection device 1100 is held to engage the target bodily fluid and is held in place until a desired fill level is reached. During this time, the device 1100 may be held horizontally to minimize gravitational force that would need to be overcome if the device 1100 were held more vertically. After a fill level is reached, the device 1100 may either be disengaged from the target fluid and then containers 1146*a* and 1146*b* engaged to draw collected fluid into the containers. Optionally, the device 1100 may be left in contact with the target fluid and the containers engaged into fluid contact with the channels so that the fill will draw fluid in the channel and perhaps also any additional sample fluid that remains at the target site. This may ensure that enough bodily fluid is drawn into the containers.

After filling the containers 1146*a* and 1146*b*, they may be prepared for shipment. Optionally, they may be sent for pre-treatment before being shipped. Some embodiments of the containers 1146*a* and 1146*b* include a material in the container of a density such that after a pre-treatment such as centrifugation, the material due to its selected density will separate one portion of the centrifuged sample from another portion of the centrifuged sample in the same container.

The container 1146*a* or 1146*b* may have a vacuum and/or negative pressure therein. The sample may be drawn into the container when the channel is brought into fluidic communication with the container. Optionally, the container may take the form of a test tube-like device in the nature of those marketed under the trademark "Vacutainer" by Becton-Dickinson Company of East Rutherford, N.J. The device may remain in a compressed state with the base 1140 closing gap 1154 while the sample is being transferred to the container. The sample may fill the entire container or a portion of the container. The entirety of the sample (and/or greater than 90%, 95%, 97%, 98%, 99%, 99.5% or 99.9% of the sample) from the channels may be transferred to the containers. Alternatively, only a portion of the sample from the channels may be transferred to the containers.

In one embodiment as described herein, a two-stage filling of the sample fluid into the sample collection device 1100 allows for i) metered collection of the sample fluid to ensure that a sufficient amount is obtained in a collection channel that is treated to prevent premature clotting and then ii) an efficient manner of transferring a high percentage of the sample fluid into the container. This low loss filling of container from pre-fill channels to meter a minimum amount of sample fluid into the container 1146 provides for multiple advantages, particularly when dealing with collecting small volumes of sample fluid. Pre-filling the channels to a desired level ensures sufficient volume is present in the container to perform the desired testing on the sample fluid.

As described herein, the entire device including the sample fill portion 1120, support 1130, and base 1140 are entirely transparent or translucent to allow for visualization of the components therein. Optionally, only one of the sample fill portion 1120, support 1130, and base 1140 are fully transparent or translucent. Optionally, only select portions of sample fill portion 1120, support 1130, or base 1140 are transparent or translucent. The user may then more accurately determine when to perform various procedures based on progression of sample fluid filling and engagement of the sample containers to the channels in sample fill portion 1120. Air bubbles in the collection channel may be visible during filling and if they are seen, a user may adjust the position of the sample collection device 1100 to better engage the target sample fluid to minimize air being drawn into the channels. It will also allow the user to know when to breakaway or disengage pieces such as the base or container holder 1140 when filling is completed.

It should be understood that other methods can be used to prevent outward sample flow from the adapter channels 1150 and 1152 if the device is held at a non-horizontal angle such as but not limited to downwardly in a vertical manner. In one embodiment, a frit 1194 can be used with needles with a central bore that are used as the adapter channels 1150 and 1152. The frits can be in the body of sample collection device or on the collection vessels. In some embodiments, the frits comprise of a material such as but not limited to PTFE. Optionally, some embodiments may use tape/adhesive over the needles that are functioning as the adapter channels 1150 and 1152. In one embodiment, the tape and/or adhesive may be used to cover the needle openings to prevent premature discharge of sample. Optionally, some embodiments may have adapter channels 1150 and 1152 having hydrophobic surface to prevent controlled outflow from the adapter channel openings leading toward the sample containers. In some embodiments, the adapter channels 1150 and 1152 are needles with hydrophobic material only on the interior surfaces near an exit. Optionally, the hydrophobic material is only on the exterior needle surfaces near an exit. Optionally, the hydrophobic material is on interior and exterior needle surfaces. Optionally, another method of preventing downward flow is increasing the surface area of the capillaries by varying the cross-section. By way of non-limiting example, some embodiments may introduce teeth- or finger-like structures within the capillary in order increase surface are in the cross-section of the capillary. Optionally, some embodiments may include fins oriented toward and/or against the fluid flow within the capillary in order increase surface are in the cross-section of the capillary. There may be variations and alternatives to the embodiments described herein and that no single embodiment should be construed to encompass the entire invention.

One Sample Collector Location to Multiple Channels

Figure 13A:
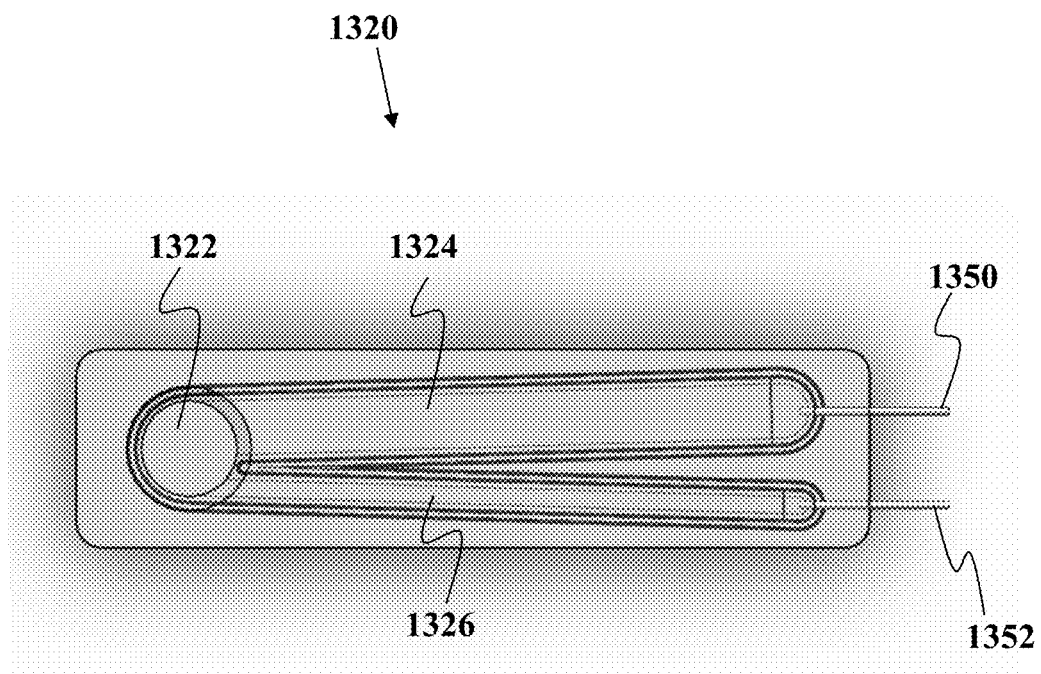
FIGS. 13A-13D show views of various collection devices with an upward facing collection location according to embodiments as described herein
Figure 13B:
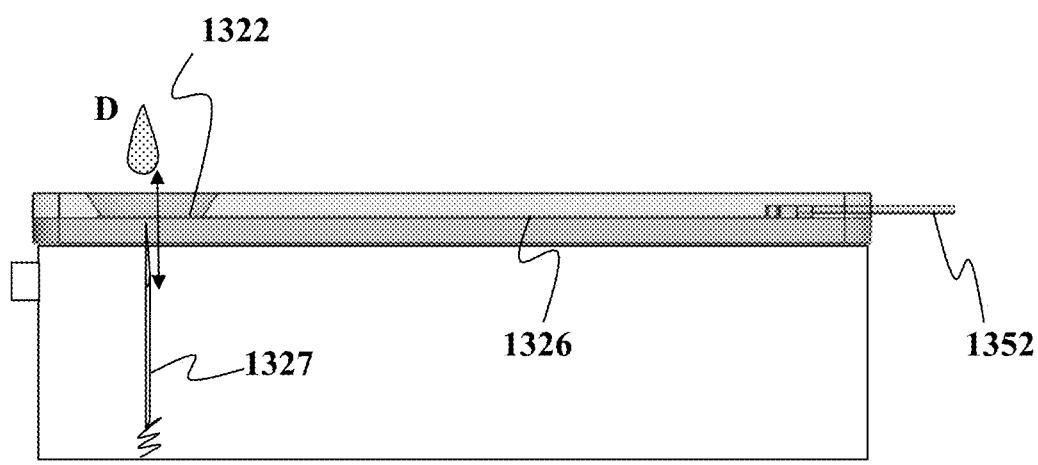

Referring now to FIGS. 13A-13B, yet another embodiment as described herein will now be described. FIG. 13A shows atop down view of a sample fill portion 1320 with a single collection location 1322 such as but not limited to a collection well where two channels 1324 and 1326 meet to draw fluid away from the single collection location 1322. Optionally, some embodiments may use an Y-split channel configuration wherein only a single channel lead away from the collection location 1322 and then splits into channels 1324 and 1326 after having been a single common channel leading away from the collection location 1322. Members providing fluid communication to the channels 1324 and 1326, such as but not limited to a needle, probe, tube, channel, hollow elongate member, or other structure, may be coupled to one end of the sample fill portion 1320.

FIG. 13B shows a side-cross-sectional view, wherein the collection location 1322 is shown and in fluidic communication with channel 1326 which is in turn in fluid communication with an adapter channel 1352 such as but not limited to a fluid communication member. Some embodiments, the fluid communication member may have sufficient stiffness and a sufficiently penetrating tip to pierce a septum, cap, or other structure of the container. Some may have the adapter channel 1352, 1150, or the like to be a non-coring structure so as not to leave behind a hole that will not seal in the septum, cap, or other structure of the container.

As seen in FIG. 13B, sample fluid may be applied or dropped into the collection location 1322 as indicated by droplet D. Optionally, some may directly apply or directly contact the collection location 1322 to apply the sample fluid. Although the embodiments herein are shown to use only a single collection location 1322, it should be understood that other embodiments where multiple channels couple to a common sample collection point are envisioned. By way of nonlimiting example, one embodiment of a collection device may have two collection locations 1322, each with its own set of channels leading away from its respective collection location. Some embodiments may combine common collection point channels shown in FIGS. 13A-B with channels that are separate such as shown in FIGS. 11A-11F. Other combinations of common collection location structure with other structures with separate channels are not excluded.

FIG. 13B also shows that this embodiment may include one or more tissue penetrating members 1327 configured to extend outward from the collection location 1322. In one embodiment, this enables the user to place target tissue simultaneously over the collection location 1322 and the wound creation location for fluid sample acquisition. Optionally, a trigger 1323 can be positioned to launch the tissue penetrating member. Optionally, the trigger is built into a tissue interface of the device to enable launch of the device when the target tissue is contacted and/or when sufficient pressure or contact is in place. This overlap of these two locations allows for simplified protocol for users to follow for successful sample acquisition. The tissue penetration member(s) 1327 may be actuated by one or more actuation techniques such as but not limited to spring actuated, spring/cam actuated, electronically actuated, or single or multiple combinations of the foregoing. It should be understood that other assist methods such as but not limited to vacuum sources, tissue stretching devices, tissue engagement nose pieces, or the like may be used alone or in combination with any of the foregoing for improved sample acquisition.

Figure 13C:
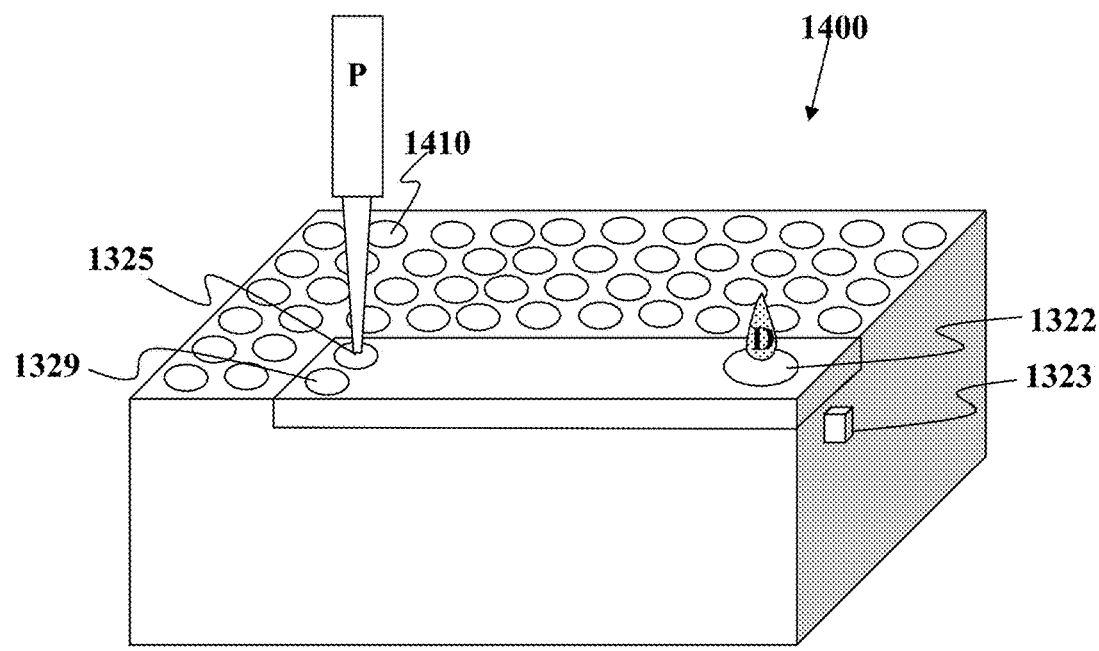

Referring now to FIG. 13C, a still further embodiment of a sample collection device will now be described. This embodiment shows a cartridge 1400 with a sample collection device 1402 integrated therein. There is a collection location 1322 and one or more sample openings 1325 and 1329 where sample collection at location 1322 can then be accessed such as but not limited to handling by a pipette tip (not shown). The sample from droplet D will travel along pathway 1326 as indicated by arrow towards the openings 1325 and 1329, where the sample in the opening and any in the pathways 1324 and/or 1326 leading towards their respective openings 1325 and 1329 are drawn into the pipette P. As indicated by arrows near the pipette P, the pipette P is movable in at least one axis to enable transport of sample fluid to the desired location(s). In this embodiment, the cartridge 1400 can have a plurality of holding containers 1410 for reagents, wash fluids, mixing area, incubation areas, or the like. Optionally, some embodiments of the cartridge 1400 may not include any holding containers or optionally, only one or two types of holding containers. Optionally, in some embodiments, the holding containers may be pipette tips. Optionally, in some embodiments, the holding containers are pipette tips that are treated to contain reagent(s) on the tip surface (typically the interior tip surface although other surfaces are not excluded). Optionally, some embodiments of the cartridge 1400 may include only the sample collection device 1402 without the tissue penetrating member or vice versa.

Figure 13D:
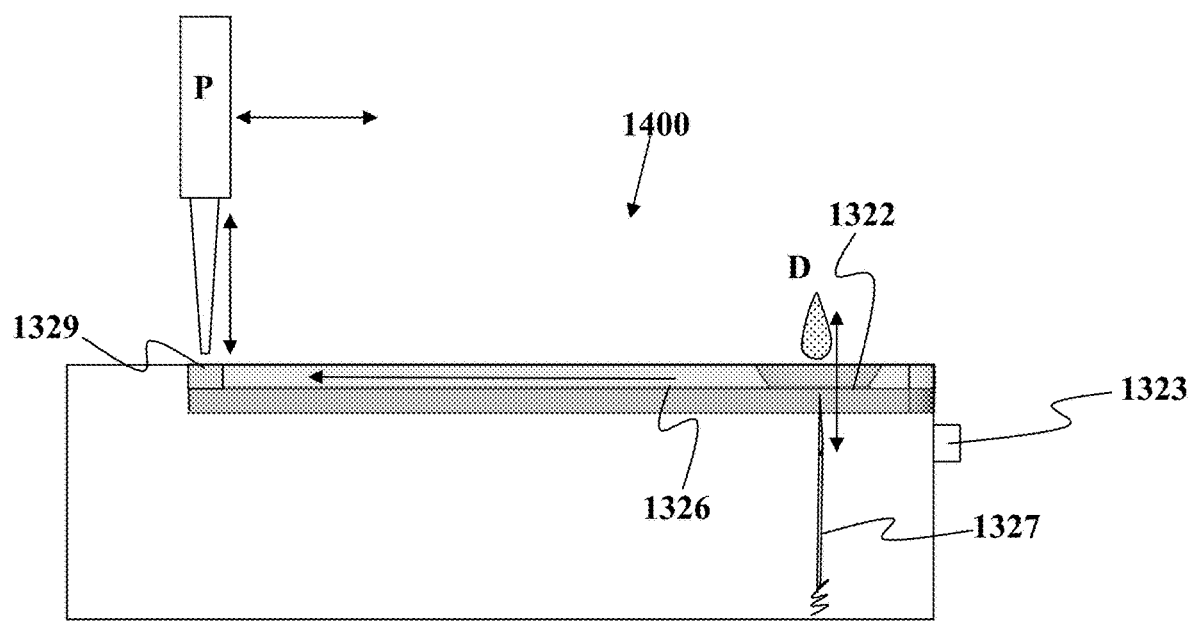

Referring now to FIG. 13D, a side cross-sectional view of the embodiment of FIG. 13C is shown. Optionally, a tissue penetrating member 1327 may be included for use with creating the wound for the sample fluid to be collected at location 1322.

Figure 14:
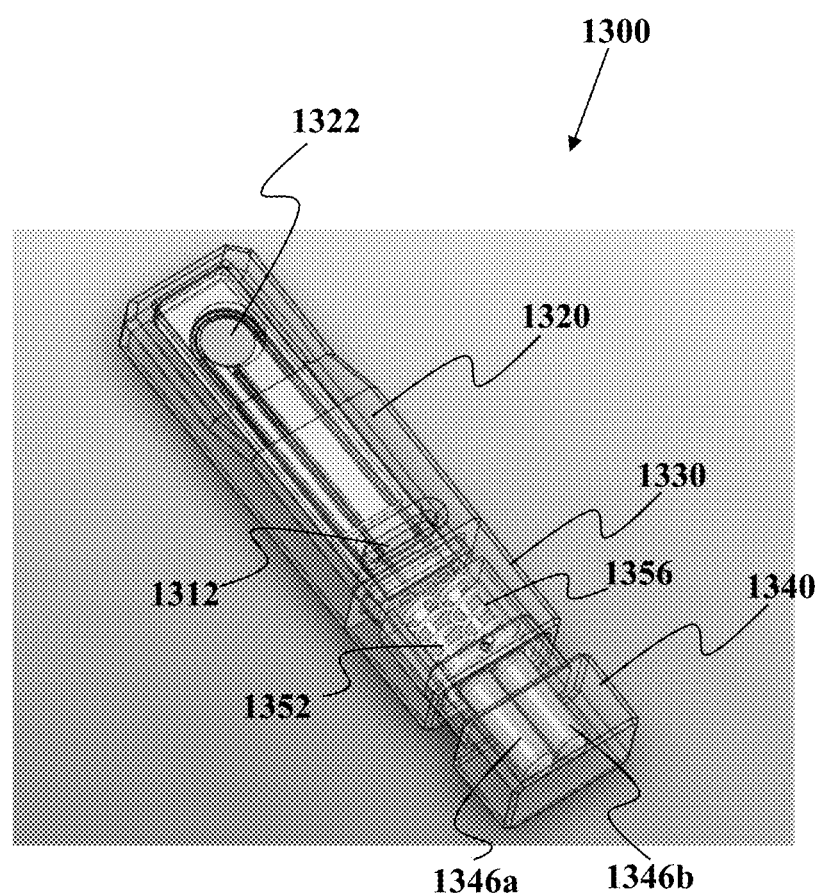
FIGS. 14-15 show various views of a collection device with a single collection location according to one embodiment as described herein.

FIG. 14 shows that the sample fill portion 1320 may be joined with support 1330 and 1340 to form the sample collection device 1300. There may be a visualization window 1312 to see if sample fluid has reached a desired fill level. A force-exerting component, such as a spring 1356 or elastic may be included. The channel holder may keep the channel affixed to the support. In one embodiment, the holder may prevent the channel from sliding relative to the support. It may use a press fit, mechanical fastening, adhesive, or other attachment technique to couple to the channel. The holder may optionally provide a support upon which a force-exerting component, such as a spring, may rest.

In one example, the engagement assemblies may include a spring 1356 which may exert a force so that the base 1340 is at an extended state, when the spring is at its natural state. When the base is at its extended state, space may be provided between the containers 1346*a*, 1346*b* and the engagement assemblies. In some instances, when the base 1340 is in its extended state, the second ends of the channels may or may not contact the caps of the containers. The second ends of the fluid communication members 1352 may be in a position where they are not in fluid communication with the interiors of the containers.

Bringing the support 1330 and the base 1340 together will bring the channels 1324 and 1326 into fluid communication with the containers 1346*a* and 1346*b* when the members 1352 penetrate through the cap on the containers and thus draw sample fluid into the containers 1346*a* and 1346*b*.

The container 1346*a* or 1346*b* may have a vacuum and/or negative pressure therein. The sample may be drawn into the container when the channel is brought into fluidic communication with the container. The device may remain in a compressed state with the base 1340 positioned so that containers are in fluid communication with the channels 1326 and 1328 when the sample fluid is being transferred to the containers. The sample may fill the entire container or a portion of the container. The entirety of the sample (and/or greater than 90%, 95%, 97%, 98%, 99%, 99.5% or 99.9% of the sample) from the channels may be transferred to the containers. Alternatively, only a portion of the sample from the channels may be transferred to the containers.

Figure 15:
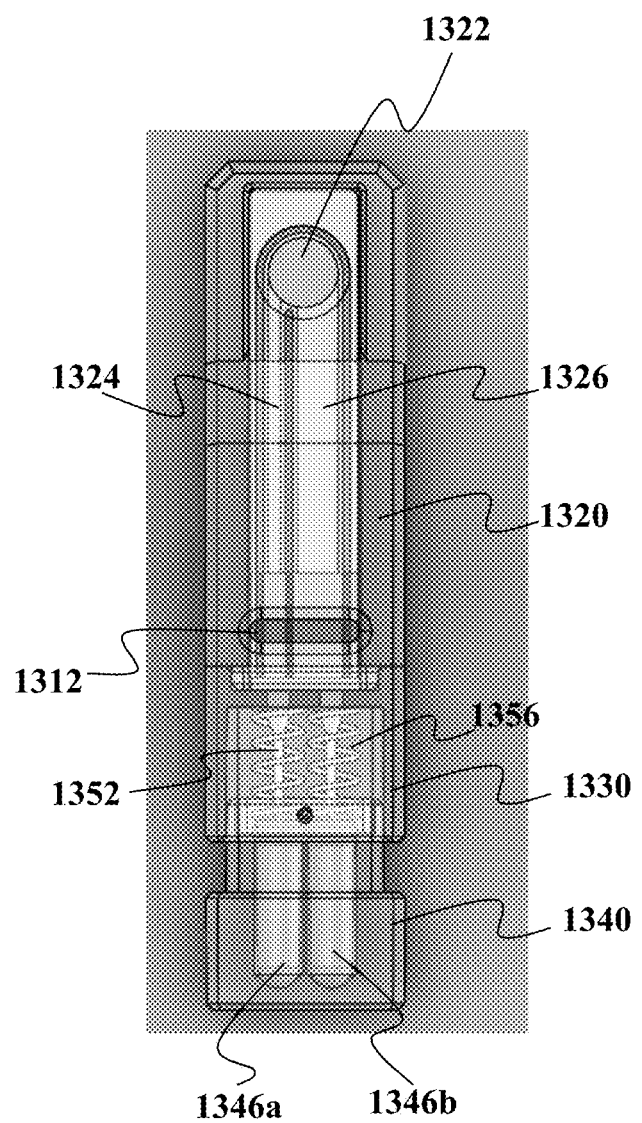

As seen in FIG. 15, in one embodiment as described herein, a two-stage filling of the sample fluid into the sample collection device 1300 allows for i) metered collection of the sample fluid to ensure that a sufficient amount is obtained in a collection channel that is treated to prevent premature clotting and then ii) an efficient manner of transferring a high percentage of the sample fluid into the container. This low loss filling of container from pre-fill channels to meter a minimum amount of sample fluid into the container 1346 provides for multiple advantages, particularly when dealing with collecting small volumes of sample fluid. Pre-filling the channels to a desired level ensures sufficient volume is present in the container to perform the desired testing on the sample fluid.

Figures 16, 17:
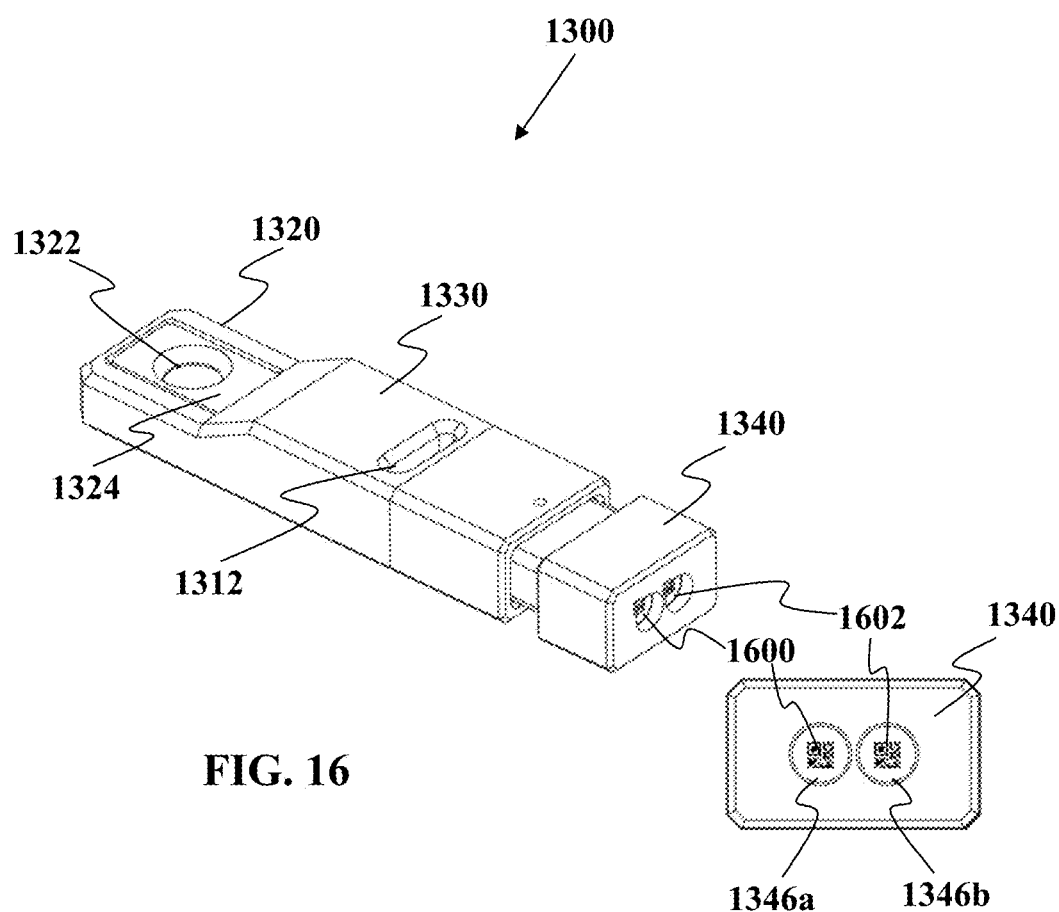
FIGS. 16-17 show perspective and end views of a sample collection device using containers having identifiers according to one embodiment as described herein.

Referring now to FIGS. 16 and 17, still further embodiments will now be described. FIG. 16 shows a blood collection device 1300 with a secondary collection area 1324 around the collection location 1322. The secondary collection area 1324 can be used to direct any overflow, spilled, or mis-directed fluid sample towards the collection location 1322.

FIG. 17 further shows that the containers 1346*a* and 1346*b* may each have an identifier associated with the containers 1346a and 1346b. FIG. 17 shows that in one nonlimiting example, the identifier 1600 and 1602 may be at least one of: a barcode (e.g., 1-D, 2-D, or 3-D), quick response (QR) code, image, shape, word, number, alphanumeric string, color, or any combination thereof, or any type of visual identifier. Others may use identifiers that are not in the visible spectrum. Others may use RFID tags, RF identifiers, IR emitting tags, or other markers that do not rely on identification through signals sent through the visual spectrum.

Identifiers 1600 and 1602 may be used to identify sample and/or types of sample in a sample collection device. There may be one or more identifiers per container. Some may also use identifiers on the container holders. Identifiers may identity the sample collection device, one or more individual containers within the device, or components of the device. In some instances, the sample collection device, a portion of the sample collection device, and/or the containers may be transported. In one example, the sample collection device, portion of the sample collection device may be transported via a delivery service, or any other service described elsewhere herein. The sample may be delivered to perform one or more test on the sample.

The sample identity and/or the identity of the individual who provided the sample could be tracked. Information associated with the individual or individuals (e.g., name, contact information, social security number, birth date, insurance information, billing information, medical history) and other information of who provided the sample may be included. In some instances, the type of sample (e.g., whole blood, plasma, urine, etc.) may be tracked. The types of reagents that the sample will have encountered (e.g., anticoagulants, labels, etc.) could also be tracked. Additional information about the sample collection, such as date and/or time of collection, circumstances under which sample was collected, types of tests to be run on the sample, insurance information, medical records information, or any other type of information may be considered.

Identifiers may assist with tracking such information. The identifiers may be associated with such information. Such information may be stored off-board the sample collection device, on-board the sample collection device, or any combination thereof. In some instances, the information may be stored on one or more external devices, such as servers, computers, databases, or any other device having a memory. In some instances, the information may be stored on a cloud computing infrastructure. One or more resources that store the information may be distributed over the cloud. In some instances, a peer-to-peer infrastructure may be provided. The information may be stored in the identifier itself, or may be associated with the identifier elsewhere, or any combination thereof.

An identifier may provide unique identification, or may provide a high likelihood of providing unique identification. In some instances, the identifier may have a visible component. The identifier may be optically detectable. In some instances, the identifier may be discernible using visible light. In some examples, the identifier may be a barcode (e.g., 1-D, 2-D, or 3-D), quick response (QR) code, image, shape, word, number, alphanumeric string, color, or any combination thereof, or any type of visual identifier.

In other embodiments, the identifier may be optically detectable via any other sort of radiation. For example, the identifier may be detectable via infrared, ultraviolet, or any other type of wavelength of the electromagnetic spectrum. The identifier may utilize luminescence, such as fluorescence, chemiluminescence, bioluminescence, or any other type of optical emission. In some instances, the identifier may be a radio transmitter and/or receiver. The identifier may be a radiofrequency identification (RFID) tag. The identifier may be any type of wireless transmitter and/or receiver. The identifier may send one or more electrical signal. In some instances, GPS or other location-related signals may be utilized with the identifier.

An identifier may include an audio component, or acoustic component. The identifier may emit a sound that may be discernible to uniquely identify the identified component.

The identifier may be detectable via an optical detection device. For example, a bar code scanner may be capable of reading the identifier. In another example, a camera (e.g., for still or video images) or other image capture device may be capable of capturing an image of the identifier and analyzing the image to determine the identification.

FIGS. 16 and 17 show examples of identifiers provided for use with a sample collection device 1300 in accordance with an embodiment described herein. In one example, a sample collection device may include a base 1340 which may support and/or contain one or more containers 1346a, 1346b. Sample may be provided to the sample collection device. The sample may be provided to the sample collection device via an inlet 1322. The sample may travel to one or more containers 1346a, 1346b within the device.

One or more identifier 1600, 1602 may be provided on the sample collection device. In some embodiments, identifiers may be positioned on a base 1340 of the sample collection device. The identifiers may be positioned on a bottom surface of the base, side surface of the base, or any other portion of the base. In one example, the base may have a flat bottom surface. The identifiers may be on the flat bottom surface of the base. One or more indentation may be provided in the base. The identifier may be located within the indentation. The indentations may be on the bottom or side surface of the base. In some embodiments, the base may include one or more protrusion. The identifier may be located on the protrusion. In some instances, the identifiers may be provided on an exterior surface of the base. The identifiers may alternatively be positioned on an interior surface of the base. The identifiers may be detected from outside the sample collection device.

In some embodiments, the identifiers may be provided on the containers 1346a, 1346b. The identifiers may be on an exterior surface of the containers or an interior surface of the containers. The identifiers may be detectable from outside the containers. In some embodiments, the identifiers may be provided on a bottom surface of the containers.

In one example, the base may include an optically transmissive portion. The optically transmissive portion may be on a bottom of the base or a side of the base. For example, a transparent or translucent window may be provided. In another example, the optically transmissive portion may be a hole without requiring a window. The optically transmissive portion may permit a portion inside the base to be visible. The identifiers may be provided on an exterior surface of the base on the optically transmissive portion, an interior surface of the base but may be visible through the optically transmissive portion, or on an exterior or interior surface of the container but may be visible through the optically transmissive portion. In some instances, the identifier may be provided on an interior surface of the container, but the container may be optically transmissive so that the identifier is viewable through the container and/or optically transmissive portion.

The identifier may be a QR code or other optical identifier that may be optically visible from outside the sample collection device. A QR code may be visible through an optical window or hole at the bottom of the base of the sample collection device. The QR code may be provided on the sample collection device base or on a portion of the container visible through the base. An image capturing device, such as a camera or scanner may be provided externally to the sample collection device, and may be capable of reading the QR code.

A single or a plurality of QR codes or other identifiers may be provided on a sample collection device. In some instances, each container may have at least one identifier, such as a QR code associated with it. In one example, at least one window may be provided in a base per container, and each window may permit a user to view a QR code or other identifier. For example, two containers 1346a, 1346b may be housed within a base 1340, each of which has an associated identifier 1600, 1602 discernible from outside the sample collection device.

The base 1340 may be separable from the support 1330 or other portions of the sample collection device. The identifier(s) may be separated from the rest of the sample collection device along with the base.

In some embodiments, the identifiers may be provided with containers housed by the base. Separating the base from the rest of the sample collection device may cause the containers to be separated from the rest of the sample collection device. The containers may remain within the base or may be removed from the base. The identifiers may remain with the containers even if they are removed from the base. Alternatively, the identifiers may remain with the base even if containers are removed. In some instances, both the base and containers may have identifiers so that the containers and bases may be individually tracked and/or matched even when separated.

In some instances, any number of containers may be provided within the sample collection device. The sample containers may be capable of receiving sample received from a subject. Each sample container may have a unique identifier. The unique identifier may be associated with any information relating to the sample, subject, device, or component of the device.

In some instances, each identifier for each container may be unique. In other embodiments, the identifier on the container need not be unique, but may be unique for the device, for the subject, or for the type of sample.

A sample collection device may receive a sample from a subject. The subject may directly contact the sample collection device or provide the sample to the device. The sample may travel through the device to one or more containers within the device. In some instances, the sample may be treated prior to reaching the containers. One or more coating or substance may be provided within a sample collection unit and/or channel that may convey the sample to the containers. Alternatively, no treatment is provided to the sample prior to reaching the container. In some embodiments, the sample may or may not be treated within the container. In some instances, a plurality of different types of treatments may be provided to a sample before or when the sample reaches the container. The treatments may be provided in a preselected order. For example, a first treatment desired first, and may be provided upstream of a second treatment. In some instances, the sample is not treated at any point.

In some embodiments, the sample may be a blood sample. A first container may receive whole blood and a second container may receive blood plasma. Anticoagulants may be provided along the fluid path and/or in the containers.

Once the sample has been provided to the containers and the containers have been sealed, the containers may be sent to a separate location for sample analysis. The separate location may be a laboratory. The separate location may be a remote facility relative to the sample collection site. The entire sample collection device may be sent to the separate location. One or more identifiers may be provided on the sample collection device and may be useful for identifying the sample collection device and/or containers therein. Alternatively, the base 1340 may be removed from the sample collection device and may be sent to the separate location with the containers therein. One or more identifiers may be provided on the base and may be useful for identifying the base and/or containers therein. In some instances, containers may be removed from the base and may be sent to the separate location. One or more identifier may be provided on each container, and may be useful for identifying the containers.

The identifiers may be read by any suitable technique. By way of example and not limitation, in some instances, the identifiers are read using an optical detector, such as an image capture device or barcode scanner. In one example, an image capture device may capture an image of a QR code. Information relating to the container may be tracked. For example, when a container arrives at a location, the identifier may be scanned, and record of the arrival of the container may be kept. The progress and/or location of the container may be updated actively and/or passively. In some instances, the identifier may need to be scanned intentionally in order to determine the location of the container. In other examples, the identifier may actively emit a signal that may be picked up by signal readers. For example, as an identifier travels through a building, signal readers may track the location of the identifier.

In some instances, reading the identifier may permit a user to access additional information associated with the identifier. For example, the user may capture an image of the identifier using a device. The device or another device may display information about the sample, subject, device, component of the device, or any other information described elsewhere herein. Information about tests to be conducted and/or test results may be included. The user may perform subsequent tests or actions with the sample based on information associated with the identifier. For example, the user may direct the container to the appropriate location for a test. In some instances, the container may be directed to an appropriate location and/or have appropriate sample processing (e.g., sample prep, assay, detection, analysis) performed on the contents of the container in an automated fashion without requiring human intervention.

Information relating to sample processing may be collected and associated with the identifier. For example, if a container has an identifier and sample processing has been performed on the contents of the container, one or more signals produced in response to the sample processing may be stored and/or associated with the identifier. Such updates may be made in an automated fashion without requiring human intervention. Alternatively, a user may initiate the storing of information or may manually enter information. Thus, medical records relating to a subject may be aggregated in an automated fashion. The identifiers may be useful for indexing and/or accessing information related to the subject.

Fluid Containers

Figures 18A, 18B:
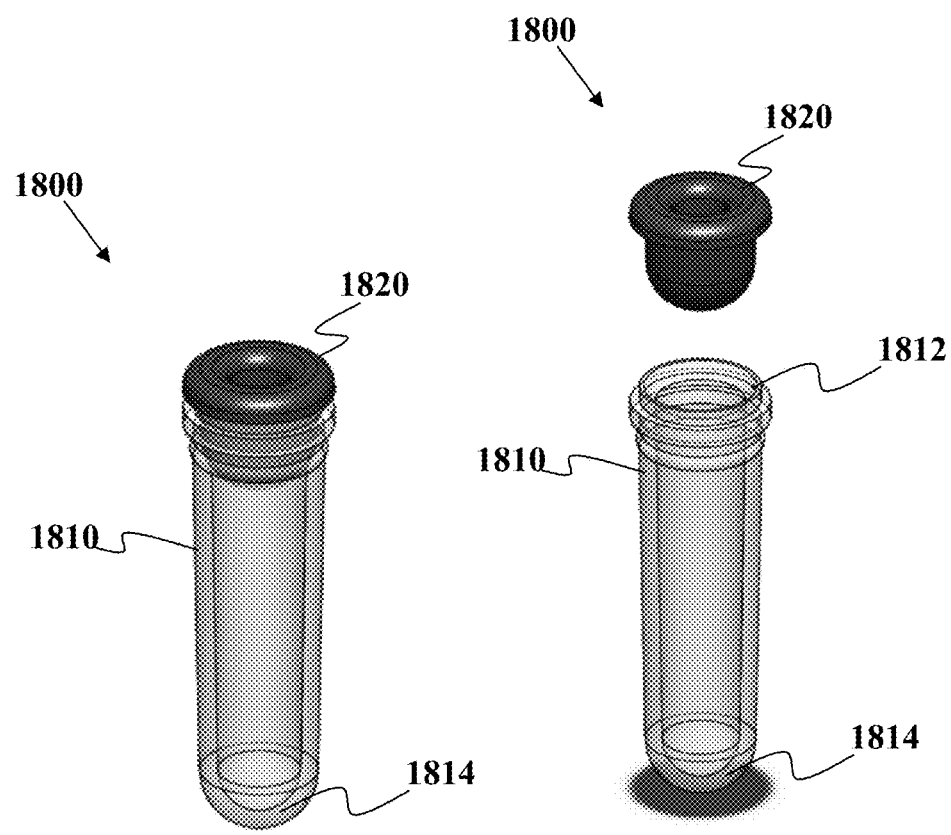
FIGS. 18A-18G show various views of sample containers according to embodiments as described herein.

FIGS. 18A-18B show one nonlimiting example of a container 1800 that may be utilized with a sample collection device in accordance with an embodiment described herein.

In some instances, the containers may be supported by the sample collection device. The containers may be encompassed or surrounded by a portion of the sample collection device. In one example, the sample collection device may have a first configuration where the containers are completely enclosed. A second configuration may be provided where the sample collection device may be opened and at least a portion of the containers may be exposed. In some examples, the containers may be supported and/or at least partially enclosed by a base of the sample collection device. The base may be separable from the rest of the sample collection device, thereby providing access to the containers therein.

In one embodiment, a container 1800 comprises a body 1810 and a cap 1820. In some instances, the container body may be formed from a transparent or translucent material. The container body may permit a sample provided within the container body to be visible when viewed from outside the container. The container body may be optically transmissive. The container body may be formed of a material that may permit electromagnetic radiation to pass through. In some instances, the container body may be formed of a material that may permit selected wavelengths of electromagnetic radiation to pass through while not permitting other non-selected wavelengths of electromagnetic radiation to pass through. In some instances a portion or all of the body may be formed of a material that is opaque along selected wavelengths of electromagnetic radiation, such as wavelengths for visible light.

An open end and a closed end may be provided on a container body 1810. The open end may be atop end 1812 of the container 1800, which may be at the end which may be configured to engage with a cap. The closed end may be a bottom end 1814 of the container, which may be at the end of the container opposite the cap. In alternative embodiments, a bottom end may also be an open end that may be closable with a floor. In some embodiments, the cross-sectional area and/or shape of the top end and the bottom end may be substantially the same. Alternatively, the cross-sectional area of the top end may be larger than the cross-sectional area of the bottom end, or vice versa. There may be variations and alternatives to the embodiments described herein and that no single embodiment should be construed to encompass the entire invention.

A container body may have an interior surface and an exterior surface. The surfaces of the container body may be smooth, rough, textured, faceted, shiny, dull, contain grooves, contain ridges, or have any other feature. The surface of the container body may be treated to provide a desired optical property. The interior surfaces and exterior surfaces may have the same properties or may be different. For example, an exterior surface may be smooth while the interior surface is rough.

The container body may have a tubular shape. In some instances, the container body may have a cylindrical portion. In some instances, the container may have a circular cross-sectional shape. Alternatively, the container may have any other cross-sectional shape which may include elliptical, triangular, quadrilateral (e.g., square, rectangular, trapezoidal, parallelogram), pentagonal, hexagonal, heptagonal, octagonal, or any other shape. The cross-sectional shape of the container may or may not have a convex and/or concave shape. The cross-sectional shape of the container may remain the same along the length of the container, or may vary. The container may have a prismatic shape along the length of the body. The prism may have a cross-sectional shape as those described herein.

The bottom 1814 of the container may be flat, tapered, rounded, or any combination thereof. In some instances, the container may have a hemispherical bottom. In other embodiments, the container may have a rounded bottom with a flat portion. The container may or may not be capable of standing on a flat surface on its own.

The containers 1800 may be sized to contain a small fluid sample. In some embodiments, the containers may be configured to contain no more than about 5 ml, 4 ml, 3 ml, 2 ml, 1.5 mL, 1 mL, 900 uL, 800 uL, 700 uL, 600 uL, 500 uL, 400 uL, 300 uL, 250 uL, 200 uL, 150 uL, 100 uL, 80 uL, 50 uL, 30 uL, 25 uL, 20 uL, 10 uL, 7 uL, 5 uL, 3 uL, 2 uL, 1 uL, 750 nL, 500 nL, 250 nL, 200 nL, 150 nL, 100 nL, 50 nL, 10 nL, 5 nL, 1 nL, 500 pL, 300 pL, 100 pL, 50 pL, 10 pL, 5 pL, or 1 pL. The containers may have the identifiers thereon such as discussed for FIGS. 16 and 17. In one non-limiting example, the containers 1800 may hold the small volume of sample fluid in liquid form without the use of a wicking material or the like to hold the sample fluid during transport. This allows the sample fluid to be substantially removed in liquid form from the container without loss due to liquid being absorbed by the wicking material.

The containers 1800 may be configured to contain no more than several drops of blood, a drop of blood, or no more than a portion of a drop of blood. For example, the container may have an interior volume of no greater than the amount of fluid sample it is configured to contain. Having a small volume container may advantageously permit storage and/or transport of a large number of containers within a small volume. This may reduce resources used to store and/or transport the containers. For example, less storage space may be required. Additionally, less cost and/or fuel may be used to transport the containers. For the same amount of exertion, a larger number of containers may be transported.

In some embodiments, the container 1800 may have a small length. For example, the container length may be no greater than 8 cm, 7 cm, 6 cm, 5 cm, 4 cm, 3.5 cm, 3 cm, 2.5 cm, 2 cm, 1.7 cm, 1.5 cm, 1.3 cm, 1.1 cm, 1 cm, 0.9 cm, 0.8 cm, 0.7 cm, 0.6 cm, 0.5 cm, 0.4 cm, 0.3 cm, 0.2 cm, 0.1 cm, 700 um, 500 m, 300 um, 100 um, 70 um, 50 um, 30 um, 10 um, 7 um, 5 um, 30 um, or 1 um. In some instances, the greatest dimension of the container (e.g., length, width, or diameter) may be no greater than 8 cm, 7 cm, 6 cm, 5 cm, 4 cm, 3.5 cm, 3 cm, 2.5 cm, 2 cm, 1.7 cm, 1.5 cm, 1.3 cm, 1.1 cm, 1 cm, 0.9 cm, 0.8 cm, 0.7 cm, 0.6 cm, 0.5 cm, 0.4 cm, 0.3 cm, 0.2 cm, 0.1 cm, 700 um, 500 m, 300 um, 100 um, 70 um, 50 um, 30 um, 10 um, 7 um, 5 um, 30 um, or 1 um.

The container 1800 may have any cross-sectional area. The cross-sectional area may be no greater than about 8 $cm^2$, 7 $cm^2$, 6 $cm^2$, 5 $cm^2$, 4 $cm^2$, 3.5 $cm^2$, 3 $cm^2$, 2.5 $cm^2$, 2 $cm^2$, 1.5 $cm^2$, 1 $cm^2$, 0.9 $cm^2$, 0.8 $cm^2$, 0.7 $cm^2$, 0.6 $cm^2$, 0.5 $cm^2$, 0.4 $cm^2$, 0.3 $cm^2$, 0.2 $cm^2$, 0.1 $cm^2$, 0.07 $cm^2$, 0.05 $cm^2$, 0.03 $cm^2$, 0.02 $cm^2$, 0.01 $cm^2$, 0.5 $cm^2$, 0.3 $cm^2$, or 0.1 $cm^2$. The cross-sectional area may remain the same or may vary along the length of the container.

The container 1800 may have any thickness. The thickness may remain the same along the length of the container or may vary. In some instances, the thickness may be selected and/or may vary in order to provide a desired optical property. In some instances, the thickness may be no greater than 5 mm, 3 mm, 2 mm, 1 mm, 700 um, 500 um, 300 um, 200 um, 150 um, 100 um, 70 um, 50 um, 30 um, 10 um, 7 um, 5 um, 3 um, 1 um, 700 nm, 500 nm, 300 nm or 100 nm.

The container 1800 may have a shape conducive to enabling centrifugation of small volume blood samples. This allows the collected sample in the containers to be taken directed to a centrifuge without having to further transfer the sample fluid to yet another container that is used in the centrifuge device.

The containers may contain a cap 1820. The cap may be configured to fit over an open end of the container. The cap may block the open end of the container. The cap may fluidically seal the container. The cap may form a fluid-tight seal with the container body. For example, the cap may be gas and/or liquid impermeable. Alternatively, the cap may permit certain gases and/or liquids to pass through. In some instances, the cap may be gas permeable while being liquid impermeable. The cap may be impermeable to the sample. For example, the cap may be impermeable to whole blood, serum or plasma.

The cap may be configured to engage with the container body in any manner. For example, the cap may be press-fit with the container body. A friction fit may permit the cap to stay on the body. In other examples, a locking mechanism may be provided, such as a sliding mechanism, clamp, fastener, or other technique. In some instances, the cap and/or the container body may be threaded to permit a screw-type engagement. In other examples, adhesives, welding, soldering, or brazing may be utilized to connect the cap to the container body. The cap may be removably attached to the container body. Alternatively, the cap may be permanently affixed to the container body.

In some instances, a portion of the cap may fit into a portion of the container body. The cap may form a stopper with the container body. In some instances, a portion of the container body may fit into a portion of the cap. The plug may include a lip or shelf that may hang over a portion of the container body. The lip or shelf may prevent the cap from sliding into the container body. In some instances, a portion of a cap may overlie a top and/or side of the container body. Optionally, some embodiments may include an additional part in the vessel assembly such as cap holder. In one embodiment, the purpose of the cap holder is to maintain a tight seal between the cap and container. In one embodiment, the cap holder engages an attachment, lip, indentation, or other attachment location on the outside of the container to hold the cap in position. Optionally, some embodiments can combine the function of both the cap and the cap holder into one component.

In some embodiments, the container body may be formed of a rigid material. For example, the container body may be formed of a polymer, such as polypropylene, polystyrene, or acrylic. In alternate embodiments, the container body may be semi-rigid or flexible. The container body may be formed from a single integral piece. Alternatively, multiple pieces may be used. The multiple pieces may be formed from the same material or from different materials.

The container cap may be formed of an elastomeric material, or any other material described elsewhere herein. In some instances, the cap may be formed from a rubber, polymer, or any other material that may be flexible and/or compressible. Alternatively, the cap may be semi-rigid or rigid. The container cap may be formed from a high friction material. The container cap may be capable of being friction-fit to engage with the container body. When the container cap is engaged with the container body, a fluid-tight seal may be formed. The interior of the container body may be fluidically isolated from the ambient air. In some instances, at least one of the cap and/or portion of the container body contacting the cap may be formed from a high friction and/or compressible material.

The container cap may be formed from a single integral piece. Alternatively, multiple pieces may be used. The multiple pieces may be formed from the same material or from different materials. The cap material may be the same as or different from the container body material. In one example, the container body may be formed from an optically transmissive material while the cap is formed from an opaque material.

The cap 1820 may be removably engaged with the body. A portion of the cap may be insertable into the body. The cap may include a lip which may rest on top of the body. The lip is not inserted into the body. In this non-limiting example, the lip may prevent the cap from being entirely inserted into the body. The lip may form a continuous flange around the cap. In some instances, a portion of the lip may overlap or overlie a portion of the body. A portion of the body may be insertable into a portion of the cap.

The portion of the cap that may be insertable into the body may have a rounded bottom. Alternatively, the portion may be flat, tapered, curved, contoured, or have any other shape. The cap may be shaped to be easily insertable into the body.

In some instances, a depression may be provided at the top of the cap. The depression may follow the portion of the cap that is inserted into the body. In some instances, a hollow or depression may be provided in the cap. The depression may be capable of accepting a portion of a channel that may be used to deliver a sample to the container. The depression may assist with guiding the channel to a desired portion of the cap. In one example, the channel may be positioned within the depression prior to bringing the channel and interior of the container into fluid communication.

The channel and cap may be pressed together so that the channel penetrates the cap and enters the interior of the container, thereby bringing the channel and interior of the container into fluid communication. In some instances, the cap may have a slit through which the channel passes. Alternatively, the channel may poke through uninterrupted cap material. The channel may be withdrawn from the container, thereby bringing the channel and container out of fluid communication. The cap may be capable of resealing when the channel is removed. For the example, the cap may be formed of a self-healing material. In some instances, the cap may have a slit that may close up when the channel is removed, thereby forming a fluid tight seal.

In some embodiments, the body may include one or more flange or other surface feature. Examples of surface features may include flanges, bumps, protrusions, grooves, ridges, threads, holes, facets, or any other surface feature. The flange and/or other surface feature may circumscribe the body. The flange and/or surface feature may be located at or near the top of the body. The flange and/or other surface feature may be located at the top half, top third, top quarter, top fifth, top sixth, top eighth, or top tenth of the body. The surface features may be useful for support of the container within a sample collection device. The surface features may be useful for removing the container from the sample collection device and/or positioning the container within the sample collection device. The flange and/or other surface feature may or may not engage with the cap.

The cap may have any dimension relative to the container body. In some instances, the cap and/or body may have similar cross-sectional areas. The cap may have the same, or a substantially similar cross-sectional area and/or shape as the top of the body. In some instances, the cap may have a lesser length than the body. For example, the cap may have a length that may be less than 60%, 50%, 40%, 30%, 25%, 20%, 15%, 10%, 7%, 5%, 3% or 1% of the length of the body.

Figure 18C:
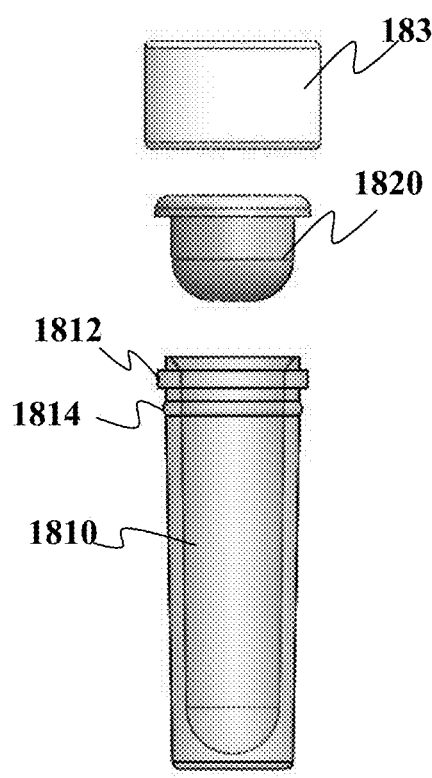
Figure 18D:
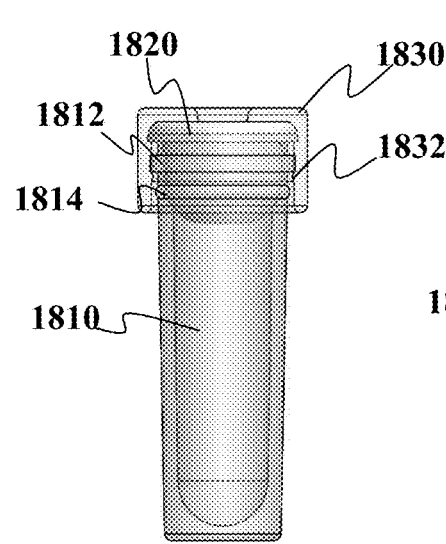
Figure 18E:
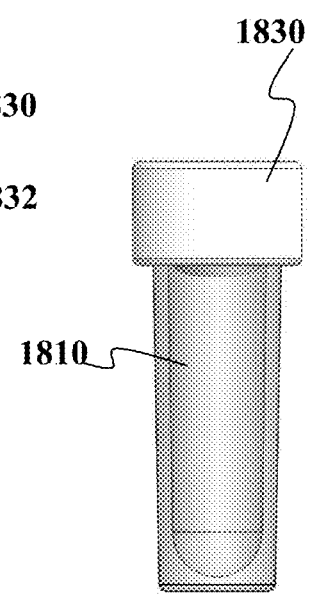

Referring now to FIGS. 18C to 18E, a still further embodiment of container 1800 may include a cap holder 1830 that fits over the cap to hold the cap in place. By way of non-limiting example, the cap holder 1830 may also include an opening in the cap holder 1830 that allows for a member such as an adapter to slide through and penetrate the cap 1820. FIG. 18C shows the parts in an exploded view.

FIG. 18D shows a cross-section view showing one embodiment wherein the container body 1810 having a cap 1820 covered by a cap holder 1830. As seen in FIG. 18D, the cap holder 1830 has a locking feature 1832 for securing the cap holder 1830 to the container body 1810 and/or the cap 1820. In one embodiment, the locking feature 1832 comprises an interior ridge which will engage one or more of the ridges 1812 and 1814 on the container body 1810. FIG. 18E shows a side view of the cap holder 1830 coupled to the container body 1810.

In some instances, a surface (interior and/or exterior) of the sample vessel may be coated and/or treated with a material. For example, an interior surface of the sample vessel may be coated with fixatives, antibodies, optical coatings, anticoagulant, and/or preservatives. These may be the same or different from any material coatings in the channels. In one non-limiting example, the coating may be but are not limited to polytetrafluoroethylene, poly-xylene, or other material as a treatment for surfaces to reduce the surface tension.

Optionally, the coating is applied on all interior surfaces of the sample vessel. Optionally, some embodiments may apply the coating in a pattern covering only select areas in the sample vessel. Some embodiments may only cover upper interior regions of the sample vessel. Optionally, some may cover only lower interior regions of the sample vessel. Optionally, some may cover strips, lanes, or other geometric patterns of the interior regions of the sample vessel. Optionally, some embodiments may also coat the surfaces of the cap, plug, or cover that is used with the sample vessel. Some embodiments may have the surfaces where sample enters the sample vessel to be coated to provide for a smooth transfer of sample away from the entry area and towards a destination site such as but not limited to a bottom portion of the container.

Optionally, the coating may be a wet or dry coating. Some embodiments may have at least one dry coating and at least one wet coating. In some instances one or more reagents may be coated and dried on the interior surface of the sample vessel. The coating may alternatively be provided in a moist environment or may be a gel. Some embodiments may include a separator gel in the sample vessel to keep select portions of the sample away from other portions of the sample. Some embodiments may include serum separator gel or plasma separator gel such as but not limited to polyester-based separator gels available from Becton Dickinson.

Optionally, one or more solid substrates may be provided within the sample vessel. For example, one or more beads or particles may be provided within the sample vessel. The beads and/or particles may be coated with reagents or any other substance described herein. The beads and/or particles may be capable of dissolving in the presence of the sample. The beads and/or particles may be formed from one or more reagents or may be useful for treating the sample. A reagent may be provided in a gaseous form within the sample vessel. The sample vessel may be sealed. The sample vessel may remain sealed before the sample is introduced into the sample vessel, after the sample has been introduced to the sample vessel, and/or while the sample is being introduced into the sample vessel. In one embodiment, the sample vessels may have smooth surfaces and/or round bottoms. This is helpful to minimize the stress on the blood sample, especially during centrifugation. Of course, in alternative embodiments, other shapes of the bottom of the sample vessel are not excluded.

Figure 18F:

FIG. 18F further shows that the sample vessels may each have at least one information storage unit associated with the sample vessels. Optionally, some embodiments may have one information storage unit convey information about a plurality of sample vessels, particularly (but not exclusively) in cases where the sample vessels all contain sample from the same subject. Such an information storage unit could be on the carrier that holds the multiple sample vessels, instead of being on the sample vessels themselves.

Figure 18G:
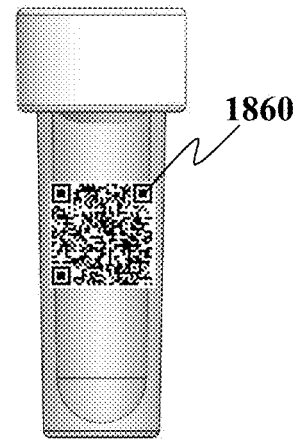

FIG. 18F shows a bottom-up view of an underside of one of the sample vessels that in one nonlimiting example, the information storage unit 1860 may be at least one of: a barcode (e.g., 1-D, 2-D, or 3-D), quick response (QR) code, image, shape, word, number, alphanumeric string, color, or any combination thereof, or any type of visual information storage unit. Others may use information storage units that are not in the visible spectrum. Others may use RFID tags, RF information storage units, IR emitting tags, or other markers that do not rely on identification through signals sent through the visual spectrum. Of course, the information storage unit 160 may also be positioned to be on a top end surface of the sample vessel. FIG. 18G shows that, optionally, an information storage unit 1860 may also be included on a side surface of the sample vessel. This may be in addition to or in place of the top or bottom positioned information storage unit(s) 1860.

In one non-limiting example, information storage unit 1860 may be used to identify sample and/or types of sample in a sample collection device. Optionally, there may be one or more information storage units per sample vessel. Some may also use information storage units on the sample vessel holders. Information storage units may identify the sample collection device, one or more individual sample vessels within the device, or components of the device. In some instances, the sample collection device, a portion of the sample collection device, and/or the sample vessels may be transported. In one example, the sample collection device or a portion of the sample collection device, may be transported via a delivery service, or any other service described elsewhere herein. The sample vessel may be delivered so that one or more tests may be performed on the sample.

Optionally, the sample identity and/or the identity of the individual who provided the sample could be tracked. By way of non-limiting example, information associated with the individual or individuals (e.g., name, contact information, social security number, birth date, insurance information, billing information, medical history) and other information of who provided the sample may be included. In some instances, the type of sample (e.g., whole blood, plasma, urine, etc.) may be tracked. Optionally, the types of reagents that the sample will have encountered (e.g., anticoagulants, labels, etc.) could also be tracked. Additional information about the sample collection, such as date and/or time of collection, circumstances under which sample was collected, types of tests to be run on the sample, setting(s) for the tests, test protocols, insurance information, medical records information, or any other type of information may be considered.

In at least one or more embodiments described herein, information storage units may assist with tracking such information. The information storage units may be associated with such information. Such information may be stored off-board the sample collection device, on-board the sample collection device, or any combination thereof. In some instances, the information may be stored on one or more external devices, such as servers, computers, databases, or any other device having a memory. In some instances, the information may be stored on a cloud computing infrastructure. One or more resources that store the information may be distributed over the cloud, through the internet from a remote server, wireless to a remote computer processor, or the like. In some instances, a peer-to-peer infrastructure may be provided. The information may be stored in the information storage unit itself, or may be associated with the information storage unit elsewhere, or any combination thereof.

Optionally, an information storage unit may provide unique identification, or may provide a high likelihood of providing unique identification. In some instances, the information storage unit may have a visible component. The information storage unit may be optically detectable. In some instances, the information storage unit may be discernible using visible light. In some examples, the information storage unit may be a barcode (e.g., 1-D, 2-D, or 3-D), quick response (QR) code, image, shape, word, number, alphanumeric string, color, or any combination thereof, or any type of visual information storage unit.

In other embodiments, the information storage unit may be optically detectable via any other sort of radiation. For example, the information storage unit may be detectable via infrared, ultraviolet, or any other type of wavelength of the electromagnetic spectrum. The information storage unit may utilize luminescence, such as fluorescence, chemiluminescence, bioluminescence, or any other type of optical emission. In some instances, the information storage unit may be a radio transmitter and/or receiver. The information storage unit may be a radiofrequency identification (RFID) tag. The information storage unit may be any type of wireless transmitter and/or receiver. The information storage unit may send one or more electrical signal. In some instances, GPS or other location-related signals may be utilized with the information storage unit.

Optionally, an information storage unit may be and/or include an audio component or acoustic component. The information storage unit may emit a sound that may be discernible to uniquely identify the identified component.

Optionally, the information storage unit may be detectable via an optical detection device. For example, a bar code scanner may be capable of reading the information storage unit. In another example, a camera (e.g., for still or video images) or other image capture device may be capable of capturing an image of the information storage unit and analyzing the image to determine the identification.

Optionally, the information storage units may be on the holder of the sample vessel(s). One or more indentation may be provided in the holder. The information storage unit may be located within the indentation. The indentations may be on the bottom or side surface of the holder. In some embodiments, the holder may include one or more protrusion. The information storage unit may be located on the protrusion. In some instances, the information storage units may be provided on an exterior surface of the holder. The information storage units may alternatively be positioned on an interior surface of the holder. The information storage units may be detected from outside the sample collection device.

In some embodiments, the information storage units may be on an exterior surface of the sample vessels or an interior surface of the sample vessels. The information storage units may be detectable from outside the sample vessels. In some embodiments, the information storage units may be provided on a bottom surface of the sample vessels.

In one non-limiting example, the holder may include an optically transmissive portion. The optically transmissive portion may be on a bottom of the holder or a side of the holder. For example, a transparent or translucent window may be provided. In another example, the optically transmissive portion may be a hole without requiring a window. The optically transmissive portion may permit a portion inside the holder to be visible. The information storage units may be provided on an exterior surface of the holder on the optically transmissive portion, an interior surface of the holder but may be visible through the optically transmissive portion, or on an exterior or interior surface of the sample vessel but may be visible through the optically transmissive portion. In some instances, the information storage unit may be provided on an interior surface of the sample vessel, but the sample vessel may be optically transmissive so that the information storage unit is viewable through the sample vessel and/or optically transmissive portion.

Optionally, the information storage unit may be a QR code, bar code, or other optical information storage unit that may be optically visible, such as but not limited to being visible from outside the sample collection device. A QR code may be visible through an optical window, hole, or the like at the bottom of the holder of the sample collection device. The QR code may be provided on the sample collection device holder or on a portion of the sample vessel visible through the holder. An image capturing device, such as a camera or scanner may be provided external to the sample vessels or the transport container, and may be capable of reading the QR code.

In some embodiments, a single or a plurality of QR codes or other information storage units may be provided on a sample collection device. In some instances, each sample vessel may have at least one information storage unit, such as a QR code associated with it. In one example, at least one window may be provided in a holder per sample vessel, and each window may permit a user to view a QR code or other information storage unit. For example, two sample vessels may be housed within a holder, each of the sample vessels having an associated information storage unit discernible from outside the holder.

In some embodiments, the information storage units may be provided with sample vessels housed by the holder. Separating the holder from the rest of the sample collection device may cause the sample vessels to be separated from the rest of the sample collection device. The sample vessels may remain within the holder or may be removed from the holder. The information storage units may remain with the sample vessels even if they are removed from the holder. Alternatively, the information storage units may remain with the holder even if sample vessels are removed. In some instances, both the holder and sample vessels may have information storage units so that the sample vessels and holders may be individually tracked and/or matched even when separated.

In some instances, any number of sample vessels may be provided within the sample collection device. Some embodiments may connect all of these sample vessels to the sample collection device all at once. Optionally, the sample vessels may be coupled in a sequential or other non-simultaneous manner. The sample vessels may be capable of receiving sample received from a subject. Each sample vessel may optionally have a unique information storage unit. The unique information storage unit may be associated with any information relating to the sample, subject, device, or component of the device.

In some instances, each information storage unit for each sample vessel may be unique or contain unique information. In other embodiments, the information storage unit on the sample vessel need not be unique. Optionally, some embodiments may have information unique for the device, for the subject, and/or for the type of sample. In some embodiments, the information on the information storage unit may be used to associate several sample vessels with the same subject or the same information.

Figure 19A:
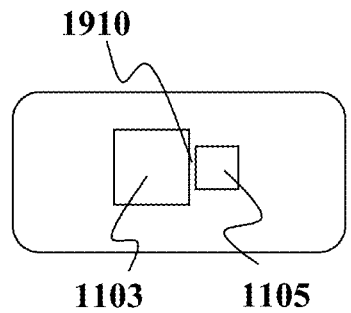
FIGS. 19A-19C show view of various embodiments of a front end of a sample collection device.
Figure 19B:
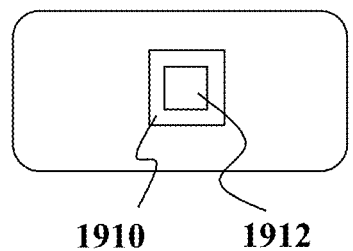
Figure 19C:
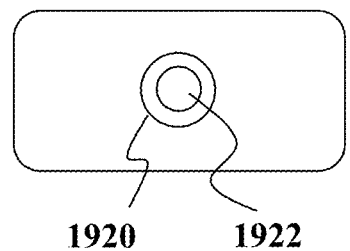

Referring now to FIGS. 19A to 19C, various embodiments of a front end of a sample collection device will now be described. FIG. 19A shows on view of a front end of the sample collection device with openings 1103 and 1105 for their respective channels. In the present embodiment, the openings 1103 and 1105 are placed in close proximity to each other with the divider wall 1910 between the openings 1103 and 1105. In one non-limiting example, the thickness of divider wall 1910 is set to be the minimum thickness that can be reliably formed through a manufacturing process used to form the sample collection device. In one embodiment, wall thickness should be about 1-10 mm. In some embodiments, instead of being side by side, the openings 1103 and 1105 may be in a top-bottom configuration, diagonal configuration, or other configuration where the two openings are in close proximity to one another.

Referring now to FIG. 19B, this embodiment shows the openings 1910 and 1912 configured to be coaxial, relative to one another. This coaxial configuration of openings 1910 and 1912 allows for greater overlap between the two openings.

Referring now to FIG. 19C, this embodiment is similar to that of FIG. 19B except that instead of square shaped openings, these openings 1920 and 1922 are round. It should be understood that any variety of shapes may be used including but not limited to circular, elliptical, triangular, quadrilateral (e.g., square, rectangular, trapezoidal), pentagonal, hexagonal, octagonal, or any other cross-sectional shape. Of course, it should be understood that different shapes can be used for each opening and that a collection device need not have the same cross-sectional shape for all openings. Some embodiments may have a one cross-sectional shape for the opening but have a different cross-sectional shape for channel downstream from the opening.

Single Channel Sample Collection Device

Figure 20A:
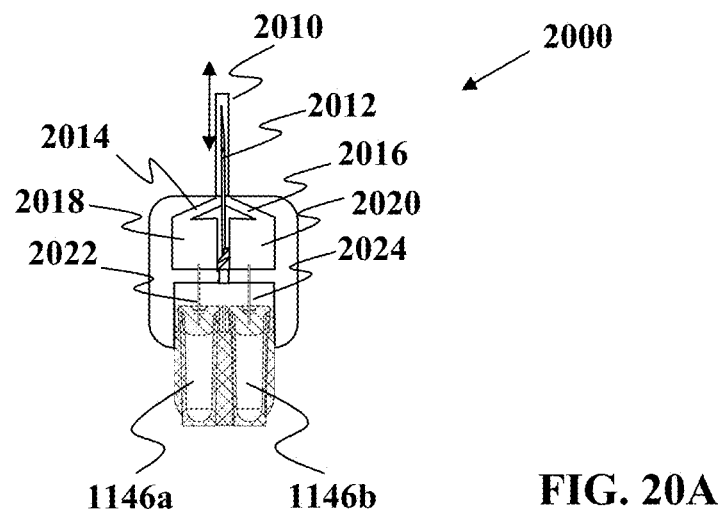
FIGS. 20A-21 show various embodiments of sample collection device with an integrated tissue penetrating member.
Figure 20B:
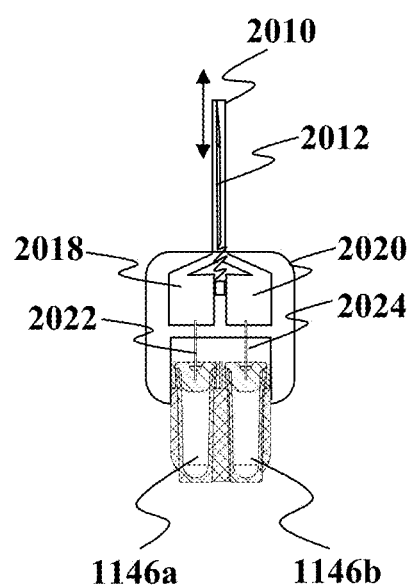

Referring now to FIGS. 20A-20B, although the embodiments herein are typically described as sample collection devices with two separate channels, it should be understood that some embodiments may use a single entry channel 2010. This single entry channel 2010 may or may not be coated. Suitable coatings include but not are limited to an anti-coagulant, plasma, or other materials.

FIG. 20A shows that in this embodiment of sample collection device 2000, a tissue penetrating member 2112 can be mounted coaxially within the single entry pathway 2010. This allows the wound at the target tissue to be formed in a manner that will be aligned with the single entry pathway 2010. The tissue penetrating member 2012 can be activated by one of a variety of techniques such as but not limited to actuation upon pressing a trigger, actuation upon contact of the device front end with the target tissue, or by pressure once the device is pressed against the target tissue with sufficient pressure. After actuation, the tissue penetrating member 2012 can remain in the single entry pathway 2010. Optionally, the tissue penetrating member 2012 may retract out of the single entry pathway 2010.

The sample fluid entering the sample collection device 2000 may split into two or more separate pathways 2014 and 2016 from the single entry pathway 2010. This enables the sample fluid to be split into at least two portions from a sample collected from a single point of contact. The two portions may optionally be held in two separate holding chambers 2018 and 2020. These chambers may each have one or more adapter channels 2022 and 2024 to transfer the sample fluid to the containers such as but not limited to containers 1146a and 1146b. It should be understood that the holding chambers 2018 and 2020 and/or the containers 1146a and 1146b may contain anti-coagulant therein to prepare the sample fluid for processing.

Referring now to FIG. 20B, this embodiment shows that the single entry pathway 2010 with a tissue penetrating member 2012 therein that, after actuation, is configured to remain in whole or in part within the single entry pathway 2010. It should be understood that this embodiment may use a solid penetrating member or one that is hollow, with a lumen therein.

Figure 21:
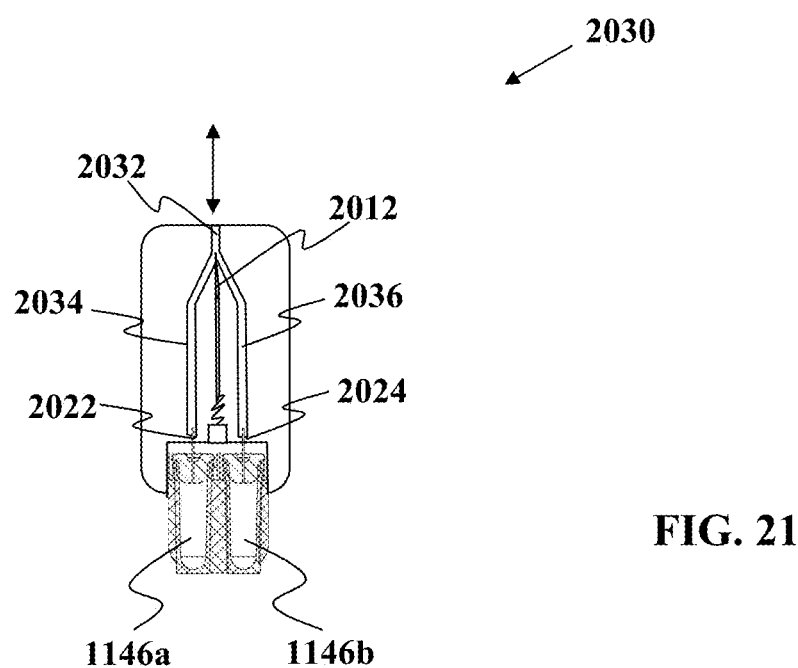

Referring now to FIG. 21, yet another embodiment of a sample collection device 2030 will now be described. This embodiment shows a reduced length single entry pathway 2032 with a tissue penetrating member 2012 configured to extend outward from the pathway 2032. After actuation, the tissue penetrating member 2012 may be in the pathway 2032 or optionally, retracted to not be in the pathway 2032. The sample fluid entering the sample collection device 2030 may split into two or more separate pathways 2034 and 2036 from the single entry pathway 2032. This enables the sample fluid to be split into at least two portions from a sample collected from a single point of contact. This embodiment shows that the pathways 2034 and 2036 remain in capillary channel configuration and do not enlarge to become chambers such as the embodiments of FIGS. 20A-20B. It should be understood that any of the embodiments herein may include one or more fill indicators for the collection pathways and/or the containers on the devices so that users can know when sufficient fill levels have been reached.

It should also be understood that due to the small sample volume collected with containers such as but not limited to containers 1146a and 1146b, the "pull" from reduced pressure, such as but not limited to vacuum pressure, in the containers is minimally or not transferred into the body of subject in a manner that may collapse or detrimentally reshape the blood vessel or other lumen from which sample fluid is being collected. For example, pediatric and geriatric patients typically have small and/or weak veins that can collapse when traditional, large volume vacutainers are used, due the higher vacuum forces associated with drawing larger sample volumes into those traditional containers. In at least one embodiment of the device, it will not have this problem because it will not impart a vacuum (suction) force on the vein. In one embodiment, the amount of vacuum force draws no more than 120 uL of sample fluid into the container 1146a. Optionally, the amount of vacuum force draws no more than 100 uL into the container 1146a. Optionally, the amount of vacuum force draws no more than 80 uL into the container 1146a. Optionally, the amount of vacuum force draws no more than 60 uL into the container 1146a. Optionally, the amount of vacuum force draws no more than 40 uL into the container 1146*a*. Optionally, the amount of vacuum force draws no more than 20 uL into the container 1146*a*. In one embodiment, this type of draw is performed without the use of a syringe and based primarily on pulling force from the containers and any force from the fluid exiting the subject. Optionally, the shaped pathway through the device to draw sample that has reached an interior of the device can assist in reducing force transfer from the containers 1146*a* and 1146*b* to the subject's blood vessel or other body lumen. Some embodiments may use about three-quarter vacuum or less in the small volume containers listed above to minimize hemolysis of the sample and to prevent collapsing of blood vessel in the subject. Some embodiments may use about half vacuum or less in the small volume containers listed above to minimize hemolysis of the sample and to prevent collapsing of blood vessel in the subject. Some embodiments may use about one quarter vacuum or less in the small volume containers listed above to minimize hemolysis of the sample and to prevent collapsing of blood vessel in the subject. Vacuum herein is full vacuum, relative to atmospheric pressure.

It should also be understood that, in one embodiment, the chamber cross-sectional area in the device is greater than the cross-sectional diameter of the needle and/or flexible tubing used for drawing the bodily fluid from the subject. This further assists in reducing the force transfer to the subject. The vacuum pull from the containers are drawing most immediately on liquid sample in the device, not directly on sample in the needle which is more proximate to the subject. The longer pathway, buffered by the larger volume chamber in the collection device dampens the pull on the blood vessel in the subject. Additionally, the initial peak force pull is substantially less in a small volume vessel versus a larger volume vessel that is also under vacuum. The duration of the "pull" is also longer to enable the larger amount of sample to enter the container. In a smaller volume, a significant portion of the sample to be collected is already in the device and there is less that is drawn from the subject that is not already in the device prior to beginning the sample pull.

Figure 22:
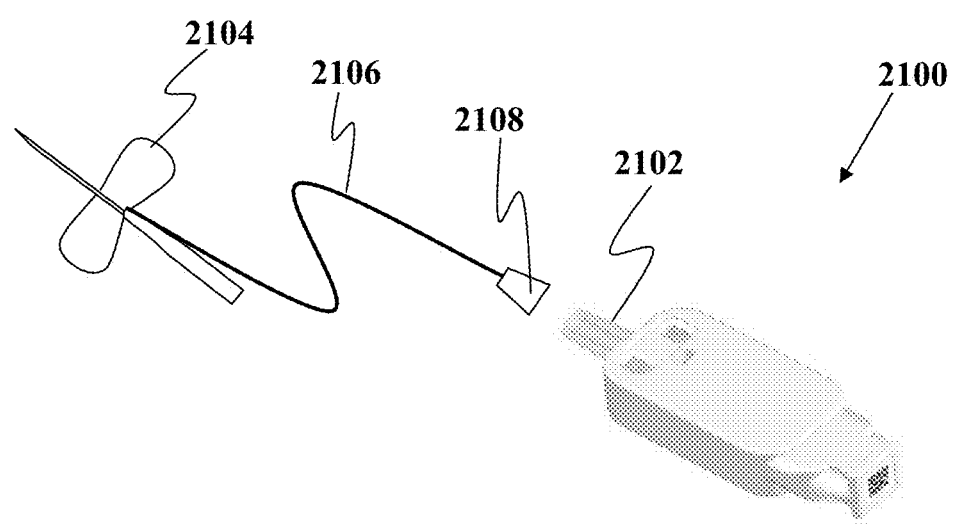
FIG. 22 shows a perspective view of a collection device for use with a blood vessel penetrator and sample collector according to an embodiment described herein.

Referring now to FIG. 22, yet another embodiment of a sample collection device will now be described. This embodiment shows a collection device 2100 that has a connector 2102 such as but not limited to Luer connector that allows for connection to a variety of sample acquisition devices such as a tissue penetrating member, needle, or the like. Some Luer connectors may use a press-fit to engage other connectors while some embodiments of the connector 2102 may include threads to facilitate engagement. FIG. 22 shows that in this current embodiment, a butterfly needle 2104 is coupled to a fluid connection pathway 2106 such as but not limited to a flexible tube that leads to a connector 2108 to connect the sample acquisition features to the sample collection device 2100. The flexible tubing 2106 allows the needle portion 2104 to be located away from but still operably fluidly coupled to the sample collection device 2100. This allows for greater flexibility in terms of positioning of the needle 2104 to acquire sample fluid without having to also move the sample collection device 2100. Optionally, some embodiments may directly couple the tissue penetrating member to the device 2100 without the use of flexible tubing.

At least some or all of the embodiments can have a fill indicator such as but not limited to a view window or opening that shows when sample is present inside the collection device and thus indicate that it is acceptable to engage the sample vessel(s). Optionally, embodiments that do not have a fill indicator are not excluded. Some embodiments may optionally include one or more vents, such as but not limited to a port, to allow air escape as the channels in the collection device are filled with sample. In most embodiments, the filled sample vessel(s) may be disconnected from the sample collection device after a desired fill level is reached. Optionally, additional sample vessel(s) can be engaged to the sample collection device to collect additional amounts of bodily fluid sample. Optionally, the interior conditions of the sample vessels are such that the vessels has a reduced pressure configure to draw in only a pre-determined amount of sample fluid.

FIG. 23 shows an exploded view of one embodiment of the sample collection device 2100. In this non-limiting example, the portion 1130 may be configured to hold the container holder 1140 and the portion with sampling device holder 2160. The device 2100 may include an anti-leakage device 2162 that can engage the open ends of the adapter channels 2022 and 2024 to minimize sample loss through the open ends until the containers in holder 1140 are engaged to draw sample in any container(s) therein. In the current embodiment, the anti-leakage device 2162 covers at least two adapter channels 2022 and 2024 and is configured to be movable. The present embodiment of anti-leakage device 2162 is sized so that it can be moved to uncover the openings on adapter channels 2022 and 2024 while still allowing the adapter channels 2022 and 2024 to engage the container(s) in the holder 1140.

Referring now to FIGS. 24 and 25, one embodiment of the sampling device holder 2160 is shown in more detail. FIG. 24 shows the sampling device holder 2160 as an assembled unit. FIG. 25 shows an exploded view of the sampling device holder 2160 with a first portion 2164 and a second portion 2166. The adapter channels 2022 and 2024 are also show as being removable from the second portion 2166. Although this embodiment of the sampling device holder 2160 is shown as two separate portions, it should be understood that some alternative embodiments can configure the sample device holder 2160 as a single unitary unit. Optionally, some embodiments may configure to have more than two portions that are assembled together to form the holder 2160. Optionally, some embodiments may create separate portions along a longitudinal axis 2165 or other axis of the holder 2160, instead of along a lateral axis of holder 2160 this is shown by the separation in FIG. 25.

Figure 26:
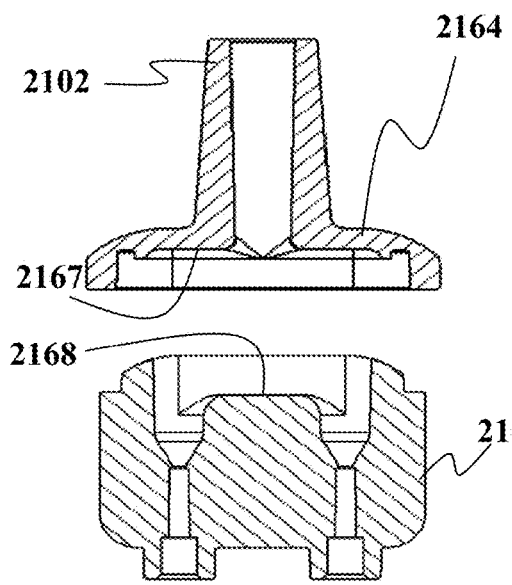
Figure 27:
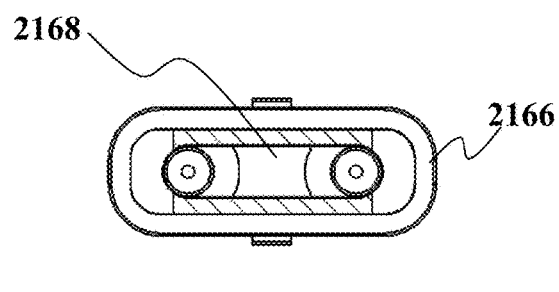
Figure 28:
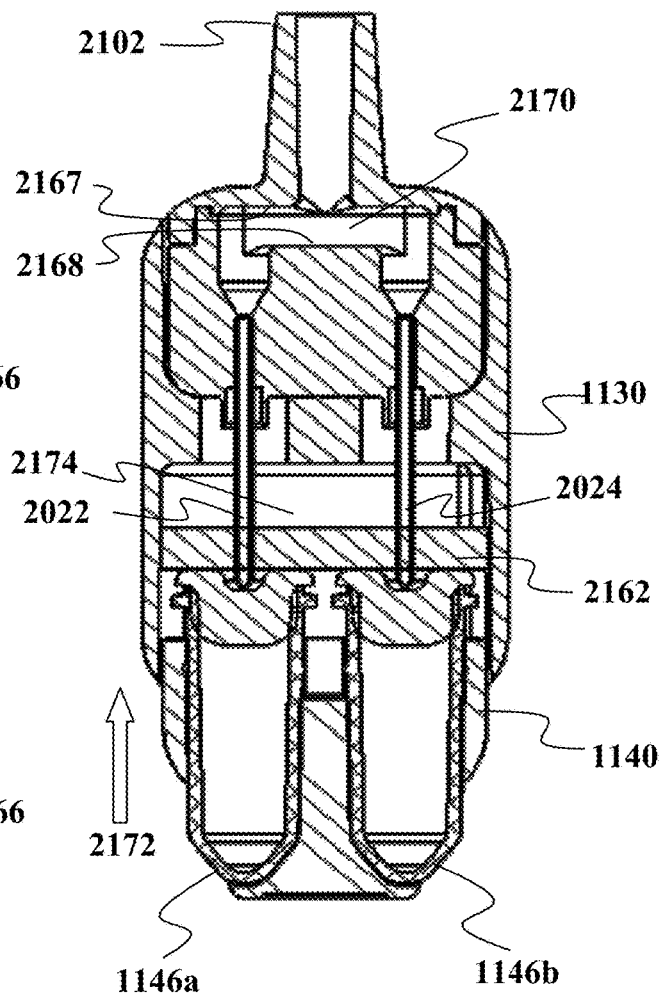

Referring now to FIGS. 26 through 28, various cross-sectional views of embodiments of the sample device holder 2160 and the device 2100 are shown. FIG. 26 shows a cross-sectional view of the portions 2164 and 2166. Although not being bound by any particular theory, the use of the separation portions 2164 and 2166 can be selected simplify manufacturing, particularly for forming the various internal channels and chambers in the holder 2160. For example, at least one wall 2167 of the chamber can be formed in the first portion 2164 while complementary walls 2168 of the chamber can be formed in the second portion 2166. FIG. 27 shows a top-down end view of the portion 2166 with the wall 2168 visible from the end view.

Referring now to FIG. 28, a cross-sectional view of the assembled device 2100 will now be described. This FIG. 28 shows that sample entering the device through the connector 2102 will enter the common chamber 2170 before leading to the adapter channels 2022 and 2024. From the adapter channels 2022 and 2024, movement of the holder 1140 in the direction indicated by arrow 2172 will operably fluidically couple the containers 1146*a* and 1146*b* to the adapter channels 2022 and 2024, moving sample from the channels into the containers. In the present embodiment, there is sufficient space 2174 to allow for movement of the containers 1146a and 1146b to have the adapter channels 2022 and 2024 penetrate the caps of the containers 1146a and 1146b so that the adapter channels 2022 and 2024 are in fluid communication with the interior of the containers 1146a and 1146b. Although only two container and adapter channel sets are shown in the figures, it should be understood that other configuration with more or less sets of containers and adapter channels can be configured for use with a device such as that shown in FIG. 28.

Modular Sample Collection Device

Figure 29A:
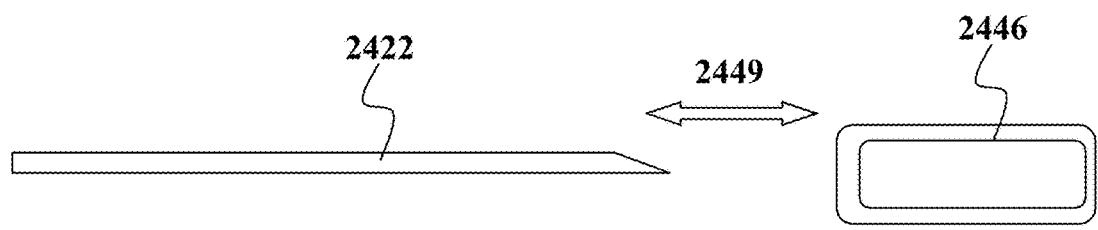
FIGS. 29A-29C show schematics of various embodiments as described herein.
Figure 29B:
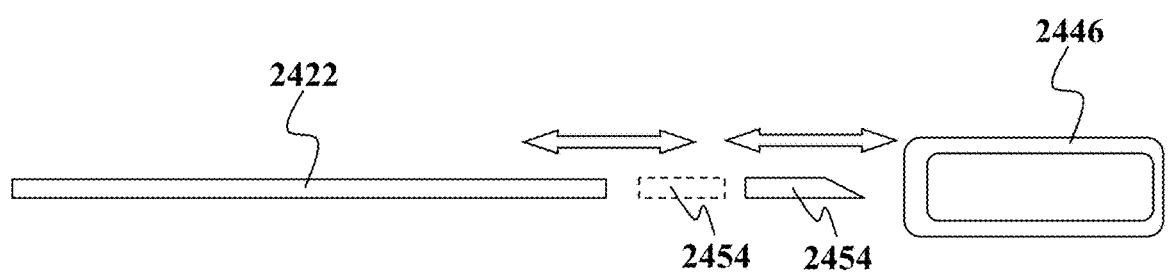
Figure 29C:
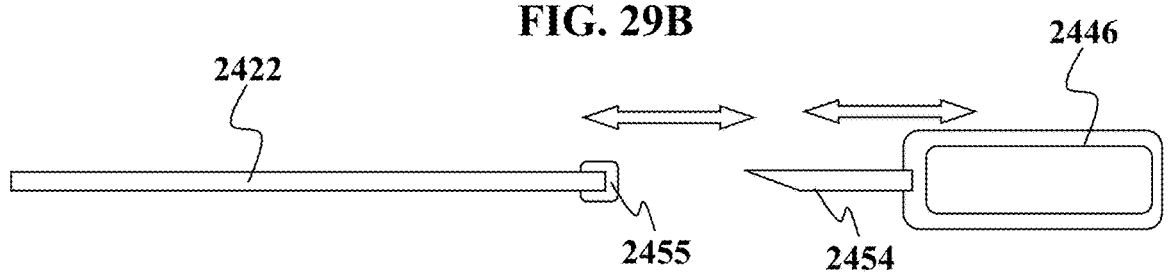

Referring now to FIGS. 29A-29C, although the embodiments herein typically describe sample collection device as having an adapter channel for connecting the sample collection channels with the containers, it should be understood that embodiments without such configurations are not excluded.

By way of non-limiting example in FIG. 29A, as previously suggested herein, some embodiments may be without a discrete, separate adapter channel. Herein the collection channel 2422 may connect directly to the container 2446 by way of relative motion between one or both of those elements as indicated by the arrow 2449.

By way of non-limiting example in FIG. 29B, one or more adapter channels 2454 may be discrete elements not initially in direct fluid communication with either the collection channel 2422 or the containers 2446. Herein the collection channel 2422 may connect to the container 2446 by way of relative motion between one or more of the collection channel, the adapter channel(s) 2454, or the container 2446 (sequentially or simultaneously) to create a fluid pathway from the collection channels through the one or more adapter channels into the containers.

By way of non-limiting example in FIG. 29C, one or more adapter channels 2454 may be elements initially in contact with the containers 2446. The adapter channels 2454 may not be directly in communication with the interior or the containers. Herein the collection channel 2400 may connect to the container by way of relative motion between one or more of those elements (sequentially or simultaneously) to create a fluid pathway from the collection channels through the one or more adapter channels into the containers. Some embodiments may have a septum, sleeve, sleeve with vent, or cover 2455 over the end of the collection channel which will be engaged by the adapter channel. The engagement of the various elements may also move the adapter channel 2454 into the interior of the container 2446, as initially, the adapter channel 2454 may not be in fluid communication with the interior. Some embodiments herein may have more than adapter channel and some embodiments may use adapter channels with pointed ends on both ends of the channel. There may be variations and alternatives to the embodiments described herein and that no single embodiment should be construed to encompass the entire invention.

It should be understood that any of the embodiments herein could be modified to include the features recited in the description for FIGS. 29A-29C.

Sample Processing

Figure 30:
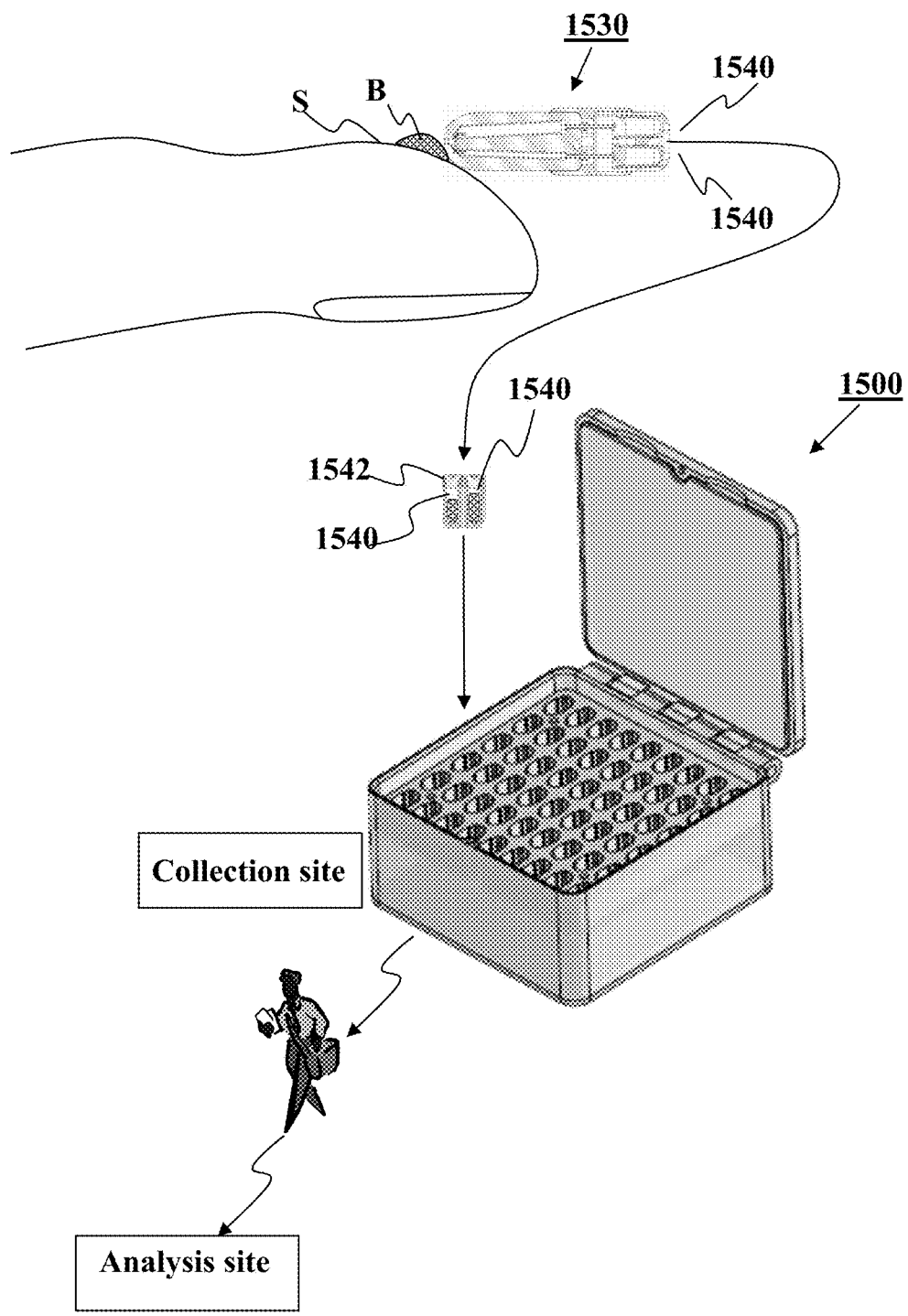
FIGS. 30-31 show schematic of methods according to embodiments described herein.

Referring now to FIG. 30, one embodiment of bodily fluid sample collection and transport system will now be described. FIG. 30 shows a bodily fluid sample B on a skin surface S of the subject. In the non-limiting example of FIG. 30, the bodily fluid sample B can be collected by one of a variety of devices. By way of non-limiting example, collection device 1530 may be but is not limited to those described in U.S. Patent Application Ser. No. 61/697,797 filed Sep. 6, 2012, which is fully incorporated herein by reference for all purposes. In the present embodiment, the bodily fluid sample B is collected by one or more capillary channels and then directed into sample vessels 1540. By way of non-limiting example, at least one of the sample vessels 1540 may have an interior that is initially under a partial vacuum that is used to draw bodily fluid sample into the sample vessel 1540. Some embodiments may simultaneously draw sample from the sample collection device into the sample vessels 1540 from the same or different collection channels in the sample collection device. Optionally, some embodiments may simultaneous draw sample into the sample vessels In the present embodiment after the bodily fluid sample is inside the sample vessels 1540, the sample vessels 1540 in their holder 1542 (or optionally, removed from their holder 1542) are loaded into the transport container 1500. In this embodiment, there may be one or more slots sized for the sample vessel holder 1542 or slots for the sample vessels in the transport container 1500. By way of non-limiting example, they may hold the sample vessels in an arrayed configuration and oriented to be vertical or some other pre-determined orientation. It should be understood that some embodiments of the sample vessels 1540 are configured so that they hold different amount of sample in each of the vessels. By way of non-limiting example, this can be controlled based on the amount of vacuum force in each of the sample vessels, the amount of sample collected in the sample collection channel(s) of the collection device, and/or other factors. Optionally, different pre-treatments such as but not limited to different anti-coagulants or the like can also be present in the sample vessels.

As seen in FIG. 30, the sample vessels 1540 are collecting sample at a first location such as but not limited to a sample collection site. By way of non-limiting example, the bodily fluid samples are then transported in the transport container 1500 to a second location such as but not limited to an analysis site. The method of transport may be by courier, postal delivery, or other shipping technique. In many embodiments, the transport may be implemented by having a yet another container that holds the transport container therein. In one embodiment, the sample collection site may be a point-of-care. Optionally, the sample collection site is a point-of-service. Optionally, the sample collection site is remote from the sample analysis site.

Although the present embodiment of FIG. 30 shows the collection of bodily fluid sample from a surface of the subject, other alternative embodiments may use collection techniques for collecting sample from other areas of the subject, such as by venipuncture, to fill the sample vessel(s) 1540. Such other collection techniques are not excluded for use as alternative to or in conjunction with surface collection. Surface collection may be on exterior surfaces of the subject. Optionally, some embodiments may collect from accessible surfaces on the interior of the subject. Presence of bodily fluid sample B on these surfaces may be naturally occurring or may occur through wound creation or other techniques to make the bodily fluid surface accessible. Although the embodiments herein may show that a collection device with at at least two collection channels are used, some embodiments may use a device with only one collection channel that collection sample that will be treated with only one anti-coagulant. Optionally, some embodiments may have at least two of the containers in the same device collecting sample that will be treated with the same anti-coagulant. In such examples, a first sample device collection sample with a first anti-coagulant such as but not limited to heparin and then a second device collects sample from the same subject from the same wound site or a different site for sample that will be treated with an anticoagulant different from the first anticoagulant. Samples from the same subject but with different anticoagulants may be shipped together in the same shipment form the site to a laboratory along with other samples from different subjects.

Figure 31:
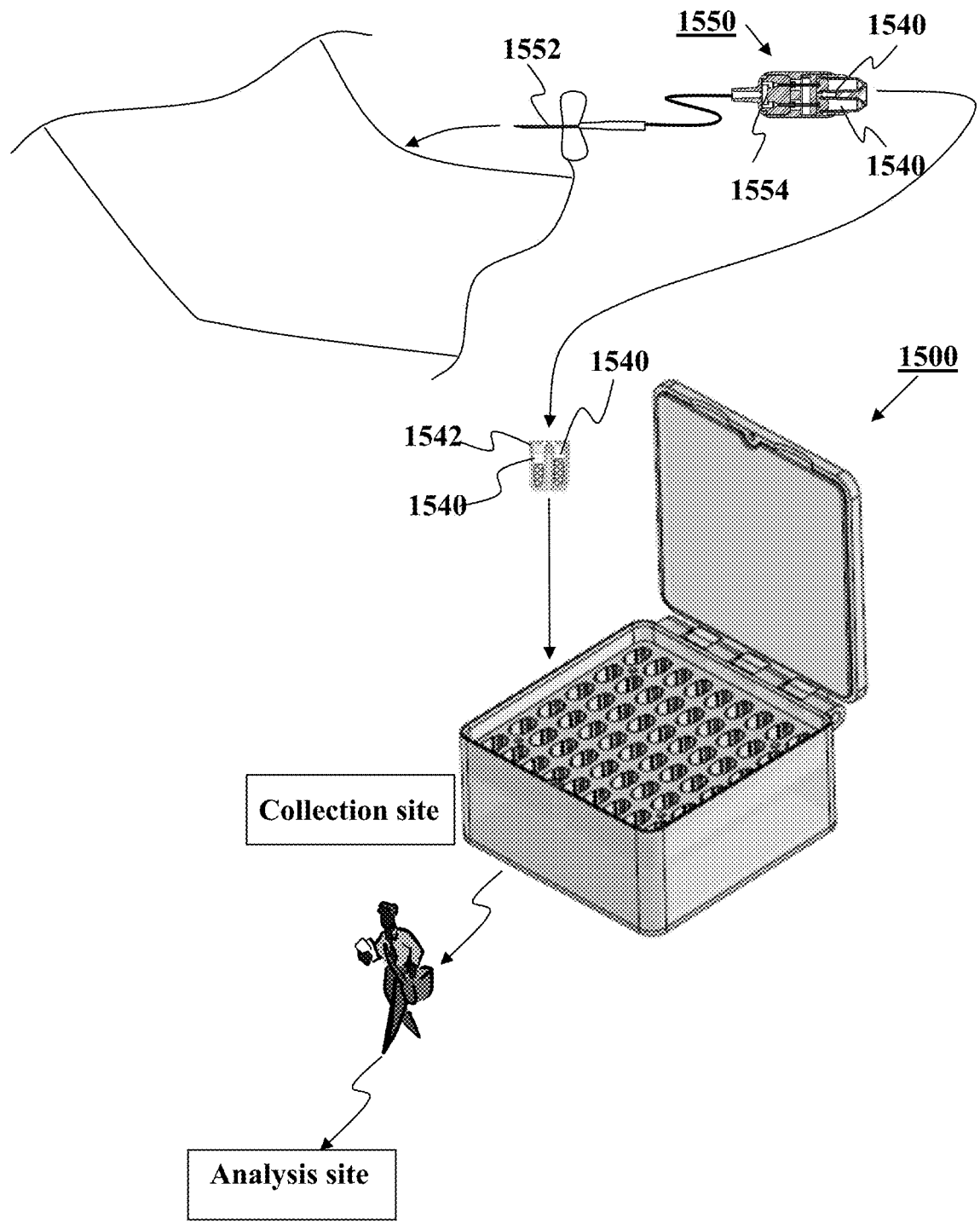

Referring now to FIG. 31, yet another embodiment is described herein wherein bodily fluid sample can be collected from an interior of the subject versus collecting sample that is pooled on a surface of the subject. This embodiment of FIG. 31 shows a collection device 1550 with a hypodermic needle 1552 that is configured to collect bodily fluid sample such as but not limited to venous blood. In one embodiment, the bodily fluid sample may fill a chamber 1554 in the device 1550 at which time sample vessel(s) 1540 may be engaged to draw the sample into the respective vessel(s). Optionally, some embodiments may not have a chamber 1554 but instead have very little void space other than channel(s), pathway(s), or tube(s) used to direct sample from the needle 1552 to the sample vessel(s) 1540. For bodily fluid samples such as blood, the pressure from within the blood vessel is such that the blood sample can fill the chamber 1554 without much if any assistance from the collection device. Such embodiments may optionally include one or more vents, such as but not limited to a port, to allow air escape as the channels in the collection device are filled with sample.

At least some or all of the embodiments can have a fill indicator such as but not limited to a view window or opening that shows when sample is present inside the collection device and thus indicate that it is acceptable to engage the sample vessel(s) 1540. Optionally, embodiments that do not have a fill indicator are not excluded. The filled sample vessel(s) 1540 may be disconnected from the sample collection device after a desired fill level is reached. Optionally, additional sample vessel(s) 1540 can be engaged to the sample collection device 1550 (or 1530) to collect additional amounts of bodily fluid sample.

Point of Service System

Figure 32:
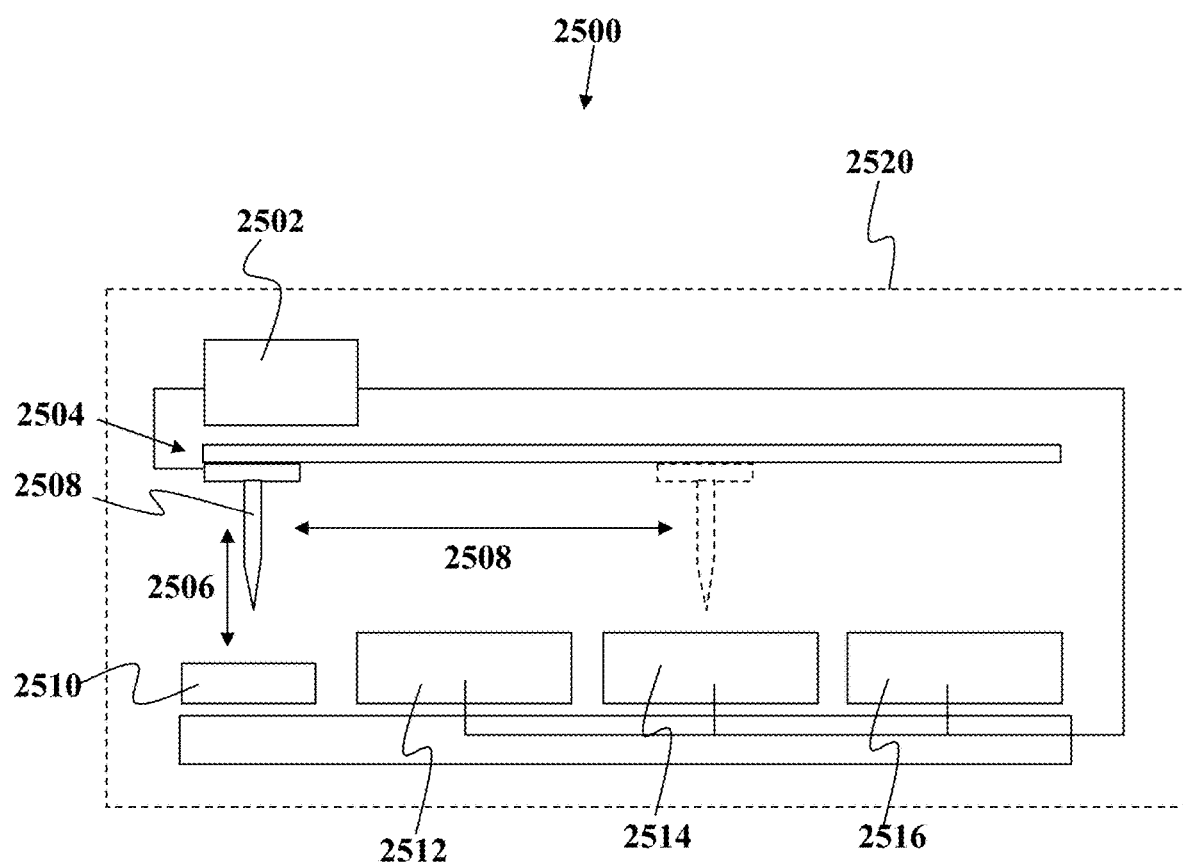
FIG. 32 shows a schematic view of one embodiment of system described herein.

Referring now to FIG. 32, it should be understood that the processes described herein may be performed using automated techniques. The automated processing may be used in an integrated, automated system. In some embodiments, this may be in a single instrument having a plurality of functional components therein and surrounded by a common housing. The processing techniques and methods for sedimentation measure can be pre-set. Optionally, that may be based on protocols or procedures that may be dynamically changed as desired in the manner described in U.S. patent application Ser. Nos. 13/355,458 and 13/244,947, both fully incorporated herein by reference for all purposes.

In one non-limiting example as shown in FIG. 32, an integrated instrument 2500 may be provided with a programmable processor 2502 which can be used to control a plurality of components of the instrument. For example, in one embodiment, the processor 2502 may control a single or multiple pipette system 2504 that is movable X-Y and Z directions as indicated by arrows 2506 and 2508. The same or different processor may also control other components 2512, 2514, or 2516 in the instrument. In one embodiment, tone of the components 2512, 2514, or 2516 comprises a centrifuge.

As seen in FIG. 32, control by the processor 2502 may allow the pipette system 2504 to acquire blood sample from cartridge 2510 and move the sample to one of the components 2512, 2514, or 2516. Such movement may involve dispensing the sample into a removable vessel in the cartridge 2510 and then transporting the removable vessel to one of the components 2512, 2514, or 2516. Optionally, blood sample is dispensed directly into a container already mounted on one of the components 2512, 2514, or 2516. In one non-limiting example, one of these components 2512, 2514, or 2516 may be a centrifuge with an imaging configuration to allow for both illumination and visualization of sample in the container. Other components 2512, 2514, or 2516 perform other analysis, assay, or detection functions.

All of the foregoing may be integrated within a single housing 2520 and configured for bench top or small footprint floor mounting. In one example, a small footprint floor mounted system may occupy a floor area of about 4 m$^2$ or less. In one example, a small footprint floor mounted system may occupy a floor area of about 3 m$^2$ or less. In one example, a small footprint floor mounted system may occupy a floor area of about 2 m$^2$ or less. In one example, a small footprint floor mounted system may occupy a floor area of about 1 m$^2$ or less. In some embodiments, the instrument footprint may be less than or equal to about 4 m$^2$, 3 m$^2$, 2.5 m$^2$, 2 m$^2$, 1.5 m$^2$, 1 m$^2$, 0.75 m$^2$, 0.5 m$^2$, 0.3 m$^2$, 0.2 m$^2$, 0.1 m$^2$, 0.08 m$^2$, 0.05 m$^2$, 0.03 m$^2$, 100 cm$^2$, 80 cm$^2$, 70 cm$^2$, 60 cm$^2$, 50 cm$^2$, 40 cm$^2$, 30 cm$^2$, 20 cm$^2$, 15 cm$^2$, or 10 cm$^2$. Some suitable systems in a point-of-service setting are described in U.S. patent application Ser. Nos. 13/355,458 and 13/244,947, both fully incorporated herein by reference for all purposes. The present embodiments may be configured for use with any of the modules or systems described in those patent applications.

Referring now to FIGS. 33 to 37, a still further embodiment of a sample collection device will now be described. This embodiment shows a sample collection region 2600 that has a capillary channel region and then a lower flow resistance region 2610 that increase the cross-sectional area of the channel to provide for lower flow resistance and increased flow rates. The increased size of the channel can also be used to store sample therein. One embodiment can be configured to have caps that go on both ends of the device so that sample is contained therein without need for transferring to containers 1146a and 1146b.

Figure 33:
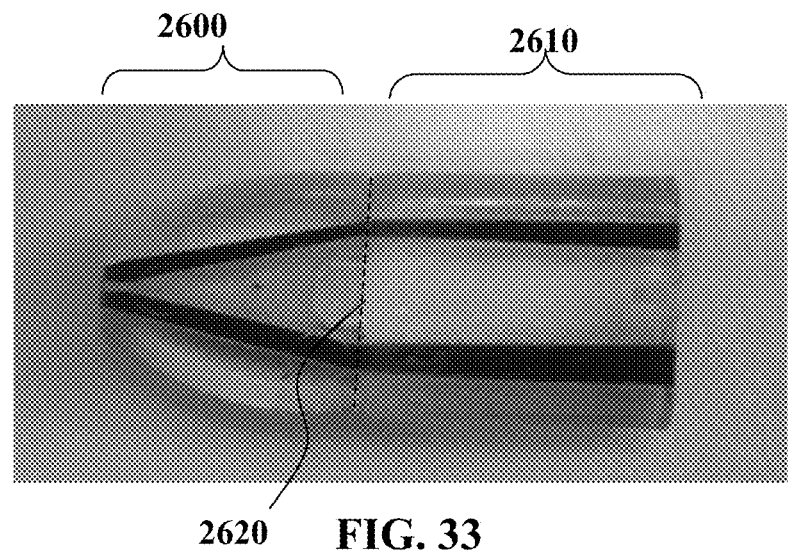
Figure 34:
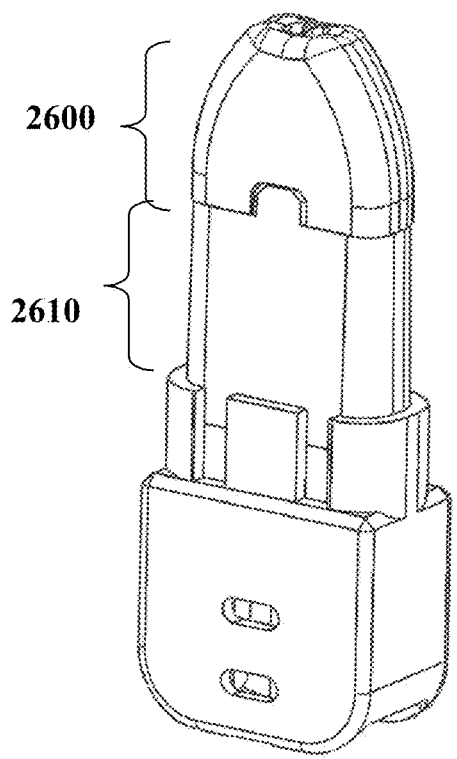

As seen in the non-limiting example of FIG. 33, because the joint between regions 2600 and 2610 can be located across the mid-line 2620, this can also reduce the amount of bonding material used to join the items together. This can also facility manufacturing as the two portions can be manufactured separately. It should also be understood that the shapes of the pathways can also be tapered or otherwise shaped in terms of cross-sectional area along the length of the pathway, although it should also be understood that non-tapered pathways are not excluded. Some embodiments may combine tapered and non-tapered pathways along portions of the same pathway. Optionally, some embodiments may have at least one pathway that is tapered and at least one pathway that is not.

In one non-limiting example, the other parts are similar to those previously described herein with regards to the containers 1146a and 1146b, adapter channels, frits, holders 130, etc. . . . . Wicking of both channels at the junction (both fill times<6-secs) has been improved (step removed) and blood got in to the channel easily and passed the junction area without need for tilting. The parts may be made of PMMA, PET, PETG, etc. . . . . This can provide a 7.5× faster fill due to the change in size of channel in region 2610 which will allow for easier flow into this region.

The flow resistance decreases to the fourth power in region 2610 based on changes in channel size as seen in the formula.

$$\dot{M} = \frac{\pi \rho g}{32\mu} \left[ \frac{\sigma}{\rho} \frac{D^3}{L} + \frac{H}{4} \frac{D^4}{L} \right]$$

Figure 35:
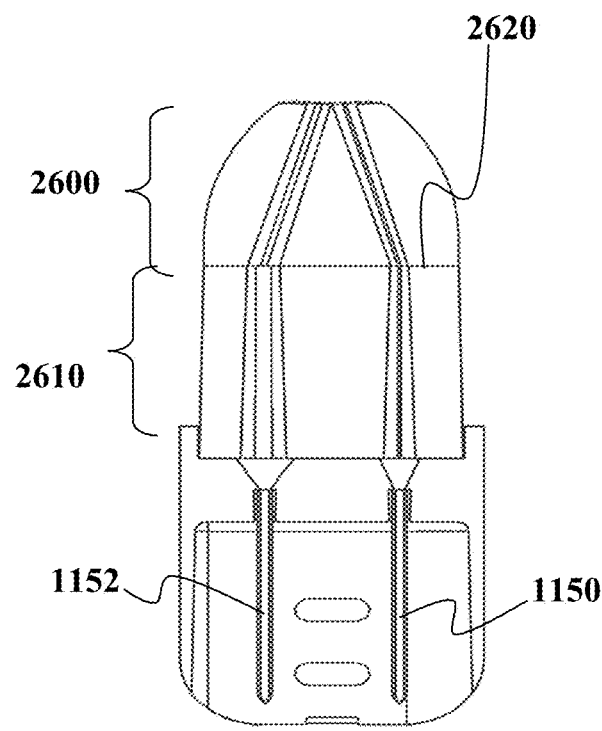

Although the non-limiting example of FIG. 35 shows that there are separate channels 1150 and 1152 incorporated, embedded, or otherwise coupled to a portion of the collection device, some embodiments may integrally form one or more of these elements as part of the collection device.

Figures 36A, 36B, 36C:
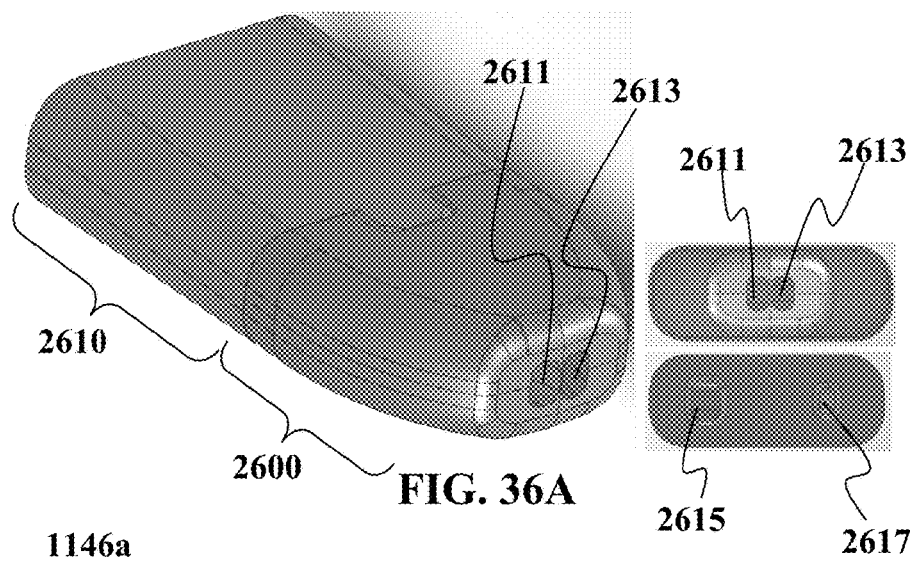
Figure 37:
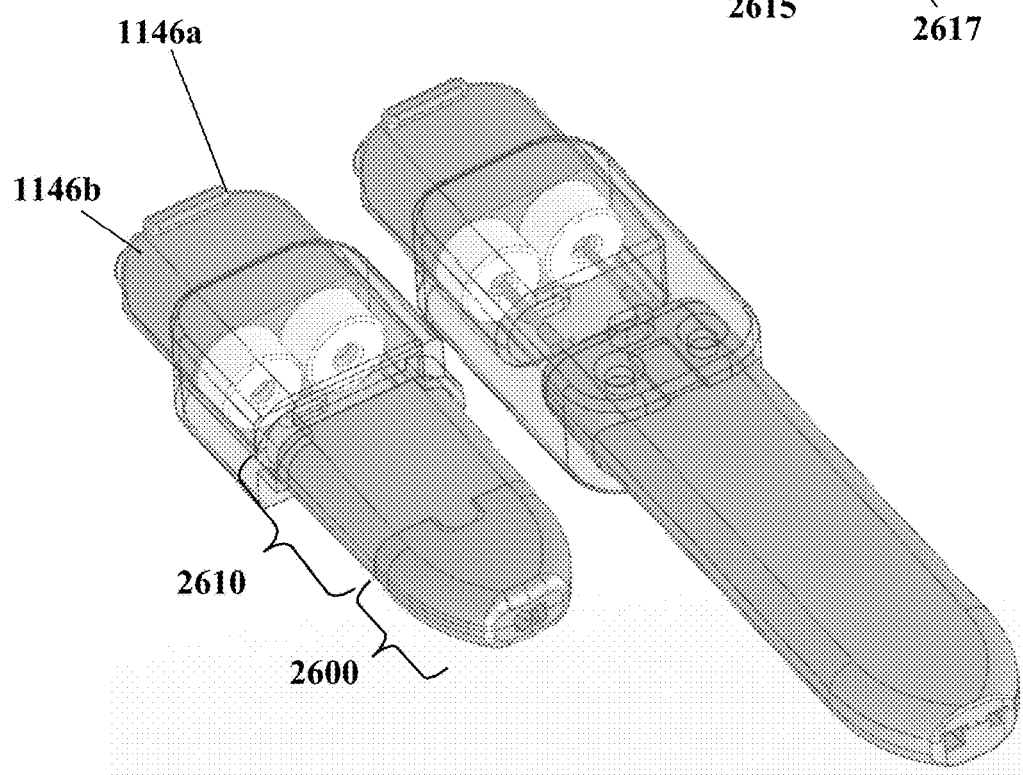

FIG. 36A shows a still further embodiment wherein the inlet ports 2611 and 2613 are shown. A non-limiting example of the exit ports 2615 and 2617 on portions 2610 are shown in FIG. 36B. Although these embodiments show the inlet ports 2611 and 2613 as separate ports, it should be understood that unified ports, co-axial ports, or other configurations for inlets as shown or described elsewhere herein can also be adapted for use in these embodiments. For example, configurations as shown in FIG. 11J (including or not including features 1166 and/or 1168) or those of FIG. 7A may also be configured for use with the collection devices shown herein.

In one non-limiting example, the portion shown in FIG. 36A may be used without the sample containers and wherein the ends with ports 2611 and 2613 are capped, closed, or otherwise sealed. In this non-limiting example, a separate cap, seal, or other closure device can be used to close ports 2615 and 2617. In this manner, the fluidic circuit is used as sample collection and sample storage. By way of non-limiting example, when the sample is desired to be accessed, the ports can be opened so that the sample can be extracted. This can reduce the amount of material used, reducing the use of a separate container(s) for storage of the collected sample. Although this embodiment in FIG. 36A shows only two passages, it should be understood that other embodiments may have three or more passages therein in the configuration shown or in different fluidic circuit configurations or alignments within the body of the device.

Figure 38A:
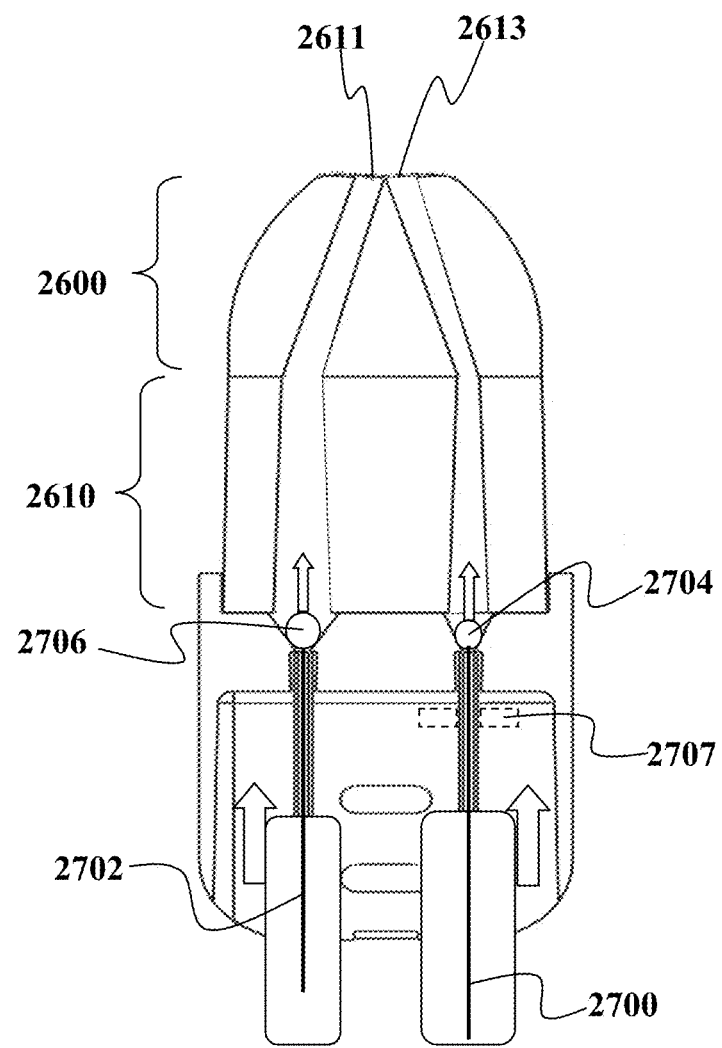

Referring now to FIG. 38A, a still further non-limiting example will now be described. FIG. 38A shows an embodiment wherein there are liquid guide elements 2700 and 2702 wherein the guide elements can assist in a bottom-up fill of the sample container so that undesired air bubble are not formed which may happen when a top-down fill occurs when sample is delivered toward a top of the sample container. FIG. 38A shows that as the sample containers are moved upward as indicated by the arrows. Moving the sample containers will move upward and first move the seal element 2704 upward on the longer guide element 2700. Unseating a seal element 2704 will allow fluid to flow in that channel into the sample container. As the sample containers a moved upward, the second seal element 2706 of the other guide element 2702 will be unseated as the element 2702 contacts a bottom or other portion of the sample container and begin to fill. By way of non-limiting example, this may be desirable if one side has a larger fill volume and will be better suited with a longer fill time. By way of non-limiting example, the guide elements 2700 and 2702 can also be useful when flow is due to a slower flow, which may be desired to prevent hemolysis of sample. A slower flow may benefit from the guide element to start with a bottom fill. In one non-limiting example, the guide element comprise a material that is inert to the sample fluid and will not corrupt or substantially corrupt the sample fluid therein for any assays to be performed on the sample. In one non-limiting example, the guide element may comprise of glass, polymer, polycarbonate, optical fiber(s), surgical grade steel, aluminum, single or multiple combinations of the foregoing, or other suitable materials that may be developed in the future. As seen in FIG. 38A, the guide elements extend from a position inside the sample container and extend to couple to flow regulating device 2704 such as but not limited to a sphere, cone, pyramid, cube, or other shape that can stop flow when in a first position and allow fluid flow when in a second position. Depending on the size of the fluid passageways, the flow regulating device 2704 may be of the same size in each passageway or at a different size, depending on what size is suitable for stopping flow in the passageway. Some embodiments may use containers on each pathway of the same interior volume. Optionally, some embodiments may use containers on a plurality of pathways of different interior volumes.

Figure 38B:
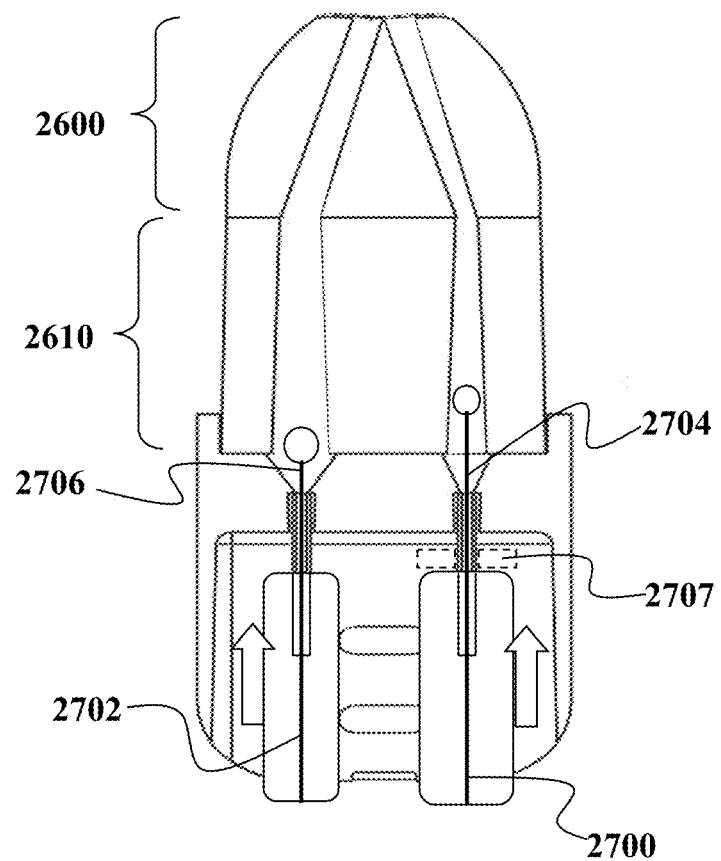

FIG. 38B also shows that some embodiments may further include one or more sealing elements 2707 that may prevent any undesired overflow. In one non-limiting example, a sealing element 2707 may include but an O-ring, frit, an elastomeric material, a self-resealing material or the like that exists or may be developed in the future. It should also be understood that although FIGS. 38A and 38B show that sealing element 2707 is only on one fluid pathway, it should understood that multiple, all, or some other combination of pathways may also each have one or more sealing elements 2707. It should also be understood that FIG. 38B shows one non-limiting example of the fluid seal elements 2704 and 2706 in a second position that allows for fluid flow.

Figure 39:
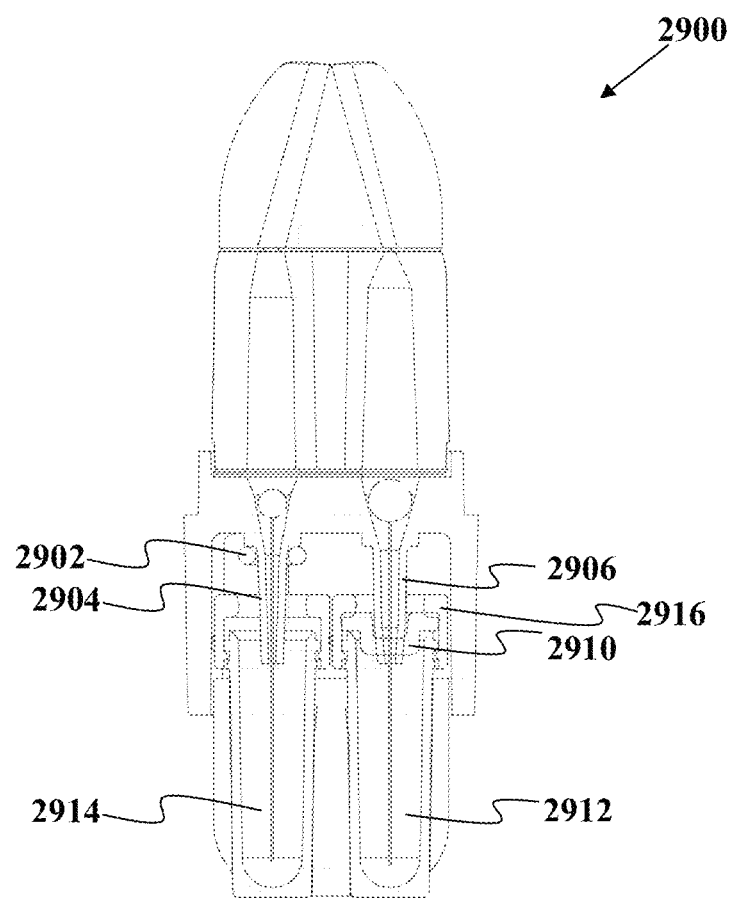

Referring now to FIG. 39, a cross-sectional view is shown of one non-limiting example wherein an inlet channel 2808, such but not limited to an adapter channel, is shown in a fluidly coupled position to at least one non-limiting example of a sample container unit 2824 (which in this embodiment is shown in a side-ways view). Although FIG. 39 only shows one of two or more sample containers, it should understood that some embodiments may have only a single sample container that has this type of container. Optionally, more than one of the sample containers can have this type of reverse-plunger type configuration. As seen in FIG. 39, the movement of the plunger 2828 of the sample container unit 2824 can be used to create a motive force such as but not limited to at least a partial vacuum to draw liquid from the channel 2808 into the sample container unit 2824. In this non-limiting example, as the plunger is displaced as shown by arrow 2831 in FIG. 68, this increases the interior volume 2829 of the sample container unit 2824 between the cap portion 2832. It should be understood that, in one non-limiting example, there may be no sample in the sample container unit 2824 until the motive force is provided to overcome any inherent capillary force of the channel 2808 which brings the sample fluid into but not out a needle end 2834 of the channel 2808, In one non-limiting example, extracting fluid from the channel 2808 may involve using one or more additional motive forces. It should be understood that this configured described herein may be similar to a reverse plunger. Optionally, some embodiments may use a conventional plunger, in place of or in combination with the structures herein, to provide motive force to draw sample into the sample container.

Referring now to FIG. 39, a still further cross-sectional view is shown of a sample collection device 2900. This embodiment is similar to that shown in FIG. 38. FIG. 39 more clearly shows at least one seal 2902 such as but not to an o-ring. This seal 2902 may be on one or both of the fluid conduits 2904 and 2906. In this non-limiting example, the fluid conduits 2904 and 2906 may be configured to penetrate a septa-based insert 2910 that may be in one or both of the containers 2912 and 2914. In one embodiment, the insert 2910 may be of a butterfly, slit, or other configuration that provides for some venting when the container 2912 and conduit 2910. Optionally, other embodiments may provide a septa or design that does not provide for the venting feature. A cap 2916 or other feature may be used to retain the insert 2910 on the container.

Figure 40:
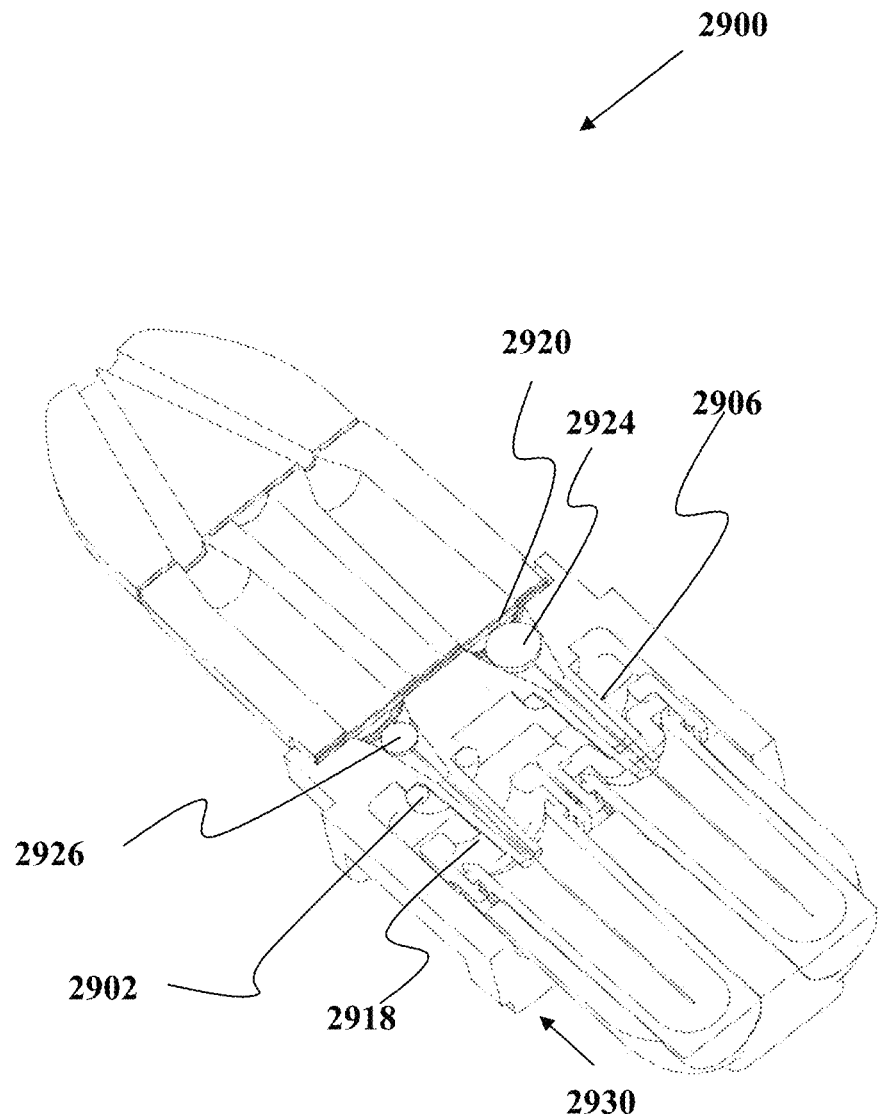

FIG. 40 shows a perspective cross-sectional view of the device 2900 of FIG. 39. As see in FIG. 40, there is a ball retaining feature 2920 to hold the ball-shaped fill stops 2924 and 2926. In one non-limiting example, the fill stops 2924 and 2926, which may be ball, conical, polygonal, or other shaped can be designed to be seated as shown but there may be sufficient clearance such that sample under pressure can flow around the fill stop, whereas sample not under pressure will not flow freely around the fill stop. FIG. 40 also more clearly shows how seal 2902 can be mated to an opening 2918 in cap 2916 when the containers are slid upward as shown by arrow 2930.

Figure 41:
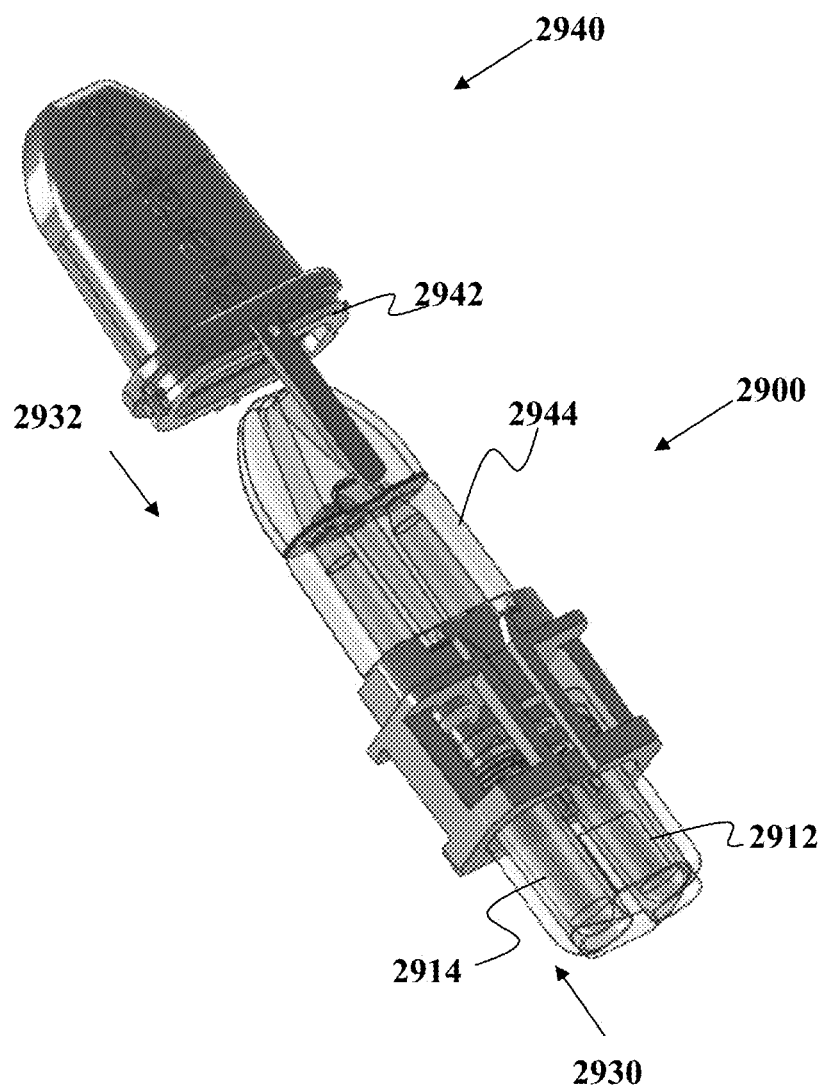

Referring now to FIG. 41, a still further feature of the embodiment will now be described. FIG. 41 shows that a sample pressurization device 2940 may be used with the device 2900. As seen in FIG. 41, to allow sample to fill the device 2900, initial position of the containers is not in a sealed position relative to seal 2902. In this non-limiting example, to transfer sample from the device to the containers 2912 and 2914, the containers are moved as indicated by arrow 2930 to create a seal with seal 2902. FIG. 41 shows that the sample pressurization device 2940 may be engaged with the device 2900 as indicated by arrow 2932. In this non-limiting example, there is a seal 2942 on the device 2940 that will seal against a surface 2944 of the device 2900.

Referring now to FIGS. 42A to 42C, the various states of the device 2900 for sample transfer are shown. FIG. 42A shows a condition wherein the containers 2912 and 2914 are in the sealed condition on the device 2900 against a seal such as seal 2902. Although only one seal is shown, some embodiments may have seals on both conduits of the device 2900. The sample pressurization device 2940 is about to be engaged. The size of the device 2940 is configured to have an interior volume that when the seal 2942 slides and seals along surface 2944, a pressurized state inside device 2900 is created. The length of overlap and volume inside the pressurization device 2940 can be used to determine the level of pressurization.

FIG. 42B shows the device 2900 in a pressurized state with the sample pressurization device 2940 engaged and the containers 2912 and 2914 are in the sealed condition on the device 2900.

FIG. 42C shows the device 2900 in a condition wherein sample is being delivered to the containers 2912 and 2914, which are no longer sealing against a seal 2902 of the device 2900. The pressure from the sample pressurization device 2940 will drive sample into the containers 2912 and 2914. The liquid guides 2950 and 2952 will deliver sample towards the bottom of the containers and minimize bubbles or other desired flow which may occur if sample is not flowing to the bottom but stays nears the top of the containers.

Figure 43:
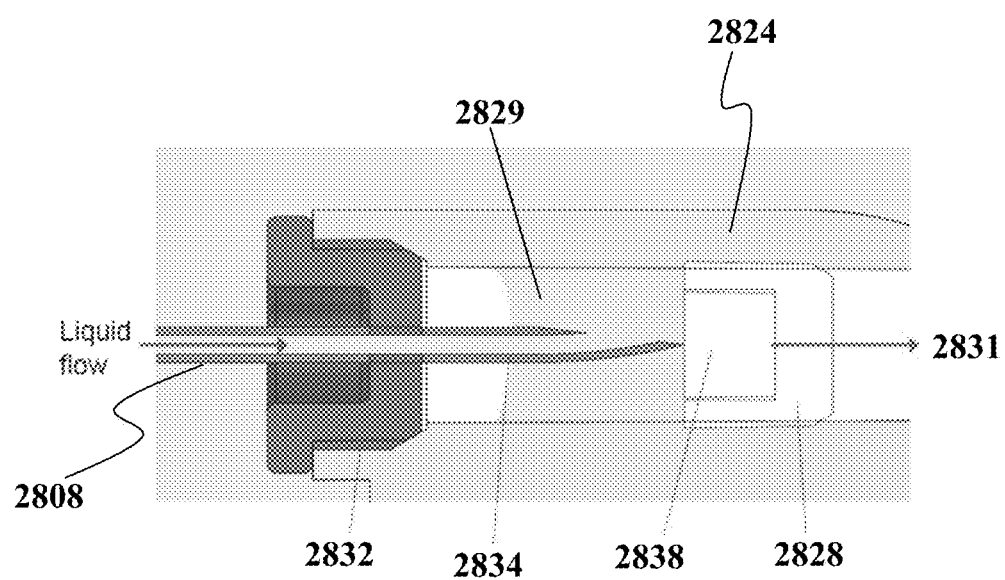

FIG. 43 also shows that, in at least one embodiment, the channel 2808 may have a pointed distal end 2834. Still further embodiments may have the channel 2808 be of a non-coring design so as not to introduce any cored portion or debris of the cap 2832 into the collected fluid. Regardless of whether a non-coring, conventional, or other shaped channel 2808, it should be understood that some embodiments of plunger 2828 may have a hardened core portion 2838 that can withstand force input from the channel 2808. As seen in FIG. 39, at least some embodiments will have a compliant material between the hardened core portion 2838 and the side walls of the sample container so as to provide at least a sufficient fluid seal as the plunger 2828 is moved from at least a first position to at least a second position. In one embodiment the hardened core portion 2838 may be at least 90% of the surface area of the plunger 2828 contacting the sample. In one embodiment the hardened core portion 2838 may be at least 80% of the surface area of the plunger 2828 contacting the sample. In one embodiment the hardened core portion 2838 may be at least 70% of the surface area of the plunger 2828 contacting the sample. In one embodiment the hardened core portion 2838 may be at least 60% of the surface area of the plunger 2828 contacting the sample. Some embodiments may have anti-coagulant coated on the walls of the container 2824 and this may be in conjunction or in place of anti-coagulant in the sample collection circuit upstream of the container. Some embodiments may use other types of coating such as but not limited to anti-hemolytic coating or a different type of anti-coagulant. Some embodiments, instead of coating, may include a dried, semi-solid, or other form of anti-coagulant in the container. Optionally, some embodiments may include a separation gel in the containers for use later during centrifugation. It should be understood that any of the embodiments described in this disclosure can be configured to use the reverse syringe container described in FIG. 43. Optionally, embodiments herein can be configured to use a syringe type device draw sample into the fluid circuit upstream of the container. Optionally, embodiments herein can be configured to use a syringe type device draw sample into the container. Optionally, embodiments herein can be configured to use a syringe type device draw sample into the fluid circuit upstream of the container and then into the container.

It should be understood that other embodiments may use one or more different motive force source(s) to move sample from the fluidic circuit collecting the sample. Some embodiments may use a syringe or other device to move a plunger 2828 or other connection to the sample container to create a vacuum or partial vacuum to draw sample into the sample container. Other embodiments may use a pump and/or other source alone or in combination with other features herein to move sample into the sample container.

It should also be understood that some embodiments may use the fluidic circuit of the collection portion 2600 and 2610 for temporary incubation or the like to provide, dissolve, or otherwise provide reagent into the sample before transferring into the sample container. Thus, in one non-limiting example, a method is used where a desired dwell time or minimum dwell time is provided to allow for the reagent, pre-treatment, or other material such as but not limited to being coated on walls of the collection circuit, to mix or enter the sample. Some embodiments may provide a timer, visual indicator, audio indicator, color change, temperature change, or other mechanism for showing that sufficient time has passed for the user to then transfer sample into the sample container.

In one embodiment, methods and devices are provided for passive filling of at least one sample container having a vented, pierceable/re-sealable closure. Optionally, the sample container is in the microliter volume range, such as greater than 1 microliter but less than 1000 microliters. Optionally, the sample container is in the microliter volume range, such as greater than 10 microliters but less than 500 microliters. Optionally, the sample container is in the microliter volume range, such as greater than 20 microliters but less than 200 microliters. Optionally, the sample container is in the microliter volume range, such as greater than 30 microliters but less than 100 microliters. Optionally, it should be understood that there may be a needle version and a capillary tube version of the device for use with such sample container(s).

Figure 64:
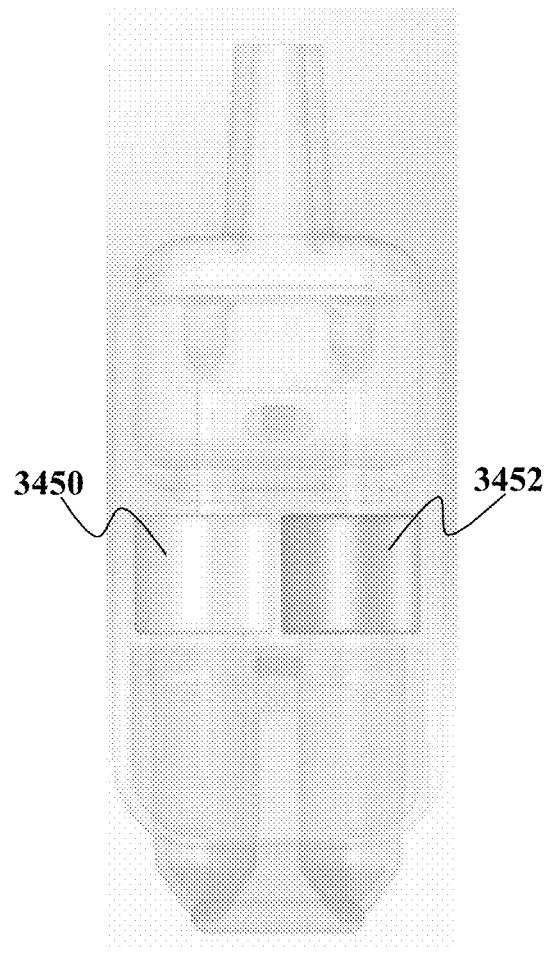

In one non-limiting example as seen in FIGS. 44A to 44B, a sample collection device 3100 is shown with containers that each have a gas-vented part 3102 is used as a part of the cap 3104 for the sample container 3106 (as seen in more detail in cross-sectional view of FIG. 44B). Non-limiting examples of such a cap are shown in FIGS. 64 and 65. It should be understood that any of the embodiments herein may be configured to use the containers herein with the flow-through design using the vented, pierceable/re-sealable closure.

The part 3102 may be but is not limited to a plastic, a polytetrafluoroethylene (PTFE), or a polyethylene (PE) part that is sufficiently porous to be gas permeable but not liquid permeable. In one embodiment, the porous material of the part 3102 may be coated with another material 3110 such as but not limited to silicone or similar material to provide a re-sealing quality around any opening that may be created through penetration of a needle, channel, penetrating member, or other fluid conduit into the gas permeable structure. This multi-layer configuration provides for a combined material that allows for qualities of at least two materials to be combined into one structure. The re-sealing quality can prevent liquid exit from any opening created in the porous material.

As seen in FIG. 44A, a fluid collection pathway is used in device 3100 with combined inlet 3150. In the embodiment of FIG. 45A, a fluid collection pathway is used in device 3120 with combined inlet 3152. In FIG. 46A, a device 3140 is provided with separate, non-cross-connecting or non-intersecting pathways 3154 and 3156, and thus, device 3140 does not have a configuration with common inlet as found in the embodiments of FIGS. 44A and 45A. FIG. 47 shows a device 3160 with a longer length fluid circuit 3162 sized to hold at least an amount that will be transferred into the containers 3164. By contrast, the devices of FIGS. 44A to 46A show devices where the length of the fluid circuits upstream of the containers 3106 are of a size that cannot fully contain a volume equal or greater than an amount to be delivered to the containers 3106. Although configurations of the fluid circuit(s) of larger volume are not excluded, it should be understood that such length is not need in all embodiments because sample begins to flow directly into the containers from the fluid circuit without having to wait until the entire amount is contained in the fluid circuit. In this manner, the length of the fluid circuit upstream of the container can be shortened because sample can flow into the container as the sample reaches the end of the pathway, without having to wait there until the entire amount is held in the fluid circuit upstream of the container(s). FIGS. 44B, 45B, and 46B shows that one of the fluid pathways into one container has a shorter length that than the other pathway into the other container. Some embodiments may have this configuration but it should be understood that other embodiments may have configurations where the fluid pathways into each of the containers are of the same length.

By way of non-limiting example, this configuration of a sample container with a gas permeable but not liquid permeable and resealing structure allows for passive filling of sample into the sample container. The passive filling may be by way of blood pressure from the subject to push sample into the sample container. It should be understood that in some embodiments, there are at least some portions that are not coated with the re-sealable material. In one non-limiting example, these non-coated area(s) are not in the target area where a penetrating member may pierce the porous material. In one embodiment, a top and/or bottom surface of the porous material may be coated but at least one side, lateral, or other surface different from the top and/or bottom surface may be uncoated to allow for venting.

The PTFE or porous material may be formed from beads into a porous material. The sealing material may be adhered, pressed, or otherwise connected. In one embodiment, at least two sides of the material, such as a compressible material, wherein on the bottom surface (if coated), there is at least one opening or a plurality of openings that allow for gas to vent through the compressible material. In this non-limiting example, the compressible material on an underside surface, such as but not limited to an O-ring of such material, provides a compressible material between the less compressible porous material and a support surface such as but not limited to ledge, protrusion, or other support structure in the sample container. The material may be a silicone or similar material which may be an inert material acceptable for use for medical purposes. Some embodiments may have shaped sidewalls such as but not limited to defining a side profile that shows a beveled, angled, or other shapes.

Although embodiments herein may have interior volumes of 500 microliters or less, it should be understood that some other embodiments may have volumes larger than 500 microliter.

Some embodiments may have an anti-coagulant crystal near an entry point of a needle in the sample container. Some embodiments may coat the anti-coagulant in the walls of the sample container. Some may optionally include at least some anti-coagulant in the walls of the capillary tube. Some embodiments may have one sample container with one anti-coagulant and a different anti-coagulant in a different container.

Figure 48A:
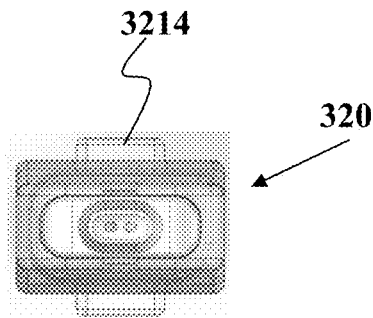
FIGS. 48A to 49 show various views of another embodiment of a device as described herein.
Figure 48B:
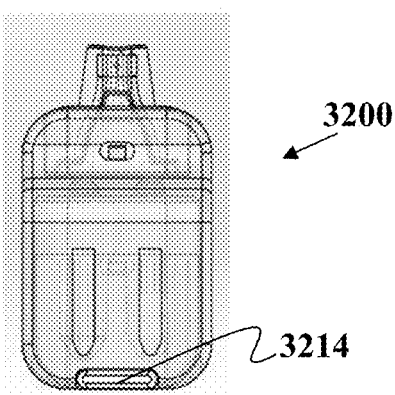
Figure 48C:
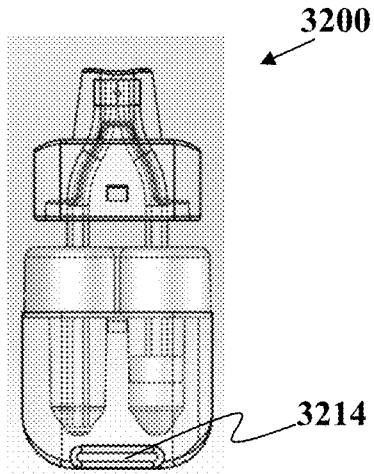
Figure 49:
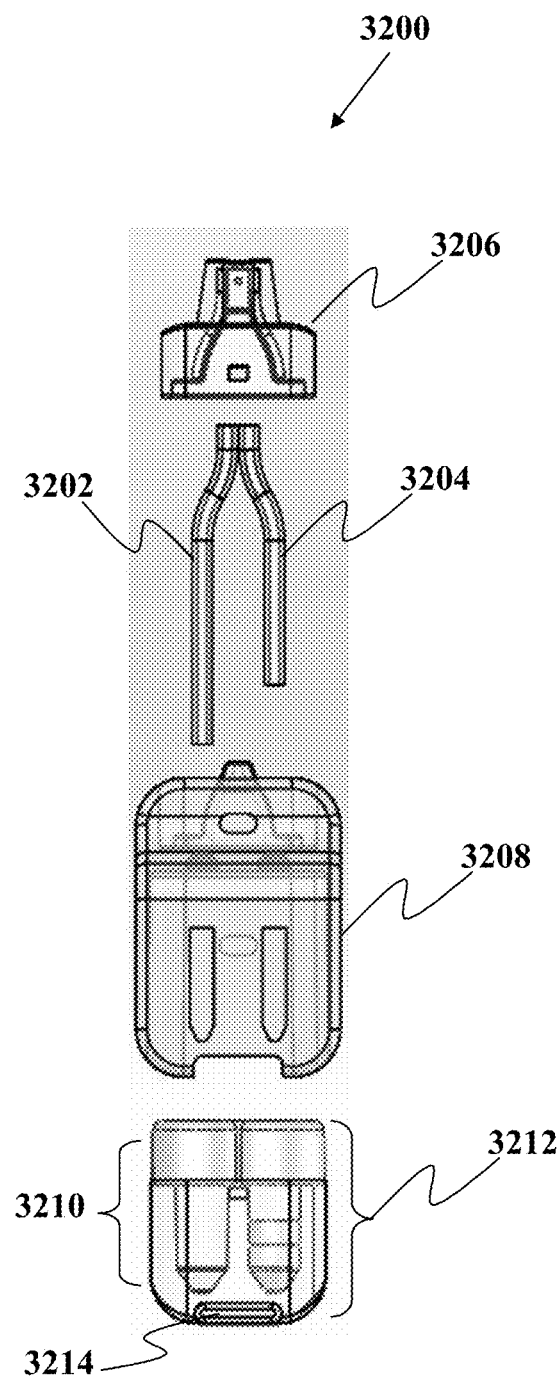

Referring now to FIG. 48A to 49, various view of a sample collection device is shown with a passive filling design, similar to that embodiments in FIGS. 44B to 46B. FIG. 48A shows a top down view of one embodiment of device 3200. FIG. 48B shows a side view of one embodiment of device 3200. FIG. 48C shows a slightly exploded view of one embodiment of device 3200.

FIG. 49 shows a fully exploded view of the embodiment of device 3200. FIG. 49 shows a first collection tube 3202 and a second collection tube 3204. FIG. 49 further shows a housing with a shaped interior that is configured to bring the first collection tube 3202 and the second collection tube 3204 in a Y-shaped configuration wherein the inlets of the tubes 3202 and 3204 are maintained in close proximity. A body is provided to join the first collection tube 3202 and the second collection tube 3204 with the containers 3210 in a unified holder 3212 with support 3214.

Figure 50:
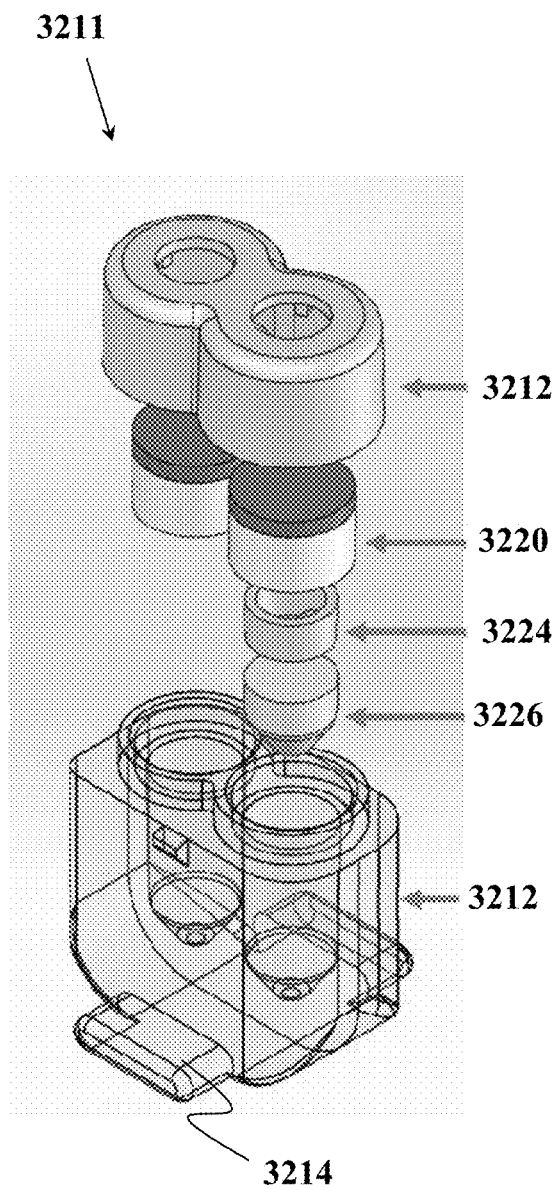
FIGS. 50 and 51 show various views of another embodiment of a device as described herein.
Figure 51:
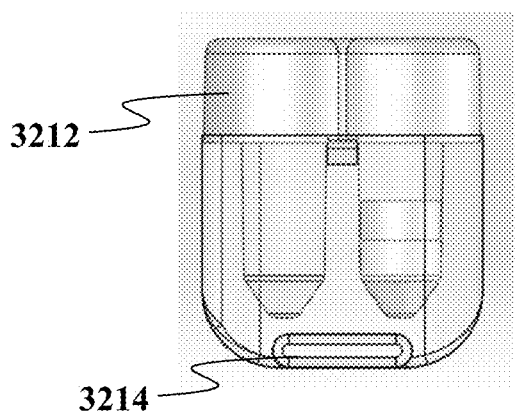

FIG. 50 shows an exploded perspective view of the sample holding portion 3211 with the containers therein a unified holder 3212. FIG. 50 shows a cap 3220 that may be for each container or an integrated cap to cover both containers. Optionally, both containers may have a vented, pierceable/re-sealable closure 3222, which may be but is not limited to a silicone coated porex disc. One embodiment may have a floater 3224 and a separation gel 3226 for a side of the container that is configured to hold sample that will be separated using a separation gel 3228. Optionally, some embodiments may have the separation gel 3226 in both containers.

Figure 52:
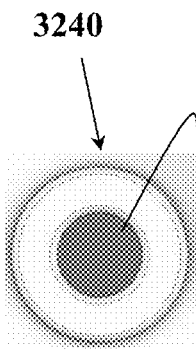
FIGS. 52 to 55 show various views of another embodiment of a sample collection container as described herein.
Figure 53:
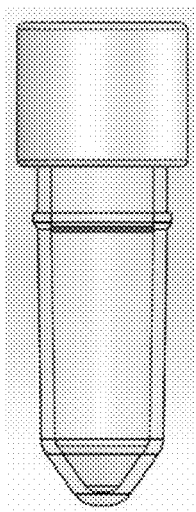

As seen in FIGS. 52 to 55, for purposes of transport, there may be an additional cap 3240 that covers the air vent area. As seen in FIG. 52, some embodiments of cap 3240 may include an opening 3242 that allows for insertion of a member into the vented, pierceable/re-sealable closure 3222. Optionally, some embodiments may provide a gas barrier by way of material that covers any vent opening(s) 3242 by way of adhesion or other attachment technique. Optionally, a still further embodiment may have a shipping container, storage container, or the like wherein a gasket is provided and a snap-fit feature may maintain contact between the vent feature of the container and the gasket on the shipping container so as to provide a gas seal. In some embodiments, the containers can be loaded and held in an inverted orientation so that the coupling feature can press the container to a support surface in the shipping or storage container. Optionally, some embodiments may be positioned in the shipping container in a lateral orientation. Optionally, some embodiments may be positioned in the shipping container in an angled orientation.

Optionally, methods and devices are provided for sealing the vented closure for sample storage and shipping and tamper proofing. In one non-limiting example, an adhesive layer such as but not limited to a sticker or the like over the opening 3242.

Figure 56A:
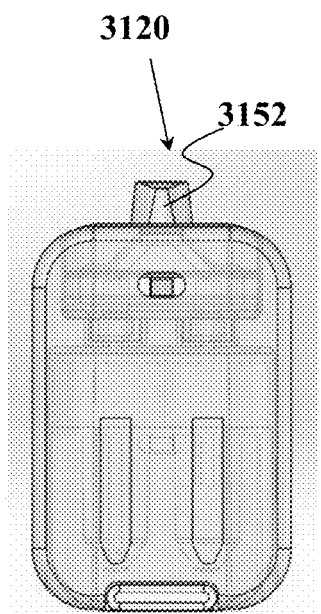
FIGS. 56A to 56C show various views of another embodiment of a device as described herein.
Figure 56B:
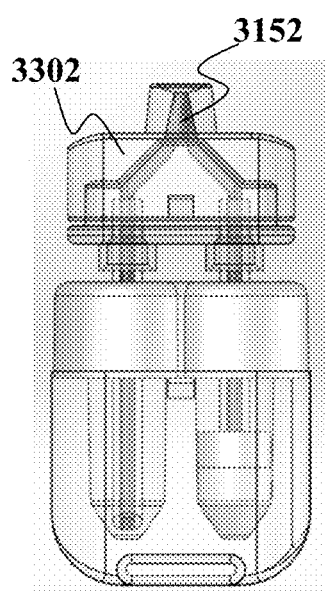
Figure 56C:
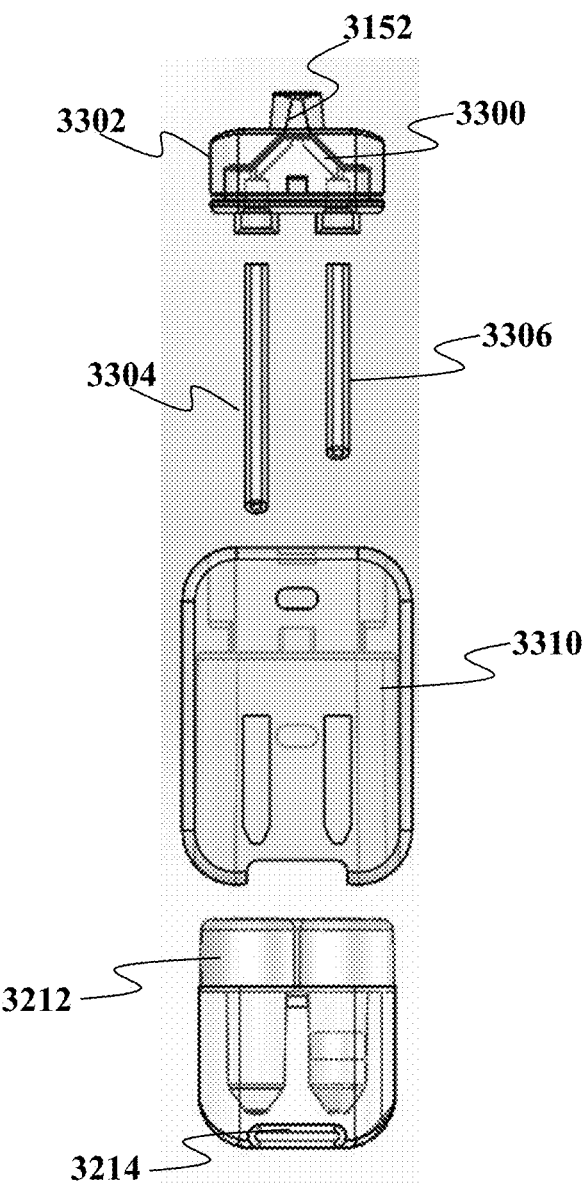

Referring now to FIGS. 56A to 56C, embodiments similar to that of FIGS. 45A and 45B are shown in further detail. As seen in the exploded view of FIG. 56C, the fluid pathway may be comprised of channels 3300 in a housing portion 3302 and individual discrete tubes 3304 or 3306 that may be of the same or different lengths. A body portion 3310 is used to hold the various components such as the tubes and the containers together.

Referring now to FIGS. 57A to 57C, various views of a housing portion 3302 is shown. In one non-limiting example, at least one "bubble popper" may be used in at least one location along the flow path, which in one non-limiting example may be a method for splitting capillary flow from a single channel to multiple channels more effectively. FIG. 18 shows one embodiment with a popper 3330. As seen in FIG. 57A, the housing portion 3302 can be formed from two different parts 3334 and 3336. The protrusion or other formation that acts as a fluid flow "popper" 3330 can be positioned on either part 3334 or 3336.

Figure 59A:
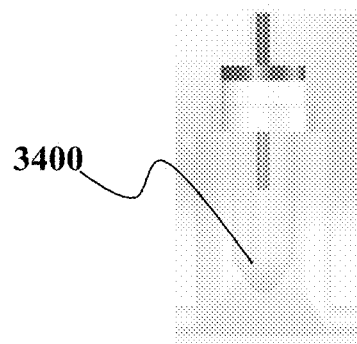
FIGS. 59A to 59D show various views of one embodiment of a method for filling container as described herein.
Figure 59B:
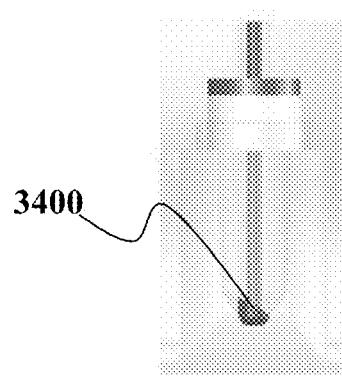
Figure 59C:
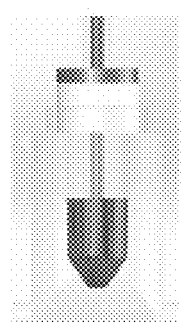
Figure 59D:
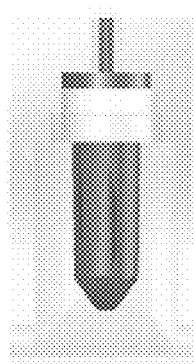

In one non-limiting example, flow through capillary device filling comprises a method for directly dispensing fluid from a capillary tube into a container (such as but not limited to a small volume sample container) using capillary driven flow. An interface between an opening of the capillary tube and an adjacent wall surface can provide a second capillary zone to pull sample fluid out of the capillary tube such as that seen in FIGS. 58A to 58C. More specifically as seen in FIGS. 58B and 59B, the close proximity with the bottom and side walls of the interior of the container and optionally with a beveled or angled opening allows for the secondary capillarity to assist in flow. Although not limited to the following, this can be of use to overcome capillary force inherent to the capillary tube with draws fluid therein but also tends to resist, to some degree, outflow for liquid from the capillary tube. Some embodiments may have beveled distal end 3400 of the capillary tube to improve outflow of liquid from the capillary tube. Optionally, a protrusion such as but not limited to a pin, shaft, pyramid, or the like can also be positioned in the vessel near an outlet of the capillary tube to assist in an initial release of fluid from the capillary tube. Once there is some liquid exiting from the capillary tube, a second capillary system comprising an outer side wall of the capillary tube and an inner side wall of the sample container will draw fluid into the container. Typically, the distance from the wall of the vessel to the outlet of the capillary tube is about 1.5 mm or less. Optionally, the distance from the wall of the vessel to the outlet of the capillary tube is about 1 mm or less. The sooner the fluid from the tip of the capillary tube makes contact with a wall of the sample container, the sooner that the secondary capillary system can begin drawing fluid out of the capillary tube. As seen herein in FIG. 59C, the capillary tube can provide for "bottom-up" filling of the sample container as its opening is located towards a bottom of the sample container. By way of non-limiting example, a bottom-up filling may be desirable to minimize air bubbles that may be created from a top-down filling of the sample container, where top-down filling increases the likelihood of bubbles. Of course, in some alternative embodiments, top-down filling of sample containers is not excluded. Optionally, some embodiments may comprise a method that has the user hold the collection device at an angle relative to horizontal so that there may be a gravity component to assist fluid flow out of the capillary tube.

In one non-limiting example, venous blood collection device that fills passively using the patient's blood flow (all the way into the small volume sample container). In one non-limiting example, this a pass-through embodiment, wherein the capillary tubes have less volume than the volumes in the sample containers. In one embodiment, the tube volume is at least 10 times less than the volume of the sample container. Optionally, the tube interior volume is at least 9 times less than the volume of the sample container. Optionally, the tube interior volume is at least 8 times less than the volume of the sample container. Optionally, the tube interior volume is at least 7 times less than the volume of the sample container. Optionally, the tube interior volume is at least 6 times less than the volume of the sample container. Optionally, the tube interior volume is at least 5 times less than the volume of the sample container. In the pass-through, the sample flows through the tube and into the sample container without a separate initiation step. Because in some embodiments there is a direct fluid circuit from the inlet to the interior of the sample container, there may be a sterility barrier over inlet or other barrier to prevent exposing the interior of the sample container to external environment prior to the collection event.

In one non-limiting example, fingerstick blood collection device that can passively fill using the flow-through technique combined with the vented closure over the vessel opening.

Figure 60:
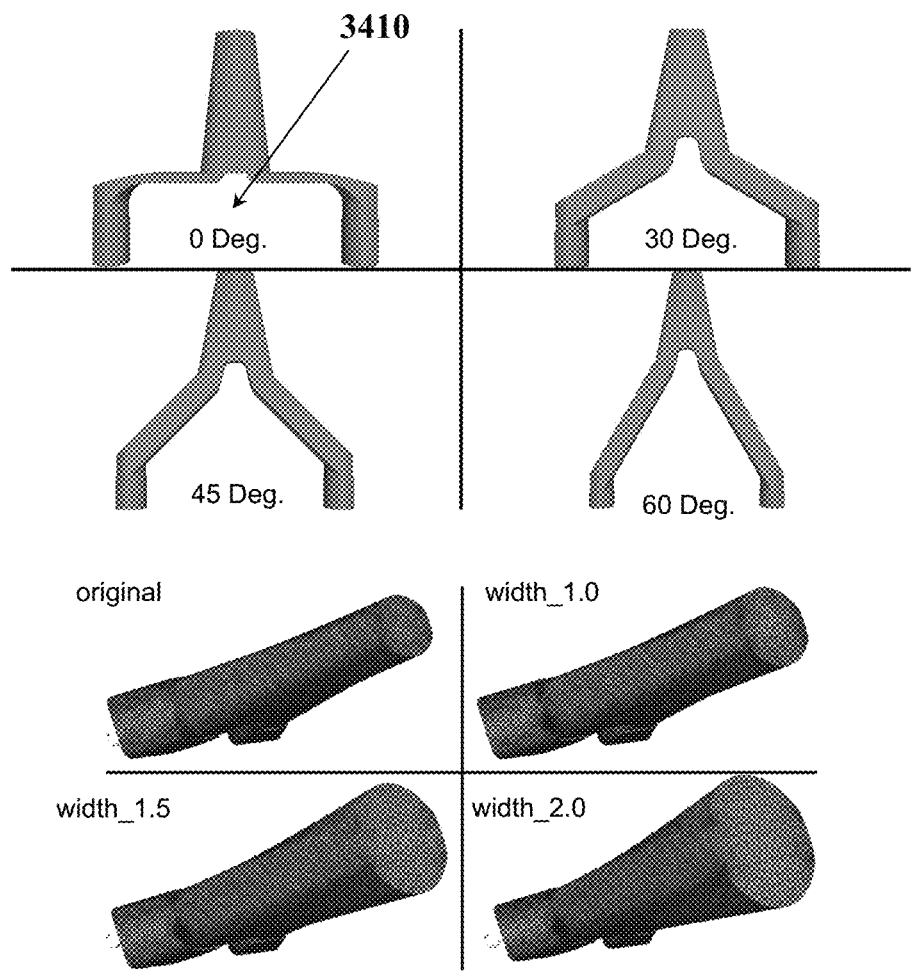
FIG. 60 shows various views of an embodiment of portions of a device as described herein.

Referring now to FIG. 60, various geometries are shown that can be adapted for use in defining the shape of channels in a housing 3302. As seen in FIG. 60, some embodiment may have funneling or other shape to the sample inlet pathway. Optionally, some embodiments may vary the angle relative to horizontal of the pathways that are splitting from off from the common inlet pathway.

Figure 63:
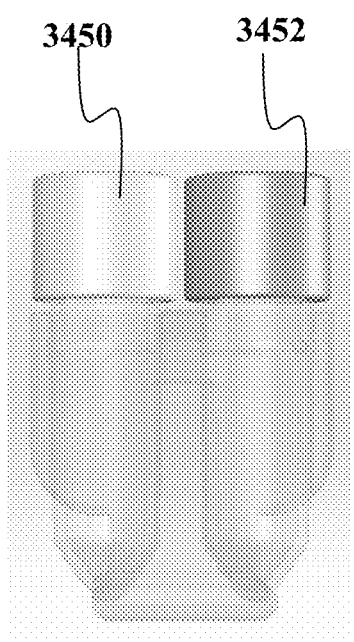
FIGS. 63 to 64 show various views of one embodiment of a portion of a device and the device as described herein.

FIGS. 61A to 62D show various sizes and shapes that be used with integrated and individual sample containers. FIGS. 63 and 64 show that one of the caps 3450 and the other cap 3452 can be different colored to alert a user as to a difference in the sample container with that cap, such as but not limited to a different anti-coagulant therein, the presence of separation gel, or other feature about the container. In the flow-through configuration, anti-coagulant may be in the container as well as or in-place of being in the sample collection channels.

Figure 54:
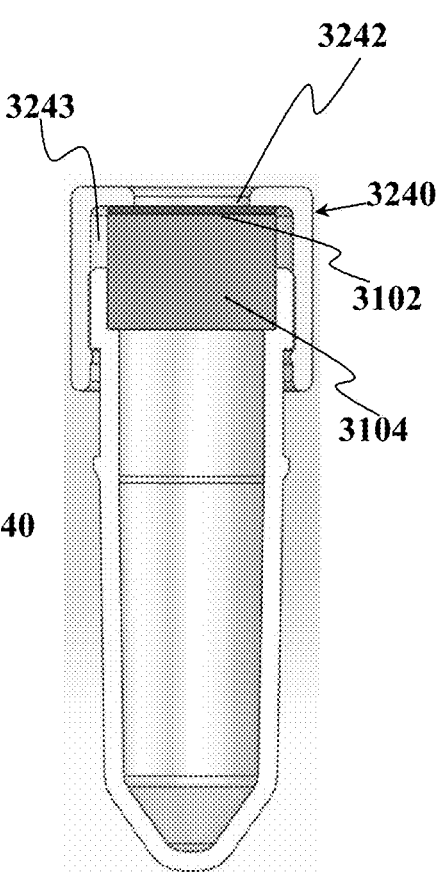
Figure 55:
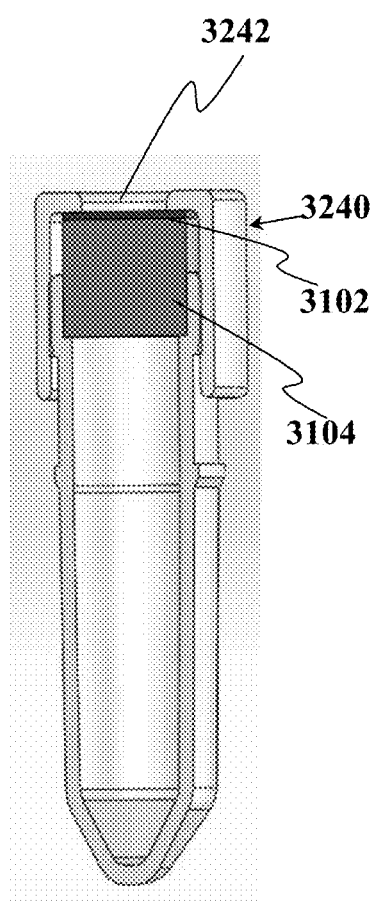

Referring now to FIGS. 65 and 66, a still further embodiment of a gas permeable, liquid impermeable, and re-sealable plug or member is shown. As seen in FIG. 65, an outward facing surface has a layer 3110 that is a re-sealable member or self-healing member that is not gas permeable. Coupled to that is a porous gas permeable member 3102. FIG. 65 shows a O-shaped lower member 3500 with a large central opening 3502. The member 3502 may be of a material that is more pliable than the material used for the porous gas permeable member 3102. In some embodiments, the porous gas permeable member 3102 may be a more rigid material and thus having the more pliable lower member 3502 may improve sealing, seating, or general fit between the container wall and the porous gas permeable member 3102. In some embodiments, the material for member 3500 may be silicone or the same material used for the layer 3110. The opening 3502 in the member 3500 allows for easy passage of a channel, needle, or capillary tube therethrough. The opening 3502 also allows for gas in the container to vent outward from the container through the opening 3502 and then out the gas porous portion 3102 without allowing liquid to escape along the same path. As seen in FIG. 54, a cap 3240 can be designed with some pathway or vent space 3243 to allow for displaced gas to escape from the vessel.

Optionally, FIG. 66 shows yet another embodiment wherein the lower member 3510 comprises a plurality of openings 3512 versus a single large opening 3502. Optionally, some embodiments may combine both the large opening 3502 and a plurality of smaller openings 3512 in the lower member to provide pliability at the interface with the container and still provide pathways for gas permeability.

While the teachings has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, with any of the above embodiments, it should be understood that the fluid sample may be whole blood, diluted blood, interstitial fluid, sample collected directly from the patient, sample that is on a surface, sample after some pre-treatment, or the like. Those of skill in the art will understand that alternative embodiments may have more than one container that may be sequentially operably coupled to the needle or opening of the channel to draw fluid in the container. Optionally, some embodiments may have the containers configured to operably couple to the channels simultaneously. Some embodiments may integrate a lancing device or other wound creation device with the sample collection device to bring targeted sample fluid to a tissue surface and then collect the sample fluid, all using a single device. By way of nonlimiting example, a spring actuated, mechanically actuated, and/or electromechanically actuated tissue penetrating member may be mounted to have a penetrating tip exiting near an end of the sample collection device near sample collection channel openings so that the wound site that is created will also be along the same end of the device as the collection openings. Optionally, an integrated device may have collection openings on one surface and tissue penetrating elements along another surface of the device. In any of the embodiments disclosed herein, the first opening of the collection channel may have a blunt shape, which is configured to not readily puncture human skin.

Additionally, the use of heat patches on the finger or other target tissue can increase blood flow to the target area and thus increase the speed with which sufficient blood or other bodily fluid can be drawn from the subject. In one non-limiting example, the heating is used to bring the target tissue to about 40 C to 50 C. Optionally, the heat brings target tissue to a temperature range of about 44 to 47 C.

Furthermore, those of skill in the art will recognize that any of the embodiments as described herein can be applied to collection of sample fluid from humans, animals, or other subjects. Some embodiments as described herein may also be suitable for collection of non-biological fluid samples. Some embodiment may use containers that are not removable from the carrier. Some may have the fluid sample, after being metered in the sample collection portion, be directed by the second motive force to a cartridge that is then placed into an analyte or other analysis device. Optionally, it should be understood although many embodiments show the containers in the carriers, embodiments where the containers are bare or not mounted in carrier are not excluded. Some embodiments may have the containers that are separate from the device and are only brought into fluid communication once the channels have reached minimum fill levels. For example, the containers may be held in a different location and are only brought into contact by a technician once sufficient amount of blood or sample fluid is in the sample collection device. At that time, the containers may be brought into fluid communication simultaneously or sequentially to one or more of the channels of the sample collection device.

Optionally, some embodiments of the collection unit may have a cross-sectional shape with an asymmetry, a protrusion, or other feature that serves as a keying feature for orienting the sample collection unit in any receiving device or structure.

By way of non-limiting example, some embodiments may handle other types of samples and necessarily biological samples. Although many illustrations are shown with only a single inlet port, it should be understood that some embodiments may have at least two inlet ports. In some embodiments, both inlet ports are on the same end of the device. Optionally, some embodiments may have inlet ports on the same surface of the device. Optionally, at least the two inlets are adjacent to each other. Optionally, there are at least three inlet ports. Optionally, at least two inlet ports are each defined by at least one capillary tube. In this embodiment where each inlet has its own capillary tube, at least one tube directs fluid to a non-separation pathway while a second tube directs fluid to a separation pathway. Optionally, some embodiments may combine inlets formed by capillary tubes with inlet(s) associated with a non-capillary pathway. Some embodiments may have the inlet along a centerline axis of the device. Optionally, some embodiments may have the inlet aligned off the centerline. Optionally, some embodiments may orient the inlet to be along or parallel to the axis of the centerline of the device. Optionally, some embodiments may orient the inlet along an axis that is at an angle to the plane of the device. Optionally, instead of having the inlet at one end of the separation device, it should be understood that some embodiments may have the inlet directly over at least one portion of the separation device. In this manner, the opening may direct fluid onto the membrane with a minimal amount of travel in a lateral tube or pathway. Optionally, having anti-coagulant in the sample collection channel allows for sample to be anti-coagulated without having the operator tilt the device up and down multiple times to mix the anticoagulant. Optionally, having anti-coagulant in the sample collection channel allows for sample to be anti-coagulated by having the operator tilt the device up and down only once to mix the anticoagulant.

Optionally, some embodiments may be configured with a co-axial design with at least one lumen within another. Optionally, some embodiments may use an outside port on a lateral surface of the collection device along with at least one port at one end of the device.

Optionally, some embodiments may have a portion of the fluid circuit portion that includes the separation member fluidly coupled to a second device portion. Some embodiments may have this combination of fluidic circuit portion 800 in fluid communication with at least a portion, such as but not limited to being in a test strip configuration. Some embodiments may have this combination in a lateral flow device configuration. Some embodiments may have a unibody structure or other merged structure that is formed to provide support to both portions. In some embodiments, the second region also provides a motive force such as but not limited to wicking force associated with such material in at least a portion of the second region.

Optionally, it should be understood that some embodiments may have at least one formed component separation pathway for use in a non-diagnostic device. By way of non-limiting example, the device may be for sample collection, where no diagnosis occur on the device. Of course, some alternative embodiments may have one or more pathways for use for diagnosis.

Optionally, some embodiments may provide a vibration motion source, such as but not limited to one built into the device and/or in an external device use to process the sample container, to assist in fluid flow within device, during the collection, or post-collection. Some embodiments may use this vibration to assist flow or to remove any air pockets that may be created, such as but not limited to when doing a top-down fill. Optionally, some embodiments may provide more periodic or pulse type force to assist in fluid flow.

It should be understood that although many components herein are shown to be in alignment in the same plane or parallel planes, some embodiments may be configured to have one or more component in a plane angled to or orthogonal to a plane of the fluid collection circuit in the fluidic collection circuit portion. The fluid collection circuit is not in a flat planar device and may be in a curved configuration. Optionally, some embodiments may have it a cone configuration. Optionally, some embodiments may have it device with a polygonal cross-sectional shape.

It should also be understood that in many embodiments, the fluidic circuit portion may be made of a transparent material. Optionally, the fluidic circuit portion may be made of a translucent material. Optionally, portions of the fluidic circuit portion may be covered with paint or other opaque material, be formed of an opaque material, or the like such that only portions that may contain fluid are transparent or translucent so as to provide an indicator of fill level. Such an embodiment may have all or only a portion of the fluidpath visible to the user. In one non-limiting example, bar codes, color-coding, visual information, instructions, instructions for use, fill-indicator, advertising, child-appealing aesthetics, texturing, texturing for grip purpose, texturing for contour, texturing to provide feedback such as orientation of the front of the device, or other coating may be used hereon.

Optionally, some embodiments may include an intermediary structure between the fluid circuit in distal end portion of the device and the sample collection unit which has the sample container(s). This intermediary structure can be in the fluid pathway and provide certain function such as but not limited to introducing a material into the collected fluid such as but not limited to anti-coagulant. Optionally, the intermediary structure in the fluid path may provide another route, such as switch or connection pathway, to add additional sample or other liquid material into the collected fluid.

Optionally, some embodiments may have disposable portion(s) and reusable portions, wherein the reusable portions can be mated with the disposable portion(s) to form another collection device. By way of non-limiting example, a reusable portion may be one that does not directly contact the sample fluid or filtered fluid.

Additionally, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a size range of about 1 nm to about 200 nm should be interpreted to include not only the explicitly recited limits of about 1 nm and about 200 nm, but also to include individual sizes such as 2 nm, 3 nm, 4 nm, and sub-ranges such as 10 nm to 50 nm, 20 nm to 100 nm, etc. . . . .

The publications discussed or cited herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All publications mentioned herein are incorporated herein by reference to disclose and describe the structures and/or methods in connection with which the publications are cited. The following applications are fully incorporated herein by reference for all purposes: U.S. Patent Application Ser. No. 61/952,125, U.S. Patent Application Ser. No. 61/952,130, U.S. Patent Application Ser. No. 62/051,906, U.S. Patent Application Ser. No. 61/952,125 filed Mar. 12, 2014, U.S. Patent Application Ser. No. 61/952,130 filed Mar. 12, 2014, U.S. Patent Application Ser. No. 61/948,542 filed Mar. 5, 2014, U.S. Patent Application Ser. No. 61/952,112 filed Mar. 12, 2014, Patent Application Ser. No. PCT/US14/30070 filed Mar. 15, 2014, U.S. Provisional Patent Application No. 61/435,250, filed Jan. 21, 2011 ("SYSTEMS AND METHODS FOR SAMPLE USE MAXIMIZATION"), and U.S. Patent Publication No. 2009/0088336 ("MODULAR POINT-OF-CARE DEVICES, SYSTEMS, AND USES THEREOF").

EMBODIMENTS

In one embodiment described herein, a device for collecting a bodily fluid sample from a subject is provided comprising: at least two sample collection pathways configured to draw the bodily fluid sample into the device from a single end of the device in contact with the subject, thereby separating the fluid sample into two separate samples; a second portion comprising a plurality of sample containers for receiving the bodily fluid sample collected in the sample collection pathways, the sample containers operably engagable to be in fluid communication with the sample collection pathways, whereupon when fluid communication is established, the containers provide a motive force to move a majority of the two separate samples from the pathways into the containers.

In another embodiment described herein, a device for collecting a bodily fluid sample is provided comprising: a first portion comprising at least one fluid collection location leading to at least two sample collection pathways configured to draw the fluid sample therein via a first type of motive force; a second portion comprising a plurality of sample containers for receiving the bodily fluid sample collected in the sample collection pathways, the sample containers operably engagable to be in fluid communication with the sample collection pathways, whereupon when fluid communication is established, the containers provide a second motive force different from the first motive force to move a majority of the bodily fluid sample from the pathways into the containers; wherein at least one of the sample collection pathways comprises a fill indicator to indicate when a minimum fill level has been reached and that at least one of the sample containers can be engaged to be in fluid communication with at least one of the sample collection pathways.

In another embodiment described herein, a device for collecting a bodily fluid sample is provided comprising a first portion comprising at least two sample collection channels configured to draw the fluid sample into the sample collection channels via a first type of motive force, wherein one of the sample collection channels has an interior coating designed to mix with the fluid sample and another of the sample collection channels has another interior coating chemically different from said interior coating; a second portion comprising a plurality of sample containers for receiving the bodily fluid sample collected in the sample collection channels, the sample containers operably engagable to be in fluid communication with the collection channels, whereupon when fluid communication is established, the containers provide a second motive force different from the first motive force to move a majority of the bodily fluid sample from the channels into the containers; wherein containers are arranged such that mixing of the fluid sample between the containers does not occur.

In another embodiment described herein, a device for collecting a bodily fluid sample is provided comprising: a first portion comprising a plurality of sample collection channels, wherein at least two of the channels are configured to simultaneously draw the fluid sample into each of the at least two sample collection channels via a first type of motive force; a second portion comprising a plurality of sample containers for receiving the bodily fluid sample collected in the sample collection channels, wherein the sample containers have a first condition where the sample containers are not in fluid communication with the sample collection channels, and a second condition where the sample containers are operably engagable to be in fluid communication with the collection channels, whereupon when fluid communication is established, the containers provide a second motive force different from the first motive force to move bodily fluid sample from the channels into the containers.

In another embodiment described herein, a sample collection device is provided comprising: (a) a collection channel comprising a first opening and a second opening, and being configured to draw a bodily fluid sample via capillary action from the first opening towards the second opening; and (b) a sample container for receiving the bodily fluid sample, the container being engagable with the collection channel, having an interior with a vacuum therein, and having a cap configured to receive a channel; wherein the second opening is defined by a portion the collection channel configured to penetrate the cap of the sample container, and to provide a fluid flow path between the collection channel and the sample container, and the sample container has an interior volume no greater than ten times larger than the interior volume of the collection channel.

In another embodiment described herein, a sample collection device is provided comprising: (a) a collection channel comprising a first opening and a second opening, and being configured to draw a bodily fluid sample via capillary action from the first opening towards the second opening; (b) a sample container for receiving the bodily fluid sample, the container being engageable with the collection channel, having an interior with a vacuum therein, and having a cap configured to receive a channel; and (c) an adaptor channel configured to provide a fluid flow path between the collection channel and the sample container, having a first opening and a second opening, the first opening being configured to contact the second opening of the collection channel, the second opening being configured to penetrate the cap of the sample container.

In another embodiment described herein, a sample collection device is provided comprising: (a) a body, containing a collection channel, the collection channel comprising a first opening and a second opening, and being configured to draw a bodily fluid via capillary action from the first opening towards the second opening; (b) a base, containing a sample container for receiving the bodily fluid sample, the sample container being engageable with the collection channel, having an interior with a vacuum therein, and having a cap configured to receive a channel; and (c) a support, wherein, the body and the base are connected to opposite ends of the support, and are configured to be movable relative to each other, such that sample collection device is configured to have an extended state and a compressed state, wherein at least a portion of the base is closer to the body in the extended state of the device than in the compressed state, the second opening of the collection channel is configured to penetrate the cap of the sample container, in the extended state of the device, the second opening of the collection channel is not in contact with the interior of the sample container, and in the compressed state of the device, the second opening of the collection channel extends into the interior of the sample container through the cap of the container, thereby providing fluidic communication between the collection channel and the sample container.

In another embodiment described herein, a sample collection device is provided comprising: (a) a body, containing a collection channel, the collection channel comprising a first opening and a second opening, and being configured to draw a bodily fluid via capillary action from the first opening towards the second opening; (b) a base, containing a sample container for receiving the bodily fluid sample, the sample container being engageable with the collection channel, having an interior with a vacuum therein and having a cap configured to receive a channel; (c) a support, and (d) an adaptor channel, having a first opening and a second opening, the first opening being configured to contact the second opening of the collection channel, and the second opening being configured to penetrate the cap of the sample container, wherein, the body and the base are connected to opposite ends of the support, and are configured to be movable relative to each other, such that sample collection device is configured to have an extended state and a compressed state, wherein at least a portion of the base is closer to the body in the extended state of the device than in the compressed state, in the extended state of the device, the adaptor channel is not in contact with one or both of the collection channel and the interior of the sample container, and in the compressed state of the device, the first opening of the adaptor channel is in contact with the second opening of the collection channel, and the second opening of the adaptor channel extends into the interior of the sample container through the cap of the container, thereby providing fluidic communication between the collection channel and the sample container.

In another embodiment described herein, a device for collecting a fluid sample from a subject is provided comprising: (a) a body containing a collection channel, the collection channel comprising a first opening and a second opening, and being configured to draw a bodily fluid via capillary action from the first opening towards the second opening; (b) a base, engageable with the body, wherein the base supports a sample container, the container being engageable with the collection channel, having an interior with a vacuum therein, and having a cap configured to receive a channel; wherein the second opening of the collection channel is configured to penetrate the cap of the sample container, and to provide a fluid flow path between the collection channel and the sample container.

In another embodiment described herein, a device for collecting a fluid sample from a subject is provided comprising: (a) a body containing a collection channel, the collection channel comprising a first opening and a second opening, and being configured to draw a bodily fluid via capillary action from the first opening towards the second opening; (b) a base, engagable with the body, wherein the base supports a sample container, the sample container being engageable with the collection channel, having an interior with a vacuum therein and having a cap configured to receive a channel; and (c) an adaptor channel, having a first opening and a second opening, the first opening being configured to contact the second opening of the collection channel, and the second opening being configured to penetrate the cap of the sample container.

It should be understood that one or more of the following features may be adapted for use with any of the embodiments described herein. By way of non-limiting example, the body may comprise of two collection channels. Optionally, the interior of the collection channel(s) are coated with an anticoagulant. Optionally, the body comprises a first collection channel and a second collection channel, and the interior of the first collection channel is coated with a different anticoagulant than the interior of the second collection channel. Optionally, the first anticoagulant is ethylenediaminetetraacetic acid (EDTA) and the second anticoagulant is different from EDTA. Optionally, the first anticoagulant is citrate and the second anticoagulant is different from citrate. Optionally, the first anticoagulant is heparin and the second anticoagulant is different from heparin. Optionally, one anticoagulant is heparin and the second anticoagulant is EDTA. Optionally, one anticoagulant is heparin and the second anticoagulant is citrate. Optionally, one anticoagulant is citrate and the second anticoagulant is EDTA. Optionally, the body is formed from an optically transmissive material. Optionally, the device includes the same number of sample containers as collection channels. Optionally, the device includes the same number of adaptor channels as collection channels. Optionally, the base contains an optical indicator that provides a visual indication of whether the sample has reached the sample container in the base. Optionally, the base is a window that allows a user to see the container in the base. Optionally, the support comprises a spring, and spring exerts a force so that the device is at the extended state when the device is at its natural state. Optionally, the second opening of the collection channel or the adaptor channel is capped by a sleeve, wherein said sleeve does not prevent movement of bodily fluid via capillary action from the first opening towards the second opening. Optionally, the sleeve contains a vent. Optionally, each collection channel can hold a volume of no greater than 500 uL. Optionally, each collection channel can hold a volume of no greater than 200 uL. Optionally, each collection channel can hold a volume of no greater than 100 uL. Optionally, each collection channel can hold a volume of no greater than 70 uL. Optionally, each collection channel can hold a volume of no greater than 500 uL. Optionally, each collection channel can hold a volume of no greater than 30 uL. Optionally, the internal circumferential perimeter of a cross-section of each collection channel is no greater than 16 mm. Optionally, the internal circumferential perimeter of a cross-section of each collection channel is no greater than 8 mm. Optionally, the internal circumferential perimeter of a cross-section of each collection channel is no greater than 4 mm. Optionally, the internal circumferential perimeter is a circumference. Optionally, the device comprises a first and a second collection channel, and the opening of the first channel is adjacent to an opening of said second channel, and the openings are configured to draw blood simultaneously from a single drop of blood. Optionally, the opening of the first channel and the opening of the second channel have a center-to-center spacing of less than or equal to about 5 mm. Optionally, each sample container has an interior volume no greater than twenty times larger than the interior volume of the collection channel with which it is engagable. Optionally, each sample container has an interior volume no greater than ten times larger than the interior volume of the collection channel with which it is engagable. Optionally, each sample container has an interior volume no greater than five times larger than the interior volume of the collection channel with which it is engagable. Optionally, each sample container has an interior volume no greater than two times larger than the interior volume of the collection channel with which it is engagable. Optionally, establishment of fluidic communication between the collection channel and the sample container results in transfer of at least 90% of the bodily fluid sample in the collection channel into the sample container.

It should be understood that one or more of the following features may be adapted for use with any of the embodiments described herein. Optionally, establishment of fluidic communication between the collection channel and the sample container results in transfer of at least 95% of the bodily fluid sample in the collection channel into the sample container. Optionally, establishment of fluidic communication between of the collection channel and the sample container results in transfer of at least 98% of the bodily fluid sample in the collection channel into the sample container. Optionally, establishment of fluidic communication between the collection channel and the sample container results in transfer of the bodily fluid sample into the sample container and in no more than ten uL of bodily fluid sample remaining in the collection channel. Optionally, establishment of fluidic communication between the collection channel and the sample container results in transfer of the bodily fluid sample into the sample container and in no more than five uL of bodily fluid sample remaining in the collection channel. Optionally, engagement of the collection channel with the sample container results in transfer of the bodily fluid sample into the sample container and in no more than 2 uL of bodily fluid sample remaining in the collection channel.

In another embodiment described herein, a method is provided comprising contacting one end of a sample collection device to a bodily fluid sample to split the sample into at least two portions by drawing the sample into at least two collection channels of the sample collection device by way of a first type of motive force; establishing fluid communication between the sample collection channels and the sample containers after a desired amount of sample fluid has been confirmed to be in at least one of the collection channels, whereupon the containers provide a second motive force different from the first motive force to move each of the portions of bodily fluid sample into their respective containers.

In another embodiment described herein, a method is provided comprising metering a minimum amount of sample into at least two channels by using a sample collection device with at least two of the sample collection channels configured to simultaneously draw the fluid sample into each of the at least two sample collection channels via a first type of motive force; after a desired amount of sample fluid has been confirmed to be in the collection channels, fluid communication is established between the sample collection channels and the sample containers, whereupon the containers provide a second motive force different from the first motive force use to collect the samples to move bodily fluid sample from the channels into the containers.

In another embodiment described herein, a method of collecting a bodily fluid sample is provided comprising (a) contacting a bodily fluid sample with a device comprising a collection channel, the collection channel comprising a first opening and a second opening, and being configured to draw a bodily fluid via capillary action from the first opening towards the second opening, such that the bodily fluid sample fills the collection channel from the first opening through the second opening; (b) establishing a fluid flow path between the collection channel and the interior of a sample container, said sample container having an interior volume no greater than ten times larger than the interior volume of the collection channel and having a vacuum prior to establishment of the fluid flow path between the collection channel and the interior of the sample container, such that establishment of the fluid flow path between the collection channel and the interior of the sample container generates a negative pressure at the second opening of the collection channel, and the fluidic sample is transferred from the collection channel to the interior of the sample container.

In another embodiment described herein, a method of collecting a bodily fluid sample is provided comprising (a) contacting a bodily fluid sample with any collection device as described herein, such that the bodily fluid sample fills the collection channel from the first opening through the second opening of at least one of the collection channel(s) in the device; and (b) establishing a fluid flow path between the collection channel and the interior of the sample container, such that establishing a fluid flow path between the collection channel and the interior of the sample container generates a negative pressure at the second opening of the collection channel, and the fluidic sample is transferred from the collection channel to the interior of the sample container.

It should be understood that one or more of the following features may be adapted for use with any of the embodiments described herein. Optionally, the collection channel and the interior of the sample container are not brought into fluid communication until the bodily fluid reaches the second opening of the collection channel. Optionally, the device comprises two collection channels, and the collection channels and the interior of the sample containers are not brought into fluidic communication until the bodily fluid reaches the second opening of both collection channels. Optionally, the second opening of the collection channel in the device is configured to penetrate the cap of the sample container, and wherein a fluidic flow path between the second opening of the collection channel and the sample container is established by providing relative movement between the second opening of the collection channel and the sample container, such that the second opening of the collection channel penetrates the cap of the sample container. Optionally, the device comprises an adaptor channel for each collection channel in the device, the adaptor channel having a first opening and a second opening, the first opening being configured to contact the second opening of the collection channel, and the second opening being configured to penetrate the cap of the sample container, and wherein a fluidic flow path between the collection channel and the sample container is established by providing relative movement between two or more of: (a) the second opening of the collection channel, (b) the adaptor channel, and (c) the sample container, such that the second opening of the adaptor channel penetrates the cap of the sample container.

In another embodiment described herein, a method for collecting a bodily fluid sample from a subject is provided comprising: (a) bringing a device comprising a first channel and a second channel into fluidic communication with a bodily fluid from the subject, each channel having an input opening configured for fluidic communication with said bodily fluid, each channel having an output opening downstream of the input opening of each channel, and each channel being configured to draw a bodily fluid via capillary action from the input opening towards the output opening; (b) bringing, through the output opening of each of the first channel and the second channel, said first channel and said second channel into fluidic communication with a first container and a second container, respectively; and (c) directing said bodily fluid within each of said first channel and second channel to each of said first container and second container with the aid of: (i) negative pressure relative to ambient pressure in said first container or said second container, wherein said negative pressure is sufficient to effect flow of said bodily fluid through said first channel or said second channel into its corresponding container, or (ii) positive pressure relative to ambient pressure upstream of said first channel or said second channel, wherein said positive pressure is sufficient to effect flow of said whole blood sample through said first channel or said second channel into its corresponding container.

In another embodiment described herein, a method of manufacturing a sample collection device is provided comprising forming one portion of a sample collection device having at least two channels configured to simultaneously draw the fluid sample into each of the at least two sample collection channels via a first type of motive force; forming sample containers, whereupon the containers are configured to be coupled to the sample collection device to the provide a second motive force different from the first motive force use to collect the samples to move bodily fluid sample from the channels into the containers.

In another embodiment described herein, computer executable instructions are provided for performing a method comprising: forming one portion of a sample collection device having at least two channels configured to simultaneously draw the fluid sample into each of the at least two sample collection channels via a first type of motive force.

In another embodiment described herein, computer executable instructions for performing a method comprising: forming sample containers, whereupon the containers are configured to be coupled to the sample collection device to provide a second motive force different from the first motive force use to collect the samples to move bodily fluid sample from the channels into the containers.

In yet another embodiment described herein, a device for collecting a bodily fluid sample from a subject, the device comprising: means for drawing the bodily fluid sample into the device from a single end of the device in contact with the subject, thereby separating the fluid sample into two separate samples; means for transferring the fluid sample into a plurality of sample containers, wherein the containers provide a motive force to move a majority of the two separate samples from the pathways into the containers.

While the above is a complete description of the preferred embodiment as described herein, it is possible to use various alternatives, modifications and equivalents. Therefore, the scope of the present invention should be determined not with reference to the above description but should, instead, be determined with reference to the appended claims, along with their full scope of equivalents. Any feature, whether preferred or not, may be combined with any other feature, whether preferred or not. The appended claims are not to be interpreted as including means-plus-function limitations, unless such a limitation is explicitly recited in a given claim using the phrase "means for." It should be understood that as used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Finally, as used in the description herein and throughout the claims that follow, the meanings of "and" and "or" include both the conjunctive and disjunctive and may be used interchangeably unless the context expressly dictates otherwise. Thus, in contexts where the terms "and" or "or" are used, usage of such conjunctions do not exclude an "and/or" meaning unless the context expressly dictates otherwise.

What is claimed is:

1. A device for collecting a bodily fluid sample, the device comprising:
   a first portion comprising a plurality of capillary collection channels;
   a second portion comprising a plurality of sample containers for receiving the bodily fluid sample collected in the collection channels, wherein the sample containers each have a gas permeable and penetration re-sealable closure comprising a first layer of re-sealable material that is liquid impermeable and a second layer of gas porous, liquid impermeable layer;
   a cap having an upper portion that seals against a portion of the re-sealable material of one of the sample containers and a sidewall portion that defines a vent space next to the gas porous, liquid impermeable layer of said one of the sample containers.

2. The device of claim 1, wherein an interior of one of the capillary collection channels is coated with a first anticoagulant different from a second anticoagulant coating an interior of another of the capillary collection channels.

3. The device of claim 2, wherein the first anticoagulant is ethylenediaminetetraacetic acid (EDTA).

4. The device of claim 2, wherein the first anticoagulant is citrate.

5. The device of claim 2, wherein the first anticoagulant is heparin.

6. The device of claim 1, wherein interiors of each of the collection channels are coated with an anti-coagulant.

7. The device of claim 1, wherein each of the capillary collection channels can hold a volume of no greater than 500 μL.

8. The device of claim 1, wherein each of the capillary collection channels can hold a volume of no greater than 200 μL.

9. The device of claim 1, wherein each sample container has an interior volume no greater than twenty times the interior volume of the capillary collection channel with which it is engagable.

10. The device of claim 9, wherein each sample container has an interior volume no greater than ten times the interior volume of the capillary collection channel with which it is engagable.

11. The device of claim 10, wherein each sample container has an interior volume no greater than five times the interior volume of the capillary collection channel with which it is engagable.

12. The device of claim 11, wherein each sample container has an interior volume no greater than two times the interior volume of the capillary collection channel with which it is engagable.

13. The device of claim 1, wherein establishment of fluidic communication between one of the capillary collection channels and one of the sample containers results in transfer of at least 90% of the bodily fluid sample in the capillary collection channel into the sample container.

14. The device of claim 13, wherein no more than five μL of bodily fluid sample remain in the capillary collection channel upon establishment of said fluidic communication.

15. A device for collecting a bodily fluid sample, the device comprising:
   a first portion comprising a plurality of capillary collection channels;
   a second portion comprising a plurality of sample containers for receiving the bodily fluid sample collected in the capillary collection channels, wherein the sample containers each have a gas permeable and penetration re-sealable enclosure comprising a first layer of re-sealable material that is liquid impermeable and a second layer of gas porous, liquid impermeable layer, wherein a flow facilitator provides a favorable pathway from at least one of the capillary collection channels into at least one of the sample containers;
   a cap having an upper portion that seals against a portion of the re-sealable material of each closure and a sidewall portion that defines a vent space next to the gas porous, liquid impermeable layer of each closure.

16. The device of claim 15, wherein an interior of one of the capillary collection channels is coated with a first anticoagulant different from a second anticoagulant coating an interior of another of the capillary collection channels.

17. The device of claim 15, wherein each of the capillary collection channels can hold a volume of no greater than 200 μL.

18. A device for collecting a bodily fluid sample, the device comprising:
   a first portion comprising a plurality of capillary collection channels;
   a second portion comprising a plurality of sample containers for receiving the bodily fluid sample collected in the collection channels, wherein the sample containers each have a gas permeable and penetration re-sealable closure comprising a first layer of re-sealable material that is liquid impermeable and a second layer of gas porous, liquid impermeable layer;

a plurality of caps, wherein each of the sample containers has one of said caps and each of said caps having an upper portion that seals against a portion of the resealable material on one of the sample containers and a sidewall portion that defines a vent space next to the gas porous, liquid impermeable layer on said one of the sample containers.

19. The device of claim 18, wherein an interior of one of the capillary collection channels is coated with a first anticoagulant different from a second anticoagulant coating an interior of another of the capillary collection channels.

20. The device of claim 19, wherein the first anticoagulant is ethylenediaminetetraacetic acid (EDTA).

21. The device of claim 19, wherein the first anticoagulant is citrate.

22. The device of claim 19, wherein the first anticoagulant is heparin.

* * * * *